(12) United States Patent
Matsushima et al.

(10) Patent No.: US 8,288,538 B2
(45) Date of Patent: *Oct. 16, 2012

(54) PYRIDINE DERIVATIVES AND PYRIMIDINE DERIVATIVES (3)

(75) Inventors: Tomohiro Matsushima, Tsukuba (JP); Keiko Takahashi, Tsukuba (JP); Setsuo Funasaka, Tsukuba (JP); Hiroshi Obaishi, Tsukuba (JP); Shuji Shirotori, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 40 days.

This patent is subject to a terminal disclaimer.

(21) Appl. No.: 12/558,982

(22) Filed: Sep. 14, 2009

(65) Prior Publication Data

US 2010/0075944 A1    Mar. 25, 2010

Related U.S. Application Data

(62) Division of application No. 11/508,322, filed on Aug. 23, 2006, now Pat. No. 7,855,290.

(60) Provisional application No. 60/710,671, filed on Aug. 24, 2005.

(51) Int. Cl.
| | |
|---|---|
| C07D 213/75 | (2006.01) |
| C07D 239/47 | (2006.01) |
| C07D 401/12 | (2006.01) |
| C07D 401/14 | (2006.01) |
| C07D 403/12 | (2006.01) |

(52) U.S. Cl. ........ 544/295; 540/575; 544/123; 544/125; 544/319; 544/360; 544/364; 546/194; 546/268.1; 546/278; 546/279.1

(58) Field of Classification Search .................. None
See application file for complete search history.

(56) References Cited

U.S. PATENT DOCUMENTS

| | | | |
|---|---|---|---|
| 6,790,852 | B2 | 9/2004 | Brandt et al. |
| 7,253,286 | B2 | 8/2007 | Funahashi et al. |
| 7,425,564 | B2 | 9/2008 | Fujiwara et al. |
| 7,531,532 | B2 | 5/2009 | Matsushima et al. |
| 7,652,022 | B2 | 1/2010 | Floersheimer et al. |
| 7,790,885 | B2 | 9/2010 | Nagai |
| 7,855,290 | B2 | 12/2010 | Matsushima et al. |
| 2003/0199691 | A1 | 10/2003 | Brandt et al. |
| 2004/0053908 | A1 | 3/2004 | Funahashi et al. |
| 2004/0214874 | A1 | 10/2004 | Brandt et al. |
| 2004/0242603 | A1 | 12/2004 | Fujiwara et al. |
| 2005/0009840 | A1 | 1/2005 | Cui et al. |
| 2005/0009842 | A1 | 1/2005 | Zemlicka et al. |
| 2005/0014753 | A1 | 1/2005 | Ding et al. |
| 2005/0245530 | A1 | 11/2005 | Borzilleri et al. |
| 2005/0277652 | A1 | 12/2005 | Matsushima et al. |
| 2006/0252777 | A1 | 11/2006 | Kim et al. |
| 2008/0214815 | A1 | 9/2008 | Nagai et al. |
| 2008/0300273 | A1 | 12/2008 | Christensen et al. |
| 2008/0318924 | A1 | 12/2008 | Matsushima et al. |
| 2008/0319188 | A1 | 12/2008 | Matsushima et al. |
| 2009/0176797 | A1 | 7/2009 | Obaishi et al. |
| 2009/0227556 | A1 | 9/2009 | Obaishi |
| 2010/0075944 | A1 | 3/2010 | Matsushima et al. |
| 2010/0311972 | A1 | 12/2010 | Nagai |

FOREIGN PATENT DOCUMENTS

| | | |
|---|---|---|
| EP | 1 411 046 A1 | 4/2004 |
| EP | 1411046 A1 | 4/2004 |
| EP | 1 415 987 A1 | 5/2004 |
| EP | 1 473 043 A1 | 11/2004 |
| EP | 1 506 962 A2 | 2/2005 |
| EP | 1506962 A2 | 2/2005 |
| EP | 1 719 762 A1 | 11/2006 |
| EP | 1 719 763 A1 | 11/2006 |
| EP | 1 889 836 A1 | 2/2008 |
| EP | 2058302 A1 | 5/2009 |

(Continued)

OTHER PUBLICATIONS

Extended European Search Report, dated Nov. 16, 2010, for European Application No. 07805959.9.
International Preliminary Report on Patentability, dated Feb. 26, 2008, for Application No. PCT/JP2006/316331.
International Search Report, dated Mar. 10, 2009, for Application No. PCT/JP2009/052401.
US Office Action, dated Aug. 13, 2010, for U.S. Appl. No. 12/031,568.
US Office Action, dated Jun. 7, 2010, for U.S. Appl. No. 12/315,291.
Berge et al., "Pharmaceutical Salts", Journal of Pharmaceutical Sciences, vol. 66, No. 1, Jan. 1977, pp. 1-19.

(Continued)

Primary Examiner — Emily Bernhardt
(74) Attorney, Agent, or Firm — Birch, Stewart, Kolasch & Birch, LLP

(57) ABSTRACT

A compound represented by the following formula, or a salt thereof or a hydrate of the foregoing, has excellent hepatocyte growth factor receptor (HGFR) inhibitory activity, and exhibits anti-tumor activity, angiogenesis inhibitory activity, and cancer metastasis inhibitory activity.

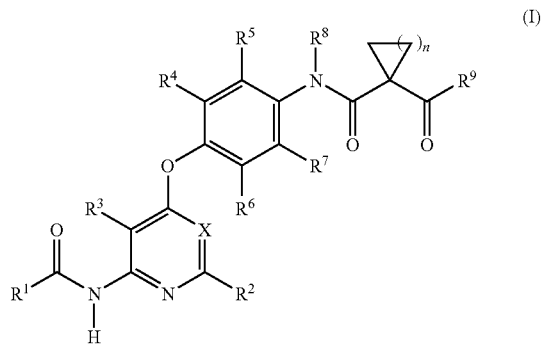

(I)

$R^1$ represents a 3- to 10-membered non-aromatic heterocyclic group or the like; $R^2$ and $R^3$ represent hydrogen; $R^4$, $R^5$, $R^6$, and $R^7$ may be the same or different and each represents hydrogen, halogen, $C_{1-6}$ alkyl or the like; $R^8$ represents hydrogen or the like; $R^9$ represents a 3- to 10-membered non-aromatic heterocyclic group or the like; n represents an integer of 1 or 2; X represents —CH=, nitrogen or the like.

14 Claims, No Drawings

FOREIGN PATENT DOCUMENTS

| | | |
|---|---|---|
| EP | 2 119 706 A1 | 11/2009 |
| JP | 2007-153894 | 6/2007 |
| JP | 2007-153894 A | 6/2007 |
| WO | WO-02/32872 A1 | 4/2002 |
| WO | WO 02/096361 A2 | 12/2002 |
| WO | WO-02/096361 A2 | 12/2002 |
| WO | WO-03/000660 A1 | 1/2003 |
| WO | WO-03/087026 A1 | 10/2003 |
| WO | WO-03/099771 A2 | 12/2003 |
| WO | WO 03/099771 A2 | 12/2003 |
| WO | WO 2004-030524 A2 | 4/2004 |
| WO | WO-2004/076412 A2 | 9/2004 |
| WO | WO-2004/089286 A2 | 10/2004 |
| WO | WO-2005/004607 A1 | 1/2005 |
| WO | WO-2005/004808 A2 | 1/2005 |
| WO | WO-2005/005378 A2 | 1/2005 |
| WO | WO-2005/005389 A2 | 1/2005 |
| WO | WO-2005/010005 A1 | 2/2005 |
| WO | WO-2005/016920 A1 | 2/2005 |
| WO | WO-2005/030140 A2 | 4/2005 |
| WO | WO-2005/040154 A1 | 5/2005 |
| WO | WO-2005/082854 A1 | 9/2005 |
| WO | WO-2005/082855 A1 | 9/2005 |
| WO | WO 2005/115478 A2 | 12/2005 |
| WO | WO-2005/117867 A2 | 12/2005 |
| WO | WO-2006/004636 A2 | 1/2006 |
| WO | WO-2006/014325 A2 | 2/2006 |
| WO | WO-2007/023768 A1 | 3/2007 |
| WO | WO 2008/026577 A1 | 3/2008 |
| WO | WO-2008/102870 A1 | 8/2008 |

OTHER PUBLICATIONS

Naran et al., "Inhibition of HGF/MET as therapy for malignancy", Expert Opinion. Ther. Tagets, vol. 13, No. 5, 2009, pp. 569-581.
Office Action issued on Feb. 5, 2010 in Co-pending U.S. Appl. No. 12/031,568.
International Preliminary Report on Patentability for Application No. PCT/JP2007/066185, dated Feb. 24, 2009.
International Search Report for Application No. PCT/IB2008/003880, dated Aug. 11, 2009.
Matsushima et a., "Preparation Phridime and Phrimidine Derivatives as Inhibitors of Hepatocyte Growth Factor Receptor (HGFR)", Updated Search, pp. 1-4.
Nakagawa et al., "Translating the Latest Discoveries Into Cancer Prevention and Cures", Proceedings, Experimental and Molecular Therapeutics 42, vol. 49, Apr. 12-16, 2008, p. 1154.
Nature Publishing Group, "MET Tyrosine Kinase Inhibitors", Nature Reviews, Drug Reviews, Drug Discovery, vol. 7, Jun. 2008, p. 499.
Notice of Allowance for U.S. Appl. No. 11/892,785, dated Apr. 5, 2010.
Obaishi, "E7050: A Novel Small Molecule Inhibitor of the c-Met and VEGFR-2 Tyrosine Kinases", AACR 2008, Abstract #4846, one page.
Pakistani Office Action for Application No. 375-2008, dated Oct. 21, 2008.
Pakistani Office Actions for Application No. 1024/2006, dated Oct. 21, 2008 and Dec. 12, 2007.
Plate et al., "Vascular Entothelial Growth Factor is a Potential Tumour Antigenesis Factor in Human Gliomas in Vivo", Nature, vol. 359, Oct. 29, 1992, pp. 845-848.
Sekido et al., "Preferential Expression of c-kit Protooncogene Transcripts in Small Cell Lunch Cancer", Cancer Research, vol. 51, May 1, 1991, pp. 2416-2419.
Kolibaba et al., "Protein tyrosine kinases and cancer", B. B. A., 1333, F217-F248, (Jul. 1997), Portland, OR.
Scheijen et al., "Tyrosine kinase oncogenes in normal hematopoiesis and hematological disease", Oncogene, 21, 3314-3333, (2002), Boston, MA.
Blume-Jensen et al., "Activation of the human c-kit product by ligand-induced dimerization mediates circular actin reorganization and chemotaxis", The EMBO Journal, 10, 4121-4128, (1991), Thousand Oaks, CA and Sweden.
Lev et al., "A specific combination of substrates is involved in signal transduction by the kit-encoded receptor" The EMBO Journal, 10, 647-654, (1991), Isreal.

Wang et al., "The Expression of the Proto-Oncogene C-Kit in the Blast Cells of Acute Myeloblastic Leukemia", Leukemia, 3, 699-702, (1989), Toronto, Canada and Cambridge, MA.
Kanakura et al., "Expression, Function and Activation of the Proto-oncogen c-kit Product in Human Leukemia Cells", Leukemia and Lymphoma, 10, 35-41, (1993), Osaka, Japan.
Ikeda et al., "Expression and Functional Role of the Proto-oncogene c-kit in Acute Myeloblastic Leukemia Cells", Blood, 78, 2962-2968, (1991).
Ikeda et al., "Changes in phenotype and proliferative potential of human acute myeloblastic leukemia cells in culture with stem cell factor", Experimental Hematology, 21, 1686-1694, (Aug. 1993), Osaka, Japan.
Furitsu et al., "Identification of Mutations in the Coding Sequence of the Proto-oncogene c-kit in a Human Mast Cell Leukemia Cell Line Causing Ligand-independent Activation of c-kit Product", J. Clin. Invest., 92, 1736-1744, (1993), Osaka, Japan; Rochester, MN and Adelaide, South Australia.
Hibi et al., "Coexpression of the stem cell factor and the c-kit genes in small-cell lung cancer", Oncogene, 6, 2291-2296, (1991), Nagoya, Japan.
Sekido et al., "Preferential Expression of c-kit Protooncogene Transcripts in Small Cell Lung Cancer", Cancer Research, 51, 2416-2419, (May 1, 1991), Nagoya, Japan.
Lasota et al., "Mutations in Exons 9 and 13 of KIT Gene Are Rare Events in Gastrointestinal Stromal Tumors", American Journal of Pathology, 157, 1091-1095, (Oct. 2000), Washington, D.C.; Helsinki, Finland and Krakow, Poland.
Taniguchi et al., Effect of c-kit Mutation on Prognosis of Gastrointestinal Stromal Tumors, Cancer Research, 59, 4297-4300, (Sep. 1, 1999), Japan.
Strohmeyer et al., "Expression of the hst-1 and c-kit Protooncogenes in Human Testicular Germ Cell Tumors", Cancer Research, 51, 1811-1816, (Apr. 1, 1991), CA and Germany.
Tian et al., "Activating c-kit Gene Mutations in Human Germ Cell Tumors", American Journal of Pathology, 154, 1643-1647, (Jun. 1999), VA.
Tonary et al., "Lack of Expression of c-Kit in Ovarian Cancers is Associated With Poor Prognosis", Int. J. Cancer (Pred. Oncol.), 89, 242-250, (2000), Ottawa, Canada.
Natali et al., "Breat Cancer Is Associated With Loss of the c-kit Ikit Oncogene Product". Int. J. Cancer, 52, 713-717, (1992), Rome, Italy.
Hines et al., "Coexpression of the c-kit and Stem Cell Factor Genes in Breast Carcinomas", Cell Growth & Differentiation, 6, 769-779, (Jun. 1995), Richmond, VA.
Berdel et al., "Recombinant Human Stem Cell Factor Stimulates Growth of a Human Glioblastoma Cell Line Expressing c-kit Protooncogene", Cancer Research, 52, 3498-3502, (Jun. 15, 1992), Germany.
Cohen et al., "Expression of Stem Cell Factor and c-kit in Human Neuroblastoma", Blood, 84, 3465-3472, (1994).
Bellone et al., "Growth Stimulation of Colorectal Carcinoma Cells Via the c-Kit Receptor Is Inhibited by TGF-β1", Journal of Cellular Physiology, 172, 1-11, (1997), Torino, Italy and Philadelphia, PA.
Hamel et al., "The road less travelled: c-kit and stem cell factor", Journal of Neuro-Oncology, 35, 327-333, (1997), Hamburg, Germany and San Francisco, CA.
Kitamura et al., "Regulation of Development, Survival and Neoplastic Growth of Mast Cells through the c-kit Receptor", Int. Arch. Allergy Immunol., 107, 54-56, (1995), Osaka, Japan.
Metcalfe, "Classification and Diagnosis of Mastocytosis: Current Status", J. Invest. Derm., 96, 2S-4S, (1991), Bethesda, MD.
Golkar et al., "Mastocytosis", The Lancet, 349, 1379-1385, (1997).
Nagata et al., "Elevated expression of the proto-oncogene c-kit in patients with mastocytosis", Leukemia, 12, 175-181, (1998), Bethesda, MD.
Longley et al., "Altered Metabolims of Mast-Cell Growth Factor (c-kit Ligand) in Cutaneous Mastocytosis", New England Journal of Medicine, 328, 1302-1307, (May 6, 1993).
Longley et al., "Somatic c-KIT activating mutation in urticaria pigmentosa and aggressive mastocytosis: establishment of clonality in a human mast cell neoplasm", Nature Genetics, 12, 312-314, (Mar. 1996).

Thomas et al., "The Eosinophil and its Role in Asthma", Gen. Pharmac., 27, 593-597, (1996), Southampton, UK.
Metcalfe et al., "Mast Cells", Physiological Reviews, 77, 1033-1079, (Oct. 1997), Tel Aviv, Israel.
Naclerio et al., "Rhinitis and Inhalant Allergens", JAMA, 278, 1842-1848, (Dec. 10, 1997).
Meltzer, "The pharmacological basis for the treatment of perennial allergic rhinitis and non-allergic rhinitis with topical corticosteroids", Allergy, 52, 33-40, (1997), San Diego, CA.
Okayama et al., "Activation of Eosinophils with Cytokines Produced by Lung Mast Cells", International Archives of Allergy and Immunology, 114, 75-77, (1997), Maebashi, Japan; Southampton, UK and Adelaide, Australia.
Okayama et al., "Human lung mast cells are enriched in the capacity to produce granulocyte-macrophage colony-stimulating factor in response to IgE-dependent stimulation", Eur. J. Immunol., 28, 708-715, (1998), Maebashi, Japan, Adelaide, Australia and Southampton, GB.
Metcalf, "Lineage commitment in the progeny of murine hematopoietic preprogenitor cells: influence of thrombopoietin and interleukin", Proc. Natl. Acad. Sci., 95, 6408-6412, (May 1998), Victoria, Australia.
Kay et al., "Eosinophils and Eosinophil-Associated Cytokines in Allergic Inflammation", International Archives of Allergy and Immunology, 113, 196-199, (1997), London, UK.
Hogaboam et al., "Novel Role of Transmembrane SCF for Mast Cell Activation and Eotaxin Production in Mast Cell-Fibroblast Interactions", The Journal of Immunology, 160, 6166-6171, Feb. 17, 1998), Ann Arbor, MI and Frederick, MD.
Luckas et al., "Stem Cell Factor (c-kit Ligand) Influences Eosinophil Recruitment and Histamine Levels in Allergic Airway Inflammation", The Journal of Immunology, 156, 3945-3951, (Feb. 28, 1996), Ann Arbor, MI; Frederick, MD and New Haven, CT.
Folkman et al., "Angiogenesis", The Journal of Biological Chemistry, 267, 10931-10934, (1992), Boston, MA.
Jakeman et al., "Developmental Expression of Binding Sites and Messenger Ribonucleic Acis for Vascular Endothelial Growth Factor Suggests a Role for This Protein in Vasculogenesis and Angiogenesis", Endocrinology, 133, 848-859, (1993), San Francisco, CA.
Folkman, "Clinical Applications of Research on Angiogenesis", The New England Journal of Medicine, 333, 1757-1763, (Dec. 28, 1995).
Folkman, "What Is the Evidence That Tumors Are Angiogenesis Dependent?", Journal of the National Cancer Institute, 82, 4-6, (Jan. 3, 1990), Boston, MA.
Ferrara et al., "Molecular and Biological Properties of the Vascular Endothelial Growth Factor Family of Proteins", Endocrine Reviews, 13, 18-32, (1992), San Francisco, CA.
Plate et al., "Vascular endothelial growth factor is a potential tumour angiogenesis factor in human gliomas in vivo", Letter to Nature, 359, 845-848, (1992), Germany.
Plate et al., "Up-Regulation of Vascular Endothelial Growth Factor and Its Cognate Receptors in a Rat Glioma Model of Tumor Angiogenesis", Cancer Research, 53, 5822-5827, (Dec. 1, 1993), Germany.
Berkman et al., "Expression of the Vascular Permeability Factor/Vascular Endothelial Growth Factor Gene in Central Nervous System Neoplasms", The Journal of Clinical Investigation, 91, 153-159, (Jan. 1993), Bethesda, MD and Memphis, TN.
Nakamura et al., "Vascular Endothelial Growth Factor Is a Potent Angiogenic Factor in AIDS-Associated Kaposi's Sarcoma-Derived Spindle Cells", The Journal of Immnology, 158, 4992-5001, (Feb. 12, 1997), Germany and CA.
Mustonen et al., "Endothelial Receptor Tyrosine Kinases Involved in Angiogenesis", The Journal of Cell Biology, 129, 895-898, (May 1995), Helsinki, Finland.
Bardella et al., "Truncated RON Tyrosine Kinase Drives Tumor Cell Progression and Abrogates Cell—Cell Adhesion Through E-Cadherin Transcriptional Repression", Cancer Research, 64, 5154-5161, (Aug. 1, 2004), Italy.
O'Toole et al., "Therapeutic Implications of a Human Neutralizing Antibody to the Macrophage-Stimulating Protein Receptor Tyrosine Kinase (RON), a c-MET Family Member", Cancer Research, 66, 9162-9170, (2006), Stonybrook, NY and Cincinnati, OH.
Carlomagno et al., "ZD6474, an Orally Available Inhibitor of KDR Tyrosine Kinase Activity, Efficiently Blocks Oncogenic RET Kinases", Cancer Research, 62, 7284-7290, (Dec. 15, 2002), Italy and UK.
Carlomagno et al., "BAY 43/9006 Inhibition of Oncogenic RET Mutants", Journal of National Cancer Institute, 98, 326-334, (Mar. 1, 2006).
Terman et al., "Identification of a new endothelial cell growth factor receptro tyrosine kinase", Oncogene, 6, 1677-1683, (1991), NY.
Park et al., "Homogeneous Proximity Tyrosine Kinase Assays: Scintillation Proximity Assay versus Homogeneous Time-Resolved Fluorescence", Analytical Biochemistry, 269, 94-104, (1999), Rahway, NJ.
"Cell Culture Technique", Lectures on New Biochemical Experiments, 18, 197-202, with English language translation.
Watson et al., "Inhibition of c-Met as a Therapeutic Strategy for Esophageal Adenocarcinoma," Neoplasia, vol. 8, No. 11, Nov. 2006, pp. 949-955.
English Translation of International Search Report and Written Opinion for PCT/IB2008/003880 issued Aug. 11, 2009.
Office Action (dated Oct. 21, 2008 and Dec. 12, 2007) in related patent application No. 1024/2006 in Pakistan, in English.
Office Action (dated Oct. 21, 2008) in related patent application No. 375/2008 in Pakistan, in English.
Notice of Allowance dated Sep. 15, 2009 in parent U.S. Appl. No. 11/508,322.
English translation of WO 2008/102870 published Aug. 28, 2008.
Smolen et al., "Amplification of MET may identify a subset of cancers with extreme sensitivity to the selective tyrosine kinase inhibitor PHA-665752" Proc. Nat. Acad. Sci. USA, 103(7): 2316-2321, 2006.
English translation of International Preliminary Report on Patentability (IPRP-Chapter I) issued in International Application No. PCT/JP2007/066185 dated Mar. 5, 2009 (6 pages).
H. Saeki et al., "Concurrent overexpression of Ets-1 and c-Met correlates with a phenotype of high cellular motility in human esophageal cancer", International Journal of Cancer, vol. 98, No. 1, pp. 8-13, 2002.
Christine Ting Ting To et al.; The roles of hepatocyte growth . . . , Oncology Reports 5: 1013-1024, 1998.
Eliot M. Rosen et al.; Scatter Factor and Angiogenesis, Advances in Cancer Research, 67, pp. 257-279, 1995.
N. Maehara et al.; NK4, a four-kringle antagonist . . . , British Journal of Cancer, 84, pp. 864-873, 2001.
Kunio Matsumoto et al.; NK4 (HGF-antagonist/angiogenesis inhibitor) . . . , Cancer Sci., 94, pp. 321-327, 2003.
Matthias Ebert et al., Coexpression of the c-met. . . , Cancer Research 54, pp. 5775-5778, 1994.
Hiroki Kumiyasu et al.; Frequent amplification . . . , Biochemical and Biophysical Research Communications, vol. 189, No. 1, pp. 227-232, Nov. 30, 1992.
Chi Liu et al., Overexpression of c-met. . . , Oncogene, 7, pp. 181-185, 1992.
Rola A. D. Choussoub et al.; Expression of c-met. . . , Cancer, 82, pp. 1513-1520, 1998.
Louis L. Pisters et al., C-met Proto-Oncogene Expression, The Journal of Urology, vol. 154, pp. 293-298, Jul. 1995.
Iwao Takanami et al., Hepatocyte Growth Factor . . . , Oncology, 53, pp. 392-397, 1996.
Laura Schmidt et al., Novel mutations of the MET . . . , Oncogene, 14, pp. 2343-2350, 1999.
Shahriar Koochekpour et al., Met and Hepatocyte Growth . . . , Cancer Research, 57, pp. 5391-5398, 1997.
Janos Tanyi et al., Evaluation of the Tyrosine . . . , Pathology Oncology Research, 5, pp. 187-191, 1999.
Yoshitaka Imaizumi et al., Expression of the c-Met . . . , Clinical Cancer Research, vol. 9, pp. 181-187, 2003.
Joachim Ulrich, "Crystallization-4.Crystal Characteristics", Kirk-Othmer Encyclopedia of Chemical Technology, Aug. 2002, 7 pages.
Sudha R. Vippagunta et al., "Crystalline Solids", Advanced Drug Delivery Reviews, 48, 2001, pp. 3-26.

Anthony R. West, "Solid Solutions", Solid State Chemistry and its applications, 1988, pp. 358-365.
E7050: "A novel orally active c-Met and VEGFR-2 tyrosine kinase inhibitor exhibited potent antitumor effect and prolongation of survival in preclinical mice model.", Nakagawa et al., Proceedings of the American Association for Cancer Research, vol. 49, p. 1154, #4845, 2008.
E7050: "A novel small molecule the c-Met and VEGFR-2 tyrosine kinase.", Obaishi et al., Proceedings of the American Association for Cancer Research, vol. 49, p. 1154, #4846, 2008.
"MET tyrosine kinase inhibitors" Nature Reviews Drug Discovery, vol. 7, Jun. 2008, p. 469.
Miller et al., "Genomic amplification of MET with boundaries within fragile site FRA7G and upregulation of MET pathways in esophageal adenocarcinoma," Oncogene, 2006, vol. 25, pp. 409-418.
Office Action dated Dec. 3, 2008 in corresponding Russian patent application No. 2008110932, with English translation.
Office Action dated Nov. 5, 2007 in corresponding patent application No. 184/2006/4959 in Bangladesh, in English.
Nakagawa et al., Poster Manuscript, "E7050: A novel orally active c-Met and VEGFR-2 tyrosine kinase inhibitor exhibited potent antitumor effect and prolongation of survival in preclinical mice model.", Proceedings of the American Association for Cancer Research 2008.
Obaishi et al., Poster Manuscript, "E7050: A novel small molecule the c-Met and VEGFR-2 tyrosine kinase.", Proceedings of the American Association for Cancer Research 2008.
"E7050: A novel orally active c-Met and VEGFR-2 tyrosine kinase inhibitor exhibited potent antitumor effect and prolongation of survival in preclinical mice model", Nakagawa et al, Nagakagawa et al., Abstract of P1-8 in Japanese Association for Molecular Target Therapy of Cancer 2008.
"E7050: A novel small molecule inhibitor of the c-Met and VEGFR-2 tyrosine kinases", Obaishi et al., Abstract of P1-7 in Japanese Association for Molecular Target Therapy of Cancer 2008.
US Office Action dated May 29, 2009 issued in U.S. Appl. No. 11/508,322.
US Office Action dated Dec. 18, 2008 issued in U.S. Appl. No. 11/508,322.
International Preliminary Report on Patentability and Written Opinion of the International Searching Authority mailed Oct. 14, 2010 for International Application No. PCT/JP2009/052401 (Forms PCT/ISA/237, PCT/IB/338 and PCT/IB/373).
Office Action issued Sep. 29, 2009 in corresponding Japanese Application No. 2006-510543.
European Office Action, dated Feb. 11, 2011, for European Application No. 05719973.9.
Nicolaus, "Symbiotic Approach to Drug Design", Decision Making in Drug Research, pp. 173-186 (BNS pp. 1-14), XP-001111439, 1983.
"Cancer Drug Design and Discovery", Stephen Neidle, editor, Failure Modes in the Discovery Process, Inadequate Preclinical Models, 2008, pp. 427-431.
European Search Report for Application No. 09713617.0, dated Apr. 28, 2011.
U.S. Office Action for U.S. Appl. No. 12/031,568, dated May 12, 2011.
International Peliminary Report on Patentability and Written Opinion of the International Searching Authority dated Jul. 14, 2011, for Application No. PCT/JP2008/071881.
Advanced Automated Peptide Protein Technologies, The Spirit of Innovation, "Coupling Reagents," published Aug. 3, 2007, 4 pages, http://www.aapptec.com.
Australian Office Action dated Dec. 22, 2011, for Application No. 2007288793.
Chinese Notice of Allowance dated Jan. 11, 2012, for Application No. 200680021939.X.
European Notice of Allowance dated Feb. 6, 2012, for Application No. 05719973.9.
European Search Report dated Sep. 7, 2011, for Application No. 06796594.7.
Indonesian Office Action dated Jan. 13, 2012, for Application No. W00200800601.
Nakagawa et al., "E7050: A dual c-Met and VEGFR-2 tyrosine kinase inhibitor promotes tumor regression and prolongs survival in mouse xenograft models," Cancer Science, vol. 101, No. 1, Jan. 2010, pp. 210-215.
Response to the invitation pursuant to Rule 70(2) and 70a(2)EPC with amended claims dated Dec. 21, 2011, for European Application No. 06796594.7.
U.S. Notice of Allowance, dated Jan. 2, 2009, for U.S. Appl. No. 11/065,631.
U.S. Notice of Allowance, dated Oct. 19, 2011, for U.S. Appl. No. 12/031,568.
U.S. Notice of Allowance, dated Sep. 9, 2008, for U.S. Appl. No. 11/065,631.
U.S. Office Action (Advisory Action), dated Mar. 24, 2011, for U.S. Appl. No. 12/315,291.
U.S. Office Action, dated Feb. 28, 2008, for U.S. Appl. No. 11/065,631.
U.S. Office Action, dated Oct. 26, 2011, for U.S. Appl. No. 12/867,646.
US Office Action, dated Jan. 12, 2011, for U.S. Appl. No. 12/315,291.
Varvoglis, "Chemical Transformations Induced by Hypervalent Iodine Reagents," Tetrahedron, vol. 53, No. 4, 1997, pp. 1179-1255.
Israeli Office Action and an English translation thereof dated Feb. 8, 2012, for Application No. 197002.
Response to the Indian First Examination Report dated Jan. 18, 2012, for National Phase Application No. 1424/CHENP/2008 of International Application No. PCT/JP06/316331.
IPP Notice of Allowability, Appl. No. 12007502319, Feb. 29, 2012.
Response to Office Action filed on Feb. 6, 2012 for PH Patent Application No. 1-2007-502319.
Australian Amendment dated Jan. 25, 2008 for AU Application No. 2006282456.
Australian Amendment dated May 29, 2009 for AU Application No. 2007288793.
Australian Notice of Acceptance dated Aug. 17, 2009 for AU Application No. 2006282456.
Australian Notice of Acceptance dated Mar. 16, 2012 for AU Application No. 2007289787.
Australian Office Action dated Jun. 12, 2009 for AU Application No. 2006282456.
Australian Voluntary Amendment dated Nov. 18, 2009 for AU Application No. 2008217931.
Bangladeshi Amendment dated May 6, 2008 for BD Application No. 184/2006.
Bangladeshi Amendment dated Sep. 26, 2007 for BD Application No. 184/2006.
Bangladeshi Letter dated Feb. 2, 2012 for BD Application No. 184/2006.
Brazilian Amendment dated May 29, 2009 for BR Application No. PI0616799-3 (with partial English translation).
Canadian Amendment dated Oct. 23, 2007 for CA Application No. 2605854.
Canadian Notice of Allowance dated Apr. 7, 2010 for CA Application No. 2605854.
Canadian Office Action dated Jul. 29, 2009 for CA Application No. 2605854.
Canadian Voluntary Amendment dated Aug. 20, 2009 for CA Application No. 2679602.
Chinese Amendment dated Aug. 7, 2009 for CN Application No. 200880004511.3 (with partial English translation).
Chinese Amendment dated Dec. 18, 2007 for CN Application No. 200680021939.X (with English translation).
Chinese Office Action dated Jul. 5, 2011 for CN Application No. 200880004511.3 (with English translation).
Chinese Office Action dated Mar. 30, 2011 for CN Application No. 200680021939.X (with English translation).
Chinese Office Action dated May 27, 2010 for CN Application No. 200680021939.X (with English translation).
Chinese Office Action dated Sep. 2, 2010 for CN Application No. 200680021939.X (with English translation).
European Amendment dated Apr. 19, 2012 for EP Application No. 06796594.7.

European Amendment dated Jan. 11, 2008 for EP Application No. 06796594.7.
European Amendment dated Nov. 16, 2007 for EP Application No. 06796594.7.
European Amendment dated Sep. 8, 2009 for EP Application No. 08711837.8.
European Decision to Grant dated Nov. 4, 2011 for EP Application No. 07805959.9.
European Invitation to Remedy Deficiencies dated Mar. 10, 2008 for EP Application No. 06796594.7.
European Office Action dated Dec. 3, 2010 for EP Application No. 07805959.9.
European Office Action dated Jun. 21, 2011 for EP Application No. 07805959.9.
European Office Action dated Sep. 26, 2011 for EP Application No. 06796594.7.
Extended European Search Report dated Mar. 28, 2011 for EP Application No. 08711837.8.
Filipino Office Action dated Dec. 16, 2011 for PH Application No. 12007502319.
Indian Amendment (complete specification) dated Mar. 24, 2008 for IN Application No. 1424/CHENP/2008.
Indian Office Action dated Sep. 19, 2011 for IN Application No. 1424/CHENP/2008, including Response thereto dated Nov. 18, 2011.
Indian Voluntary Amendment dated Sep. 23, 2009 for IN Application No. 5625/CHENP/2009.
Israeli Amendment dated Aug. 18, 2009 for IL Application No. 200466.
Israeli Notice Prior to Allowance dated Sep. 12, 2011 for IL Application No. 188670 (with English translation).
Israeli Notice Prior to Examination dated Aug. 13, 2009 for IL Application No. 188670 (with English translation).
Israeli Notice Prior to Examination dated Jun. 22, 2010 for IL Application No. 200466 (with English translation).
Israeli Notice Prior to Examination dated Mar. 23, 2010 for IL Application No. 197141 (with English translation).
Israeli Office Action dated Feb. 22, 2012 for IL Application No. 197141 (with English translation).
Israeli Office Action dated Feb. 8, 2012 for IL Application No. 197002 (with English translation).
Israeli Office Action dated Jul. 3, 2011 for IL Application No. 188670 (with English translation).
Japanese Amendment dated Dec. 25, 2007 for JP Application No. 2007-532099 (with English translation).
Japanese Amendment dated Sep. 25, 2007 for JP Application No. 2007-532099.
Japanese Decision to Grant dated Jan. 8, 2008 for JP Application No. 2007-532099 (with English translation).
Japanese Petition dated Dec. 25, 2007 for JP Application No. 2007-532099 (with English translation).
Japanese Petition dated Sep. 25, 2007 for JP Application No. 2007-532099 (with English translation).
Jordanian Amendment dated Oct. 19, 2007 for JO Application No. 280/2006 (with partial English translation).
Korean Amendment dated Aug. 10, 2009 for KR Application No. 10-2009-7013723 (with partial English translation).
Korean Amendment dated Dec. 27, 2007 for KR Application No. 10-2007-7026886 (with partial English translation).
Korean Amendment dated Nov. 21, 2007 for KR Application No. 10-2007-7026886 (with partial English translation).
Korean Amendment dated Oct. 27, 2009 for KR Application No. 10-2007-7026886 (with partial English translation).
Korean Argument Brief dated Oct. 27, 2009 for KR Application No. 10-2007-7026886 (with partial English translation).
Korean Notice of Decision to Grant dated Dec. 31, 2009 for KR Application No. 10-2007-7026886 (with English translation).
Korean Notice of Final Rejection dated Jul. 29, 2011 for KR Application No. 10-2009-7013723 (with English translation).
Korean Office Action dated Aug. 27, 2009 for KR Application No. 10-2007-7026886 (with English translation).
Korean Office Action dated May 19, 2011 for KR Application No. 10-2009-7013723 (with English translation).
Malaysian Amendment dated Jul. 17, 2008 for MY Application No. PI20071922.
Malaysian Office Action dated Jan. 15, 2010 for MY Application No. PI20071922.
Maltese Registration Letter dated Oct. 29, 2007 for MT Application No. 3723.
Maltese Registration Letter dated Sep. 29, 2007 for MT Application No. 3723.
Mexican Notice of Allowance dated Oct. 15, 2010 for MX Application No. MX/a/2008/002156 (with English translation).
New Zealand Notice of Acceptance dated Feb. 12, 2010 for NZ Application No. 566793.
New Zealand Office Action dated Dec. 4, 2009 for NZ Application No. 566793.
Pakistani Notice of Acceptance dated Nov. 2, 2010 for PK Application No. 1024/2006.
Pakistani Notice of Acceptance dated Nov. 2, 2010 for PK Application No. 375/2008.
Pakistani Office Action dated Feb. 24, 2009 for PK Application No. 1024/2006.
Pakistani Office Action dated Jul. 20, 2009 for PK Application No. 375/2008.
Response to Australian Office Action dated Jul. 16, 2009 for AU Application No. 2006282456.
Response to Australian Office Action dated Mar. 30, 2012 for AU Application No. 2007288793.
Response to Bangladeshi Office Action dated Dec. 13, 2007 for BD Application No. 184/2006.
Response to Canadian Office Action dated Oct. 8, 2009 for CA Application No. 2605854.
Response to Chinese Office Action dated Jul. 27, 2010 for CN Application No. 200680021939.X (with English translation).
Response to Chinese Office Action dated May 20, 2011 for CN Application No. 200680021939.X (with English translation).
Response to Chinese Office Action dated Oct. 28, 2010 for CN Application No. 200680021939.X (with English translation).
Response to European Invitation to Remedy Deficiencies dated Mar. 31, 2008 for EP Application No. 06796594.7.
Response to European Office Action dated Dec. 21, 2011 for EP Application No. 06796594.7.
Response to European Office Action dated Mar. 29, 2011 for EP Application No. 07805959.9.
Response to Israeli Notice Prior to Examination dated Jun. 1, 2010 for IL Application No. 197141 (with English translation).
Response to Israeli Notice Prior to Examination dated Nov. 22, 2009 for IL Application No. 188670 (with English translation).
Response to Israeli Office Action dated Aug. 15, 2011 for IL Application No. 188670 (with English translation).
Response to Israeli Office Action dated Oct. 25, 2011 for IL Application No. 188670 (with English translation).
Response to New Zealand Office Action dated Jan. 27, 2010 for NZ Application No. 566793.
Response to Pakistani Office Action dated Apr. 20, 2009 for PK Application No. 1024/2006.
Response to Pakistani Office Action dated Apr. 7, 2008 for PK Application No. 1024/2006.
Response to Pakistani Office Action dated Apr. 8, 2009 for PK Application No. 375/2008.
Response to Pakistani Office Action dated Jan. 29, 2009 for PK Application No. 1024/2006.
Response to Pakistani Office Action dated Sep. 1, 2009 for PK Application No. 375/2008.
Response to Russian Office Action dated Jan. 26, 2009 for RU Application No. 2008110932/04 (with English translation).
Response to Vietnamese Office Action dated May 10, 2010 for VN Application No. 1-2008-00723 (with English translation).
Russian Decision on Grant dated Feb. 6, 2009 for RU Application No. 2008110932/04 (with English translation).
Saudi Arabian Amendment dated Oct. 22, 2007 for SA Application No. 06270287 (with partial English translation).
Saudi Arabian Appeal dated Jun. 23, 2010 for SA Application No. 06270287 (with English translation).

Singaporean Amendment dated on Aug. 24, 2010 for SG Application No. 200718614-1.
South African Notification of Acceptance dated Mar. 12, 2009 for ZA Application No. 2007/09572.
Sri Lankan Amendment dated Mar. 31, 2011 for LK Application No. 14703.
Supplementary European Search Report dated Apr. 14, 2011 for EP Application No. 08711837.8.
Taiwanese Amendment dated Mar. 20, 2009 for TW Application No. 95130665 (with English translation).
Thai Amendment dated on Sep. 25, 2007 for TH Application No. 0601004017 (with English translation).
U.S. Notice of Allowance dated Apr. 26, 2011 for U.S. Appl. No. 12/315,291.
Vietnamese Intention to Grant dated Aug. 19, 2010 for VN Application No. 1-2008-00723 (with English translation).
Vietnamese Office Action dated Mar. 11, 2010 for VN Application No. 1-2008-00723 (with English translation).
Office Action for Chinese Application No. 200780019200.X, dated Apr. 6, 2012.
Israel Amendment filed May 2, 2012 for IL Patent Application No. 188670 (w/ English Translation).
TW Office Action dated Mar. 2, 2012 for Appl. No. 095130665 (w/ English translation).
Australian Notice of Acceptance for AU Patent Application No. 2007288793 dated Apr. 10, 2012.
Australian Second Statement of Proposed Amendments for AU Patent Application No. 2006282456 filed Apr. 26, 2012.
India Amendment for IN Patent Application No. 1424/CHENP/2008 filed Apr. 27, 2012.
Norwegian Amendment for NO Patent Application No. 20080460 filed May 14, 2012 (w/ English translation).
Philippines Amendment for PH Patent Application No. 1-2007-502319 filed May 14, 2012.
European Decision to Grant a Patent, dated Jun. 1, 2012, for European Application No. 05719973.9.
Israeli Response to Notice of Defects, dated Jun. 10, 2012, for Israeli Application No. 197141.
US Notice of Allowance, dated Jun. 1, 2012, for U.S. Appl. No. 12/031,568.
Request for Examination dated Jun. 26, 2012 for Canadian Patent Application No. 2661702.
Response to the Result of Substantative Examination Stage I filed on Jun. 11, 2012 for Indonesian Patent Application No. W-00200800601 (w/ English translation).
Submission Document(s) Before the Patent Office dated May 29, 2012 for Brazilian Patent Application No. PI0616799-3 (w/ English translation).
Australian Office Action dated Jun. 28, 2012 for AU Application No. 2008217931.
Response to Chinese Office Action dated Jul. 24, 2012, for Chinese Patent Application No. 200780019200.X (with English translation).
U.S. Office Action, dated Aug. 13, 2012, for U.S. Appl. No. 12/527,633.

SEQUENCE LISTING

<160> NUMBER OF SEQ ID NOS: 2

<210> SEQ ID NO 1
<211> LENGTH: 33
<212> TYPE: DNA
<213> ORGANISM: Artificial Sequence
<220> FEATURE:

```
<223> OTHER INFORMATION: Artificially synthesized primer sequence

<400> SEQUENCE: 1
ccggccggat ccaaaaagag aaagcaaatt aaa                            33

<210> SEQ ID NO 2
<211> LENGTH: 33
<212> TYPE: DNA
<213> ORGANISM: Artificial Sequence
<220> FEATURE:
<223> OTHER INFORMATION: Artificially synthesized primer sequence

<400> SEQUENCE: 2
ttaattctgc agctatgatg tctcccagaa gga                            33
```

PYRIDINE DERIVATIVES AND PYRIMIDINE DERIVATIVES (3)

CROSS-REFERENCE TO RELATED APPLICATIONS

This application is a divisional of, and claims the benefit of, U.S. application Ser. No. 11/508,322, filed Aug. 23, 2006, now U.S. Pat. No. 7,855,290, which in turn claims the benefit of U.S. Provisional Application Ser. No. 60/710,671, filed on Aug. 24, 2005. The entire contents of both of these applications is hereby incorporated by reference.

BACKGROUND OF THE INVENTION

1. Field of the Invention

The present invention relates to a novel pyridine derivative and pyrimidine derivative, a salt thereof or a hydrate of the foregoing, having inhibitory activity against hepatocyte growth factor receptor, anti-tumor activity, inhibitory activity against angiogenesis, inhibitory activity against cancer metastasis or the like.

2. Related Background of the Invention

Overexpression of hepatocyte growth factor receptor (hereafter referred to as "HGFR") is reported in various kinds of tumors such as a pancreatic cancer, a gastric cancer, a colorectal cancer, a breast cancer, a prostate cancer, a lung cancer, a renal cancer, a brain tumor or an ovarian cancer (non-patent document 1). HGFR expressed in these cancer cells is considered to be involved in cancer malignancy (aberrant growth, invasion or enhanced metastasis), because HGFR cause autophosphorylation of intracellular tyrosine kinase constitutively or upon stimulation by hepatocyte growth factor (hereafter referred to as HGF).

It is also reported that HGFR is expressed in vascular endothelial cells and is involved in tumor angiogenesis since HGF stimulates HGFR to facilitate proliferation and migration of vascular endothelial cells (non-patent document 2).

Furthermore, NK4, an antagonistic peptide for HGF, is reported to block HGF-HGFR signal to inhibit invasion of cancer cells and tumor angiogenesis (non-patent documents 3 and 4).

Therefore, a compound having inhibitory activity against HGFR is expected to be useful as an anti-tumor agent, an angiogenesis inhibitor or an inhibitor for cancer metastasis.

With regard to documents disclosing a low molecular weight compound having inhibitory activity against HGFR, the patent documents 1 to 11 are listed. However, the patent documents 1 and 2 disclose indolinone derivatives; the patent documents 3 and 4 disclose quinoline derivatives and quinazoline derivatives; the patent documents 5 and 6 disclose imidazole derivatives; the patent document 7 discloses aminopyridine derivatives and aminopyrazine derivatives; the patent document 8 discloses triazolopyrazine derivatives and imidazopyrazine derivatives; the patent document 9 discloses tetracyclic derivatives; the patent document 10 discloses triazolotriazine derivatives; the patent document 11 discloses pyrrole derivatives; therefore the compounds disclosed in these documents are obviously different in the structure from pyridine derivatives and pyrimidine derivatives according to the present invention.

The patent documents 12 and 13 disclose pyridine derivatives and pyrimidine derivatives similar in the structure to the compounds according to the present invention. The patent documents 12 and 13, however, do not disclose inhibitory activity against HGFR of the compounds disclosed in the patent documents 12 and 13 as well as the compounds according to the present invention.

[Patent document 1] WO 02/096361
[Patent document 2] WO 2005/005378
[Patent document 3] WO 03/000660
[Patent document 4] WO 2005/030140
[Patent document 5] WO 03/087026
[Patent document 6] WO 2005/040154
[Patent document 7] WO 2004/076412
[Patent document 8] WO 2005/004607
[Patent document 9] WO 2005/004808
[Patent document 10] WO 2005/010005
[Patent document 11] WO 2005/016920
[Patent document 12] WO 02/032872
[Patent document 13] WO 2005/005389
[Non-patent document 1] Oncology Reports, 5, 1013-1024 (1998)
[Non-patent document 2] Advances in Cancer Research, 67, 257-279 (1995)
[Non-patent document 3] British Journal of Cancer, 84, 864-873 (2001)
[Non-patent document 4] Cancer Sci., 94, 321-327 (2003)

SUMMARY OF THE INVENTION

An object of the present invention is to provide a compound showing anti-tumor activity, inhibitory activity against angiogenesis or inhibitory activity against cancer metastasis by inhibiting cellular aberrant growth, morphological change and hypermobility via HGFR in vivo.

As a result of diligent studies in view of the above situation, the present inventors have succeeded in synthesizing novel pyridine derivatives and pyrimidine derivatives represented by the formula (I), salts thereof or hydrates of the foregoing, found out that the compounds, salts thereof or hydrates of the foregoing have excellent inhibitory activity against HGFR and also exhibit anti-tumor activity, inhibitory activity against angiogenesis or inhibitory activity against cancer metastasis, and completed the present invention.

Namely, the present invention provides [1] to [35] below:

[1] A compound represented by the following formula, a salt thereof or a hydrate of the foregoing:

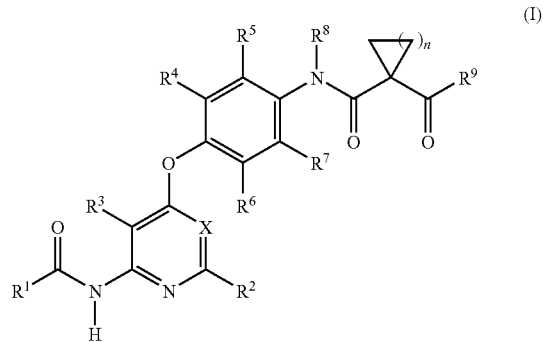

(I)

wherein $R^1$ represents a 3- to 10-membered non-aromatic heterocyclic group wherein the group is limited to a group having nitrogen as a ring constituent atom and the nitrogen having a bonding hand, or a group represented by the formula $-NR^{11a}R^{11b}$, wherein $R^{11a}$ and $R^{11b}$) may be the same or different and each represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{11a}$ and $R^{11b}$ may be substituted with a substituent selected from Substituent Group A or Substituent Group B and $R^1$ may be substituted with a substituent selected from Substituent Group A or Substituent Group B;

$R^2$ and $R^3$ represent hydrogen;

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino;

$R^8$ represents hydrogen or $C_{1-6}$ alkyl;

$R^9$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ represent the same meaning as described above and $R^9$ may be substituted with a substituent selected from Substituent Group A or Substituent Group B;

n represents an integer of 1 or 2; and

X represents a group represented by the formula —$C(R^{10})$= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO— $R^{12}$, wherein $R^{12}$ represents the same meaning as recited above;

wherein Substituent Group A consists of halogen, hydroxyl, mercapto, nitro, cyano and oxo;

wherein Substituent Group B consists of $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{3-6}$ alkenyloxy, $C_{3-6}$ alkynyloxy, $C_{3-10}$ cycloalkoxy, $C_{6-10}$ aryloxy, 5- to 10-membered heteroaryloxy, 4- to 10-membered non-aromatic heterocyclicoxy, $C_{1-6}$ alkylthio, $C_{3-6}$ alkenylthio, $C_{3-6}$ alkynylthio, $C_{3-10}$ cycloalkylthio, $C_{6-10}$ arylthio, 5- to 10-membered heteroarylthio, 4- to 10-membered non-aromatic heterocyclicthio and a group represented by the formula -$T^1$-$T^2$-$T^3$, and each group in Substituent Group B may be substituted with a substituent selected from Substituent Group C, wherein $T^1$ represents a direct bond or $C_{1-6}$ alkylene, $T^2$ represents carbonyl, sulfinyl, sulfonyl, a group represented by the formula —C(=O)—O—, a group represented by the formula —O—C(=O)—, a group represented by the formula —$SO_2$—O—, a group represented by the formula —O—$SO_2$—, a group represented by the formula —$NR^{T1}$—, a group represented by the formula —C(=O)—$NR^{T1}$—, a group represented by the formula —$NR^{T1}$—C(=O)—, a group represented by the formula —$SO_2$—$NR^{T1}$— or a group represented by the formula —$NR^{T1}$—$SO_2$—, $T^3$ represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{T1}$ represents hydrogen or $C_{1-6}$ alkyl; and wherein Substituent Group C consists of halogen, hydroxyl, mercapto, nitro, cyano, oxo, $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{1-6}$ alkylthio, mono-$C_{1-6}$ alkylamino and di-$C_{1-6}$ alkylamino.

[2] A compound according to [1], a salt thereof or a hydrate of the foregoing, wherein $R^1$ represents a 3- to 10-membered non-aromatic heterocyclic group optionally substituted with a substituent selected from Substituent Group A or Substituent Group B recited in [1], wherein the group is limited to a group having nitrogen as a ring constituent atom and the nitrogen having a bonding hand.

[3] A compound according to [1], a salt thereof or a hydrate of the foregoing, wherein $R^1$ represents a group represented by the formula (II):

wherein a represents an integer of 1 to 4;

or a group represented by the formula (III):

wherein b represents an integer of 1 to 3, and Z represents oxygen, sulfur, carbonyl, sulfonyl, or a group represented by the formula —$NR^Z$—, wherein $R^Z$ represents hydrogen or $C_{1-6}$ alkyl, and the groups represented by the formula (II) or (III) may be substituted with a substituent selected from Substituent Group A or Substituent Group B recited in [1].

[4] A compound according to [1], a salt thereof or a hydrate of the foregoing, wherein $R^1$ represents azetidin-1-yl optionally substituted with a substituent selected from Substituent Group D, pyrrolidin-1-yl optionally substituted with a substituent selected from Substituent Group D, piperidin-1-yl optionally substituted with a substituent selected from Substituent Group D, azepan-1-yl optionally substituted with a substituent selected from Substituent Group D, piperazin-1-yl optionally substituted with a substituent selected from Substituent Group D, diazepan-1-yl optionally substituted with a substituent selected from Substituent Group D, morpholin-4-yl optionally substituted with a substituent selected from Substituent Group D, thiomorpholin-4-yl optionally substituted with a substituent selected from Substituent Group D, 1,1-dioxothiomorpholin-4-yl optionally substituted with a substituent selected from Substituent Group D, wherein Substituent Group D consists of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, diazepanyl and a group represented by -$T^4$-$T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino, where each group included in Substituent Group D may be substituted with hydroxyl, $C_{1-6}$ alkyl, di-$C_{1-6}$ alkylamino, azetidinyl or pyrrolidinyl.

[5] A compound according to [1], a salt thereof or a hydrate of the foregoing, wherein $R^1$ represent azetidin-1-yl optionally substituted with a substituent selected from Substituent Group E, pyrrolidin-1-yl optionally substituted with a substituent selected from Substituent Group E, piperidin-1-yl optionally substituted with a substituent selected from Substituent Group E, piperazin-1-yl optionally substituted with a substituent selected from Substituent Group E, diazepan-1-yl optionally substituted with a substituent selected from Substituent Group E or morpholin-4-yl optionally substituted with a substituent selected from Substituent Group E, wherein Substituent Group E consists of methyl, ethyl, dimethylamino, azetidinyl, pyrrolidinyl, piperidinyl and piperazinyl, where each group included in Substituent Group E may be substituted with hydroxyl, methyl, dimethylamino, azetidinyl, pyrrolidinyl or piperidinyl.

[6] A compound according to [1], a salt thereof or a hydrate of the foregoing, wherein $R^1$ represents azetidin-1-yl optionally substituted with a substituent selected from Substituent Group G, pyrrolidin-1-yl optionally substituted with a substituent selected from Substituent Group G, piperidin-1-yl optionally substituted with a substituent selected from Substituent Group G or piperazin-1-yl optionally substituted with a substituent selected from Substituent Group G, wherein Substituent Group G consists of dimethylamino, azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl, where each group included in Substituent Group G may be substituted with methyl or dimethylamino.

[6-1] A compound according to [1], a salt thereof or a hydrate of the foregoing, wherein $R^1$ represents azetidin-1-yl optionally substituted with a substituent selected from Substituent Group G-1, pyrrolidin-1-yl optionally substituted with a substituent selected from Substituent Group G-1, piperidin-1-yl optionally substituted with a substituent selected from Substituent Group G-1 or piperazin-1-yl optionally substituted with a substituent selected from Substituent Group G-1, wherein Substituent Group G-1 consists of azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl, where each group included in Substituent Group G-1 may be substituted with methyl or dimethylamino.

[6-2] A compound according to [1], a salt thereof or a hydrate of the foregoing, wherein $R^1$ represents azetidin-1-yl having dimethylamino, pyrrolidin-1-yl having dimethylamino or piperidin-1-yl having dimethylamino.

[6-3] A compound according to [1], a salt thereof or a hydrate of the foregoing, wherein $R^1$ represents azetidin-1-yl optionally substituted with a substituent selected from Substituent Group G-2, pyrrolidin-1-yl substituted with a substituent selected from Substituent Group G-2 or piperidin-1-yl substituted with a substituent selected from Substituent Group G-2, wherein Substituent Group G-2 consists of hydroxyl, methoxy, hydroxymethyl and dimethylaminoacetoxy.

[6-4] A compound according to [1], a salt thereof or a hydrate of the foregoing, wherein $R^1$ represents [2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl or 3-(2-dimethylaminoacetoxy)azetidin-1-yl.

[7] A compound according to [1], a salt thereof or a hydrate of the foregoing, wherein $R^1$ represents a group represented by the formula $-NR^{11a}R^{11b}$, wherein $R^{11a}$ and $R^{11a}$ and $R^{11b}$ represent the same meaning as recited in [1].

[8] A compound according to [1], a salt thereof or a hydrate of the foregoing, wherein $R^1$ represents a group represented by the formula $-NR^{11c}R^{11d}$, wherein $R^{11c}$ represents hydrogen or $C_{1-6}$ alkyl, and $R^{11d}$ represents $C_{1-6}$ alkyl or a group represented by the formula (IV):

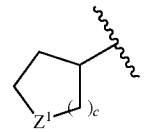

(IV)

wherein c represents an integer of 1 to 3, and $Z^1$ represents oxygen, sulfur, carbonyl, sulfonyl or a group represented by the formula $-NR^{Z1}-$, wherein $R^{Z1}$ represents hydrogen or $C_{1-6}$ alkyl, and $R^{11d}$ may be substituted with a substituent selected from Substituent Group A or Substituent Group B recited in [1].

[9] A compound according to [1], a salt thereof or a hydrate of the foregoing, wherein $R^1$ represents a group represented by the formula $-NR^{11e}R^{11f}$, wherein $R^{11e}$ represents hydrogen or $C_{1-6}$ alkyl, and $R^{11f}$ represents $C_{1-6}$ alkyl, pyrrolidin-3-yl, piperidin-3-yl, piperidin-4-yl or tetrahydropyran-4-yl, and $R^{11f}$ may be substituted with a substituent selected from Substituent Group D recited in [4].

[10] A compound according to [1], a salt thereof or a hydrate of the foregoing, wherein $R^1$ represents a group represented by the formula $-NR^{11g}R^{11h}$, wherein $R^{11g}$ represents hydrogen or methyl, and $R^{11h}$ represents n-propyl, n-butyl, pyrrolidin-3-yl, piperidin-3-yl, piperidin-4-yl or tetrahydropyran-4-yl, and $R^{11h}$ may be substituted with a substituent selected from Substituent Group F, wherein Substituent Group F consists of methyl, ethyl, n-propyl, acetyl, dimethylamino, diethylamino, azetidinyl, pyrrolidinyl and piperazinyl, where each group included in Substituent Group F may be substituted with methyl or dimethylamino.

[11] A compound according to [1], a salt thereof or a hydrate of the foregoing, wherein $R^1$ represents a group represented by the formula $-N(CH_3)R^{11i}$, wherein $R^{11i}$ represents n-propyl, n-butyl, pyrrolidin-3-yl or piperidin-4-yl, and $R^{11i}$ may be substituted with a substituent selected from Substituent Group H, wherein Substituent Group H consists of dimethylamino, diethylamino, dimethylaminoethyl, dimethylaminopropyl and 1-methylazetidin-3-yl.

[12] A compound according to [1], a salt thereof or a hydrate of the foregoing, wherein $R^1$ represents a group represented by the formula $-N(CH_3)R^{11j}$, wherein $R^{11j}$ represents 1-methylpiperidin-4-yl or 1-ethylpiperidin-4-yl.

[12-1] A compound according to [1], a salt thereof or a hydrate of the foregoing, wherein $R^1$ represents a group represented by the formula $-N(CH_3)R^{11k}$, wherein $R^{11k}$ represents 3-(dimethylamino)propyl or 1-[2-(dimethylamino)ethyl]piperidin-4-yl.

[12-2] A compound according to [1], a salt thereof or a hydrate of the foregoing, wherein $R^1$ represents methyl(1-methylpiperidin-4-yl)amino, (1-ethylpiperidin-4-yl)(methyl)amino, [3-(dimethylamino)propyl](methyl)amino or {1-[2-(dimethylamino)ethyl]piperidin-4-yl}(methyl) amino.

[13] A compound according to any one of [1] to [12-2], a salt thereof or a hydrate of the foregoing, wherein $R^4$, $R^5$, $R^6$ and $R^7$ may be the same or different and each represents hydrogen, halogen or $C_{1-6}$ alkyl.

[14] A compound according to any one of [1] to [13], a salt thereof or a hydrate of the foregoing, wherein $R^8$ represents hydrogen.

[15] A compound according to any one of [1] to [14], a salt thereof or a hydrate of the foregoing, wherein X represents a group represented by the formula —C($R^{10a}$)=, wherein $R^{10a}$ represents hydrogen, halogen or cyano.

[16] A compound according to any one of [1] to [14], a salt thereof or a hydrate of the foregoing, wherein X represents nitrogen.

[17] A compound according to any one of [1] to [16], a salt thereof or a hydrate of the foregoing, wherein n represents 1.

[18] A compound according to any one of [1] to [17], a salt thereof or a hydrate of the foregoing, wherein $R^9$ represents mono-$C_{1-6}$ alkylamino optionally substituted with a substituent selected from Substituent Group A or Substituent Group B recited in [1], mono-$C_{3-10}$ cycloalkylamino optionally substituted with a substituent selected from Substituent Group A or Substituent Group B recited in [1], mono-$C_{6-10}$ arylamino optionally substituted with a substituent selected from Substituent Group A or Substituent Group B recited in [1], mono-5- to 10-membered heteroarylamino optionally substituted with a substituent selected from Substituent Group A or Substituent Group B recited in [1] or mono-4- to 10-membered non-aromatic heterocyclic amino optionally substituted with a substituent selected from Substituent Group A or Substituent Group B recited in [1].

[19] A compound according to any one of [1] to [17], a salt thereof or a hydrate of the foregoing, wherein $R^9$ represents mono-$C_{3-10}$ cycloalkylamino optionally substituted with a substituent selected from Substituent Group A or Substituent Group B recited in [1] or mono-$C_{6-10}$ arylamino optionally substituted with a substituent selected from Substituent Group A or Substituent Group B recited in [1].

[19-1] A compound according to any one of [1] to [17], a salt thereof or a hydrate of the foregoing, wherein $R^9$ represents mono-$C_{3-10}$ cycloalkylamino optionally substituted with a substituent selected from Substituent Group I or mono-$C_{6-10}$ arylamino optionally substituted with a substituent selected from Substituent Group I, wherein Substituent Group I consists of halogen, trifluoromethyl, cyano, $C_{1-6}$ alkyl and $C_{1-6}$ alkoxy.

[19-2] A compound according to any one of [1] to [17], a salt thereof or a hydrate of the foregoing, wherein $R^9$ represents cyclopentylamino optionally substituted with a substituent selected from Substituent Group I recited in [19-1], cyclohexylamino optionally substituted with a substituent selected from Substituent Group I recited in [19-1], cycloheptylamino optionally substituted with a substituent selected from Substituent Group I recited in [19-1] or phenylamino optionally substituted with a substituent selected from Substituent Group I recited in [19-1].

[19-3] A compound according to [1], a salt thereof or a hydrate of the foregoing, wherein a compound represented by the formula (I) is (1) N-[4-({2-[({4-[2-(Dimethylamino)ethyl]piperazin-1-yl}carbonyl)amino]pyridin-4-yl}oxy)-2-fluorophenyl]-N'-(4-fluorophenyl)cyclopropane-1,1-dicarboxamide, (2) N-(2-Fluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide, (3) N-(4-Fluorophenyl)-N'-{2-fluoro-4-[2-{[(4-pyrrolidin-1-ylpiperidin-1-yl)carbonyl]amino}pyridin-4-yl)oxy] phenyl}cyclopropane-1,1-dicarboxamide, (4) N-[4-({2-[({4-[(Dimethylamino)methyl]piperidin-1-yl}carbonyl)amino]pyridin-4-yl}oxy)-2-fluorophenyl]-N'-(4-fluorophenyl)cyclopropane-1,1-dicarboxamide, (5) N-{4-[(2-{[(4-Azetidin-1-ylpiperidin-1-yl)carbonyl] amino}pyridin-4-yl)oxy]-2-fluorophenyl}-N'-(4-fluorophenyl)cyclopropane-1,1-dicarboxamide, (6) N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide, (7) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide, (8) N-(2-Fluoro-4-{[2-({[4-(1-methylpiperidin-4-yl)piperazin-1-yl]carbonyl}amino)pyridin-4-yl]oxy}phenyl)-N'-(4-fluorophenyl)cyclopropane-1,1-dicarboxamide, (9) N-(2-Fluoro-4-{[2-({[4-(1-methylazetidin-3-yl)piperazin-1-yl]carbonyl}amino)pyridin-4-yl]oxy}phenyl)-N'-(4-fluorophenyl)cyclopropane-1,1-dicarboxamide,

(10) N-(4-{[2-({[4-(Dimethylamino)piperidin-1-yl] carbonyl}amino)pyridin-4-yl]oxy}-2-fluorophenyl)-N'-(4-fluorophenyl)cyclopropane-1,1-dicarboxamide,

(11) N-(4-{[2-({[4-(Azetidin-1-ylmethyl)piperidin-1-yl] carbonyl}amino)pyridin-4-yl]oxy}-2-fluorophenyl)-N'-(4-fluorophenyl)cyclopropane-1,1-dicarboxamide,

(12) N-(4-Fluorophenyl)-N'-(2-fluoro-4-{[2-({[4-(pyrrolidin-1-ylmethyl)piperidin-1-yl]carbonyl}amino)pyridin-4-yl]oxy}phenyl)cyclopropane-1,1-dicarboxamide,

(13) N-(4-{[2-({[(3S)-3-(Dimethylamino)pyrrolidin-1-yl] carbonyl}amino)pyridin-4-yl]oxy}-2-fluorophenyl)-N'-(4-fluorophenyl)cyclopropane-1,1-dicarboxamide,

(14) N-(4-{[2-({[(3R)-3-(Dimethylamino)pyrrolidin-1-yl] carbonyl}amino)pyridin-4-yl]oxy}-2-fluorophenyl)-N'-(4-fluorophenyl)cyclopropane-1,1-dicarboxamide,

(15) N-(2-Fluoro-4-{[2-({[methyl(1-methylpiperidin-4-yl) amino]carbonyl}amino)pyridin-4-yl]oxy}phenyl)-N'-phenylcyclopropane-1,1-dicarboxamide,

(16) N-(2-Fluoro-4-{[2-({[4-(4-methylpiperazin-1-yl)piperidin-1-yl]carbonyl}amino)pyridin-4-yl]oxy}phenyl)-N'-phenylcyclopropane-1,1-dicarboxamide,

(17) N-[4-({2-[({4-[3-(Dimethylamino)azetidin-1-yl]piperidin-1-yl}carbonyl)amino]pyridin-4-yl}oxy)-2-fluorophenyl]-N'-phenylcyclopropane-1,1-dicarboxamide,

(18) N-(4-{[2-({[(1-Ethylpiperidin-4-yl)(methyl)amino] carbonyl}amino)pyridin-4-yl]oxy}-2-fluorophenyl)-N'-phenylcyclopropane-1,1-dicarboxamide,

(19) N-[4-({2-[(Azetidin-1-ylcarbonyl)amino]pyridin-4-yl}oxy)-2-fluorophenyl]-N'-(4-fluorophenyl)cyclopropane-1,1-dicarboxamide,

(20) N-(4-Fluorophenyl)-N'-[2-fluoro-4-({2-[(pyrrolidin-1-ylcarbonyl)amino]pyridin-4-yl}oxy)phenyl]cyclopropane-1,1-dicarboxamide,

(21) N-{2-Fluoro-4-[(2-{[(3-hydroxyazetidin-1-yl)carbonyl]amino}pyridin-4-yl)oxy]phenyl}-N'-(4-fluorophenyl) cyclopropane-1,1-dicarboxamide,

(22) N-[4-({2-[(1,3'-Biazetidin-1'-ylcarbonyl)amino]pyridin-4-yl}oxy)-2-fluorophenyl]-N'-(4-fluorophenyl)cyclopropane-1,1-dicarboxamide,

(23) N-(2-Fluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,
(24) N-(4-{[2-({[3-(Dimethylamino)azetidin-1-yl]carbonyl}amino)pyridin-4-yl]oxy}-2-fluorophenyl)-N'-(4-fluorophenyl)cyclopropane-1,1-dicarboxamide,
(25) N-[4-({2-[({3-[(Dimethylamino)methyl]azetidin-1-yl}carbonyl)amino]pyridin-4-yl}oxy)-2-fluorophenyl]-N'-(4-fluorophenyl)cyclopropane-1,1-dicarboxamide,
(26) N-{2-Fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,
(27) N-(2-Fluoro-4-{[2-({[4-(hydroxymethyl)piperidin-1-yl]carbonyl}amino)pyridin-4-yl]oxy}phenyl)-N'-(4-fluorophenyl)cyclopropane-1,1-dicarboxamide,
(28) N-(2-Fluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide,
(29) N-(2-Fluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide,
(30) N-[4-({2-[(Azetidin-1-ylcarbonyl)amino]pyridin-4-yl}oxy)-2,5-difluorophenyl]-N'-(4-fluorophenyl)cyclopropane-1,1-dicarboxamide,
(31) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,
(32) N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
(33) N-[2,5-Difluoro-4-({2-[({3-[(dimethylamino)methyl]azetidin-1-yl}carbonyl)amino]pyridin-4-yl}oxy)phenyl]-N'-(4-fluorophenyl)cyclopropane-1,1-dicarboxamide,
(34) N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide,
(35) N-{4-[(2-{[3-(Azetidin-1-ylmethyl)azetidin-1-ylcarbonyl]amino}pyridin-4-yl)oxy]-2,5-difluorophenyl}-N'-(4-fluorophenyl)cyclopropane-1,1-dicarboxamide,
(36) N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,
(37) N-{2,5-Difluoro-4-[(4-{[(3-hydroxyazetidin-1-yl)carbonyl]amino}pyrimidin-6-yl)oxy]phenyl}-N'-(4-fluorophenyl)cyclopropane-1,1-dicarboxamide,
(38) N-[4-({4-[({3-[(Dimethylamino)methyl]azetidin-1-yl}carbonyl)amino]pyrimidin-6-yl}oxy)-2,5-difluorophenyl]-N'-(4-fluorophenyl)cyclopropane-1,1-dicarboxamide,
(39) N-(2,5-Difluoro-4-{[4-({[3-(hydroxymethyl)azetidin-1-yl]carbonyl}amino)pyrimidin-6-yl]oxy}phenyl)-N'-(4-fluorophenyl)cyclopropane-1,1-dicarboxamide,
(40) N-(2,5-Difluoro-4-{[4-({[methyl(1-methylpiperidin-4-yl)amino]carbonyl}amino)pyrimidin-6-yl]oxy}phenyl)-N'-(4-fluorophenyl)cyclopropane-1,1-dicarboxamide,
(41) N-(2,5-Difluoro-4-{[4-({[4-(4-methylpiperazin-1-yl)piperidin-1-yl]carbonyl}amino)pyrimidin-6-yl]oxy}phenyl)-N'-(4-fluorophenyl)cyclopropane-1,1-dicarboxamide,
(42) N-(4-{[2-({[4-(Dimethylamino)piperidin-1-yl]carbonyl}amino)pyridin-4-yl]oxy}-2,5-difluorophenyl)-N'-(4-fluorophenyl)cyclopropane-1,1-dicarboxamide,
(43) N-{2,5-Difluoro-4-[(2-{[(4-methylpiperazin-1-yl)carbonyl]amino}pyridin-4-yl)oxy]phenyl}-N'-(4-fluorophenyl)cyclopropane-1,1-dicarboxamide,
(44) N-{2,5-Difluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,
(45) N-{4-[(2-{[(4-Azetidin-1-ylpiperidin-1-yl)carbonyl]amino}pyridin-4-yl)oxy]oxy}-2,5-difluorophenyl}-N'-(4-fluorophenyl)cyclopropane-1,1-dicarboxamide,
(46) N-(2,5-Difluoro-4-{[2-({[3-(2-dimethylaminoacetoxy)azetidin-1-yl]carbonyl}amino)pyridin-4-yl]oxy}phenyl)-N'-(4-fluorophenyl)cyclopropane-1,1-dicarboxamide,
(47) N-(2,5-Difluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide or
(48) N-(2,5-Difluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide.

[20] A pharmaceutical composition comprising a compound according to [1], a salt thereof or a hydrate of the foregoing.

[21] An inhibitor against hepatocyte growth factor receptor, comprising a compound according to [1], a salt thereof or a hydrate of the foregoing.

[22] An angiogenesis inhibitor comprising a compound according to [1], a salt thereof or a hydrate of the foregoing.

[23] An anti-tumor agent comprising a compound according to [1], a salt thereof or a hydrate of the foregoing.

[24] An anti-tumor agent according to [23], wherein tumor is a pancreatic cancer, a gastric cancer, a colorectal cancer, a breast cancer, a prostate cancer, a lung cancer, a renal cancer, a brain tumor or an ovarian cancer.

[25] An inhibitor against cancer metastasis, comprising a compound according to [1], a salt thereof or a hydrate of the foregoing.

[26] A prophylactic or therapeutic method for a disease for which inhibition of hepatocyte growth factor receptor is effective, comprising administering to a patient, a pharmacologically effective dose of a compound according to [1], a salt thereof or a hydrate of the foregoing.

[27] A prophylactic or therapeutic method for a disease for which angiogenesis inhibition is effective, comprising administering to a patient, a pharmacologically effective dose of a compound according to [1], a salt thereof or a hydrate of the foregoing.

[28] A prophylactic or therapeutic method for a tumor, comprising administering to a patient, a pharmacologically effective dose of a compound according to [1], a salt thereof or a hydrate of the foregoing.

[29] A prophylactic or therapeutic method for a tumor according to [28], wherein tumor is a pancreatic cancer, a gastric cancer, a colorectal cancer, a breast cancer, a prostate cancer, a lung cancer, a renal cancer, a brain tumor or an ovarian cancer.

[30] A prophylactic or therapeutic method for a cancer metastasis, comprising administering to a patient, a pharmacologically effective dose of a compound according to [1], a salt thereof or a hydrate of the foregoing.

[31] Use of a compound according to [1], a salt thereof or a hydrate of the foregoing for the manufacture of an inhibitor against hepatocyte growth factor receptor.

[32] Use of a compound according to [1], a salt thereof or a hydrate of the foregoing for the manufacture of an angiogenesis inhibitor.

[33] Use of a compound according to [1], a salt thereof or a hydrate of the foregoing for the manufacture of an anti-tumor agent.

[34] Use according to [33], wherein tumor is a pancreatic cancer, a gastric cancer, a colorectal cancer, a breast cancer, a prostate cancer, a lung cancer, a renal cancer, a brain tumor or an ovarian cancer.

[35] Use of a compound according to [1], a salt thereof or a hydrate of the foregoing for the manufacture of an inhibitor against cancer metastasis.

Effect of the Invention

The compound according to the present invention has an inhibitory activity against HGFR tyrosine kinase (Pharmacological Test Examples 1 and 3), and thus inhibits proliferation of human cancer cells caused by HGFR activation (Pharmacological Test Example 2). The compound according to the present invention also inhibits migration of human cancer cells (Pharmacological Test Example 4). Furthermore, the compound according to the present invention inhibits proliferation of vascular endothelial cells via HGF-HGFR signal (Pharmacological Test Example 7).

Overexpression of HGFR is reported to involve in malignancy of cancer (overgrowth, invasion and enhanced metastasis) in a pancreatic cancer, a gastric cancer, a colorectal cancer, a breast cancer, a prostate cancer, a lung cancer, a renal cancer, a brain tumor, an ovarian cancer and a blood cancer (Cancer Research, 54, 5775-5778 (1994); Biochemical and Biophysical Research Communication, 189, 227-232 (1992); Oncogene, 7, 181-185 (1992); Cancer, 82, 1513-1520 (1998); J. Urology, 154, 293-298 (1995); Oncology, 53, 392-397 (1996); Oncogene, 14, 2343-2350 (1999); Cancer Research, 57, 5391-5398 (1997); Pathology Oncology Research, 5, 187-191 (1999); Clinical Cancer Research, 9, 181-187 (2003)).

Additionally, HGFR activation in vascular endothelial cells is reported to facilitate tumor angiogenesis (Advances in Cancer Research, 67, 257-279 (1995)).

Therefore, the compound according to the present invention which has excellent inhibitory activity against HGFR is useful as an anti-tumor agent, an inhibitor against angiogenesis or a cancer metastasis inhibitor against various kinds of cancers such as a pancreatic cancer, a gastric cancer, a colorectal cancer, a breast cancer, a prostate cancer, a lung cancer, a renal cancer, a brain tumor and an ovarian cancer.

DESCRIPTION OF THE PREFERRED EMBODIMENTS

The symbols and terms as used herein will be defined and the present invention will be described in details below.

Several of the structural formulas for the compounds throughout the present specification represent only one isomeric form for convenience, but the invention encompasses any and all of the geometric isomers as well as optical isomers based on asymmetric carbons, stereoisomers and tautomers, and mixtures of those isomers, which are implied by the structures of the compounds, without being limited to any of the formulas shown for convenience. The compounds of the invention therefore include all those having asymmetric carbons therein and existing in optically active or racemic form, with no particular restrictions on the invention. There are also no restrictions when polymorphic crystalline forms thereof exist, and the compounds may be in one crystalline form or a mixture of different crystalline forms, while anhydrates and hydrates of the compounds of the invention are also included.

The so-called metabolite, a compound which a compound according to the present invention is metabolized in a living body through oxidation, reduction, hydrolysis, conjugation and the others to provide, and the so-called prodrug, a compound which is metabolized in a living body through oxidation, reduction, hydrolysis, conjugation and the others to provide a compound according to the present invention, are also included within the claimed scope of the present invention.

The "salt" includes a salt of an inorganic acid, a salt of an organic acid, a salt of an inorganic base, a salt of an organic base and a salt of an acidic or basic amino acid, among them, a pharmacologically acceptable salt is preferable.

The preferable salt of an inorganic acid includes, for example, a salt of hydrochloric acid, hydrobromic acid, sulfuric acid, nitric acid and phosphoric acid. The preferable salt of an organic acid includes, for example, a salt of acetic acid, succinic acid, fumaric acid, maleic acid, tartaric acid, citric acid, lactic acid, stearic acid, benzoic acid, methanesulfonic acid, ethanesulfonic acid, and p-toluenesulfonic acid.

The preferable salt of an inorganic base includes, for example, an alkali metal salt such as sodium salt and potassium salt, an alkali earth metal salt such as calcium salt and magnesium salt, aluminum salt, and ammonium salt. The preferable salt of an organic base includes, for example, a salt of diethylamine, diethanolamine, meglumine, and N,N-dibenzylethylenediamine.

The preferable salt of an acidic amino acid includes, for example, a salt of aspartic acid and glutamic acid. The preferable salt of a basic amino acid includes, for example, a salt of arginine, lysine and ornithine.

The "halogen" represents fluorine, chlorine, bromine or iodine.

The "$C_{1-6}$ alkyl" represents an alkyl of straight or branched chain having a carbon number of 1 to 6, and includes, for specific example, methyl, ethyl, 1-propyl(n-propyl), 2-propyl (i-propyl), 2-methyl-1-propyl(i-butyl), 2-methyl-2-propyl(t-butyl), 1-butyl(n-butyl), 2-butyl(s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl.

The "$C_{2-6}$ alkenyl" represents an alkenyl of straight or branched chain having one double bond and a carbon number of 2 to 6, and includes, for specific example, ethenyl (vinyl), 1-propenyl, 2-propenyl(allyl), 1-butenyl, 2-butenyl, 3-butenyl, pentenyl, and hexenyl.

The "$C_{3-6}$ alkenyl" represents an alkenyl of straight or branched chain having one double bond and a carbon number of 3 to 6, and includes, for specific example, 2-propenyl (allyl), 2-butenyl, 3-butenyl, pentenyl, and hexenyl.

The "$C_{2-6}$ alkynyl" represents an alkynyl of straight or branched chain having one triple bond and a carbon number of 2 to 6, and includes, for specific example, ethynyl, 1-propynyl, 2-propynyl, 1-butynyl, 2-butynyl, 3-butynyl, pentynyl, and hexynyl.

The "$C_{3-6}$ alkynyl" represents an alkynyl of straight or branched chain having one triple bond and a carbon number of 3 to 6, and includes, for specific example, 2-propynyl, 2-butynyl, 3-butynyl, pentynyl, and hexynyl.

The "$C_{1-6}$ alkylene" represents a divalent group derived by eliminating further any one hydrogen from the "$C_{1-6}$ alkyl" defined above, and includes, for specific example, methylene, 1,2-ethylene, 1,1-ethylene, 1,3-propylene, tetramethylene, pentamethylene, and hexamethylene.

The "$C_{3-10}$ cycloalkyl" represents a mono- or di-cyclic saturated aliphatic hydrocarbon group having a carbon number of 3 to 10, and includes, for specific example, cyclopropyl, cyclobutyl, cyclopentyl, cyclohexyl, cycloheptyl, cyclooctyl, cyclononyl, cyclodecyl, bicyclo[2.1.0]pentyl, bicyclo[3.1.0]hexyl, bicyclo[2.1.1]hexyl, bicyclo[4.1.0]heptyl, bicyclo[2.2.1]heptyl(norbornyl), bicyclo[3.3.0]octyl, bicyclo[3.2.1]octyl, bicyclo[2.2.2]octyl, bicyclo[4.3.0]nonyl, bicyclo[3.3.1]nonyl, bicyclo[4.4.0]decyl(decalyl), and bicyclo[3.3.2]decyl.

The "$C_{6-10}$ aryl" represents an aromatic hydrocarbon ring group having a carbon number of 6 to 10, and includes, for specific example, phenyl, 1-naphthyl, 2-naphthyl, indenyl, azulenyl, and heptalenyl.

The "heteroatom" represents nitrogen, oxygen, or sulfur.

The "5- to 10-membered heteroaryl" represents an aromatic ring group having 5 to 10 atoms forming the ring and containing 1 to 5 heteroatoms, and includes, for specific example, furyl, thienyl, pyrrolyl, imidazolyl, triazolyl, tetrazolyl, thiazolyl, pyrazolyl, oxazolyl, isoxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthalazinyl, imidazopyridyl, imidazothiazolyl, imidazoxazolyl, benzothiazolyl, benzoxazolyl, benzimidazolyl, indolyl, isoindolyl, indazolyl, pyrrolopyridyl, thienopyridyl, furopyridyl, benzothiadiazolyl, benzoxadiazolyl, pyridopyrimidinyl, benzofuryl, benzothienyl, and thienofuryl.

The preferable example of the "5- to 10-membered heteroaryl" includes furyl, thienyl, pyrrolyl, imidazolyl, thiazolyl, pyrazolyl, oxazolyl, isoxazolyl, isothiazolyl, pyridyl, and pyrimidinyl.

The "3- to 10-membered non-aromatic heterocyclic group" represents
(1) a monocyclic or a bicyclic non-aromatic heterocyclic group
(2) having 3 to 10 atoms in the ring,
(3) containing 1 to 2 heteroatoms among the atoms of the ring,
(4) optionally containing 1 to 2 double bonds in the ring,
(5) optionally containing 1 to 3 carbonyl, sulfinyl, or sulfonyl in the ring.

If the group contains nitrogen in the ring, the nitrogen may have a bond not participating in the formation of the ring. The group includes, for specific example, aziridinyl, azetidinyl, pyrrolidinyl, piperidinyl, azepanyl, azocanyl, piperazinyl, diazepanyl, diazocanyl, diazabicyclo[2.2.1]heptyl, morpholinyl, thiomorpholinyl, 1,1-dioxothiomorpholinyl, oxiranyl, oxetanyl, tetrahydrofuryl, tetrahydropyranyl, dioxanyl, tetrahydrothienyl, tetrahydrothiopyranyl, oxazolidinyl, and thiazolidinyl.

The preferable example of the "3- to 10-membered non-aromatic heterocyclic group" includes aziridinyl, azetidinyl, pyrrolidinyl, piperidinyl, azepanyl, piperazinyl, diazepanyl, morpholinyl, thiomorpholinyl, 1,1-dioxothiomorpholinyl, tetrahydrofuryl, and tetrahydropyranyl.

The "4- to 10-membered non-aromatic heterocyclic group" represents
(1) a monocyclic or a bicyclic non-aromatic heterocyclic group
(2) having 4 to 10 atoms in the ring,
(3) containing 1 to 2 heteroatoms among the atoms of the ring,
(4) optionally containing 1 to 2 double bonds in the ring,
(5) optionally containing 1 to 3 carbonyl, sulfinyl, or sulfonyl in the ring.

If the group contains nitrogen in the ring, the nitrogen may have a bond not participating in the formation of the ring. The group includes, for specific example, azetidinyl, pyrrolidinyl, piperidinyl, azepanyl, azocanyl, piperazinyl, diazepanyl, diazocanyl, diazabicyclo[2.2.1]heptyl, morpholinyl, thiomorpholinyl, 1,1-dioxothiomorpholinyl, oxetanyl, tetrahydrofuryl, tetrahydropyranyl, dioxanyl, tetrahydrothienyl, tetrahydrothiopyranyl, oxazolidinyl, and thiazolidinyl.

The preferable example of the "4- to 10-membered non-aromatic heterocyclic group" includes azetidinyl, pyrrolidinyl, piperidinyl, azepanyl, piperazinyl, diazepanyl, morpholinyl, thiomorpholinyl, 1,1-dioxothiomorpholinyl, tetrahydrofuryl, and tetrahydropyranyl.

The "$C_{3-10}$ cycloalkyl-$C_{1-6}$ alkyl" represents a group obtained by substituting any one hydrogen of the above defined "$C_{1-6}$ alkyl" with the above defined "$C_{3-10}$ cycloalkyl", and includes, for specific example, cyclopropylmethyl, cyclobutylmethyl, cyclopentylmethyl, cyclohexylmethyl, cycloheptylmethyl, cyclooctylmethyl, cyclononylmethyl, cyclodecylmethyl, bicyclo[2.2.1]heptylmethyl (norbornylmethyl), and bicyclo[4.4.0]decylmethyl (decarylmethyl).

The "$C_{6-10}$ aryl-$C_{1-6}$ alkyl" represents a group obtained by substituting any one hydrogen of the above defined "$C_{1-6}$ alkyl" with the above defined "$C_{6-10}$ aryl", and includes, for specific example, benzyl, 1-naphthylmethyl, 2-naphthylmethyl, phenethyl, 1-naphthylethyl, and 2-naphthylethyl.

The "5- to 10-membered heteroaryl-$C_{1-6}$ alkyl" represents a group obtained by substituting any one hydrogen of the above defined "$C_{1-6}$ alkyl" with the above defined "5- to 10-membered heteroaryl", and includes, for specific example, furylmethyl, thienylmethyl, pyrrolylmethyl, imidazolylmethyl, triazolylmethyl, tetrazolylmethyl, thiazolylmethyl, pyrazolylmethyl, oxazolylmethyl, isoxazolylmethyl, isothiazolylmethyl, furazanylmethyl, thiadiazolylmethyl, oxadiazolylmethyl, pyridylmethyl, pyrazinylmethyl, pyridazinylmethyl, pyrimidinylmethyl, triazinylmethyl, furylethyl, thienylethyl, pyrrolylethyl, imidazolylethyl, triazolylethyl, tetrazolylethyl, thiazolylethyl, pyrazolylethyl, oxazolylethyl, isoxazolylethyl, isothiazolylethyl, furazanylethyl, thiadiazolylethyl, oxadiazolylethyl, pyridylethyl, pyrazinylethyl, pyridazinylethyl, pyrimidinylethyl, and triazinylethyl.

The preferable example of the "5- to 10-membered heteroaryl $C_{1-6}$ alkyl" includes furylmethyl, thienylmethyl, pyrrolylmethyl, imidazolylmethyl, thiazolylmethyl, pyrazolylmethyl, oxazolylmethyl, isoxazolylmethyl, isothiazolylmethyl, pyridylmethyl, pyrimidinylmethyl, furylethyl, thienylethyl, pyrrolylethyl, imidazolylethyl, thiazolylethyl, pyrazolylethyl, oxazolylethyl, isoxazolylethyl, isothiazolylethyl, pyridylethyl, and pyrimidinylethyl.

The "3- to 10-membered non-aromatic heterocyclic-$C_{1-6}$ alkyl" represents a group obtained by substituting any one hydrogen of the above defined "$C_{1-6}$ alkyl" with the above defined "3- to 10-membered heterocyclic group", and includes, for specific example, aziridinylmethyl, azetidinylmethyl, pyrrolidinylmethyl, piperidinylmethyl, azepanylmethyl, azocanylmethyl, piperazinylmethyl, diazepanylmethyl, diazocanylmethyl, morpholinylmethyl, thiomorpholinylmethyl, 1,1-dioxothiomorpholinylmethyl, oxiranylmethyl, oxetanylmethyl, tetrahydrofurylmethyl, tetrahydropyranylmethyl, dioxanylmethyl, tetrahydrothienylmethyl, tetrahydrothiopyranylmethyl, oxazolidinylmethyl, thiazolidinylmethyl, aziridinylethyl, azetidinylethyl, pyrrolidinylethyl, piperidinylethyl, azepanylethyl, azocanylethyl, piperazinylethyl, diazepanylethyl, diazocanylethyl, morpholinylethyl, thiomorpholinylethyl, 1,1-dioxothiomorpholinylethyl, oxiranylethyl, oxetanylethyl, tetrahydrofurylethyl, tetrahydropyranylethyl, dioxanylethyl, tetrahydrothienylethyl, tetrahydrothiopyranylethyl, oxazolidinylethyl, and thiazolidinylethyl.

The preferable example of the "3- to 10-membered non-aromatic heterocyclic-$C_{1-6}$ alkyl" includes azetidinylmethyl, pyrrolidinylmethyl, piperidinylmethyl, azepanylmethyl, piperazinylmethyl, diazepanylmethyl, morpholinylmethyl, thiomorpholinylmethyl, tetrahydrofurylmethyl, azetidinylethyl, pyrrolidinylethyl, piperidinylethyl, azepanylethyl, piperazinylethyl, diazepanylethyl, morpholinylethyl, thiomorpholinylethyl, and tetrahydrofurylethyl.

The "$C_{1-6}$ alkoxy" represents a group obtained by adding oxygen to the terminal of the above defined "$C_{1-6}$ alkyl", and includes, for specific example, methoxy, ethoxy, 1-propoxy (n-propoxy), 2-propoxy(i-propoxy), 2-methyl-1-propoxy(i-butoxy), 2-methyl-2-propoxy(t-butoxy), 1-butoxy(n-butoxy), 2-butoxy(s-butoxy), 1-pentyloxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propoxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, and 2,3-dimethyl-2-butoxy.

The "$C_{1-6}$ alkylthio" represents a group obtained by adding sulfur to the terminal of the above defined "$C_{1-6}$ alkyl", and includes, for specific example, methylthio, ethylthio, 1-propylthio(n-propylthio), 2-propylthio(i-propylthio), 2-methyl-1-propylthio(i-butylthio), 2-methyl-2-propylthio(t-butylthio), 1-butylthio(n-butylthio), 2-butylthio(s-butylthio), 1-pentylthio, 2-pentylthio, 3-pentylthio, 2-methyl-1-butylthio, 3-methyl-1-butylthio, 2-methyl-2-butylthio, 3-methyl-2-butylthio, 2,2-dimethyl-1-propylthio, 1-hexylthio, 2-hexylthio, 3-hexylthio, 2-methyl-1-pentylthio, 3-methyl-1-pentylthio, 4-methyl-1-pentylthio, 2-methyl-2-pentylthio, 3-methyl-2-pentylthio, 4-methyl-2-pentylthio, 2-methyl-3-pentylthio, 3-methyl-3-pentylthio, 2,3-dimethyl-1-butylthio, 3,3-dimethyl-1-butylthio, 2,2-dimethyl-1-butylthio, 2-ethyl-1-butylthio, 3,3-dimethyl-2-butylthio, and 2,3-dimethyl-2-butylthio.

The "$C_{3-6}$ alkenyloxy" represents a group obtained by adding oxygen to the terminal of the above defined "$C_{3-6}$ alkenyl", and includes, for specific example, 2-propenyloxy(allyloxy), 2-butenyloxy, 3-butenyloxy, pentenyloxy, and hexenyloxy.

The "$C_{3-6}$ alkenylthio" represents a group obtained by adding sulfur to the terminal of the above defined "$C_{3-6}$ alkenyl", and includes, for specific example, 2-propenylthio(allylthio), 2-butenylthio, 3-butenylthio, pentenylthio, and hexenylthio.

The "$C_{3-6}$ alkynyloxy" represents a group obtained by adding oxygen to the terminal of the above defined "$C_{3-6}$ alkynyl", and includes, for specific example, 2-propynyloxy, 2-butynyloxy, 3-butynyloxy, pentynyloxy, and hexynyloxy.

The "$C_{3-6}$ alkynylthio" represents a group obtained by adding sulfur to the terminal of the above defined "$C_{3-6}$ alkynyl", and includes, for specific example, 2-propynylthio, 2-butynylthio, 3-butynylthio, pentynylthio, and hexynylthio.

The "$C_{3-10}$ cycloalkoxy" represents a group obtained by adding oxygen to the terminal of the above defined "$C_{3-10}$ cycloalkyl", and includes, for specific example, cyclopropoxy, cyclobutoxy, cyclopentyloxy, cyclohexyloxy, cycloheptyloxy, and cyclooctyloxy.

The "$C_{3-10}$ cycloalkylthio" represents a group obtained by adding sulfur to the terminal of the above defined "$C_{3-10}$ cycloalkyl", and includes, for specific example, cyclopropylthio, cyclobutylthio, cyclopentylthio, cyclohexylthio, cycloheptylthio, and cyclooctylthio.

The "$C_{6-10}$ aryloxy" represents a group obtained by adding oxygen to the terminal of the above defined "$C_{6-10}$ aryl", and includes, for specific example, phenoxy, 1-naphthoxy, 2-naphthoxy, indenyloxy, azulenyloxy, and heptalenyloxy.

The "$C_{6-10}$ arylthio" represents a group obtained by adding sulfur to the terminal of the above defined "$C_{6-10}$ aryl", and includes, for specific example, phenylthio, 1-naphthylthio, 2-naphthylthio, indenylthio, azulenylthio, and heptalenylthio.

The "5- to 10-membered heteroaryloxy" represents a group obtained by adding oxygen to the terminal of the above defined "5- to 10-membered heteroaryl", and includes, for specific example, furyloxy, thienyloxy, pyrrolyloxy, imidazolyloxy, triazolyloxy, thiazolyloxy, pyrazolyloxy, oxazolyloxy, isoxazolyloxy, isothiazolyloxy, furazanyloxy, thiadiazolyloxy, oxadiazolyloxy, pyridyloxy, pyrazinyloxy, pyridazinyloxy, pyrimidinyloxy, and triazinyloxy.

The "5- to 10-membered heteroarylthio" represents a group obtained by adding sulfur to the terminal of the above defined "5- to 10-membered heteroaryl", and includes, for specific example, furylthio, thienylthio, pyrrolylthio, imidazolylthio, triazolylthio, thiazolylthio, pyrazolylthio, oxazolylthio, isoxazolylthio, isothiazolylthio, furazanylthio, thiadiazolylthio, oxadiazolylthio, pyridylthio, pyrazinylthio, pyridazinylthio, pyrimidinylthio, and triazinylthio.

The "4- to 10-membered non-aromatic heterocyclicoxy group" represents a group obtained by adding oxygen to the terminal of the above defined "4- to 10-membered non-aromatic heterocyclic group", and includes, for specific example, azetidinyloxy, pyrrolidinyloxy, piperidinyloxy, azepanyloxy, azocanyloxy, piperazinyloxy, diazepanyloxy, diazocanyloxy, morpholinyloxy, thiomorpholinyloxy, 1,1-dioxothiomorpholinyloxy, oxetanyloxy, tetrahydrofuryloxy, tetrahydropyranyloxy, tetrahydrothienyloxy, and tetrahydrothiopyranyloxy.

The "4- to 10-membered non-aromatic heterocyclicthio group" represents a group obtained by adding sulfur to the terminal of the above defined "4- to 10-membered non-aromatic heterocyclic group", and includes, for specific example, azetidinylthio, pyrrolidinylthio, piperidinylthio, azepanylthio, azocanylthio, piperazinylthio, diazepanylthio, diazocanylthio, oxetanylthio, tetrahydrofurylthio, tetrahydropyranylthio, tetrahydrothienylthio, and tetrahydrothiopyranylthio.

The "mono-$C_{1-6}$ alkylamino" represents a group obtained by substituting one hydrogen of amino with the above defined "$C_{1-6}$ alkyl", and includes, for specific example, methylamino, ethylamino, 1-propylamino(n-propylamino), 2-propylamino(i-propylamino), 2-methyl-1-propylamino(i-butylamino), 2-methyl-2-propylamino(t-butylamino), 1-butylamino(n-butylamino), 2-butylamino(s-butylamino), 1-pentylamino, 2-pentylamino, 3-pentylamino, 2-methyl-1-butylamino, 3-methyl-1-butylamino, 2-methyl-2-butylamino, 3-methyl-2-butylamino, 2,2-dimethyl-1-propylamino, 1-hexylamino, 2-hexylamino, 3-hexylamino, 2-methyl-1-pentylamino, 3-methyl-1-pentylamino, 4-methyl-1-pentylamino, 2-methyl-2-pentylamino, 3-methyl-2-pentylamino, 4-methyl-2-pentylamino, 2-methyl-3-pentylamino, 3-methyl-3-pentylamino, 2,3-dimethyl-1-butylamino, 3,3-dimethyl-1-butylamino, 2,2-dimethyl-1-butylamino, 2-ethyl-1-butylamino, 3,3-dimethyl-2-butylamino, and 2,3-dimethyl-2-butylamino.

The "mono-$C_{3-10}$ cycloalkylamino" represents a group obtained by substituting one hydrogen of amino with the above defined "$C_{3-10}$ cycloalkyl", and includes, for specific example, cyclopropylamino, cyclobutylamino, cyclopentylamino, cyclohexylamino, cycloheptylamino, and cyclooctylamino.

The "mono-$C_{6-10}$ arylamino" represents a group obtained by substituting one hydrogen of amino with the above defined "$C_{6-10}$ aryl", and includes, for specific example, phenylamino, 1-naphthylamino, 2-naphthylamino, indenylamino, azulenylamino, and heptalenylamino.

The "mono-5- to 10-membered heteroarylamino" represents a group obtained by substituting one hydrogen of amino with the above defined "5- to 10-membered heteroaryl", and includes, for specific example, furylamino, thienylamino, pyrrolylamino, imidazolylamino, triazolylamino, tetrazolylamino, thiazolylamino, pyrazolylamino, oxazolylamino, isoxazolylamino, isothiazolylamino, furazanylamino, thiadiazolylamino, oxadiazolylamino, pyridylamino, pyrazinylamino, pyridazinylamino, pyrimidinylamino, and triazinylamino.

The preferable example of the "mono-5- to 10-membered heteroarylamino" includes furylamino, thienylamino, pyrrolylamino, imidazolylamino, thiazolylamino, pyrazolylamino, oxazolylamino, isoxazolylamino, isothiazolylamino, pyridylamino, and pyrimidinylamino.

The "mono-4- to 10-membered non-aromatic heterocyclic amino" represents a group obtained by substituting one hydrogen of amino with the above defined "4- to 10-membered non-aromatic heterocyclic group", and includes, for specific example, azetidinylamino, pyrrolidinylamino, piperidinylamino, azepanylamino, azocanylamino, piperazinylamino, diazepanylamino, diazocanylamino, morpholinylamino, thiomorpholinylamino, 1,1-dioxothiomorpholinylamino, oxetanylamino, tetrahydrofurylamino, tetrahydropyranylamino, tetrahydrothienylamino, and tetrahydrothiopyranylamino.

The preferable example of the "mono-4- to 10-membered non-aromatic heterocyclic amino" includes pyrrolidinylamino, piperidinylamino, azepanylamino, piperazinylamino, diazepanylamino, morpholinylamino, thiomorpholinylamino, and tetrahydrofurylamino.

The "di-$C_{1-6}$ alkylamino" represents a group obtained by substituting two hydrogen of amino with the same or different groups of the above defined "$C_{1-6}$ alkyl", and includes, for specific example, N,N-dimethylamino, N,N-diethylamino, N,N-di-n-propylamino, N,N-di-i-propylamino, N,N-di-n-butylamino, N,N-di-i-butylamino, N,N-di-s-butylamino, N,N-di-t-butylamino, N-ethyl-N-methylamino, N-n-propyl-N-methylamino, N-i-propyl-N-methylamino, N-n-butyl-N-methylamino, N-i-butyl-N-methylamino, N-s-butyl-N-methylamino, and N-t-butyl-N-methylamino.

Each of the substituents in the compound of the present invention represented by the above formula (I) will be described below.

(Meaning of $R^1$)

$R^1$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ may be the same or different and each represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{11a}$ and $R^{11b}$ may be substituted with a substituent selected from Substituent Group A or Substituent Group B.

$R^1$ may be substituted with a substituent selected from Substituent Group A or Substituent Group B.

The preferable example of $R^1$ includes a group represented by the formula (II):

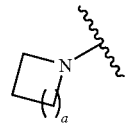

wherein a represents an integer of 1 to 4;
a group represented by the formula (III):

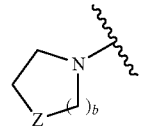

wherein b represents an integer of 1 to 3, and Z represents oxygen, sulfur, carbonyl, sulfonyl, or a group represented by the formula —$NR^Z$—, wherein $R^Z$ represents hydrogen or $C_{1-6}$ alkyl, and the groups represented by the formula (II) or (III) may be substituted with a substituent selected from Substituent Group A or Substituent Group B; or
a group represented by the formula —$NR^{11c}R^{11d}$, wherein $R^{11c}$ represents hydrogen or $C_{1-6}$ alkyl, and $R^{11d}$ represents $C_{1-6}$ alkyl or a group represented by the formula (IV):

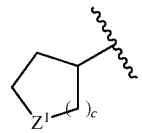

wherein c represents an integer of 1 to 3, and $Z^1$ represents oxygen, sulfur, carbonyl, sulfonyl or a group represented by the formula —$NR^{Z1}$—, wherein $R^{Z1}$ represents hydrogen or $C_{1-6}$ alkyl, and $R^{11d}$ may be substituted with a substituent selected from Substituent Group A or Substituent Group B.

The more preferable example of $R^1$ includes azetidin-1-yl, pyrrolidin-1-yl, piperidin-1-yl, azepan-1-yl, piperazin-1-yl, diazepan-1-yl, morpholin-4-yl, thiomorpholin-4-yl, 1,1-dioxothiomorpholin-4-yl, or a group represented by the formula —$NR^{11e}R^{11f}$, wherein $R^{11e}$ represents hydrogen or $C_{1-6}$ alkyl, $R^{11f}$ represents $C_{1-6}$ alkyl, pyrrolidin-3-yl, piperidin-3-yl, piperidin-4-yl or tetrahydropyran-4-yl, and $R^{11f}$ may be substituted with a substituent selected from Substituent Group D, and each of the above substituents may be substituted with a substituent selected from Substituent Group D.

The even more preferable example of $R^1$ includes azetidin-1-yl, pyrrolidin-1-yl, piperidin-1-yl, piperazin-1-yl, diazepan-1-yl, morpholin-4-yl, and each of the above substituents may be substituted with a substituent selected from Substituent Group E, or a group represented by the formula —$NR^{11g}R^{11h}$, wherein $R^{11g}$ represents hydrogen or methyl, $R^{11h}$ represents n-propyl, n-butyl, pyrrolidin-3-yl, piperidin-3-yl, piperidin-4-yl or tetrahydropyran-4-yl, and $R^{11h}$ may be substituted with a substituent selected from Substituent Group F.

The especially preferable example of $R^1$ includes azetidin-1-yl, pyrrolidin-1-yl, piperidin-1-yl or piperazin-1-yl, wherein azetidin-1-yl may be substituted with a substituent selected from Substituent Group G and pyrrolidin-1-yl, piperidin-1-yl and piperazin-1-yl are substituted with a substituent selected from Substituent Group G, or a group represented by the formula —N(CH$_3$)R$^{11i}$ wherein R$^{11i}$ represents n-propyl, n-butyl, pyrrolidin-3-yl or piperidin-4-yl, and R$^{11i}$ is substituted with a substituent selected from Substituent Group H.

The most preferable example of R$^1$ includes azetidin-1-yl, pyrrolidin-1-yl, piperidin-1-yl or piperazin-1-yl, wherein azetidin-1-yl may be substituted with a substituent selected from Substituent Group G-1 and pyrrolidin-1-yl, piperidin-1-yl and piperazin-1-yl are substituted with a substituent selected from Substituent Group G-1, or azetidin-1-yl having dimethylamino, pyrrolidin-1-yl having dimethylamino or piperidin-1-yl having dimethylamino, a group represented by the formula —N(CH$_3$)R$^{11j}$ wherein R$^{11j}$ represents 1-methylpiperidin-4-yl or 1-ethylpiperidin-4-yl, azetidin-1-yl optionally substituted with a substituent selected from Substituent Group G-2, pyrrolidin-1-yl substituted with a substituent selected from Substituent Group G-2, piperidin-1-yl substituted with a substituent selected from Substituent Group G-2 or a group represented by the formula —N(CH$_3$)R$^{11k}$, wherein R$^{11k}$ represents 3-(dimethylamino)propyl or 1-[2-(dimethylamino)ethyl]piperidin-4-yl.

The most preferable example of R$^1$ also includes [2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl(1-methylpiperidin-4-yl)amino, (1-ethylpiperidin-4-yl)(methyl)amino, [3-(dimethylamino)propyl](methyl)amino or {1-[2-(dimethylamino)ethyl]piperidin-4-yl}(methyl)amino.

(Meaning of Substituent Group A)

The Substituent Group A represents a group consisting of halogen, hydroxyl, mercapto, nitro, cyano and oxo.

(Meaning of Substituent Group B)

The Substituent Group B represents a group consisting of C$_{1-6}$ alkyl, C$_{2-6}$ alkenyl, C$_{2-6}$ alkynyl, C$_{3-10}$ cycloalkyl, C$_{6-10}$ aryl, 5- to 10-membered heteroaryl, a 3- to 10-membered non-aromatic heterocyclic group, C$_{1-6}$ alkoxy, C$_{3-6}$ alkenyloxy, C$_{3-6}$ alkynyloxy, C$_{3-10}$ cycloalkoxy, C$_{6-10}$ aryloxy, 5- to 10-membered heteroaryloxy, 4- to 10-membered non-aromatic heterocyclicoxy, C$_{1-6}$ alkylthio, C$_{3-6}$ alkenylthio, C$_{3-6}$ alkynylthio, C$_{3-10}$ cycloalkylthio, C$_{6-10}$ arylthio, 5- to 10-membered heteroarylthio, 4- to 10-membered non-aromatic heterocyclicthio and a group represented by the formula -T$^1$-T$^2$-T$^3$, wherein T$^1$ represents a direct bond or C$_{1-6}$ alkylene, T$^2$ represents carbonyl, sulfinyl, sulfonyl, a group represented by the formula —C(=O)—O—, a group represented by the formula —O—C(=O)—, a group represented by the formula —SO$_2$—O—, a group represented by the formula —O—SO$_2$—, a group represented by the formula —NR$^{T1}$—, a group represented by the formula —C(=O)—NR$^{T1}$—, a group represented by the formula —NR$^{T1}$—C(=O)—, a group represented by the formula —SO$_2$—NR$^{T1}$— or a group represented by the formula —NR$^{T1}$—SO$_2$—, T$^3$ represents hydrogen, C$_{1-6}$ alkyl, C$_{3-6}$ alkenyl, C$_{3-6}$ alkynyl, C$_{3-10}$ cycloalkyl, C$_{6-10}$ aryl, 5- to 10-membered heteroaryl or a 4- to 10-membered non-aromatic heterocyclic group, and R$^{T1}$ represents hydrogen or C$_{1-6}$ alkyl.

Each group included in Substituent Group B may be substituted with a substituent selected from Substituent Group C.

(Meaning of Substituent Group C)

The Substituent Group C represents a group consisting of halogen, hydroxyl, mercapto, nitro, cyano, oxo, C$_{1-6}$ alkyl, C$_{2-6}$ alkenyl, C$_{2-6}$ alkynyl, C$_{3-10}$ cycloalkyl, C$_{6-10}$ aryl, 5- to 10-membered heteroaryl, a 3- to 10-membered non-aromatic heterocyclic group, C$_{1-6}$ alkoxy, C$_{1-6}$ alkylthio, mono-C$_{1-6}$ alkylamino and di-C$_{1-6}$ alkylamino.

(Meaning of Substituent Group D)

The Substituent Group D represents a group consisting of halogen, hydroxyl, mercapto, cyano, formyl, oxo, C$_{1-6}$ alkyl, C$_{3-10}$ cycloalkyl, C$_{1-6}$ alkoxy, amino, mono-C$_{1-6}$ alkylamino, di-C$_{1-6}$ alkylamino, azetidinyl, pyrrolidinyl, piperidinyl, piperazinyl, diazepanyl and a group represented by -T$^4$-T$^5$, wherein T$^4$ represents carbonyl or sulfonyl, and T$^5$ represents C$_{1-6}$ alkyl, C$_{3-10}$ cycloalkyl, azetidinyl, pyrrolidinyl, piperidinyl, hydroxyl, C$_{1-6}$ alkoxy, amino, mono-C$_{1-6}$ alkylamino or di-C$_{1-6}$ alkylamino.

Each group included in Substituent Group D may be substituted with hydroxyl, C$_{1-6}$ alkyl, di-C$_{1-6}$ alkylamino, azetidinyl or pyrrolidinyl.

(Meaning of Substituent Group E)

The Substituent Group E represents a group consisting of methyl, ethyl, dimethylamino, azetidinyl, pyrrolidinyl, piperidinyl and piperazinyl.

Each group included in Substituent Group E may be substituted with hydroxyl, methyl, dimethylamino, azetidinyl, pyrrolidinyl or piperidinyl.

(Meaning of Substituent Group F)

The Substituent Group F represents a group consisting of methyl, ethyl, n-propyl, acetyl, dimethylamino, diethylamino, azetidinyl, pyrrolidinyl and piperazinyl.

Each group included in Substituent Group F may be substituted with methyl or dimethylamino.

(Meaning of Substituent Group G)

The Substituent Group G represents a group consisting of dimethylamino, azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl.

Each group included in Substituent Group G may be substituted with methyl or dimethylamino.

(Meaning of Substituent Group G-1)

The Substituent Group G-1 represents a group consisting of azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl.

Each group included in Substituent Group G-1 may be substituted with methyl or dimethylamino.

(Meaning of Substituent Group G-2)

The Substituent Group G-2 represents a group consisting of hydroxyl, methoxy, hydroxymethyl and dimethylaminoacetoxy.

(Meaning of Substituent Group H)

The Substituent Group H represents a group consisting of dimethylamino, diethylamino, dimethylaminoethyl, dimethylaminopropyl and 1-methylazetidin-3-yl.

(Meaning of R$^2$ and R$^3$)

R$^2$ and R$^3$ represent hydrogen.

(Meaning of R$^4$, R$^5$, R$^6$ and R$^7$)

R$^4$, R$^5$, R$^6$ and R$^7$ may be the same or different and each represents hydrogen, halogen, hydroxyl, cyano, trifluoromethyl, C$_{1-6}$ alkyl, C$_{2-6}$ alkenyl, C$_{2-6}$ alkynyl, C$_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino.

The preferable example of $R^4$, $R^5$, $R^6$ and $R^7$ includes hydrogen, halogen, $C_{1-6}$ alkyl, $C_{1-6}$ alkoxy and trifluoromethyl.

The more preferable example of $R^4$, $R^5$, $R^6$ and $R^7$ includes hydrogen, halogen and $C_{1-6}$ alkyl.

The even more preferable example of $R^4$, $R^5$, $R^6$ and $R^7$ includes hydrogen, fluorine, chlorine and methyl.

$R^4$, $R^5$, $R^6$ and $R^7$ may be in any one of the following cases: (1) all of them represent hydrogen, (2) all of them represent substituents other than hydrogen, and (3) some of them represent hydrogen and the others represent substituents other than hydrogen. Preferably, 2 to 4 of $R^4$, $R^5$, $R^6$ and $R^7$ represent hydrogen.

Preferable example for a group represented by the formula:

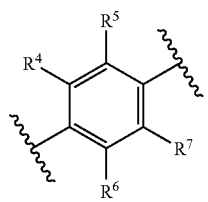

includes groups represented by the formulas:

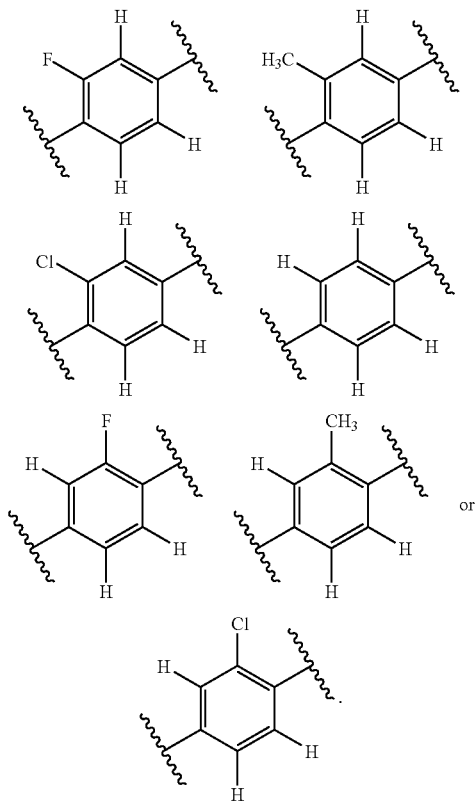

or a group represented by the formula:

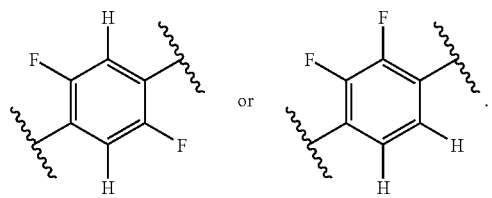

(Meaning of $R^8$)
$R^8$ represents hydrogen or $C_{1-6}$ alkyl.
The preferable example of $R^8$ includes hydrogen.
(Meaning of $R^9$)
$R^9$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ represent the same meaning as described above.

$R^9$ may be substituted with a substituent selected from Substituent Group A or Substituent Group B.

The preferable example of $R^9$ includes mono-$C_{1-6}$ alkylamino, mono-$C_{3-10}$ cycloalkylamino, mono-$C_{6-10}$ arylamino, mono-5- to 10-membered heteroarylamino or mono-4- to 10-membered non-aromatic heterocyclic amino, wherein $R^9$ may be substituted with a substituent selected from Substituent Group A or Substituent Group B.

The more preferable example of $R^9$ includes mono-$C_{3-10}$ cycloalkylamino or mono-$C_{6-10}$ arylamino, wherein $R^9$ may be substituted with a substituent selected from Substituent Group A or Substituent Group B.

The even more preferable example of $R^9$ includes mono-$C_{3-10}$ cycloalkylamino or mono-$C_{6-10}$ arylamino, wherein $R^9$ may be substituted with a substituent selected from Substituent Group I.

The Substituent Group I represents a group consisting of halogen, trifluoromethyl, cyano, $C_{1-6}$ alkyl and $C_{1-6}$ alkoxy.

The especially preferable example of $R^9$ includes cyclopentylamino, cyclohexylamino, cycloheptylamino and phenylamino, wherein $R^9$ may be substituted with a substituent selected from Substituent Group I.

The most preferable example of $R^9$ includes phenylamino optionally substituted with a substituent selected from the above Substituent Group I.

(Meaning of n)
n represents an integer of 1 or 2.
The preferable example of n includes 1.
(Meaning of X)
X represents a group represented by the formula —$C(R^{10})$= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as described above.

The preferable example of X includes a group represented by the formula —$C(R^{10a})$= or nitrogen, wherein $R^{10a}$ represents hydrogen, halogen or cyano.

The more preferable example of X includes a group represented by the formula —CH= or nitrogen.

The preferable compound of the formula (I) includes a compound obtained by selecting respective aspects of $R^1$, $R^2$, $R^3$, $R^4$, $R^5$, $R^6$, $R^7$, $R^8$, $R^9$, X and n in the compound and combining them arbitrarily.

The preferable compound of the formula (I) includes, other than the compounds described in Examples, the compounds illustrated below; but the present invention is not limited to the compounds described in Examples and the compounds illustrated below.

(1) N-(4-{[2-({[(1-ethylpiperidin-4-yl)(methyl)amino]carbonyl}amino)pyridin-4-yl]oxy}-2-fluorophenyl)-N'-(4-fluorophenyl)cyclopropane-1,1-dicarboxamide, (2) N-(4-{[2-({[(1-ethylpiperidin-4-yl)(methyl)amino]carbonyl}amino)pyridin-4-yl]oxy}phenyl)-N'-(4-fluorophenyl)cyclopropane-1,1-dicarboxamide, (3) N-{2-fluoro-4-[(2-{[(4-methyl-1,4-diazepan-1-yl)carbonyl]amino}pyridin-4-yl)oxy]phenyl}-N'-(4-fluorophenyl)cyclopropane-1,1-dicarboxamide, (4) N-(4-fluorophenyl)-N'-{2-fluoro-4-[(2-{[(3-pyrrolidin-1-ylazetidin-1-yl)carbonyl]amino}pyridin-4-yl)oxy]phenyl}cyclopropane-1,1-dicarboxamide, (5) N-{2-fluoro-4-[(2-{[(4-methylpiperazin-1-yl)carbonyl]amino}pyridin-4-yl)oxy]phenyl}-N'-(4-fluorophenyl)cyclopropane-1,1-dicarboxamide, (6) N-[4-({2-[({4-[2-(dimethylamino)ethyl]-1,4-diazepan-1-yl}carbonyl)amino]pyridin-4-yl}oxy)-2-fluorophenyl]-N'-phenylcyclopropane-1,1-dicarboxamide, (7) N-(4-{[2-({[3-(dimethylamino)azetidin-1-yl]carbonyl}amino)pyridin-4-yl]oxy}-2-fluorophenyl)-N'-(4-fluorophenyl)cyclopropane-1,1-dicarboxamide, (8) N-(4-{[2-({[3-(dimethylamino)azetidin-1-yl]carbonyl}amino)pyridin-4-yl]oxy}phenyl)-N'-(4-fluorophenyl)cyclopropane-1,1-dicarboxamide, (9) N-(4-{[2-({[3-(dimethylamino)azetidin-1-yl]carbonyl}amino)pyridin-4-yl]oxy}-2-fluorophenyl)-N'-phenylcyclopropane-1,1-dicarboxamide,

(10) N-[2-fluoro-4-({2-[({methyl[1-(1-methylazetidin-3-yl)piperidin-4-yl]amino}carbonyl)amino]pyridin-4-yl}oxy)phenyl]-N'-phenylcyclopropane-1,1-dicarboxamide,

(11) N-(2-fluoro-4-{[2-({[4-(1-methylazetidin-3-yl)piperazin-1-yl]carbonyl}amino)pyridin-4-yl]oxy}phenyl)-N'-phenylcyclopropane-1,1-dicarboxamide,

(12) N-(4-fluorophenyl)-N'-(4-{[2-({[4-(1-methylazetidin-3-yl)piperazin-1-yl]carbonyl}amino)pyridin-4-yl]oxy}phenyl)cyclopropane-1,1-dicarboxamide,

(13) N-(2-fluoro-4-{[2-({[(1-methylpiperidin-4-yl)amino]carbonyl}amino)pyridin-4-yl]oxy}phenyl)-N'-(4-fluorophenyl)cyclopropane-1,1-dicarboxamide,

(14) N-{2-fluoro-4-[(2-{[(4-hydroxy-1,4'-bipiperidin-1'-yl)carbonyl]amino}pyridin-4-yl)oxy]phenyl}-N'-phenylcyclopropane-1,1-dicarboxamide,

(15) N-(4-{[2-({[{1-[3-(dimethylamino)propyl]piperidin-4-yl}(methyl)amino]carbonyl}amino)pyridin-4-yl]oxy}-2-fluorophenyl)-N'-phenylcyclopropane-1,1-dicarboxamide,

(16) N-(4-{[2-({[(3-azetidin-1-ylpropyl)(methyl)amino]carbonyl}amino)pyridin-4-yl]oxy}-2-fluorophenyl)-N'-(4-fluorophenyl)cyclopropane-1,1-dicarboxamide,

(17) N-(2-fluoro-4-{[2-({[methyl(3-pyrrolidin-1-ylpropyl)amino]carbonyl}amino)pyridin-4-yl]oxy}phenyl)-N'-(4-fluorophenyl)cyclopropane-1,1-dicarboxamide,

(18) N-(4-{[2-({[[3-(dimethylamino)propyl](methyl)amino]carbonyl}amino)pyridin-4-yl]oxy}-2-fluorophenyl)-N'-(4-fluorophenyl)cyclopropane-1,1-dicarboxamide,

(19) N-(2-fluoro-4-{[2-({[methyl(4-pyrrolidin-1-ylbutyl)amino]carbonyl}amino)pyridin-4-yl]oxy}phenyl)-N'-phenylcyclopropane-1,1-dicarboxamide,

(20) N-[2-fluoro-4-({2-[(morpholin-4-ylcarbonyl)amino]pyridin-4-yl}oxy)phenyl]-N'-(4-fluorophenyl)cyclopropane-1,1-dicarboxamide,

(21) N-[4-({2-[(azetidin-1-ylcarbonyl)amino]pyridin-4-yl}oxy)-2-fluorophenyl]-N'-(4-fluorophenyl)cyclopropane-1,1-dicarboxamide,

(22) N-(2-fluoro-4-{[2-({[methyl(3-morpholin-4-ylpropyl)amino]carbonyl}amino)pyridin-4-yl]oxy}phenyl)-N'-(4-fluorophenyl)cyclopropane-1,1-dicarboxamide,

(23) N-[2-fluoro-4-({2-[({methyl[3-(4-methylpiperazin-1-yl)propyl]amino}carbonyl)amino]pyridin-4-yl}oxy)phenyl]-N'-(4-fluorophenyl)cyclopropane-1,1-dicarboxamide,

(24) N-(4-fluorophenyl)-N'-[2-fluoro-4-({2-[(pyrrolidin-1-ylcarbonyl)amino]pyridin-4-yl}oxy)phenyl]cyclopropane-1,1-dicarboxamide,

(25) N-(2-fluoro-4-{[2-({[methyl(1-methylpiperidin-4-yl)amino]carbonyl}amino)pyridin-4-yl]oxy}phenyl)-N'-2-thienylcyclopropane-1,1-dicarboxamide,

(26) N-(2-fluoro-4-{[2-({[methyl(1-methylpiperidin-4-yl)amino]carbonyl}amino)pyridin-4-yl]oxy}phenyl)-N'-1,3-thiazol-2-ylcyclopropane-1,1-dicarboxamide,

(27) N-(2-fluoro-4-{[2-({[methyl(1-methylpiperidin-4-yl)amino]carbonyl}amino)pyridin-4-yl]oxy}phenyl)-N'-(5-methylisoxazol-3-yl)cyclopropane-1,1-dicarboxamide,

(28) N-(2-fluoro-4-{[2-({[methyl(1-methylpiperidin-4-yl)amino]carbonyl}amino)pyridin-4-yl]oxy}phenyl)-N'-(3-methylisoxazol-5-yl)cyclopropane-1,1-dicarboxamide,

(29) N-{2-fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,

(30) N-{2-fluoro-4-[(2-{[(4-methoxypiperidin-1-yl)carbonyl]amino}pyridin-4-yl)oxy]phenyl}-N'-(4-fluorophenyl)cyclopropane-1,1-dicarboxamide,

(31) N-{2-fluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,

(32) N-{2-fluoro-4-[(2-{[(3-methoxyazetidin-1-yl)carbonyl]amino}pyridin-4-yl)oxy]phenyl}-N'-(4-fluorophenyl)cyclopropane-1,1-dicarboxamide,

(33) N-(2-fluoro-4-{[2-({[(2-methoxyethyl)(methyl)amino]carbonyl}amino)pyridin-4-yl]oxy}phenyl)-N'-(4-fluorophenyl)cyclopropane-1,1-dicarboxamide,

(34) N-(2-fluoro-4-{[2-({[4-(3-hydroxyazetidin-1-yl)piperidin-1-yl]carbonyl}amino)pyridin-4-yl]oxy}phenyl)-N'-(4-fluorophenyl)cyclopropane-1,1-dicarboxamide,

(35) N-(2-fluoro-4-{[2-({[methyl(tetrahydro-2H-pyran-4-yl)amino]carbonyl}amino)pyridin-4-yl]oxy}phenyl)-N'-(4-fluorophenyl)cyclopropane-1,1-dicarboxamide,

(36) N-(2-fluoro-4-{[2-({[methyl(1-methylpiperidin-3-yl)amino]carbonyl}amino)pyridin-4-yl]oxy}phenyl)-N'-(4-fluorophenyl)cyclopropane-1,1-dicarboxamide,

(37) N-[4-({2-[({3-[(dimethylamino)methyl]piperidin-1-yl}carbonyl)amino]pyridin-4-yl}oxy)phenyl]-N'-(4-fluorophenyl)cyclopropane-1,1-dicarboxamide,

(38) N-[4-({2-[({3-[(dimethylamino)methyl]pyrrolidin-1-yl}carbonyl)amino]pyridin-4-yl}oxy)-2-fluorophenyl]-N'-(4-fluorophenyl)cyclopropane-1,1-dicarboxamide,

(39) N-(2-fluoro-4-{[2-({[methyl(1-methylpyrrolidin-3-yl)amino]carbonyl}amino)pyridin-4-yl]oxy}phenyl)-N'-(4-fluorophenyl)cyclopropane-1,1-dicarboxamide,

(40) N-{2-fluoro-4-[(2-{[(3-hydroxypyrrolidin-1-yl)carbonyl]amino}pyridin-4-yl)oxy]phenyl}-N'-(4-fluorophenyl)cyclopropane-1,1-dicarboxamide,

(41) N-{2-fluoro-4-[(2-{[(3-methoxypyrrolidin-1-yl)carbonyl]amino}pyridin-4-yl)oxy]phenyl}-N'-(4-fluorophenyl)cyclopropane-1,1-dicarboxamide,

(42) N-{4-[(2-{[(3,4-dihydroxypyrrolidin-1-yl)carbonyl]amino}pyridin-4-yl)oxy]-2-fluorophenyl}-N'-(4-fluorophenyl)cyclopropane-1,1-dicarboxamide,

(43) N-{2-fluoro-4-[(2-{[(3-hydroxy-4-methoxypyrrolidin-1-yl)carbonyl]amino}pyridin-4-yl)oxy]phenyl}-N'-(4-fluorophenyl)cyclopropane-1,1-dicarboxamide,

(44) N-{4-[(2-{[(3,4-dimethoxypyrrolidin-1-yl)carbonyl]amino}pyridin-4-yl)oxy]-2-fluorophenyl}-N'-(4-fluorophenyl)cyclopropane-1,1-dicarboxamide,
(45) N-{2-fluoro-4-[(2-{[(3-hydroxypiperidin-1-yl)carbonyl]amino}pyridin-4-yl)oxy]phenyl}-N'-(4-fluorophenyl)cyclopropane-1,1-dicarboxamide,
(46) N-{2-fluoro-4-[(2-{[(3-methoxypiperidin-1-yl)carbonyl]amino}pyridin-4-yl)oxy]phenyl}-N'-(4-fluorophenyl)cyclopropane-1,1-dicarboxamide,
(47) N-(4-{[2-({[3-(dimethylamino)piperidin-1-yl]carbonyl}amino)pyridin-4-yl]oxy}-2-fluorophenyl)-N'-(4-fluorophenyl)cyclopropane-1,1-dicarboxamide The more preferable compound of the formula (I) includes the compounds illustrated below;

(1) N-[4-({2-[({4-[2-(Dimethylamino)ethyl]piperazin-1-yl}carbonyl)amino]pyridin-4-yl}oxy)-2-fluorophenyl]-N'-(4-fluorophenyl)cyclopropane-1,1-dicarboxamide,
(2) N-(2-Fluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide,
(3) N-(4-Fluorophenyl)-N'-{2-fluoro-4-[(2-{[(4-pyrrolidin-1-ylpiperidin-1-yl)carbonyl]amino}pyridin-4-yl)oxy]phenyl}cyclopropane-1,1-dicarboxamide,
(4) N-[4-({2-[({4-[(Dimethylamino)methyl]piperidin-1-yl}carbonyl)amino]pyridin-4-yl}oxy)-2-fluorophenyl]-N'-(4-fluorophenyl)cyclopropane-1,1-dicarboxamide,
(5) N-{4-[(2-{[(4-Azetidin-1-ylpiperidin-1-yl)carbonyl]amino}pyridin-4-yl)oxy]-2-fluorophenyl}-N'-(4-fluorophenyl)cyclopropane-1,1-dicarboxamide,
(6) N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide,
(7) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
(8) N-(2-Fluoro-4-{[2-({[4-(1-methylpiperidin-4-yl)piperazin-1-yl]carbonyl}amino)pyridin-4-yl]oxy}phenyl)-N'-(4-fluorophenyl)cyclopropane-1,1-dicarboxamide,
(9) N-(2-Fluoro-4-{[2-({[4-(1-methylazetidin-3-yl)piperazin-1-yl]carbonyl}amino)pyridin-4-yl]oxy}phenyl)-N'-(4-fluorophenyl)cyclopropane-1,1-dicarboxamide,
(10) N-(4-{[2-({[4-(Dimethylamino)piperidin-1-yl]carbonyl}amino)pyridin-4-yl]oxy}-2-fluorophenyl)-N'-(4-fluorophenyl)cyclopropane-1,1-dicarboxamide,
(11) N-(4-{[2-({[4-(Azetidin-1-ylmethyl)piperidin-1-yl]carbonyl}amino)pyridin-4-yl]oxy}-2-fluorophenyl)-N'-(4-fluorophenyl)cyclopropane-1,1-dicarboxamide,
(12) N-(4-Fluorophenyl)-N'-(2-fluoro-4-{[2-({[4-(pyrrolidin-1-ylmethyl)piperidin-1-yl]carbonyl}amino)pyridin-4-yl]oxy}phenyl)cyclopropane-1,1-dicarboxamide,
(13) N-(4-{[2-({[(3S)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide,
(14) N-(4-{[2-({[(3R)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide,
(15) N-(2-Fluoro-4-{[2-({[methyl(1-methylpiperidin-4-yl)amino]carbonyl}amino)pyridin-4-yl]oxy}phenyl)-N'-phenylcyclopropane-1,1-dicarboxamide,
(16) N-(2-Fluoro-4-{[2-({[4-(4-methylpiperazin-1-yl)piperidin-1-yl]carbonyl}amino)pyridin-4-yl]oxy}phenyl)-N'-phenylcyclopropane-1,1-dicarboxamide,
(17) N-[4-({2-[({4-[3-(Dimethylamino)azetidin-1-yl]piperidin-1-yl}carbonyl)amino]pyridin-4-yl}oxy)-2-fluorophenyl]-N'-phenylcyclopropane-1,1-dicarboxamide,
(18) N-(4-{[2-({[(1-Ethylpiperidin-4-yl)(methyl)amino]carbonyl}amino)pyridin-4-yl]oxy}-2-fluorophenyl)-N'-phenylcyclopropane-1,1-dicarboxamide,
(19) N-[4-({2-[(Azetidin-1-ylcarbonyl)amino]pyridin-4-yl}oxy)-2-fluorophenyl]-N'-(4-fluorophenyl)cyclopropane-1,1-dicarboxamide,
(20) N-(4-Fluorophenyl)-N'-[2-fluoro-4-({2-[(pyrrolidin-1-ylcarbonyl)amino]pyridin-4-yl}oxy)phenyl]cyclopropane-1,1-dicarboxamide,
(21) N-{2-Fluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,
(22) N-[4-({2-[(1,3'-Biazetidin-1'-ylcarbonyl)amino]pyridin-4-yl}oxy)-2-fluorophenyl]-N'-(4-fluorophenyl)cyclopropane-1,1-dicarboxamide,
(23) N-(2-Fluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,
(24) N-(4-{[2-({[3-(Dimethylamino)azetidin-1-yl]carbonyl}amino)pyridin-4-yl]oxy}-2-fluorophenyl)-N'-(4-fluorophenyl)cyclopropane-1,1-dicarboxamide,
(25) N-[4-({2-[({3-[(Dimethylamino)methyl]azetidin-1-yl}carbonyl)amino]pyridin-4-yl}oxy)-2-fluorophenyl]-N'-(4-fluorophenyl)cyclopropane-1,1-dicarboxamide,
(26) N-{2-Fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,
(27) N-(2-Fluoro-4-{[2-({[4-(hydroxymethyl)piperidin-1-yl]carbonyl}amino)pyridin-4-yl]oxy}phenyl)-N'-(4-fluorophenyl)cyclopropane-1,1-dicarboxamide,
(28) N-(2-Fluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide,
(29) N-(2-Fluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide,
(30) N-[4-({2-[(Azetidin-1-ylcarbonyl)amino]pyridin-4-yl}oxy)-2,5-difluorophenyl]-N'-(4-fluorophenyl)cyclopropane-1,1-dicarboxamide,
(31) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,
(32) N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
(33) N-[2,5-Difluoro-4-({2-[({3-[(dimethylamino)methyl]azetidin-1-yl}carbonyl)amino]pyridin-4-yl}oxy)phenyl]-N'-(4-fluorophenyl)cyclopropane-1,1-dicarboxamide,
(34) N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide,
(35) N-{4-[(2-{[3-(Azetidin-1-ylmethyl)azetidin-1-ylcarbonyl]amino}pyridin-4-yl)oxy]-2,5-difluorophenyl}-N'-(4-fluorophenyl)cyclopropane-1,1-dicarboxamide,
(36) N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,
(37) N-{2,5-Difluoro-4-[(4-{[(3-hydroxyazetidin-1-yl)carbonyl]amino}pyrimidin-6-yl)oxy]phenyl}-N'-(4-fluorophenyl)cyclopropane-1,1-dicarboxamide,
(38) N-[4-({4-[({3-[(Dimethylamino)methyl]azetidin-1-yl}carbonyl)amino]pyrimidin-6-yl}oxy)-2,5-difluorophenyl]-N'-(4-fluorophenyl)cyclopropane-1,1-dicarboxamide,

(39) N-(2,5-Difluoro-4-{[4-({[3-(hydroxymethyl)azetidin-1-yl]carbonyl}amino)pyrimidin-6-yl]oxy}phenyl)-N'-(4-fluorophenyl)cyclopropane-1,1-dicarboxamide,

(40) N-(2,5-Difluoro-4-{[4-({[methyl(1-methylpiperidin-4-yl)amino]carbonyl}amino)pyrimidin-6-yl]oxy}phenyl)-N'-(4-fluorophenyl)cyclopropane-1,1-dicarboxamide,

(41) N-(2,5-Difluoro-4-{[4-({[4-(4-methylpiperazin-1-yl)piperidin-1-yl]carbonyl}amino)pyrimidin-6-yl]oxy}phenyl)-N'-(4-fluorophenyl)cyclopropane-1,1-dicarboxamide,

(42) N-(4-{[2-({[4-(Dimethylamino)piperidin-1-yl]carbonyl}amino)pyridin-4-yl]oxy}-2,5-difluorophenyl)-N'-(4-fluorophenyl)cyclopropane-1,1-dicarboxamide,

(43) N-{2,5-Difluoro-4-[(2-{[(4-methylpiperazin-1-yl)carbonyl]amino}pyridin-4-yl]oxy]phenyl)-N'-(4-fluorophenyl)cyclopropane-1,1-dicarboxamide,

(44) N-{2,5-Difluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,

(45) N-{4-[(2-{[(4-Azetidin-1-ylpiperidin-1-yl)carbonyl]amino}pyridin-4-yl)oxy]oxy}-2,5-difluorophenyl}-N'-(4-fluorophenyl)cyclopropane-1,1-dicarboxamide,

(46) N-(2,5-Difluoro-4-{[2-({[3-(2-dimethylaminoacetoxy)azetidin-1-yl]carbonyl}amino)pyridin-4-yl]oxy}phenyl)-N'-(4-fluorophenyl)cyclopropane-1,1-dicarboxamide,

(47) N-(2,5-Difluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide,

(48) N-(2,5-Difluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide.

The phrase "may be substituted with a substituent selected from Substituent Group" or "optionally substituted with a substituent selected from Substituent Group" means "may be substituted with 1 to 3 substituents selected arbitrarily from the substituents described in the Substituent Group."

(General Production Method)

The compound of the present invention can be produced by methods described below. But the method for producing the compound of the present invention is not limited to these methods.

[Production method 1] A method for producing intermediates (1m) and (1n)

[Production method 1-A] A method for producing intermediates (1m) and (1n) via coupling of a derivative of 2-aminopyridine or 6-aminopyrimidine with phenol

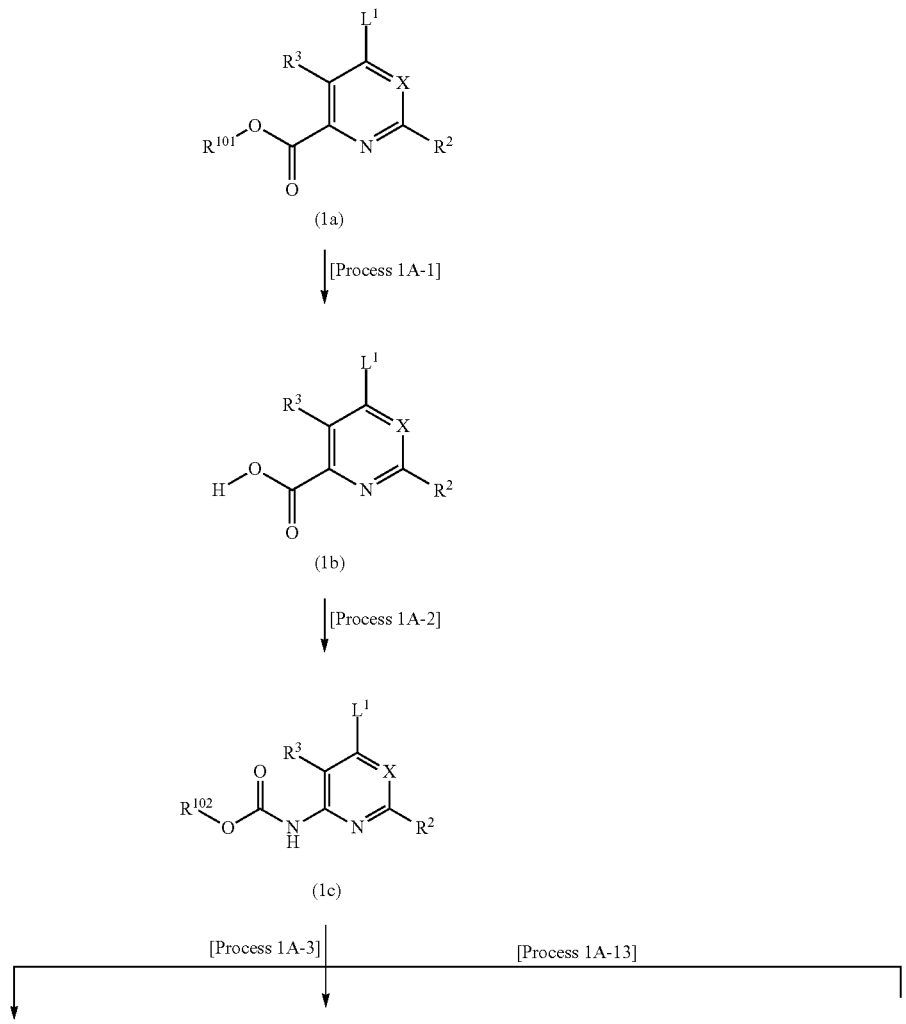

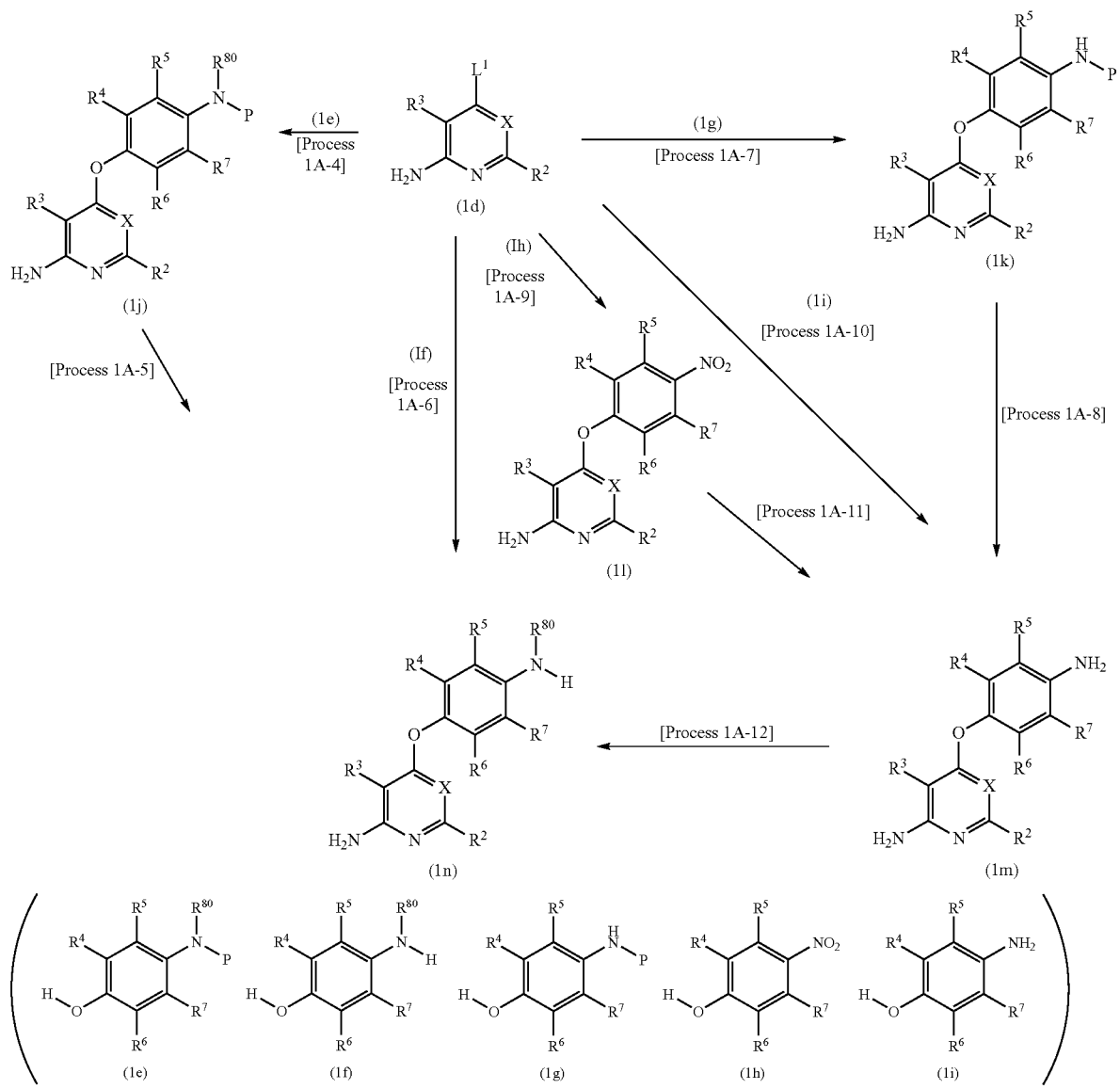

In the scheme, $L^1$ represents a leaving group; $R^{101}$ represents $C_{1-6}$ alkyl or benzyl; $R^{102}$ represents $C_{1-6}$ alkyl, benzyl or 2-(trimethylsilyl)ethyl; $R^{80}$ represents $C_{1-6}$ alkyl; P represents a protecting group for amino; and the other symbols represent the same meaning as defined above.

The compound (1a) includes, for example, 4-nitropicolinic acid ester, 4-chloropicolinic acid ester, 6-chloropyrimidine-4-carboxylic acid ester. 4-nitropicolinic acid ester and 4-chloropicolinic acid ester can be obtained by the esterification of 4-nitropicolinic acid and 4-chloropicolinic acid, both of which are commercially available. Among 6-chloropyrimidine-4-carboxylic acid ester, methyl 6-chloropyrimidine-4-carboxylate is described in Ukr. Kihm. Zh., 1982, Vol. 48, p 67 (CAS No. 6627-22-1). 6-chloropyrimidine-4-carboxylic acid ester also can be produced according to a method described in J. Heterocycl. Chem., 1, 130 (1964).

The compound (1d) includes, for example, commercially available compounds such as 2-amino-4-chloropyridine and 4-amino-6-chloropyrimidine. The compound (1d) also can be produced via <Process 1A-1>, <Process 1A-2> and <Process 1A-3> described below, using the compound (1a) as a starting material.

The compound (1f) includes, for example, commercially available compounds such as p-methylaminophenol sulfate.

The compound (1e) can be obtained by protecting a group represented by the formula $R^{80}NH-$ of the compound (1f). The general reaction for protecting amino can be used. For example, the compound (1e) can be obtained by a reaction of the compound (1f) with ethyl chloroformate, methyl chloroformate, benzyl chloroformate, di-t-butyl dicarbonate or trifluoroacetic anhydride.

The compound (1g) includes, for example, commercially available compounds such as 4-acetoamidophenol, N-(4-hydroxyphenyl)formamide, 4-(N-t-butoxycarbonylamino)phenol and 4-trifluoroacetoamidophenol.

The compound (1h) includes, for example, commercially available compounds such as 4-nitrophenol, 2-chloro-4-nitrophenol, 2-fluoro-4-nitrophenol, 3-fluoro-4-nitrophenol and 3-methyl-4-nitrophenol.

The compound (1i) includes, for example, commercially available compounds such as 4-aminophenol, 4-amino-3-chlorophenol hydrochloride, 4-amino-2,5-dimethylphenol, 4-amino-2,6-dichlorophenol and 5-amino-2-hydroxybenzonitrile.

The above compounds can also be produced from commercially available compounds by a known method.

<Process 1A-1>

The process is a process for producing the compound (1b) from the compound (1a). For example, hydrolysis using a base can be used. As the base, an inorganic base such as sodium hydroxide, potassium hydroxide and lithium hydroxide can be used. As the solvent, methanol, ethanol, water or the like can be used. The reaction temperature is between 0° C. and a reflux temperature. The reaction time is between 10 minutes and 30 hours.

<Process 1A-2>

The process is a process for rearrangement of the compound (1b) to the compound (1c). The compound (1c) can be obtained by a reaction of the compound (1b) with an alcohol represented by the formula $R^{102}$—OH in the presence of diphenylphosphoryl azide and triethylamine. The preferable example of $R^{102}$ includes t-butyl, benzyl and 2-(trimethylsilyl)ethyl. As the solvent, N,N-dimethylformamide, N-methylpyrrolidone, toluene or the like can be used as well as t-butanol or benzylalcohol. The reaction temperature is between room temperature and a reflux temperature. The reaction time is between 10 minutes and 30 hours.

<Process 1A-3>

The process is a process for producing the compound (1d) from the compound (1c) by deprotection of carbamate. For the reaction, general deprotection for amino can be used and specific examples are deprotection using an acid such as hydrochloric acid and trifluoroacetic acid, deprotection using an inorganic base such as sodium hydroxide and potassium hydroxide, and deprotection using tetrabutylammonium fluoride. As the solvent, methanol, ethanol, water, tetrahydrofuran, N,N-dimethylformamide or the like can be used. The reaction temperature is between room temperature and a reflux temperature. The reaction time is between 10 minutes and 30 hours.

<Process 1A-4> <Process 1A-6> <Process 1A-7> <Process 1A-9> <Process 1A-10>

These processes are processes for coupling the compound (1d) with the compounds (1e), (1f), (1g), (1h) or (1i) to produce the compounds (1j), (1n), (1k), (1l) or (1m), respectively. As the solvent, N-methylpyrrolidone, N,N-dimethylformamide, dimethyl sulfoxide, 2-ethoxyethanol, chlorobenzene or the like can be used. A base or an acid may be added in the reaction system, and specifically an organic base such as triethylamine and diisopropylethylamine, an inorganic base such as potassium carbonate, cesium carbonate and sodium hydride, or an acid such as pyridine hydrochloride and hydrochloric acid can be used. The reaction temperature is between room temperature and a reflux temperature. The reaction time is between 10 minutes and 30 hours.

<Process 1A-5>

The process is a process for deprotecting the compound (1j) to produce the compound (1n). For the reaction, general deprotection for amino can be applied, for specific example, deprotection using an acid such as hydrochloric acid and trifluoroacetic acid, deprotection using an inorganic base such as sodium hydroxide and potassium hydroxide, and deprotection using tetrabutylammonium fluoride. When a protecting group is benzyloxycarbonyl and $R^4$, $R^5$, $R^6$, $R^7$ and $R^{10}$ are not any of chlorine, bromine and iodine, deprotection by catalytic hydrogenation using palladium-carbon or palladium hydroxide as a catalyst can also be used. As the solvent, methanol, ethanol, water, tetrahydrofuran, N,N-dimethylformamide or the like can be used. The reaction temperature is between room temperature and a reflux temperature. The reaction time is between 10 minutes and 30 hours.

<Process 1A-8>

The process is a process for deprotecting the compound (1k) to produce the compound (1m). The conditions similar to those in <Process 1A-5> can be used.

<Process 1A-11>

The process is a process for reducing nitro of the compound (1l) to produce the compound (1m). Generally used conditions for reduction from nitro to amino can be applied, for specific example, reduction using iron-ammonium chloride, or iron-acetic acid. When $R^4$, $R^5$, $R^6$, $R^7$ and $R^{10}$ are not any of chlorine, bromine and iodine, catalytic hydrogenation using palladium hydroxide or palladium-carbon as a catalyst also can be used. As the solvent, methanol, ethanol, water, N,N-dimethylformamide, ethyl acetate, tetrahydrofuran or the like can be used. The reaction temperature is between room temperature and a reflux temperature. The reaction time is between 10 minutes and 30 hours.

<Process 1A-12>

The process is a process for alkylating the compound (1m) to produce the compound (1n). Reductive amination of aldehyde or ketone can convert hydrogen to $C_{1-6}$ alkyl. As the reducing agent, sodium cyanoborohydride and sodium triacetoxyborohydride can be used. As the solvent, methanol, tetrahydrofuran, dichloromethane, dichloroethane or the like can be used.

A method for reducing a benzotriazole derivative with sodium borohydride can also be used, as described in Tetrahedron, 47(16), 2683(1991). Specifically for example, the compound (1n) wherein $R^{80}$ is methyl can be obtained by reduction with sodium borohydride, a benzotriazol-1-ylmethylaniline derivative obtained by a reaction of the compound (1m) with 1-(hydroxymethyl)-1H-benzotriazole. In the process for producing a benzotriazol-1-ylmethylaniline derivative, an alcohol such as methanol or ethanol, or a mixed solvent of an alcohol with N,N-dimethylformamide, acetic acid or water can be used for the solvent. The reaction temperature is between −5° C. and a reflux temperature. The reaction time is between 10 minutes and 30 hours. In the process of reduction with sodium borohydride, tetrahydrofuran, dioxane, an alcohol such as methanol or ethanol, or a mixed solvent of an alcohol with N,N-dimethylformamide or the like can be used as the solvent. The reaction temperature is between −5° C. and a reflux temperature. The reaction time is between 10 minutes and 30 hours.

<Process 1A-13>

The process is an alternative method for producing the compound (1j) by alkylating the compound (1k) to produce the compound (1j). The compound (1j) can be obtained by a reaction with alkyl halide in the presence of a base such as potassium carbonate or sodium hydride. As the solvent, tetrahydrofuran, N,N-dimethylformamide or the like can be used. The reaction temperature is between 0° C. and a reflux temperature. The reaction time is between 10 minutes and 30 hours.

[Production method 1-B] A method for producing an intermediate (1x) via coupling of pyridine-2-carboxylic acid ester or pyrimidine-6-carboxylic acid ester with a derivative of phenol

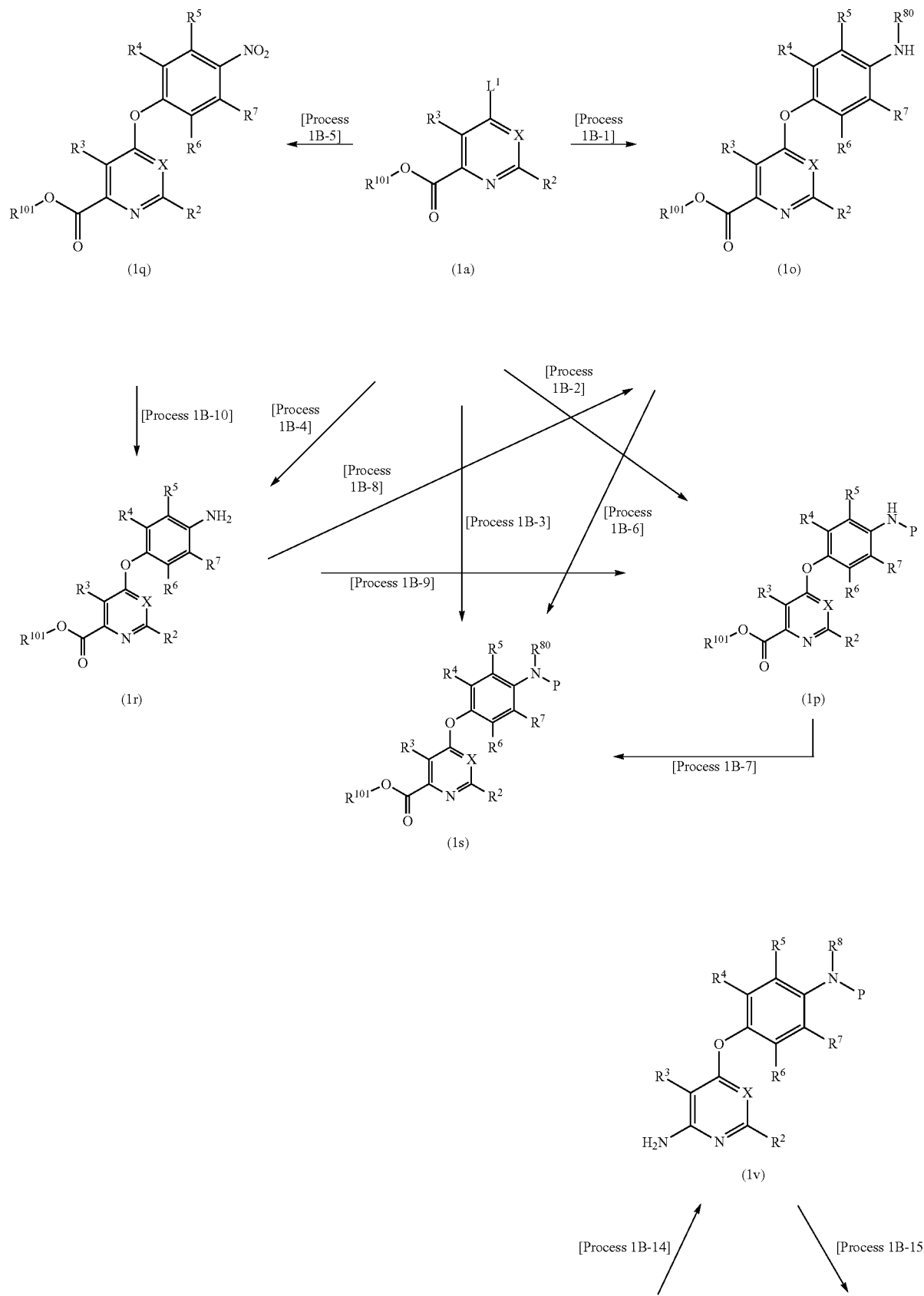

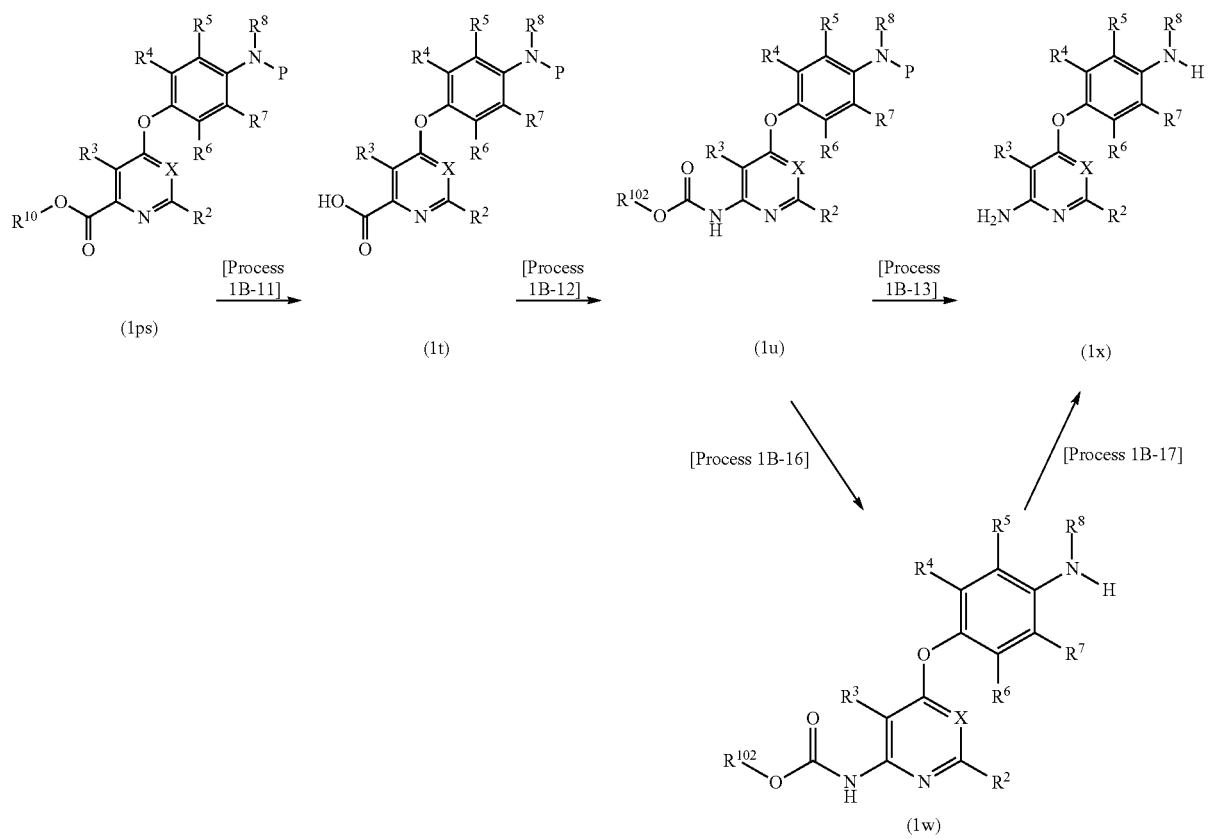

In the scheme, the symbols represent the same meaning as defined above.

<Process 1B-1> <Process 1B-2> <Process 1B-3> <Process 1B-4> <Process 1B-5>

These processes are processes for coupling the compound (1a) with the compound (1f), (1g), (1e), (1i) or (1h) to produce the compound (1o), (1p), (1s), (1r) or (1q), respectively. The methods similar to those in <Process 1A-4> can be used.

<Process 1B-6>

The process is a process for protecting amino of the compound (1o) to produce the compound (1s). A general reaction for protecting amino can be used. Specifically for example, a reaction with ethyl chloroformate, methyl chloroformate, benzyl chloroformate, di-t-butyl dicarbonate and trifluoroacetic anhydride can be used. A base may be added in the reaction system, and an organic base such as pyridine, triethylamine and diisopropylethylamine, and an inorganic base such as sodium carbonate, potassium carbonate and sodium hydrogencarbonate can be used. As the solvent, tetrahydrofuran, acetone, water, dioxane or the like can be used. The reaction temperature is between room temperature and a reflux temperature. The reaction time is between 10 minutes and 30 hours.

<Process 1B-7>

The process is a process for alkylating the compound (1p) to produce the compound (1s). The methods similar to those in <Process 1A-13> can be used.

<Process 1B-8>

The process is a process for alkylating the compound (1r) to produce the compound (1o). The methods similar to those in <Process 1A-12> can be used.

<Process 1B-9>

The process is a process for protecting amino of the compound (1r) to produce the compound (1p). The methods similar to those in <Process 1B-6> can be used.

<Process 1B-10>

The process is a process for reducing nitro of the compound (1q) to produce the compound (1r). The methods similar to those in <Process 1A-11> can be used.

<Process 1B-11>

The process is a process for producing the compound (1t) from the compound (1ps) (the compound (1ps) represents the compound (1p) and the compound (1s) described in [Production method 1-B]). The methods similar to those in <Process 1A-1> can be used.

<Process 1B-12>

The process is a process for producing the compound (1u) from the compound (1t). The methods similar to those in <Process 1A-2> can be used.

<Process 1B-13>

The process is a process for deprotecting the two protecting groups "$R^{102}$—O—C(=O)—" and "P" of the compound (1u) to produce the compound (1x). Depending on the kind of the protecting groups, deprotection using an acid such as hydrochloric acid and trifluoroacetic acid, deprotection using an inorganic base such as sodium hydroxide and potassium hydroxide, deprotection using tetrabutylammonium fluoride, and deprotection by catalytic hydrogenation using palladium-carbon or palladium hydroxide as a catalyst can be appropriately combined to produce the compound (1x).

<Production 1B-14> <Production 1B-16>

These processes are processes for deprotecting only one of the two protecting groups "$R^{102}$—O—C(=O)—" and "P" of the compound (1u) to produce the compound (1v) or the compound (1w), respectively. The process is applicable only when the two protecting groups "$R^{102}$—O—C(=O)—" and "P" are different. Specifically, for example, when a group represented by the formula $R^{102}$—O—C(=O)— is 2-(trimethylsilyl)ethoxycarbonyl and P is benzyloxycarbonyl, deprotection using tetrabutylammonium fluoride or deprotection by catalytic hydrogenation can be applied to deprotect selectively only one of the two protecting groups.

<Process 1B-15>

The process is a process for deprotecting the compound (1v) to produce the compound (1x). The method described in <Process 1A-5> can be used.

<Process 1B-17>

The process is a process for deprotecting the compound (1w) to produce the compound (1x). The method described in <Process 1A-5> can be used.

[Production method 2] An alternative production method of intermediates (1l), (1m), (1k), (1j) and (1n) from a pyridine or pyrimidine derivative (2a) having leaving groups $L^1$ at the 4-position and $L^2$ at the 2-position or 6-position In the scheme, $L^2$ represents a leaving group. The other symbols represent the same meanings as defined above.

The compound (2a) includes, for example, commercially available compounds such as 4,6-dichloropyrimidine, 2-chloro-4-nitropyridine, and 2,4-dichloropyridine. The compound (2a) also can be produced from commercially available compounds by a known method.

<Process 2-1> <Process 2-2> <Process 2-3> <Process 2-4> <Process 2-5>

These processes are processes for coupling the compound (2a) with the compound (1h), (1i), (1g), (1e) or (1f) to produce the compound (2b), (2c), (2d), (2e) or (2f), respectively. Preferably, in (2a), $L^1$ is a reactive group having higher reactivity than $L^2$. In a specific combination, for example, $L^1$ is nitro and $L^2$ is chlorine. The methods similar to those in <Process 1A-4> can be used for these processes.

<Process 2-6>

The process is a process for reducing nitro of the compound (2b) to produce the compound (2c). Generally used conditions of reduction from nitro to amino can be used. Specifically, for example a reduction using iron-ammonium chloride or iron-acetic acid can be used. As the solvent, methanol, ethanol, water, N,N-dimethylformamide, tetrahydrofuran or the like can be used. The reaction temperature is between room temperature and a reflux temperature. The reaction time is between 10 minutes and 30 hours.

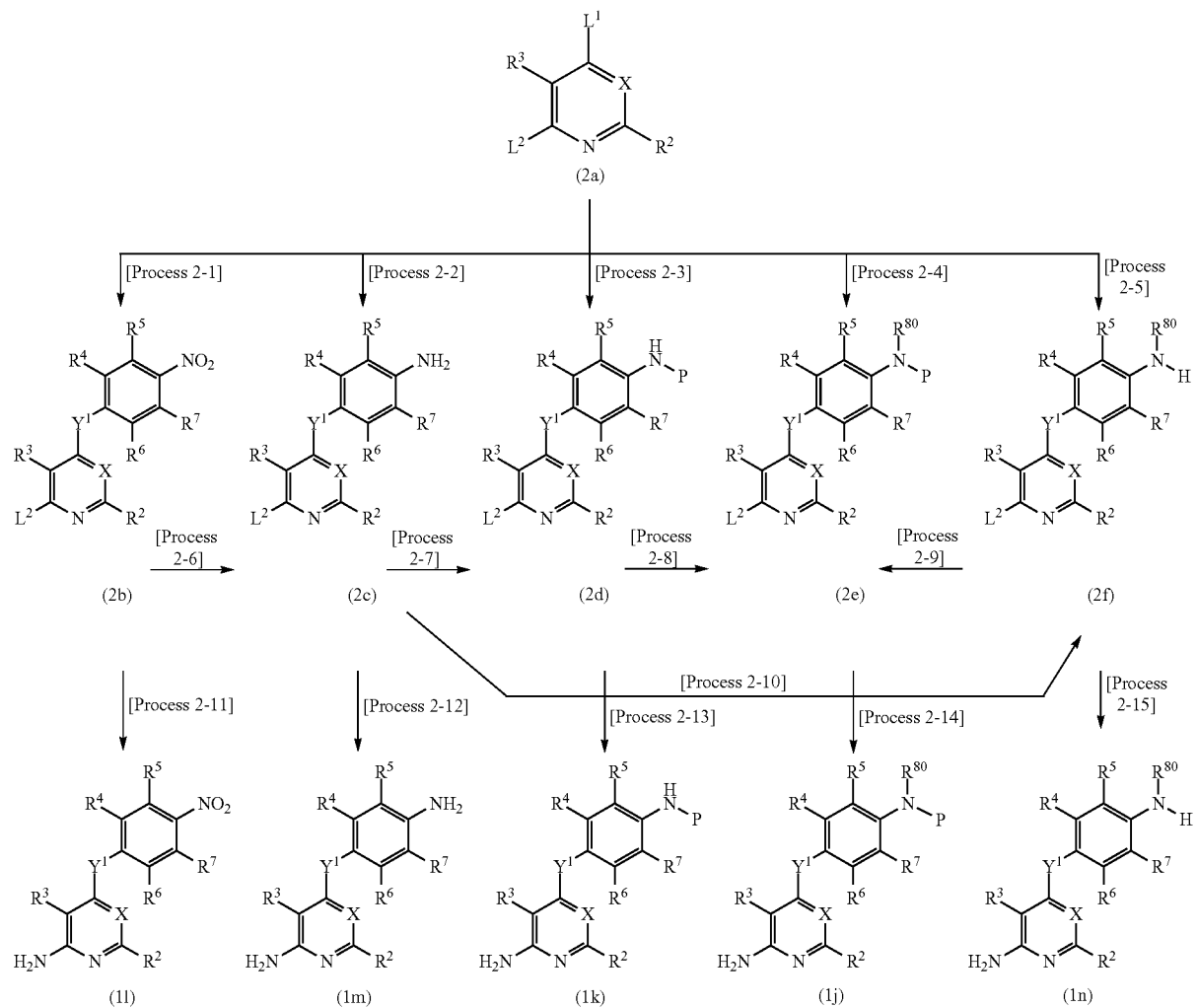

<Process 2-7>

The process is a process for protecting amino of the compound (2c) to produce the compound (2d). The methods similar to those in <Process 1B-6> can be used.

<Process 2-8>

The process is a process for alkylating the compound (2d) to produce the compound (2e). The methods similar to those in <Process 1A-13> can be used.

<Process 2-9>

The process is a process for protecting amino of the compound (2f) to produce the compound (2e). The methods similar to those in <Process 1B-6> can be used.

<Process 2-10>

The process is a process for alkylating the compound (2c) to produce the compound (2f). The methods similar to those in <Process 1A-12> can be used.

<Process 2-11> <Process 2-12> <Process 2-13> <Process 2-14> <Process 2-15>

These process are processes for converting the leaving group $L^2$ of the compound (2b), (2c), (2d), (2e) or (2f) to amino to produce the compound (1l), (1m), (1k), (1j) or (1n), respectively. The process can be carried out using, for example, an ammonia-ethanol solution in a sealed tube. The reaction temperature is a reflux temperature. The reaction time is between 10 minutes and 100 hours.

[Production method 3] A method for producing an intermediate represented by the formula (XI)

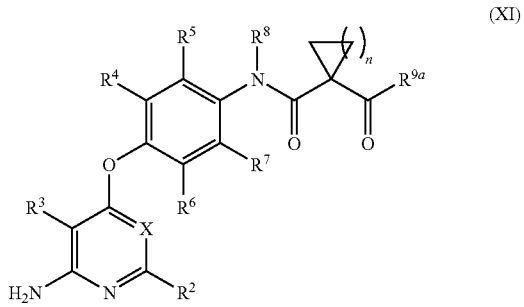

In the formula, $R^{9a}$ represents a 3- to 10-membered non-aromatic heterocyclic group wherein the group is limited to a group having nitrogen as a ring constituent atom and the nitrogen having a bonding hand, or a group represented by the formula $-NR^{11a}R^{11b}$, wherein $R^{11a}$ and $R^{11b}$ represent the same meaning as described above. $R^{9a}$ may be substituted with a substituent selected from Substituent Group A or Substituent Group B. Where $R^{9a}$ has hydroxyl, primary amino or secondary amino as a substituent group, the group may be protected by a suitable protecting group. The other symbols represent the same meanings as defined above.

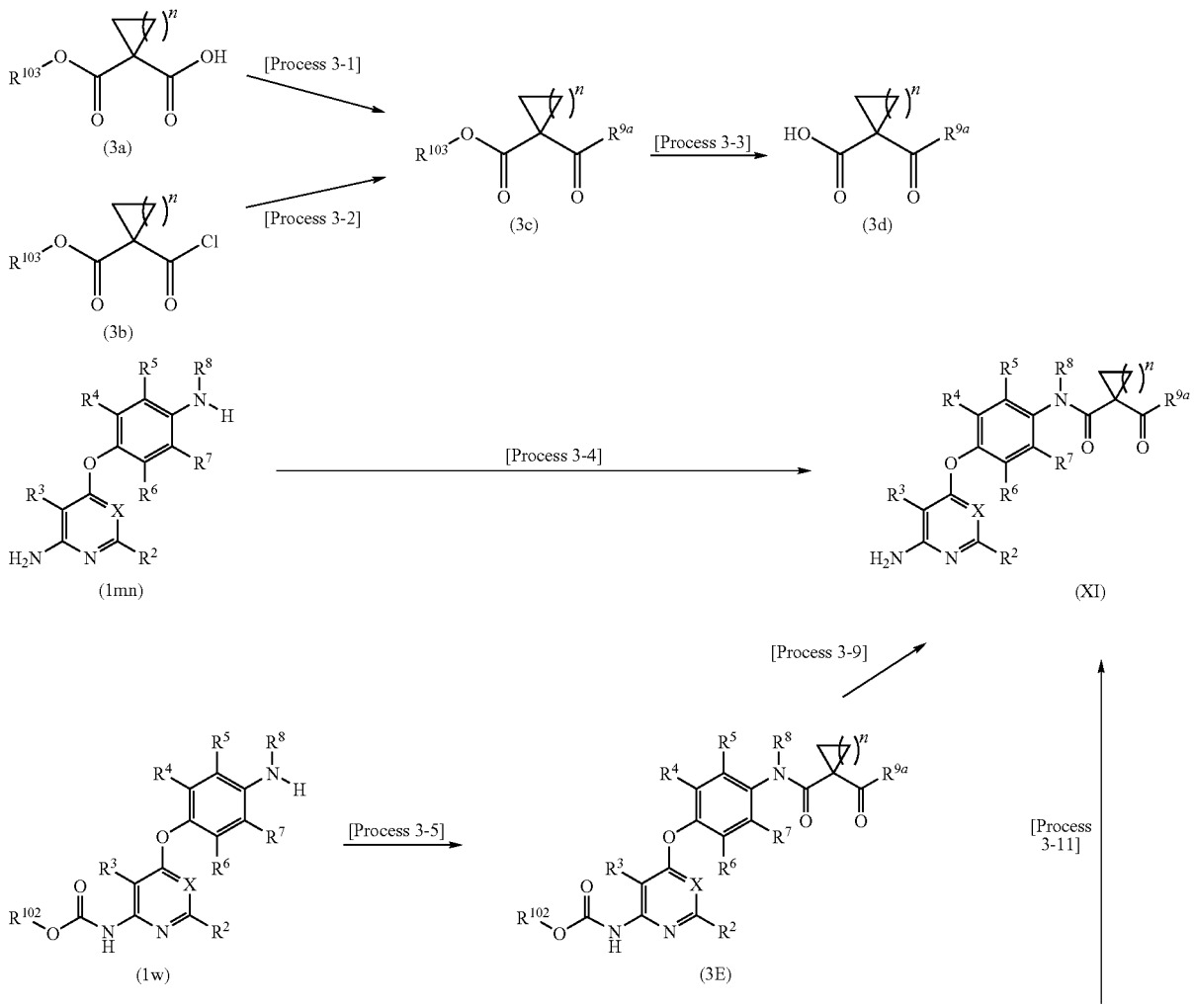

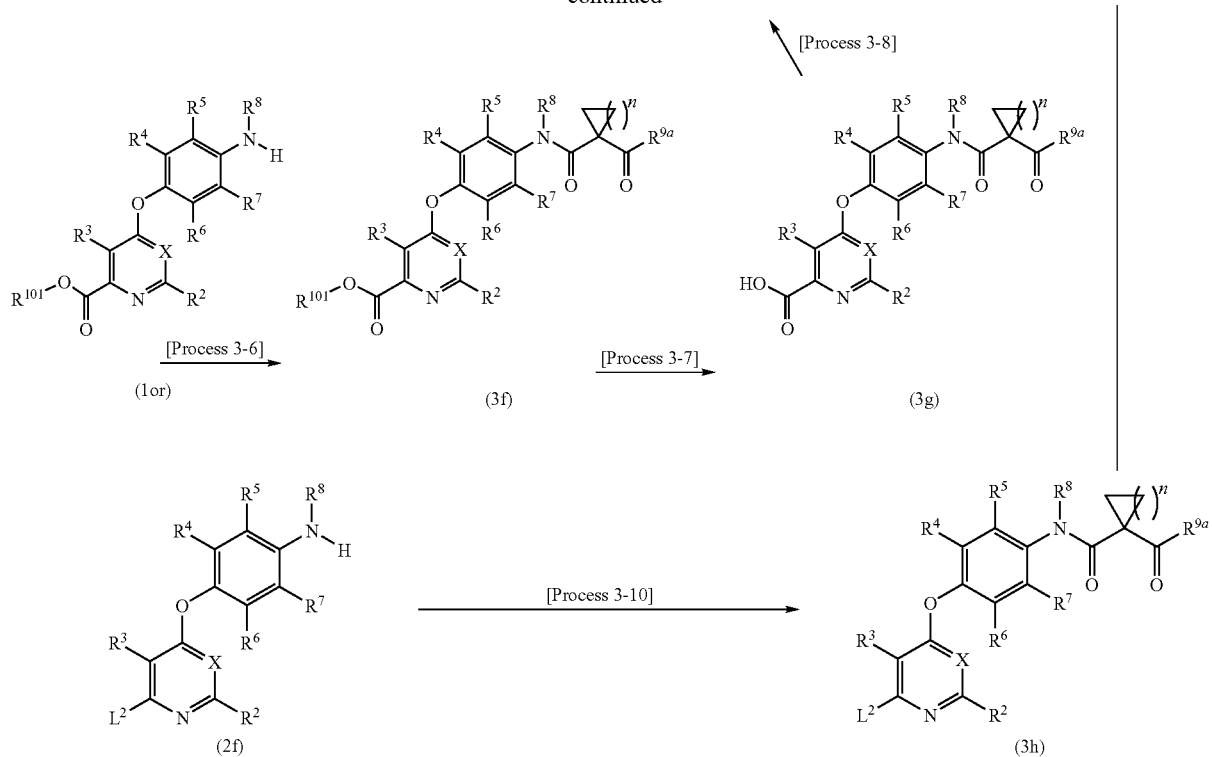

In the formula, $R^{103}$ represents $C_{1-6}$ alkyl or benzyl. The other symbols represent the same meanings as defined above.

The compound (3a) includes, for example, 1-ethoxycarbonylcyclopropanecarboxylic acid, 1-methoxycarbonylcyclopropanecarboxylic acid, 1-benzyloxycarbonylcyclobutanecarboxylic acid and 1-ethoxycarbonylcyclobutanecarboxylic acid.

The compound (3b) includes, for example, 1-chlorocarbonylcyclopropanecarboxylic acid ethyl ester and 1-chlorocarbonylcyclobutanecarboxylic acid ethyl ester.

The above compounds can also be produced from commercially available compounds by a known method.

<Process 3-1>

The process is a process for condensing the compound (3a) with an amine represented by the formula $R^{9a}$—H or a salt thereof to produce the compound (3c). For the process, a general condensation of a carboxylic acid with an amine can be used. For specific example, as the solvent, N,N-dimethylformamide and tetrahydrofuran can be used, and for the condensing agent, carbonyldiimidazole, dicyclohexylcarbodiimide, 1-ethyl-3-(3-dimethylaminopropyl)carbodiimide hydrochloride, and (1H-1,2,3-benzotriazol-1-yloxy)(tri(dimethylamino))phosphonium hexafluorophosphate can be used. An organic base such as triethylamine also can be appropriately used. The reaction temperature is between 0° C. and a reflux temperature. The reaction time is between 10 minutes and 30 hours.

<Process 3-2>

The process is a process for condensing the compound (3b) with an amine represented by the formula $R^{9a}$—H or a salt thereof to produce the compound (3c). As the solvent, N,N-dimethylformamide, tetrahydrofuran, dichloromethane or the like can be used. An organic base such as triethylamine also can be appropriately used. The reaction temperature is between 0° C. and a reflux temperature. The reaction time is between 10 minutes and 30 hours.

<Process 3-3>

The process is a process for producing the compound (3d) from the compound (3c). For the process, hydrolysis using a base can be used. For the base, lithium hydroxide or the like can be used. If $R^{103}$ is benzyl and $R^{9a}$ does not have chlorine, bromine and iodine as a substituent group, catalytic hydrogenation using palladium-carbon or palladium hydroxide as a catalyst also can be used. As the solvent, methanol, ethanol, water, N,N-dimethylformamide, tetrahydrofuran, ethyl acetate or the like can be used. The reaction temperature is between 0° C. and a reflux temperature. The reaction time is between 10 minutes and 30 hours.

<Process 3-4>

The process is a process for condensing the compound (1mn) (the compound (1mn) represents the compounds (1m) and (1n) described in [Production method 1-A]) with the compound (3d) to produce the compound (XI). For the condensing agent, 1-ethyl-3-(3-dimethylaminopropyl)carbodiimide hydrochloride, (1H-1,2,3-benzotriazol-1-yloxy)(tri(dimethylamino))phosphonium hexafluorophosphate or the like can be used. An organic base such as triethylamine also can be appropriately used. As the solvent, tetrahydrofuran, N,N-dimethylformamide or the like can be used. The reaction temperature is between 0° C. and a reflux temperature. The reaction time is between 10 minutes and 30 hours.

<Process 3-5> <Process 3-6> <Process 3-10>

These processes are processes for producing the compounds (3e), (3f) or (3h) from the compound (1w), (1or) (the compound (1or) represents the compounds (1o) and (1r) described in [Production method 1-B], the same applies hereinafter), or (2f), respectively. The methods similar to those in <Process 3-4> can be used.

<Process 3-7>

The process is a process for producing the compound (3g) from the compound (3f). The methods similar to those in <Process 1A-1> can be used.

<Process 3-8>

The process is a process for rearrangement of the compound (3g) to the compound (3e). The methods similar to those in <Process 1A-2> can be used.

<Process 3-9>

The process is a process for deprotecting the compound (3e) to produce the compound (XI). The methods similar to those in <Process 1A-5> can be used.

<Process 3-11>

The process is a process for converting the leaving group $L^2$ of the compound (3h) to amino to produce the compound (XI). The methods similar to those in <Process 2-11> can be used.

[Production method 4] An alternative method for synthesizing various intermediates in [Production method 3]

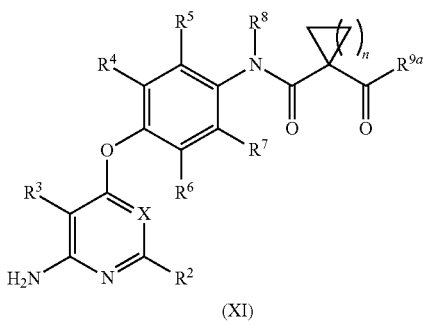

(XI)

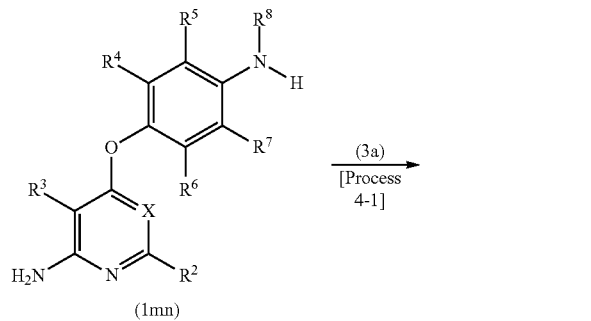

(1mn)

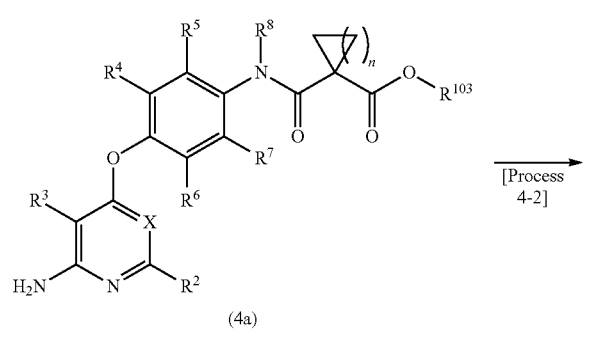

(4a)

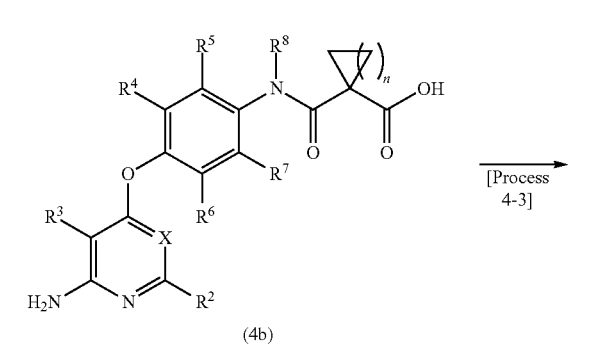

(4b)

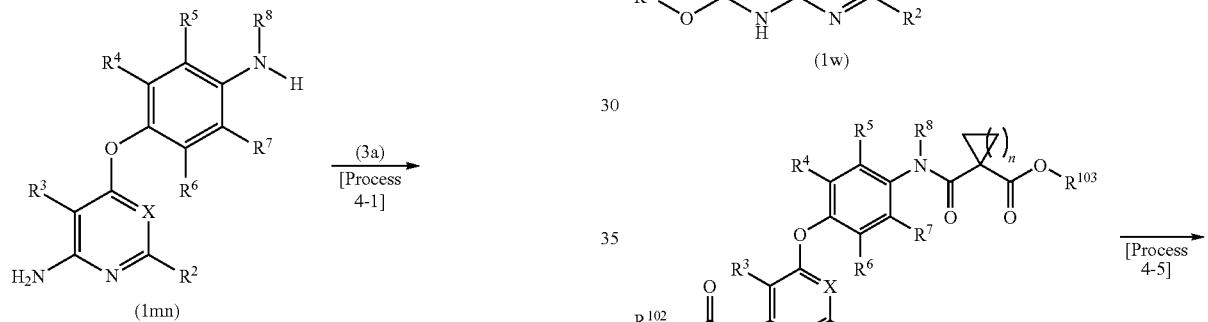

(1w)

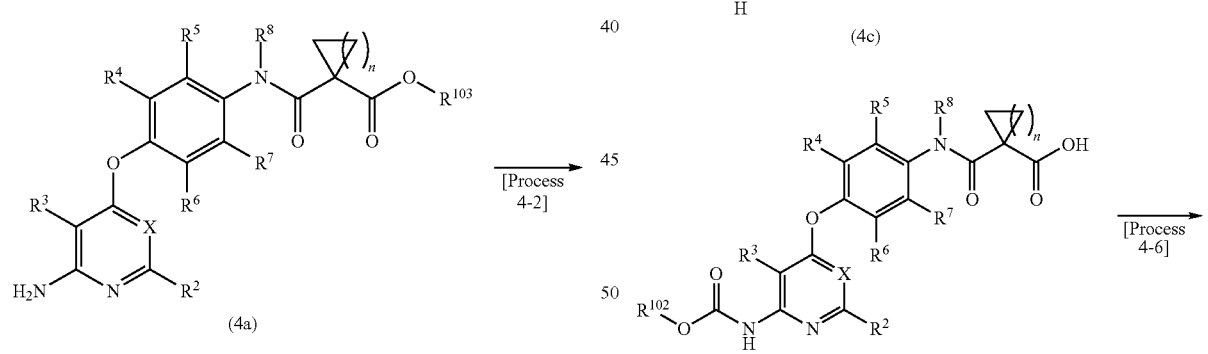

(4c)

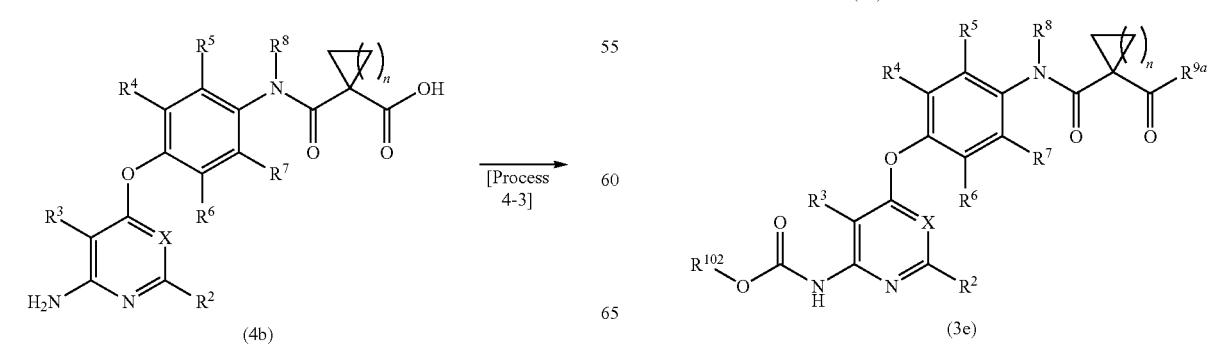

(4d)

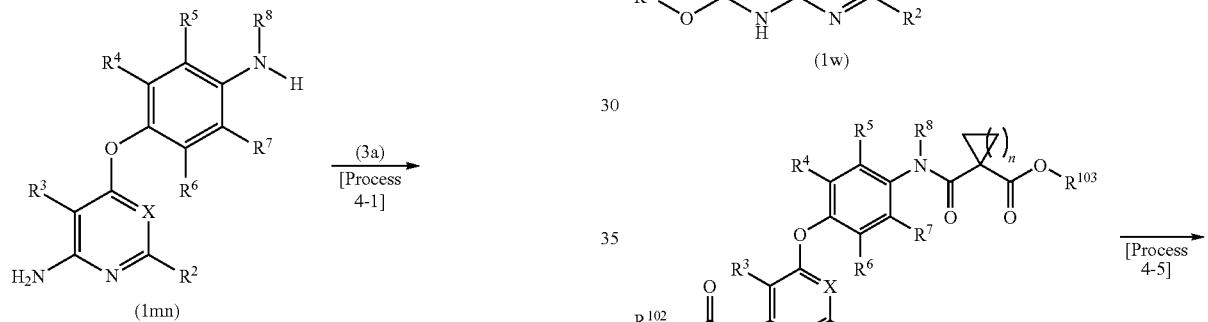

(3e)

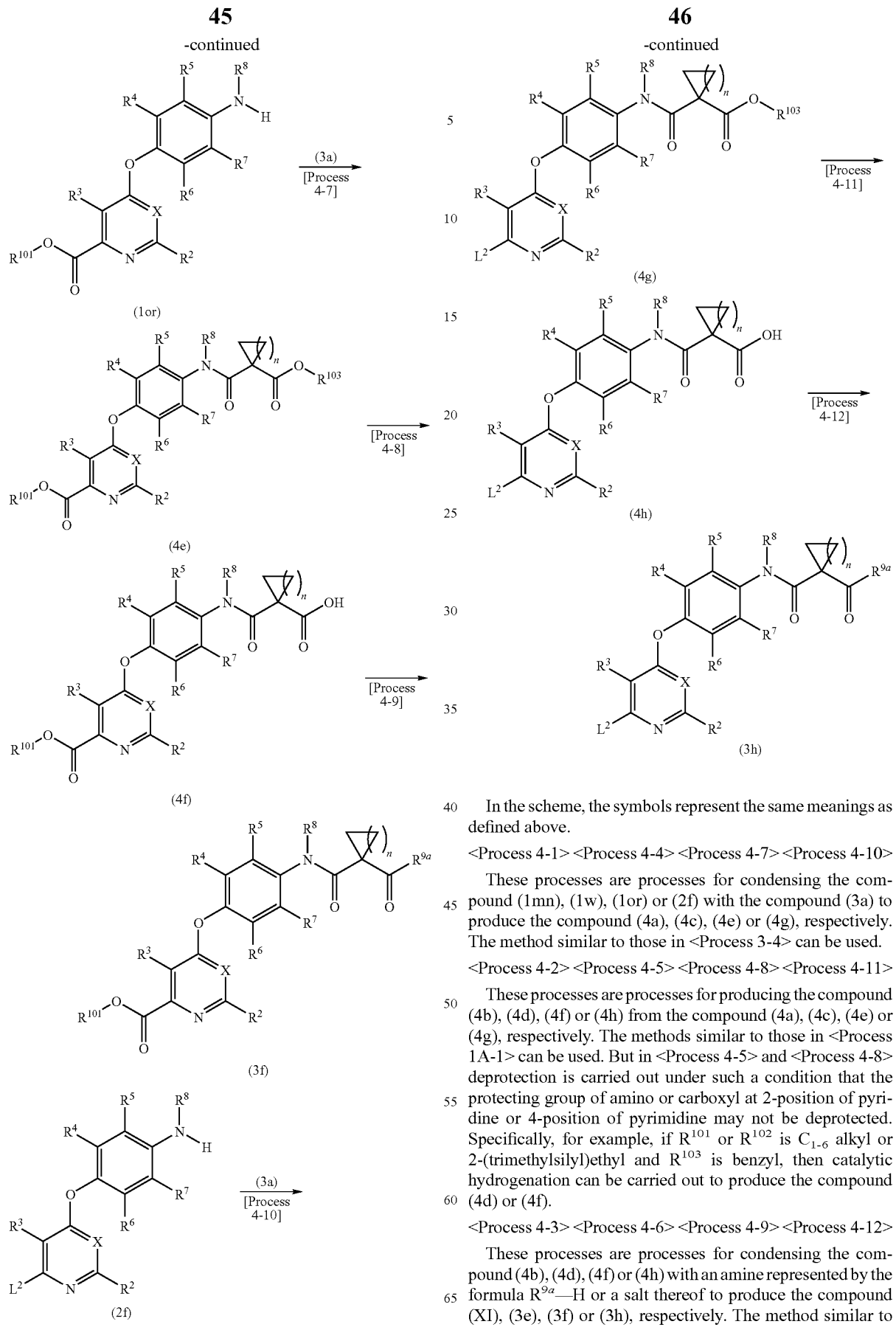

In the scheme, the symbols represent the same meanings as defined above.

<Process 4-1> <Process 4-4> <Process 4-7> <Process 4-10>

These processes are processes for condensing the compound (1mn), (1w), (1or) or (2f) with the compound (3a) to produce the compound (4a), (4c), (4e) or (4g), respectively. The method similar to those in <Process 3-4> can be used.

<Process 4-2> <Process 4-5> <Process 4-8> <Process 4-11>

These processes are processes for producing the compound (4b), (4d), (4f) or (4h) from the compound (4a), (4c), (4e) or (4g), respectively. The methods similar to those in <Process 1A-1> can be used. But in <Process 4-5> and <Process 4-8> deprotection is carried out under such a condition that the protecting group of amino or carboxyl at 2-position of pyridine or 4-position of pyrimidine may not be deprotected. Specifically, for example, if $R^{101}$ or $R^{102}$ is $C_{1-6}$ alkyl or 2-(trimethylsilyl)ethyl and $R^{103}$ is benzyl, then catalytic hydrogenation can be carried out to produce the compound (4d) or (4f).

<Process 4-3> <Process 4-6> <Process 4-9> <Process 4-12>

These processes are processes for condensing the compound (4b), (4d), (4f) or (4h) with an amine represented by the formula $R^{9a}$—H or a salt thereof to produce the compound (XI), (3e), (3f) or (3h), respectively. The method similar to those in <Process 3-1> can be used.

[Production method 5] An alternative method (2) for synthesizing various intermediates in [Production method 3]

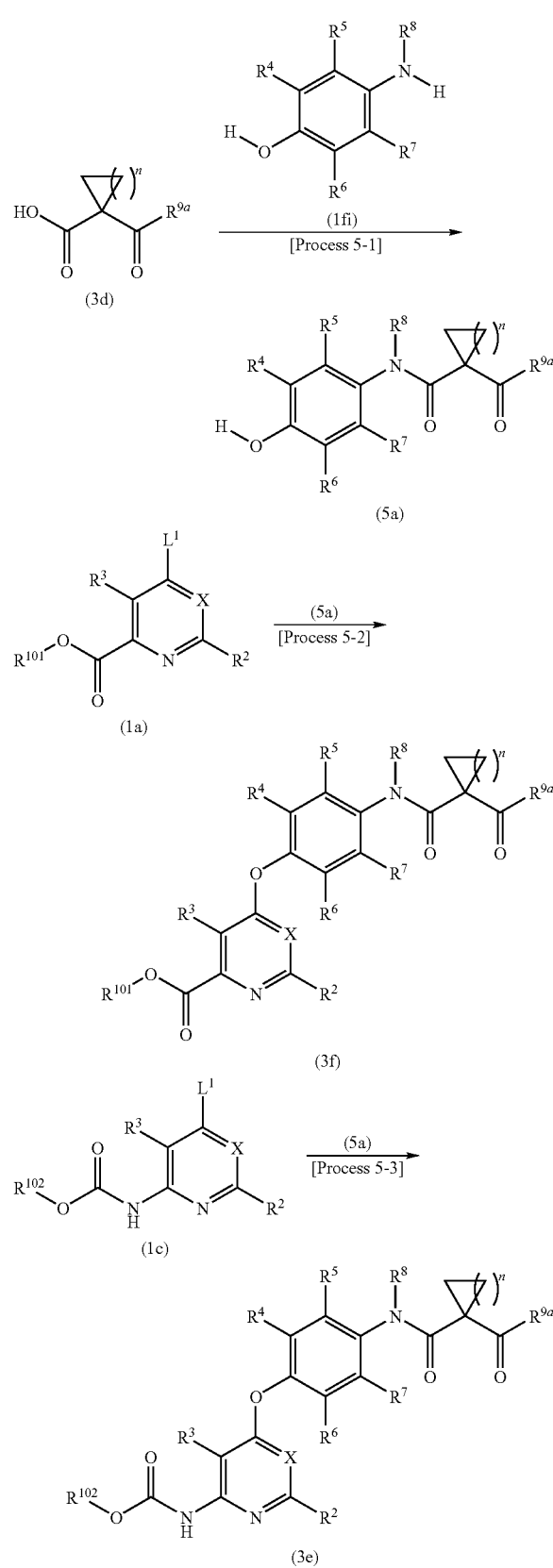
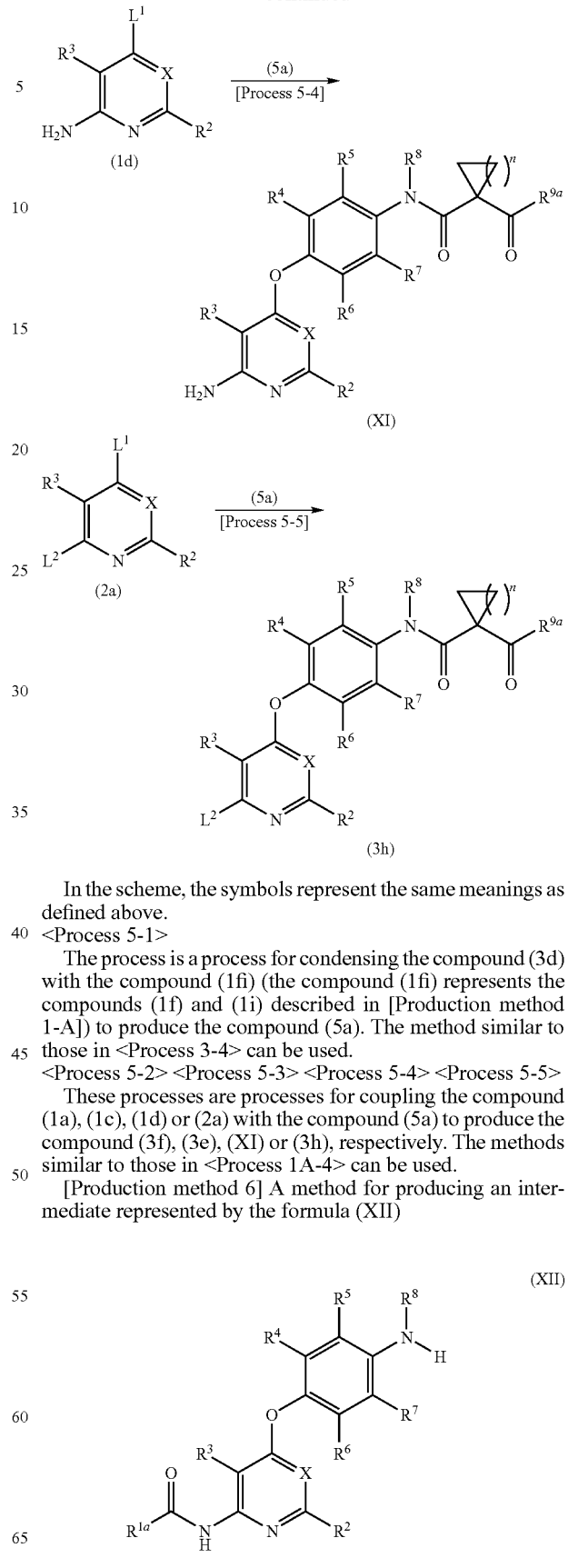

In the scheme, the symbols represent the same meanings as defined above.

<Process 5-1>

The process is a process for condensing the compound (3d) with the compound (1fi) (the compound (1fi) represents the compounds (1f) and (1i) described in [Production method 1-A]) to produce the compound (5a). The method similar to those in <Process 3-4> can be used.

<Process 5-2> <Process 5-3> <Process 5-4> <Process 5-5>

These processes are processes for coupling the compound (1a), (1c), (1d) or (2a) with the compound (5a) to produce the compound (3f), (3e), (XI) or (3h), respectively. The methods similar to those in <Process 1A-4> can be used.

[Production method 6] A method for producing an intermediate represented by the formula (XII)

In the formula, $R^{1a}$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ represent the same meaning as described above. $R^{1a}$ may be substituted with a substituent selected from Substituent Group A or Substituent Group B. Where $R^{1a}$ has hydroxyl, primary amino or secondary amino as a substituent group, the group may be protected by a suitable protecting group. The other symbols represent the same meanings as defined above.

represented by the formula Ar—OC(=O)—Cl, wherein Ar represents a phenyl group optionally substituted with one or two substituent(s) selected from halogen, methyl, methoxy and nitro, followed by reacting with an amine can be used. Alternatively, the compound (1l), (1m), (1k), (1j) or (1n) can be reacted with a carbamate derivative, an isocyanate derivative to convert to a corresponding urea derivative. As the solvent, chloroform, toluene, N-methylpyrrolidone, N,N-dimethylformamide, dimethylsulfoxide, chlorobenzene or the like can be used. A mixed solvent of the above solvent and water also can be used. A base also can be used. Specifically,

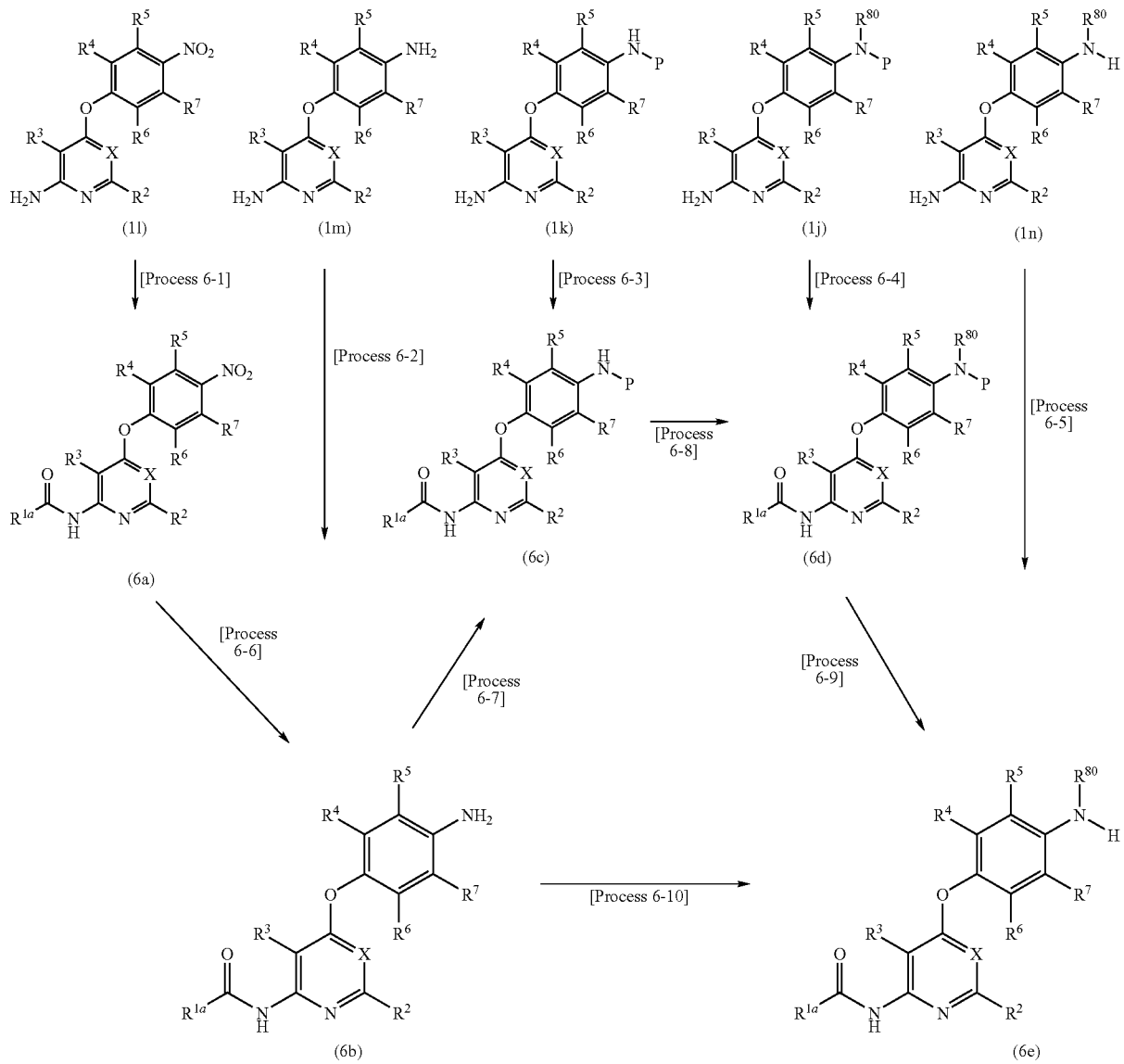

In the scheme, the symbols represent the same meanings as defined above.

<Process 6-1> <Process 6-2> <Process 6-3> <Process 6-4> <Process 6-5>

These processes are processes for producing the compound (6a), (6b), (6c), (6d) or (6e) from the compound (1l), (1m), (1k), (1j) or (1n), respectively. For example, a method wherein the compound (1l), (1m), (1k), (1j) or (1n) is converted to a carbamic acid ester derivative using a compound an organic base such as pyridine, triethylamine and diisopropylethylamine, and an inorganic base such as potassium carbonate, cesium carbonate, sodium hydride and sodium hydroxide can be used. The reaction temperature is between 0° C. and a reflux temperature. The reaction time is between 10 minutes and 30 hours.

After the process, in order to convert substituent groups on $R^{1a}$, generally used reactions such as oxidation, reduction, esterification, amidation, introduction of protecting groups, deprotection and hydrolysis can also be carried out in a suitable succeeding process. Specifically, for example, the method includes a method wherein the compound (1l), (1k) or (1j) is reacted with a ketone or aldehyde-containing amine, followed by reductive amination with an amine to introduce an amine side chain on $R^{1a}$. As the reducing agent, sodium cyanoborohydride and sodium triacetoxyborohydride or the like can be used. As the solvent, methanol, tetrahydrofuran, dichloromethane, dichloroethane or the like can be used. Furthermore, the compound (1l), (1k) or (1j) can be reacted with an ester-containing amine to produce a compound, an ester portion of which is then hydrolyzed with a base such as lithium hydroxide, sodium hydroxide and potassium hydroxide in hydrous ethanol, followed by converting with a condensing agent to an amide derivative. As the solvent, N,N-dimethylformamide, tetrahydrofuran or the like can be used. As the condensing agent, 1-ethyl-3-(3-dimethylaminopropyl)carbodiimide hydrochloride and (1H-1,2,3-benzotriazol-1-yloxy)(tri(dimethylamino))phosphonium hexafluorophosphate can be used. The reaction temperature is between 0° C. and a reflux temperature. The reaction time is between 10 minutes and 30 hours.

<Process 6-6>
The process is a process for reducing the compound (6a) to produce the compound (6b). The methods similar to those in <Process 1A-11> can be used.

<Process 6-7>
The process is a process for protecting amino of the compound (6b) to produce the compound (6c). The methods similar to those in <Process 1B-6> can be used.

<Process 6-8>
The process is a process for alkylating the compound (6c) to produce the compound (6d). The methods similar to those in <Process 1A-13> can be used.

<Process 6-9>
The process is a process for deprotecting the compound (6d) to produce the compound (6e). The methods similar to those in <Process 1A-5> can be used.

<Process 6-10>
The process is a process for alkylating the compound (6b) to produce the compound (6e). The methods similar to those in <Process 1A-12> can be used.

[Production method 7] A method for producing the compound of the present invention represented by the formula (I)

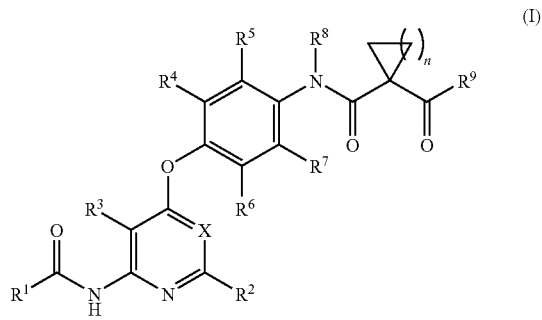

In the formula, the symbols represent the same meanings as defined above.

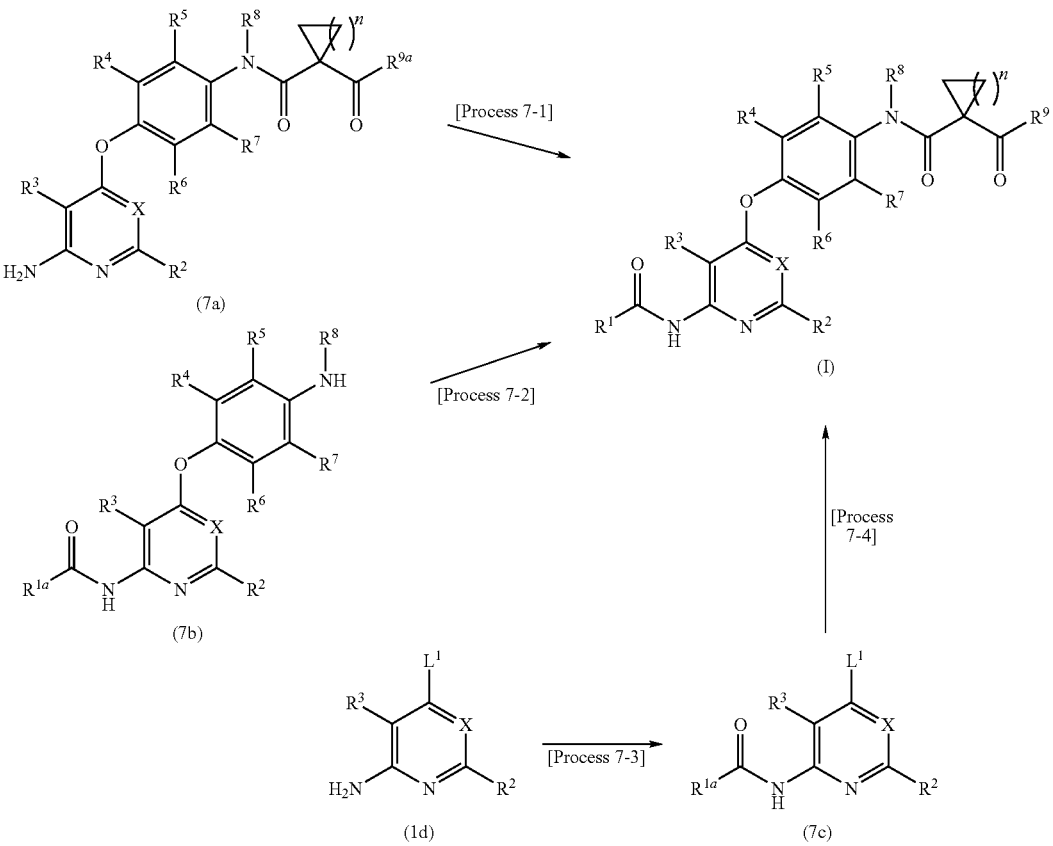

In the scheme, the symbols represent the same meanings as defined above.

<Process 7-1>

The process is a process for producing the compound (I) of the present invention from the compound (7a), that is, the above intermediate (XI).

(1) When $R^{1a}$ or $R^{9a}$ does not contain hydroxyl, primary amino or secondary amino:

Using a compound represented by the formula Ar—OC(=O)—Cl, wherein Ar represents the same meaning as defined above, the compound (7a) can be converted to a carbamic acid ester derivative, which is then reacted with an amine to produce the compound (I) of the present invention. Alternatively, the compound (7a) can be reacted with a carbamate derivative, an isocyanate derivative to convert to the compound (I) of the present invention. As the solvent, chloroform, toluene, N-methylpyrrolidone, N,N-dimethylformamide, dimethyl sulfoxide, chlorobenzene or the like can be used. A mixed solvent of the above solvent and water also can be used. A base also can be used, and specifically, an organic base such as pyridine, triethylamine and diisopropylethylamine, and an inorganic base such as potassium carbonate, cesium carbonate, sodium hydride and sodium hydroxide can be used. The reaction temperature is between 0° C. and a reflux temperature. The reaction time is between 10 minutes and 30 hours.

(2) When $R^{1a}$ or $R^{9a}$ contains hydroxyl, primary amino or secondary amino:

After these substituents are suitably protected, the above reaction can be carried out followed by deprotecting suitably to produce the compound (I) of the present invention.

(3) After the process, in order to convert substituent groups on $R^{1a}$ or $R^{9a}$, generally used reactions such as oxidation, reduction, esterification, amidation, protection, deprotection and hydrolysis can also be carried out in a suitable succeeding process, as described in <Process 6-1> of the above [Production method 6].

<Process 7-2>

The process is a process for producing the compound (I) of the present invention from the compound (7b), that is, the above intermediate (XII).

(1) When $R^{1a}$ or $R^{9a}$ does not contain hydroxyl, primary amino or secondary amino:

(Method 1)

The compound (7b) can be condensed with the compound (3d) to produce the compound (I) of the present invention. As a condensing agent, 1-ethyl-3-(3-dimethylaminopropyl)carbodiimide hydrochloride, (1H-1,2,3-benzotriazol-1-yloxy)(tri(dimethylamino))phosphonium hexafluorophosphate or the like can be used. An organic base such as triethylamine also can be used. As the solvent, tetrahydrofuran, N,N-dimethylformamide or the like can be used. The reaction temperature is between 0° C. and a reflux temperature. The reaction time is between 10 minutes and 30 hours.

(Method 2) When $R^{1a}$, $R^{9a}$ or $R^{10}$ Does not Contain alkoxycarbonyl:

The compound (7b) can be condensed with the compound (3a), $R^{103}$ of the resultant compound is then deprotected, followed by condensing with an amine or a salt thereof to produce the compound (I) of the present invention.

In condensation of the compound (7b) with the compound (3a), as the condensing agent, 1-ethyl-3-(3-dimethylaminopropyl)carbodiimide hydrochloride, (1H-1,2,3-benzotriazol-1-yloxy)(tri(dimethylamino))phosphonium hexafluorophosphate or the like can be used. A base such as triethylamine can also be suitably used. As the solvent, tetrahydrofuran, N,N-dimethylformamide or the like can be used. The reaction temperature is between 0° C. and a reflux temperature. The reaction time is between 10 minutes and 30 hours.

For the deprotection of $R^{103}$, hydrolysis using a base or the like can be used.

In condensation with an amine or a salt thereof, general condensation of a carboxylic acid with an amine can be used. Specifically for example, as the solvent, N,N-dimethylformamide and tetrahydrofuran can be used, and as the condensing agent, carbonyl diimidazole, dicyclohexyl carbodiimide, 1-ethyl-3-(3-dimethylaminopropyl)carbodiimide hydrochloride and (1H-1,2,3-benzotriazol-1-yloxy)(tri(dimethylamino))phosphonium hexafluorophosphate can be used. A base such as triethylamine can also be suitably used. The reaction temperature is between 0° C. and a reflux temperature. The reaction time is between 10 minutes and 30 hours.

(2) When $R^{1a}$ or $R^{9a}$ contains hydroxyl, primary amino or secondary amino:

After the substituent is protected if necessary, the above reaction can be carried out, followed by deprotecting suitably to produce the compound (I) of the present invention.

(3) After the process, in order to convert substituent groups on $R^{1a}$ or $R^{9a}$, generally used reactions such as oxidation, reduction, esterification, amidation, protection, deprotection and hydrolysis can also be carried out, as described in <Process 6-1> of the above [Production method 6].

<Process 7-3>

The process is a process for producing the compound (7c) from the compound (1d). The methods similar to those in <Process 6-1> can be used, for example, a method wherein the compound (1d) is converted to a carbamic acid ester derivative using a compound represented by the formula Ar—OC(=O)—Cl, wherein Ar represents the same meaning as defined above, followed by reacting with an amine can be used. Alternatively, the compound (1d) can be reacted with a carbamate derivative, an isocyanate derivative to convert to a corresponding urea derivative. As the solvent, chloroform, toluene, N-methylpyrrolidone, N,N-dimethylformamide, dimethylsulfoxide, chlorobenzene or the like can be used. A mixed solvent of the above solvent and water also can be used. A base also can be used. Specifically, an organic base such as pyridine, triethylamine and diisopropylethylamine, and an inorganic base such as potassium carbonate, cesium carbonate, sodium hydride and sodium hydroxide can be used. The reaction temperature is between 0° C. and a reflux temperature. The reaction time is between 10 minutes and 30 hours.

<Process 7-4>

The process is a process for producing the compound (I) of the present invention from the compound (7c).

(1) When $R^{1a}$ or $R^{9a}$ does not contain hydroxyl, primary amino or secondary amino:

The compound (I) of the present invention can be obtained by a coupling reaction of the compound (7c) and the compound (5a). The methods similar to those in <Process 1A-4> can be used. As the solvent, N-methylpyrrolidone, N,N-dimethylformamide, dimethyl sulfoxide, 2-ethoxyethanol, chlorobenzene or the like can be used. A base or an acid may be added in the reaction system, and specifically an organic base such as triethylamine and diisopropylethylamine, an inorganic base such as potassium carbonate, cesium carbonate and sodium hydride, or an acid such as pyridine hydrochloride and hydrochloric acid can be used. The reaction temperature is between room temperature and a reflux temperature. The reaction time is between 10 minutes and 30 hours.

(2) When $R^{1a}$ or $R^{9a}$ contains hydroxyl, primary amino or secondary amino:

After these substituents are suitably protected, the above reaction can be carried out followed by deprotecting suitably to produce the compound (I) of the present invention.

(3) After the process, in order to convert substituent groups on $R^{1a}$ or $R^{9a}$, generally used reactions such as oxidation, reduction, esterification, amidation, protection, deprotection and hydrolysis can also be carried out in a suitable succeeding process, as described in <Process 6-1> of the above [Production method 6].

[Production Method 8] A method for producing an intermediate (1d), wherein X is a group represented by the formula—

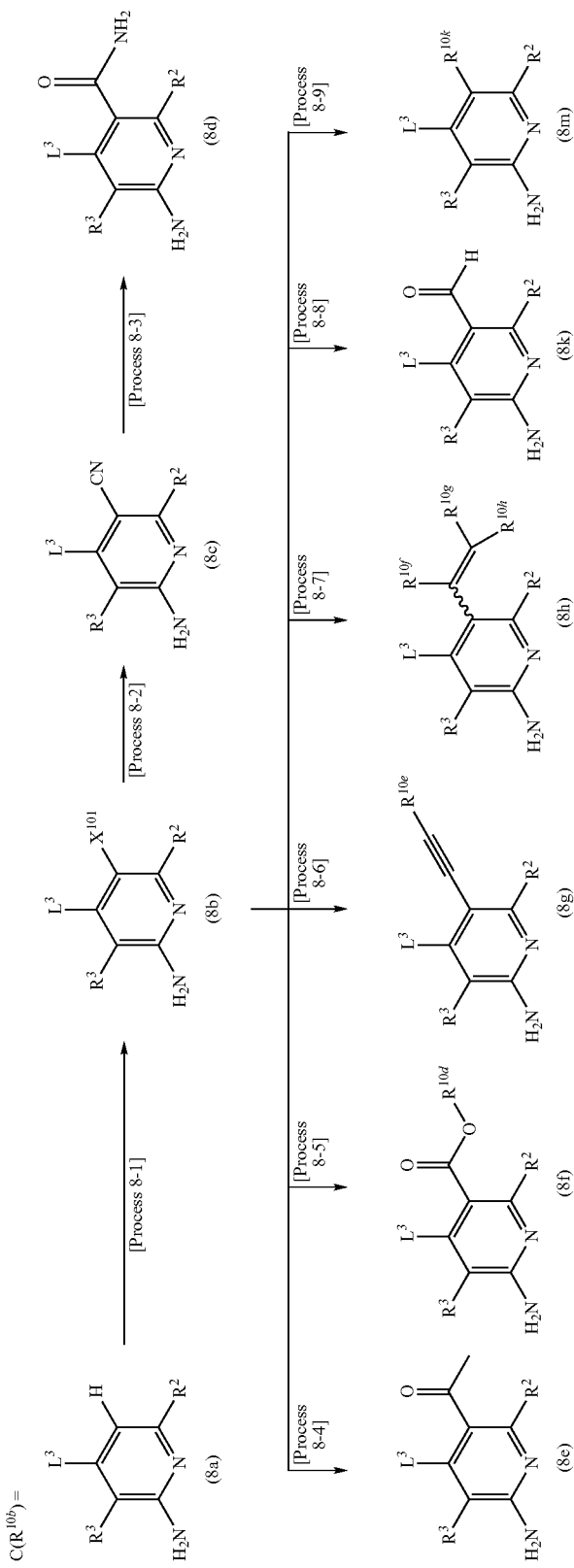

In the scheme, $L^3$ represents chlorine or bromine; $X^{101}$ represents chlorine, bromine or iodine; $R^{10b}$ represents halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as defined above; $R^{10d}$ represents $C_{1-6}$ alkyl; $R^{10e}$ represents hydrogen or $C_{1-4}$ alkyl; $R^{10f}$, $R^{10g}$ and $R^{10h}$ may be the same or different and each represents hydrogen or $C_{1-4}$ alkyl, with the proviso that the total carbon number of $R^{10f}$, $R^{10g}$ and $R^{10h}$ is 0 or more to 4 or less; $R^{10k}$ represents $C_{1-6}$ alkyl; and the other symbols represent the same meanings as defined above.

<Process 8-1>

The process is a process for chlorinating, brominating or iodinating the 5-position of the compound (8a) to produce the compound (8b). For example, a halogenating agent such as iodine, N-iodosuccinimide, bromine, N-bromosuccinimide and N-chlorosuccinimide can be used. As the solvent, for example, N,N-dimethylformamide, dimethyl sulfoxide, dichloromethane and acetonitrile can be used. The reaction temperature is between 0° C. and a reflux temperature. The reaction time is between 10 minutes and 48 hours.

<Process 8-2>

The process is a process for converting $X^{101}$ of the compound (8b) to cyano to produce the compound (8c). Concerning the combination of $L^3$ and $X^{101}$ upon cyanation, $X^{101}$ is preferably iodine or bromine when $L^3$ is chlorine, and $X^{101}$ is preferably iodine when $L^3$ is bromine. For example, in the presence of a palladium catalyst such as tetrakis(triphenylphosphine)palladium(0) and dichlorobis(triphenylphosphine)palladium(II), 0.5-0.6 equivalent of zinc cyanide is used relative to the compound (8b), or 1.0-1.2 equivalent of potassium cyanide or trimethylsilyl cyanide is used relative to the compound (8b). As the solvent, for example, N,N-dimethylformamide, dioxane or tetrahydrofuran can be used. The reaction temperature is between room temperature and a reflux temperature. The reaction time is between 10 minutes and 10 hours.

<Process 8-3>

The process is a process for producing the compound (8d) from the compound (8c). Hydrolysis using an inorganic base such as potassium carbonate and a hydrogen peroxide can be used. As the solvent, dimethyl sulfoxide or the like can be used. The reaction temperature is between 0° C. and a reflux temperature. The reaction time is between 10 minutes and 10 hours. A method of heating under reflux in a solvent such as toluene and tetrahydrofuran in the presence of potassium trimethylsilanolate, as described in Tetrahedron Lett., 41, 3747 (2000), also can be used. The reaction time is between 10 minutes and 60 hours.

<Process 8-4>

The process is a process for producing the compound (8e) from the compound (8b). A method of reacting with (1-ethoxyvinyl)tributyltin in the presence of a palladium catalyst such as dichlorobis(triphenylphosphine)palladium(II) and tetrakis(triphenylphosphine)palladium(0) can be used. In the reaction system, a salt such as lithium chloride may be added. As the solvent, tetrahydrofuran, N,N-dimethylformamide, N-methylpyrrolidone or the like can be used. The reaction temperature is between room temperature and a reflux temperature. The reaction time is between 10 minutes and 60 hours.

As for a document that complements the above method, Tetrahedron, 53 (14), 5159 (1997) can be mentioned.

<Process 8-5>

The process is a process for producing the compound (8f) from the compound (8b). A method of reacting an alcohol represented by the formula $R^{10d}$—OH with carbon monoxide in the presence of a palladium catalyst such as dichlorobis(triphenylphosphine)palladium(II) can be used. In the reaction system, a base such as triethylamine and diisopropylethylamine may be added. As the solvent, an alcohol represented by the formula $R^{10d}$—OH, tetrahydrofuran, N,N-dimethylformamide, N-methylpyrrolidone, dimethyl sulfoxide or the like can be used. The reaction temperature is between room temperature and a reflux temperature. The reaction time is between 10 minutes and 60 hours.

As for a document that complements the above method, Tetrahedron Lett., 25 (51), 5939 (1984) can be mentioned.

<Process 8-6>

The process is a process for producing the compound (8g) from the compound (8b). The compound (8b) can be reacted with an acetylene derivative in the presence of a palladium catalyst such as dichlorobis(triphenylphosphine)palladium (II) to produce the compound (8g). In the reaction system, an organic base such as triethylamine or an inorganic base such as potassium carbonate and sodium hydroxide may be added. A monovalent copper halide may coexist. As the solvent, tetrahydrofuran, N,N-dimethylformamide, N-methylpyrrolidone, dioxane, 1,2-dimethoxyethane, toluene, benzene, acetonitrile or the like can be used. The reaction temperature is between room temperature and a reflux temperature. The reaction time is between 10 minutes and 60 hours.

<Process 8-7>

The process is a process for producing the compound (8h) from the compound (8b). The compound (8b) can be reacted with a trialkylvinyltin derivative in the presence of a palladium catalyst such as dichlorobis(triphenylphosphine)palladium(II) to produce the compound (8h). In the reaction system, hexamethylphosphoramide or the like may be added. As the solvent, tetrahydrofuran, N,N-dimethylformamide, N-methylpyrrolidone, dimethyl sulfoxide or the like can be used. The reaction temperature is between room temperature and a reflux temperature. The reaction time is between 10 minutes and 60 hours.

As for a document that complements the above method, Tetrahedron, 53 (14), 5159 (1997) can be mentioned.

<Process 8-8>

The process is a process for producing the compound (8k) from the compound (8b). A method of reacting with carbon monoxide in the presence of a palladium catalyst such as dichlorobis(triphenylphosphine)palladium(II), and sodium formate, as described in Bull. Chem. Soc. Jpn., 67 (8), 2329 (1994), can be used. As the solvent, tetrahydrofuran, N,N-dimethylformamide, N-methylpyrrolidone, dimethyl sulfoxide or the like can be used. The reaction temperature is between room temperature and a reflux temperature. The reaction time is between 10 minutes and 60 hours.

<Process 8-9>

The process is a process for producing the compound (8m) from the compound (8b). A method of reacting with a reagent prepared from alkyl magnesium halide and zinc(II)chloride in the presence of a palladium catalyst such as dichlorobis(triphenylphosphine)palladium(II), as described in J. Org. Chem., 2001, 66 (20), 605, can be used. As the solvent, tetrahydrofuran or the like can be used. The reaction temperature is between room temperature and a reflux temperature. The reaction time is between 10 minutes and 60 hours. Alternatively, a method of reacting with tetraalkyltin in the presence of a palladium catalyst such as dichlorobis(triphenylphosphine)palladium(II), as described in Tetrahedron Lett. 1996, 37 (14), 2409-2412, can be used. As the solvent, toluene or the like can be used. The reaction temperature is between room temperature and a reflux temperature. The reaction time is between 10 minutes and 60 hours.

The reactions similar to described in the processes of <Process 8-1> to <Process 8-9> can be applied to the conversion of the substituent at the 5-position ($R^{10}$) of the pyridine ring of various intermediates described in [Production Method 1] to [Production Method 7].

The "leaving group" may be any group generally known as a leaving group in organic synthesis, and is not particularly limited. Specifically for example, it includes halogen such as chlorine, bromine and iodine; nitro; alkylsulfonyloxy such as methanesulfonyloxy, trifluoromethanesulfonyloxy and ethanesulfonyloxy; arylsulfonyloxy such as benzenesulfonyloxy and p-toluenesulfonyloxy; and alkanoyloxy such as acetoxy and trifluoroacetoxy.

The amino-protecting group may be any group generally known as an amino-protecting group in organic synthesis, and is not particularly limited. Specifically for example, it includes substituted or unsubstituted acyl such as formyl, acetyl, chloroacetyl, dichloroacetyl, propionyl, phenylacetyl, phenoxyacetyl and thienylacetyl; alkoxycarbonyl such as t-butoxycarbonyl; substituted or unsubstituted benzyloxycarbonyl such as benzyloxycarbonyl and 4-nitrobenzyloxycarbonyl; substituted or unsubstituted alkyl such as methyl, t-butyl and 2,2,2-trichloroethyl; substituted benzyl such as trityl, 4-methoxybenzyl, 4-nitrobenzyl and diphenylmethyl; alkylcarbonyloxyalkyl such as pivaloyloxymethyl; alkylsilyl such as trimethylsilyl and t-butyldimethylsilyl; and alkylsilylalkoxyalkyl such as trimethylsilylmethoxymethyl, trimethylsilylethoxymethyl, t-butyldimethylsilylmethoxymethyl, t-butyldimethylsilylethoxymethyl.

These protecting groups can be deprotected by a conventional method such as hydrolysis and reduction depending on the kind of the protecting group used.

The hydroxyl-protecting group may be any group generally known as a hydroxyl-protecting group in organic synthesis, and is not particularly limited. Specifically for example, it includes alkylsilyl such as trimethylsilyl and t-butyldimethylsilyl; alkoxymethyl such as methoxymethyl and 2-methoxyethoxymethyl; tetrahydropyranyl; substituted or unsubstituted benzyl such as benzyl, 4-methoxybenzyl, 2,4-dimethoxybenzyl, 2-nitrobenzyl, 4-nitrobenzyl and trityl; alkenyl such as allyl; and acyl such as formyl and acetyl.

These protecting groups can be deprotected by a conventional method such as hydrolysis and reduction depending on the kind of the protecting group used.

The carboxyl-protecting group may be any group generally known as a carboxyl-protecting group in organic synthesis, and is not particularly limited. For example, it includes substituted or unsubstituted alkyl such as methyl, ethyl, i-propyl, t-butyl, 2-iodoethyl and 2,2,2-trichloroethyl; alkoxymethyl such as methoxymethyl, ethoxymethyl and i-butoxymethyl; acyloxymethyl such as butylyloxymethyl and pivaloyloxymethyl; alkoxycarbonyloxyethyl such as 1-methoxycarbonyloxyethyl and 1-ethoxycarbonyloxyethyl; and substituted or unsubstituted benzyl such as benzyl, 4-methoxybenzyl, 2-nitrobenzyl and 4-nitrobenzyl.

These protecting groups can be deprotected by a conventional method such as hydrolysis and reduction depending on the kind of the protecting group used.

In addition to the above protecting groups, groups described in Greene et al., "Protective Groups in Organic Synthesis", 3rd Edition, JOHN WILEY & SONS, INC. can be used.

There have been described above the typical examples of a method for producing the compound (I) according to the present invention. Each of the starting materials and various reagents may be a salt, a hydrate or a solvate, varies depending on a starting material, a solvent and the like to be used, and is not limited to a particular one as long as it does not inhibit a reaction. A solvent to be used varies depending on a starting material, a reagent and the like, and is not limited to a particular one as long as it does not inhibit a reaction and can dissolve the starting material to some extent.

The compound (I) according to the present invention, if provided as a free form, can be converted to a form of a salt or a hydrate which the forgoing may form by a conventional method.

The compound (I) according to the present invention, if provided as the form of a salt or a hydrate of the compound (I), can be converted to a free form of the compound (I) by a conventional method.

The compound (I) according to the present invention and the various isomers (such as geometric isomers and optical isomers) of the compound (I) according to the present invention can be purified and isolated by a conventional separation means, including recrystallization, diastereomer salt method, enzyme separation method, and various chromatographies such as thin-layer chromatography, column chromatography and gas chromatography.

The compound (I) of the present invention is generally mixed with an appropriate additive and formulated to use as a medicament. But the compound of the present invention may be used alone without any additive.

The above additives include excipients, binders, lubricants, disintegrators, coloring agents, taste correctives, emulsifiers, surfactants, dissolving aids, suspending agents, isotonizing agents, buffering agents, antiseptics, antioxidants, stabilizers, absorption accelerators and the like. These also may be appropriately combined to use if desired.

The excipients include, for example, lactose, white soft sugar, glucose, corn starch, mannitol, sorbitol, starch, pregelatinized starch, dextrin, crystalline cellulose, soft silicic anhydride, aluminum silicate, calcium silicate, magnesium aluminometasilicate and calcium hydrogenphosphate.

The binders include, for example, polyvinyl alcohol, methylcellulose, ethylcellulose, gum arabic, tragacanth, gelatin, shellac, hydroxypropylmethylcellulose, hydroxypropylcellulose, carboxymethylcellulose sodium, polyvinylpyrrolidone and macrogol.

The lubricants includes magnesium stearate, calcium stearate, sodium stearyl fumarate, talc, polyethylene glycol and colloidal silica.

The disintegrators includes, for example, crystalline cellulose, agar, gelatin, calcium carbonate, sodium hydrogencarbonate, calcium citrate, dextrin, pectin, low-substituted hydroxypropylcellulose, carboxymethylcellulose, carboxymethylcellulose calcium, croscarmellose sodium, carboxymethyl starch and carboxymethyl starch sodium.

The coloring agents include, for example, those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

The taste correctives include cocoa powder, menthol, aromatic powders, mentha oil, borneol, powdered cinnamon bark and the like.

The emulsifiers or surfactants include, for example, stearyl triethanolamine, sodium lauryl sulfate, lauryl aminopropionic acid, lecitin, glycerin monostearate, sucrose fatty acid esters and glycerin fatty acid esters.

The dissolving aids include, for example, polyethylene glycol, propylene glycol, benzyl benzoate, ethanol, cholesterol, triethanolamine, sodium carbonate, sodium citrate, polysorbate 80 and nicotinamide.

The suspending agents include, for example, hydrophilic polymers such as polyvinyl alcohol, polyvinylpyrrolidone, methylcellulose, hydroxymethylcellulose, hydroxyethylcellulose and hydroxypropylcellulose, in addition to the above surfactants.

The isotonizing agents include, for example, glucose, sodium chloride, mannitol and sorbitol.

The buffering agents include, for example, buffer solutions of phosphate, acetate, carbonate and citrate.

The antiseptics include, for example, methylparaben, propylparaben, chlorobutanol, benzyl alcohol, phenethyl alcohol, dehydroacetic acid and sorbic acid.

The antioxidants include, for example, sulfite, ascorbic acid and α-tocopherol.

The stabilizers include those commonly used in pharmaceuticals.

The absorption accelerators include those commonly used in pharmaceuticals.

The formulation may be in an oral form such as tablets, powders, granules, capsules, syrups, lozenges and inhalants; an external application form such as suppositories, ointment, eye salve, tape, eye drops, nose drops, ear drops, pap and lotion; and an injection.

An oral formulation may be formulated by combining appropriately the above additives, and may be coated on the surface if necessary.

An external application may be formulated by combining appropriately the above additives, particularly excipients, binders, taste correctives, emulsifiers, surfactants, dissolving aids, suspending agents, isotonizing agents, antiseptics, antioxidants, stabilizers and absorption accelerators.

An injection may be formulated by combining appropriately the above additives, particularly emulsifiers, surfactants, dissolving aids, suspending agents, isotonizing agents, buffering agents, antiseptics, antioxidants, stabilizers and absorption accelerators.

The dose of the compound according to the present invention for the pharmaceutical use varies depending on symptoms and age of the patients, but it will ordinary be 0.1 mg to 10 g (preferably 1 mg to 2 g) for an oral formulation, 0.01 mg to 10 g (preferably 0.1 mg to 2 g) for an external application, and 0.01 mg to 10 g (preferably 0.1 mg to 2 g) for an injection, which is administrated once or divided over two to four times a day.

Examples

The compound according to the present invention can be produced, for example, by the methods described in the below Production Examples and Examples. But these Examples are for illustrative purposes, and the compound according to the present invention is not limited to the following specific Examples in any case.

In the Production Examples and Examples, YMC SIL-60-400/230W was used as silica gel for purification unless otherwise described.

For conditions of purification by LC-MS, the two conditions described below (Gradient Condition 1 or Gradient Condition 2) was used unless otherwise described.
ODS column: CAPCELL PAK C-18
Solvent
Solution A: Water
Solution B: Acetonitrile
Solution C: 1% trifluoroacetic acid in water
Flow rate: 30 ml/min
Stop time: 10 min
Gradient Condition 1
0.00 min A: 80%, B: 10%, C: 10%
7.80 min A: 30%, B: 60%, C: 10%
8.00 min A: 0%, B: 100%, C: 0%
Gradient Condition 2
0.00 min A: 80%, B: 10%, C: 10%
2.00 min A: 70%, B: 20%, C: 10%
7.50 min A: 40%, B: 50%, C: 10%
8.00 min A: 0%, B: 100%, C: 0%

Production Example 1 tert-Butyl 3-dimethylaminoazetidine-1-carboxylate

To a solution of 1-Boc-azetidin-3-one (3.45 g) in methanol (175 ml) were added a 2M solution of dimethylamine in tetrahydrofuran (21.9 ml), acetic acid (1.73 ml), 10% palladium on carbon (2.15 g), followed by stirring at room temperature under a hydrogen atmosphere for 14 hr. The catalyst was removed by filtration and the filtrate was concentrated under reduced pressure. The residue was partitioned between ethyl acetate and a saturated aqueous solution of sodium hydrogencarbonate. The combined organic layer was dried over anhydrous sodium sulfate, which was concentrated to provide the titled compound as a colorless oil (4.07 g, 101%).
$^1$H-NMR Spectrum (CDCl$_3$) δ (ppm): 1.43 (9H, m), 2.17 (6H, s), 3.01 (1H, m), 3.79 (2H, m), 3.91 (2H, m).

Production Example 2

N-[1-(1-Benzylpiperidin-4-yl)azetidin-3-yl]-N,N-dimethylamine trihydrochloride tert-Butyl 3-dimethylaminoazetidine-1-carboxylate (7.00 g) was stirred in an ice bath, and trifluoroacetic acid (21.6 ml) was added thereto, followed by stirring in an ice bath for 30 min, then at room temperature for 1.5 hr. The reaction mixture was concentrated to provide a crude product of 3-(dimethylamino)azetidine ditrifluoroacetate as a brown oil (ESI-MS (m/z): 101[M+H]$^+$). This was dissolved in dichloromethane (350 ml), and 1-benzyl-4-piperidone (6.49 ml) was added thereto, followed by stirring at room temperature for 10 min. This was cooled in an ice bath, and sodium triacetoxyborohydride (11.1 g) was added thereto, followed by stirring at room temperature for 2 hr. The reaction mixture was concentrated. To the residue were added ethyl acetate (300 ml), brine and potassium carbonate, followed by stirring at room temperature for 20 min and liquid-liquid separation was carried out. The aqueous layer was extracted with ethyl acetate:tetrahydrofuran=1:1. The organic layer was combined and dried, followed by addition of a 4N solution of hydrochloric acid in ethyl acetate (26.3 ml). This was concentrated to provide a crude product of the titled compound as colorless crystals (14.1 g).
ESI-MS (m/z): 274 [M+H]$^+$.

Production Example 3

N,N-Dimethyl-N-[1-(piperidin-4-yl)azetidin-3-yl] amine trihydrochloride

To a solution of a crude product of N-[1-(1-benzylpiperidin-4-yl)azetidin-3-yl]-N,N-dimethylamine trihydrochloride (14.1 g) in 2-propanol (380 ml)-water (380 ml) was added 10% palladium on carbon (5.0 g), followed by stirring at room temperature under a hydrogen atmosphere for 12 hr. The catalyst was removed by filtration. Concentration of the filtrate provided a crude product of the titled compound as colorless crystals (10.7 g).

ESI-MS (m/z): 184 [M+H]$^+$.

Production Example 4

1-(1-Methylazetidin-3-yl)piperazine trihydrochloride

To a solution of 1-benzylpiperazine (0.500 ml) in methanol (25 ml) were added 1-Boc-azetidin-3-one (495 mg), acetic acid (0.182 ml), followed by stirring at room temperature for 5 min. 10% palladium on carbon (308 mg) was added thereto, followed by stirring at room temperature under a hydrogen atmosphere for 15 hr. The catalyst was removed by filtration. The residue was partitioned between ethyl acetate and a saturated aqueous solution of sodium hydrogencarbonate. The organic layer was washed with brine, and dried over anhydrous sodium sulfate. This was concentrated to provide a crude product of 4-benzyl-1-(1-Boc-azetidin-3-yl)piperazine (ESI-MS (m/z): 332 [M+H]$^+$). This was dissolved in tetrahydrofuran (10 ml). Lithium aluminum hydride (219 mg) was added thereto while stirring in an ice bath. The mixture was stirred under a nitrogen atmosphere in an ice bath for 15 min, at room temperature for 15 min, and was heated to reflux at 100° C. for 3.5 hr. The reaction mixture was cooled in an ice bath. Water (0.22 ml), a 5N aqueous solution of sodium hydroxide (0.22 ml) and water (1.1 ml) were added thereto, followed by stirring in an ice bath for 1 hr. Insoluble matter was removed by filtration. To the filtrate was added a 4N solution of hydrochloric acid in ethyl acetate (2.17 ml), which was concentrated to provide a crude product of 4-benzyl-1-(1-methylazetidin-3-yl)piperazine trihydrochloride (ESI-MS (m/z): 246[M+H]$^+$). This was dissolved in water (25 ml) and 2-propanol (25 ml). 10% palladium on carbon (615 mg) was added thereto, followed by stirring under a hydrogen atmosphere at room temperature for 12 hr. The catalyst was removed by filtration. Concentration of the filtrate provided a crude product of the titled compound as a white solid (382 mg).

ESI-MS (m/z): 156 [M+H]$^+$.

Production Example 5 tert-Butyl[1-(2-dimethylaminoacetyl)piperidin-4-yl]carbamate

To a solution of 4-(tert-butoxycarbonylamino)piperidine (5.0 g) in N,N-dimethylformamide (70 ml) were added N,N-dimethylglycine (2.97 g), 1-hydroxybenzotriazole (3.89 g) and 1-ethyl-3-(3-dimethylaminopropyl)carbodiimide hydrochloride (5.27 g), followed by stirring under a nitrogen atmosphere at room temperature for 46 hr. To the reaction mixture were added ethyl acetate (400 ml), brine (200 ml) and a 1N aqueous solution of sodium hydroxide (50 ml), followed by stirring at room temperature for 30 min and liquid-liquid separation was carried out. The aqueous layer was extracted with ethyl acetate. The organic layer was collected, washed with a 1N aqueous solution of sodium hydroxide and brine in this order, and dried over anhydrous sodium sulfate. The organic layer was concentrated under reduced pressure to provide the titled compound as colorless crystals (8.03 g, quantitative).

ESI-MS (m/z): 286 [M+H]$^+$.

Production Example 6

N-[1-(2-Dimethylaminoethyl)piperidin-4-yl]-N-methylamine

A solution of tert-butyl[1-(2-dimethylaminoacetyl)piperidin-4-yl]carbamate (7.07 g) in tetrahydrofuran (100 ml) was stirred under a nitrogen atmosphere in an ice bath. Lithium aluminum hydride (280 mg) was added thereto, followed by stirring in an ice bath for 15 min, then at room temperature for 15 min. The reaction mixture was heated to reflux at 100° C. under a nitrogen atmosphere for 11 hr. The reaction mixture was cooled in an ice bath. Water (2.8 ml), a 5N aqueous solution of sodium hydroxide (2.8 ml) and water (14.0 ml) were added thereto in this order, followed by stirring for 2 hr. Insoluble matter was removed by filtration. The filtrate was concentrated to provide the titled compound as a yellow oil (4.65 g, quantitative).

$^1$H-NMR Spectrum (CDCl$_3$) δ (ppm): 1.34-1.43 (2H, m), 1.87-1.90 (2H, m), 2.02-2.08 (2H, m), 2.25 (6H, s), 2.31-2.50 (7H, m), 2.90 (2H, m), 3.14-3.27 (1H, m).

ESI-MS (m/z): 186 [M+H]$^+$.

Production Example 7

N,N-Diethyl-N'-methylpropane-1,3-diamine

To a solution of N,N-diethyl-1,3-propanediamine (10.0 ml) and triethylamine (10.0 ml) in tetrahydrofuran (150 ml) was added dropwise methyl chloroformate (5.15 ml) while stirring in an ice bath. After stirring at room temperature for 30 min, a saturated aqueous solution of sodium hydrogencarbonate (10 ml) was added to the reaction mixture, and liquid-liquid separation was carried out. The organic layer was dried over anhydrous sodium sulfate, and concentrated under reduced pressure. The residue was dissolved again in ethyl acetate (200 ml), dried over potassium carbonate, and concentrated under reduced pressure to provide a pale yellow oil (8.90 g, ESI-MS (m/z): 189). The residue was dissolved in tetrahydrofuran (200 ml), and lithium aluminum hydride (2.00 g) was gradually added thereto while stirring in an ice bath. The reaction mixture was stirred under a nitrogen atmosphere at room temperature for 15 min, then at 65° C. for 1.5 hr. The reaction mixture was cooled in an ice bath, water (2.0 ml), a 5N aqueous solution of sodium hydroxide (2.0 ml) and water (10.0 ml) were added thereto in this order, followed by stirring in an ice bath for 1 hr. Insoluble matter was removed by filtration and washed with tetrahydrofuran, and the filtrate was concentrated under reduced pressure to provide the titled compound as a pale yellow oil (9.2 g, 72%).

$^1$H-NMR Spectrum (CDCl$_3$) δ (ppm): 1.01 (6H, t, J=7.0 Hz), 1.65 (2H, m), 2.42 (3H, s), 2.47 (2H, t, J=7.0 Hz), 2.51 (4H, q, J=7.0 Hz), 2.62 (2H, t, J=7.0 Hz).

ESI-MS (m/z): 145 [M+H]$^+$.

Production Example 8

(4-Benzoylpiperazin-1-yl)acetic acid ethyl ester 1-(Ethoxycarbonylmethyl)piperazine (5.1 g) was dissolved in tetrahydrofuran (300 ml) under a nitrogen atmosphere, and triethylamine (8.25 ml) and benzoyl chloride (3.44 ml) were added thereto while stirring in an ice water bath. The reaction mixture was allowed to warm up to room temperature and stirred for 4 hr. The reaction mixture was partitioned between ethyl acetate (200 ml) and a saturated aqueous solution of sodium hydrogencarbonate (100 ml). The separated organic layer was washed with a saturated aqueous solution of sodium hydrogencarbonate (100 ml), water (100 ml) and brine (100 ml), and dried over sodium sulfate. The solvent was removed under reduced pressure to provide the titled compound as a colorless oil (8.19 g, quantitative).

$^1$H-NMR Spectrum (CDCl$_3$) δ (ppm): 1.28 (3H, t, J=7.2 Hz), 2.20-2.85 (4H, m), 3.26 (2H, m), 3.48 (2H, m), 3.85 (2H, m), 4.19 (2H, m), 7.41 (5H, m).

Production Example 9

1-(Azetidin-1-yl)-2-(4-benzoylpiperazin-1-yl)ethanone

To (4-benzoylpiperazin-1-yl)acetic acid ethyl ester (8.19 g) were added methanol (300 ml) and water (50 ml), and lithium hydroxide (1.34 g) was added thereto in an ice water bath, followed by stirring for 10 min. The reaction mixture was allowed to warm up to room temperature and stirred for 24 hr. After addition of 1N hydrochloric acid (55.9 ml), the reaction mixture was concentrated under reduced pressure, and ethanol (200 ml) was added to the resultant residue. Precipitated insoluble matter was filtered through celite. The filtrate was concentrated to provide a crude product of (4-benzoylpiperazin-1-yl)acetic acid as a white solid (8.6 g). To (4-benzoylpiperazin-1-yl)acetic acid (2 g) was added N,N-dimethylformamide (80 ml) under a nitrogen atmosphere at room temperature, and azetidine hydrochloride (1.51 g), triethylamine (4.49 ml), 1-ethyl-3-(3-dimethylaminopropyl) carbodiimide hydrochloride (3.09 g) and 1-hydroxybenzotriazole (2.18 g) were added thereto in this order, followed by stirring at room temperature for 66 hr. Liquid-liquid separation was carried out after addition of ethyl acetate (100 ml) and a saturated aqueous solution of sodium hydrogencarbonate (50 ml) to the reaction mixture. The organic layer was washed with a saturated aqueous solution of sodium hydrogencarbonate (50 ml), water (50 ml) and brine (50 ml) in this order, and dried over anhydrous sodium sulfate. The solvent was removed under reduced pressure, and the resultant residue was purified by silica gel column chromatography (Fuji Silysia NH, eluent; ethyl acetate). Fractions containing the target compound were concentrated under reduced pressure, the resultant residue was suspended in diethyl ether (10 ml). The solid was collected by filtration, and dried under aeration to provide the titled compound as white powder (731.5 mg).

$^1$H-NMR Spectrum (CDCl$_3$) δ (ppm): 2.40-2.80 (6H, m), 3.03 (2H, s), 3.47 (2H, m), 3.83 (2H, m), 4.06 (2H, m), 4.22 (2H, m), 7.30-7.50 (5H, m).

Production Example 10

1-[2-(Azetidin-1-yl)ethyl]-4-benzylpiperazine

Lithium aluminum hydride (405 mg) was suspended in tetrahydrofuran (10 ml) under a nitrogen atmosphere while stirring in an ice water bath, and 1-(azetidin-1-yl)-2-(4-benzoylpiperazin-1-yl)ethanone (730 mg) and tetrahydrofuran (5 ml×3) were added thereto. The reaction mixture was stirred at 60° C. for 3 hr. After the reaction mixture was allowed to cool down to room temperature, water (0.4 ml), a 5N aqueous solution of sodium hydroxide (0.4 ml) and water (1.2 ml) was added thereto, followed by stirring for 13 hr. Insoluble matter in the reaction mixture was filtered through celite, and washed with ethyl acetate (100 ml). The solvent was removed under reduced pressure to provide a crude product of the titled compound as a pale yellow oil (687 mg).

ESI-MS (m/z): 260 [M+H]$^+$.

Production Example 11

1-[2-(Azetidin-1-yl)ethyl]piperazine trihydrochloride

1-[2-(Azetidin-1-yl)ethyl]-4-benzylpiperazine (687 mg) was dissolved in methanol (30 ml), and 20% palladium hydroxide on carbon (372 mg) was added thereto, followed by stirring under pressurized hydrogen atmosphere (0.4 MPa) for 10 hr. The catalyst was removed by filtration and washed with methanol. To the filtrate was added a 4N solution of hydrochloric acid in ethyl acetate (1.33 ml), followed by stirring. Excess hydrochloric acid was removed under reduced pressure while stirring. The solvent was removed under reduced pressure to provide the titled compound as a pale brown oil (736 mg, quantitative).

ESI-MS (m/z): 170 [M+H]$^+$.

Production Example 12

2-Amino-4-(2-fluoro-4-nitrophenoxy)pyridine

2-Amino-4-chloropyridine (8.00 g) was dissolved in N-methylpyrrolidone (65 ml), and 2-fluoro-4-nitrophenol (19.55 g) and N,N-diisopropylethylamine (43.36 ml) were added thereto, followed by stirring at 160° C. for 41 hr. The reaction mixture was allowed to cool down to room temperature, and was partitioned between ethyl acetate-tetrahydrofuran (1:1) and a 2N aqueous solution of sodium hydroxide. The organic layer was washed with water and brine in this order. The aqueous layer was re-extracted with ethyl acetate, and the combined organic layer was dried over anhydrous sodium sulfate. The solvent was removed under reduced pressure, the residue was purified by silica gel column chromatography (eluent; hexane:ethyl acetate=1:2, then ethyl acetate). Fractions containing the target compound were concentrated, and crystals were precipitated by addition of ethyl acetate to the residue. The crystals were collected by filtration and dried under aeration to provide the titled compound as opalescent crystals (3.02 g, 20%).

$^1$H-NMR Spectrum (CDCl$_3$) δ (ppm): 4.52 (2H, brs), 6.05 (1H, d, J=1.6 Hz), 6.30 (1H, dd, J=1.6, 5.6 Hz), 7.20-7.30 (1H, m), 8.02 (1H, d, J=5.6 Hz), 8.05-8.15 (2H, m).

Production Example 13

3-[4-(2-Fluoro-4-nitrophenoxy)pyridin-2-yl]-1-methyl-1-(1-methylpiperidin-4-yl)urea 2-Amino-4-(2-fluoro-4-nitrophenoxy)pyridine (200 mg) was dissolved in tetrahydrofuran (8 ml) under a nitrogen atmosphere, and triethylamine (0.336 ml) and phenyl chloroformate (0.302 ml) were added dropwise thereto, followed by stirring at room temperature for 30 min. The reaction mixture was concentrated under reduced pressure, the resultant residue was dissolved in N,N-dimethylformamide (5 ml), and N-methyl-N-(1-methylpiperidin-4-yl)amine (0.467 ml) was added at room temperature, followed by stirring for 4 hr. The reaction mixture was partitioned between ethyl acetate and a saturated aqueous solution of ammonium chloride. The organic layer was washed with a saturated aqueous solution of ammonium chloride, water and brine in this order, and dried over anhydrous sodium sulfate. The solvent was concentrated under reduced pressure, the resultant residue was purified by silica gel column chromatography (Fuji Silysia NH, eluent; ethyl acetate). The solvent was concentrated under reduced pressure and dried under reduced pressure to provide the titled compound as a yellow solid (245 mg, 75.5%).

$^1$H-NMR Spectrum (CDCl$_3$) δ (ppm): 1.50-1.70 (2H, m), 1.79 (2H, m), 2.04-2.13 (2H, m), 2.29 (3H, s), 2.88-2.98 (5H, m), 4.09-4.22 (1H, m), 6.66 (1H, dd, J=2.4, 5.6 Hz), 7.26-7.35 (1H, m), 7.74-7.78 (1H, m), 8.06-8.13 (2H, m), 8.13-8.19 (2H, m).

Production Example 14

3-[4-(4-Amino-2-fluorophenoxy)pyridin-2-yl]-1-methyl-1-(1-methylpiperidin-4-yl)urea 3-[4-(2-Fluoro-4-nitrophenoxy)pyridin-2-yl]-1-methyl-1-(1-methylpiperidin-4-yl)urea (243 mg) was dissolved in tetrahydrofuran (6 ml)-methanol (6 ml), and 10% palladium on carbon (128 mg) was added thereto, followed by stirring under a hydrogen atmosphere for 3 hr. The atmosphere in the reaction vessel was replaced with nitrogen, and the catalyst was removed by filtration and washed with methanol. The filtrate was concentrated under reduced pressure, and the resultant residue was purified by silica gel column chromatography (Fuji Silysia NH, eluent; ethyl acetate) and concentrated under reduced pressure to provide the titled compound as pale yellow powder (175 mg, 78.0%).

$^1$H-NMR Spectrum (CDCl$_3$) δ (ppm): 1.50-1.70 (2H, m), 1.78 (2H, m), 1.98-2.18 (2H, m), 2.20-2.38 (3H, m), 2.82-3.02 (5H, m), 3.75 (2H, m), 4.08-4.26 (1H, m), 6.45 (1H, dd, J=3.2, 8.4 Hz), 6.47-6.66 (2H, m), 6.97 (1H, m), 7.17 (1H, brs), 7.65 (1H, d, J=2.0 Hz), 8.03 (1H, d, J=5.6 Hz).

ESI-MS (m/z): 374 [M+H]$^+$.

Production Example 15

Ethyl 4-chloropyridine-2-carboxylate

A mixture of 4-chloropyridine-2-carboxylic acid (39.4 g) and thionyl chloride (64 ml) was heated and stirred at 100° C. under a nitrogen atmosphere for 6 hr. The reaction mixture was allowed to cool down to room temperature. This was concentrated under reduced pressure and distilled azeotropically with toluene. The resultant residue was gradually added to ethanol while stirring in an ice bath. The reaction mixture was stirred at room temperature for 25.5 hr. The reaction mixture was concentrated under reduced pressure. To the residue was added a saturated aqueous solution of sodium hydrogencarbonate and extracted with ethyl acetate. The organic layer was washed with brine, dried over anhydrous sodium sulfate, and concentrated under reduced pressure to provide the titled compound as a brown oil (38.8 g, 83.6%).

$^1$H-NMR Spectrum (CDCl$_3$) δ (ppm): 1.46 (3H, t, J=7.2 Hz), 4.50 (2H, q, J=7.2 Hz), 7.49 (1H, dd, J=2.0, 5.2 Hz), 8.15 (1H, d, J=2.0 Hz), 8.67 (1H, d, J=5.2 Hz).

Production Example 16

Ethyl 4-(3-fluoro-4-nitrophenoxy)pyridine-2-carboxylate

To ethyl 4-chloropyridine-2-carboxylate (19.4 g) were added 3-fluoro-4-nitrophenol (24.7 g) and chlorobenzene (7.0 ml), followed by heating and stirring under a nitrogen atmosphere at 120° C. for 4 hr. The reaction mixture was allowed to cool down to room temperature. Ethyl acetate (400 ml) and a saturated aqueous solution of sodium hydrogencarbonate (400 ml) were added thereto, followed by stirring at room temperature for 27 hr. Stirring was stopped and the aqueous layer was separated. To the organic layer was added again a saturated aqueous solution of sodium hydrogencarbonate, followed by stirring at room temperature for 2 days. Stirring was stopped and the aqueous layer was separated. The aqueous layer was extracted with ethyl acetate (300 ml). The organic layers were combined and washed with brine. The organic layer was dried over anhydrous sodium sulfate and concentrated under reduced pressure. The residue was purified by silica gel column chromatography (eluent; heptane:ethyl acetate=2:1, 1:1, then ethyl acetate). Fractions containing the target compound were concentrated to provide the titled compound as a brown oil (12.9 g, 40.2%).

$^1$H-NMR Spectrum (CDCl$_3$) δ (ppm): 1.45 (3H, t, J=7.2 Hz), 4.49 (2H, q, J=7.2 Hz), 6.97-7.01 (2H, m), 7.16 (1H, dd, J=2.4, 5.6 Hz), 7.79 (1H, d, J=2.4 Hz), 8.20 (1H, m), 8.76 (1H, d, J=5.6 Hz).

ESI-MS (m/z): 329 [M+Na]$^+$.

Production Example 17

4-(4-Benzyloxycarbonylamino-3-fluorophenoxy) pyridine-2-carboxylic acid

To a solution of ethyl 4-(3-fluoro-4-nitrophenoxy)pyridine-2-carboxylate (8.56 g) in ethanol (150 ml) was added 20% palladium hydroxide on carbon (1.0 g), followed by stirring under a hydrogen atmosphere at room temperature for 9.5 hr. The catalyst was removed by filtration. To the filtrate was added a 4N solution of hydrochloric acid in ethyl acetate (14 ml) and concentrated. Concentration was stopped before dryness. Water (75 ml), acetone (150 ml) and sodium hydrogencarbonate (11.8 g) was added thereto. This was cooled in an ice bath, and benzyloxycarbonyl chloride (6.00 ml) was added. The reaction mixture was stirred at room temperature for 4 hr. The reaction mixture was concentrated under reduced pressure. The residue was extracted with ethyl acetate. The organic layer was washed with brine and dried over anhydrous sodium sulfate. This was concentrated under reduced pressure, and the residue was purified by silica gel column chromatography (eluent; heptane:ethyl acetate=1:1, 1:2, then ethyl acetate). Fractions containing the target compound were concentrated under reduced pressure. The resultant solid was suspended in hexane and allowed to stand for a while, then the supernatant was removed by using a pipette. This residue was dried to provide ethyl 4-(4-benzyloxycarbonylamino-3-fluorophenoxy)pyridine-2-carboxylate as pale yellow solid (7.51 g, 65.4%).

$^1$H-NMR Spectrum (CDCl$_3$) δ (ppm): 1.43 (3H, m), 4.45-4.52 (2H, m), 5.24 (2H, s), 6.87-6.92 (2H, m), 6.99 (1H, dd, J=2.4, 5.6 Hz), 7.35-7.45 (6H, m), 7.65 (1H, d, J=2.4 Hz), 8.19 (1H, m), 8.60 (1H, d, J=5.6 Hz).

Ethyl 4-(4-benzyloxycarbonylamino-3-fluorophenyl)pyridine-2-carboxylate (7.95 g) was dissolved in ethanol (120 ml), and water (25 ml) was added thereto. Lithium hydroxide (783 mg) was added thereto while stirring at room temperature, followed by stirring at room temperature for 1 hr. To the reaction mixture was added 1N hydrochloric acid (60 ml) and concentrated under reduced pressure. After concentration, precipitated crystals in the reaction mixture were collected by filtration and washed with water. The crystals were dissolved in ethyl acetate-tetrahydrofuran, and dried over anhydrous sodium sulfate. The solution after drying was concentrated under reduced pressure. The resultant crystals were suspended in hexane and collected by filtration. The crystals were dried to provide the target compound as pale yellow crystals (5.04 g, 72.0%).

¹H-NMR Spectrum (DMSO-d₆) δ (ppm): 5.18 (2H, s), 7.08 (1H, m), 7.23 (1H, m), 7.24-7.46 (8H, m), 7.75 (1H, m), 8.59 (1H, d, J=5.6 Hz), 9.59 (1H, s).

Production Example 18 tert-Butyl[4-(4-benzyloxycarbonylamino-3-fluorophenoxy)pyridin-2-yl]carbamate

To a suspension of 4-(4-benzyloxycarbonylamino-3-fluorophenoxy)pyridine-2-carboxylic acid (5.04 g) in tert-butanol (50 ml) was added triethylamine (4.6 ml) at room temperature, followed by stirring. Diphenylphosphoryl azide (3.13 ml) was added thereto at room temperature, followed by stirring under a nitrogen atmosphere at room temperature for 30 min. Then the reaction mixture was heated and stirred at 90° C. for 30 min and at 100° C. for 4 hr. The reaction mixture was allowed to cool down to room temperature. Ethyl acetate (25 ml) was added thereto, and the reaction mixture was stirred in an ice bath for 30 min. Precipitated crystals were collected by filtration and washed with diethyl ether. These crystals were dried under aeration at room temperature for 1 hr to provide the titled compound as colorless crystals (3.92 g, 65.5%).
¹H-NMR Spectrum (DMSO-d₆) δ (ppm): 1.42 (9H, s), 5.17 (2H, s), 6.62 (1H, dd, J=2.4, 5.6 Hz), 7.01 (1H, dd, J=2.2, 8.8 Hz), 7.21 (1H, dd, J=2.2, 11.2 Hz), 7.35-7.42 (6H, m), 7.70 (1H, m), 8.14 (1H, d, J=5.6 Hz), 9.53 (1H, s), 9.83 (1H, s).

Production Example 19

Benzyl[4-(2-aminopyridin-4-yloxy)-2-fluorophenyl]carbamate

A 4N solution of hydrochloric acid in ethyl acetate (120 ml) was cooled in an ice bath. tert-Butyl[4-(4-benzyloxycarbonylamino-3-fluorophenoxy)pyridin-2-yl]carbamate (3.92 g) was added thereto while stirring, followed by stirring in an ice bath for 10 min. The reaction mixture was then stirred at room temperature for 3.5 hr. The reaction mixture was concentrated under reduced pressure. Ethyl acetate (150 ml) and a saturated aqueous solution of sodium hydrogencarbonate (70 ml) were added thereto, and liquid-liquid separation was carried out. The aqueous layer was extracted with ethyl acetate (50 ml). The combined organic layer was washed with brine and dried over anhydrous sodium sulfate. The organic layer after drying was concentrated under reduced pressure. The resultant crystals were suspended in a mixed solvent of hexane-ethyl acetate (5:1). The crystals were collected by filtration and washed with a mixed solvent of hexane-ethyl acetate (5:1). The crystals were sucked to dryness at room temperature to provide the titled compound as pale yellow crystals (2.93 g, 95.9%).
¹H-NMR Spectrum (CDCl₃) δ (ppm): 4.49 (2H, m), 5.23 (2H, s), 5.95 (1H, d, J=2.0 Hz), 6.26 (1H, dd, J=2.0, 6.0 Hz), 6.84-6.90 (2H, m), 7.00 (1H, m), 7.34-7.42 (5H, m), 7.94 (1H, d, J=6.0 Hz), 8.10 (1H, m).
ESI-MS (m/z): 354 [M+H]⁺.

Production Example 20

Phenyl[4-(3-fluoro-4-{[1-(4-fluorophenylcarbamoyl)cyclopropanecarbonyl]amino}phenoxy)pyridin-2-yl]-N-phenoxycarbonylcarbamate To a solution of benzyl[4-(2-aminopyridin-4-yloxy)-2-fluorophenyl]carbamate (1.25 g) in tetrahydrofuran (100 ml) were added triethylamine (1.48 ml) and phenyl chloroformate (1.11 ml), followed by stirring at room temperature for 1 hr. The reaction mixture was partitioned between ethyl acetate and a 1N aqueous solution of sodium hydroxide. The organic layer was washed with brine, dried over anhydrous sodium sulfate. The solvent was removed to provide a crude product of phenyl N-[4-(4-benzyloxycarbonylamino-3-fluorophenoxy)pyridin-2-yl]-N-phenoxycarbonylcarbamate as a brown oil (ESI-MS (m/z): 616 [M+Na]⁺). This was dissolved in tetrahydrofuran (200 ml), 20% palladium hydroxide (497 mg) was added thereto, and the mixture was stirred under a hydrogen atmosphere at room temperature for 4 hr. The catalyst was removed by filtration and washed with tetrahydrofuran. The filtrate was concentrated to 20 ml to provide a solution of phenyl N-[4-(4-amino-3-fluorophenoxy)pyridin-2-yl]-N-phenoxycarbonylcarbamate (ESI-MS (m/z): 482 [M+Na]⁺, 941 [2M+Na]⁺) in tetrahydrofuran. This was dissolved in N,N-dimethylformamide (50 ml). 1-(4-Fluorophenylcarbamoyl)cyclopropanecarboxylic acid (1.58 g), benzotriazol-1-yloxytris(dimethylamino)phosphonium hexafluorophosphate (3.13 g) and triethylamine (0.987 ml) were added thereto, followed by stirring at room temperature for 13.5 hr. The reaction mixture was partitioned between ethyl acetate and brine. The organic layer was washed with a 1N aqueous solution of sodium hydroxide and brine in this order, and dried over anhydrous sodium sulfate. This was concentrated, and the residue was purified by silica gel column chromatography (heptane:ethyl acetate=3:2, 1:1 then 1:2) to provide the titled compound as colorless foam (940 mg, 40.0%).
¹H-NMR Spectrum (CDCl₃) δ (ppm): 1.68-1.76 (4H, m), 6.90 (1H, dd, J=2.4, 5.6 Hz), 6.95 (1H, m), 6.98 (1H, m), 7.03-7.07 (3H, m), 7.18 (4H, d, J=8.4 Hz), 7.25 (2H, m), 7.38 (4H, m), 7.48 (2H, m), 8.27 (1H, m), 8.46 (1H, d, J=5.6 Hz), 8.75 (1H, s), 9.40 (1H, s).
ESI-MS (m/z): 687 [M+Na]⁺.

Production Example 21

Methyl 4-chloropyridine-2-carboxylate

To thionyl chloride (500 ml) stirred at room temperature was gradually added picolinic acid (200 g). The reaction mixture was stirred under a nitrogen atmosphere at 85° C. for 20 min and further at 100° C. for 157 hr. The reaction mixture was allowed to cool down to room temperature, then thionyl chloride was removed under reduced pressure. Methanol (500 ml) was gradually added to the residue while stirring in an ice bath. The reaction mixture was stirred in an ice bath for 1 hr, then at room temperature for 17.5 hr. The reaction mixture was concentrated under reduced pressure, and the residue was partitioned between ethyl acetate:tetrahydrofuran=2:1 (1.0 l) and a 1N aqueous solution of sodium hydroxide (500 ml). The aqueous layer was extracted twice with ethyl acetate (500 ml). The combined organic layer was washed with brine (500 ml) and dried over anhydrous sodium sulfate. The solvent was removed, and hexane (200 ml) and diethyl ether (40 ml) were added to the resultant residue and stirred at room temperature for 13 hr. The precipitated solid was collected by filtration, washed twice with a mixed solvent of hexane (100 ml)-diethyl ether (20 ml), and dried under aeration to provide the titled compound as a pale yellow solid (182 g, 65.2%).
¹H-NMR Spectrum (DMSO-d₆) δ (ppm): 3.99 (3H, s), 7.83 (1H, dd, J=2.0, 5.2 Hz), 8.09 (1H, d, J=2.0 Hz), 8.70 (1H, d, J=5.2 Hz).

Production Example 22

4-(4-Amino-2-fluorophenoxy)pyridine-2-carboxylic acid methyl ester dihydrochloride 4-Chloropyridine-2-carboxylic acid methyl ester (30 g) and 2-fluoro-4-nitrophenol (41.2 g) were dissolved in chlorobenzene (24 ml), followed by stirring under a nitrogen atmosphere at 120° C. for 4 hr. The reaction mixture was allowed to cool down to room temperature, methanol (100 ml) was added, and stirred for 30 min. The solvent was removed under reduced pressure, then the resultant residue was partitioned between ethyl acetate (300 ml) and a 1N aqueous solution of sodium hydroxide (150 ml). The separated organic layer was washed with a 1N aqueous solution of sodium hydroxide (100 ml) and brine (150 ml) and dried over anhydrous sodium sulfate. The solvent was removed under reduced pressure, ethanol (200 ml) was added to the resultant residue, followed by stirring for 30 min. The solid was collected by filtration and the filtrate was purified by silica gel column chromatography (YMC, SIL-60-400/230W, eluent; heptane:ethyl acetate=1:1). Fractions containing the target compound were concentrated under reduced pressure, the resultant solid was combined to the solid above to provide 4-(2-fluoro-4-nitrophenoxy)pyridine-2-carboxylic acid methyl ester as a pale brown solid (20.0 g, 40.0%).

The above purified product (9.90 g) was dissolved in methanol (340 ml) and tetrahydrofuran (340 ml), 20% palladium hydroxide on carbon (2.4 g) was added thereto, followed by stirring under a hydrogen atmosphere for 16 hr. The atmosphere in the reaction vessel was replaced with nitrogen, and the catalyst was removed by filtration and washed with methanol. A 4N solution of hydrochloric acid in ethyl acetate (4.18 ml) was added to the filtrate, and concentration under reduced pressure provided a crude product of the titled compound as a pale yellow solid (11.5 g).

ESI-MS (m/z): 263 [M+H]$^+$

Production Example 23

4-(4-Benzyloxycarbonylamino-2-fluorophenoxy)pyridine-2-carboxylic acid methyl ester 4-(4-amino-2-fluorophenoxy)pyridine-2-carboxylic acid methyl ester (11.5 g) was dissolved in acetone (340 ml) and water (170 ml). To the reaction mixture was added sodium hydrogencarbonate (17.3 g), then benzyl chloroformate (9.79 ml) while stirring in an ice water bath, followed by stirring for 15 min. The reaction mixture was allowed to warm up to room temperature, then stirred for 2 hr. To the reaction mixture cooled in an ice water bath was further added benzyl chloroformate (2.45 ml), followed by stirring for 18 hr. The reaction mixture was concentrated under reduced pressure, and to the resultant residue were added ethyl acetate (500 ml) and brine (200 ml), and liquid-liquid separation was carried out. The separated organic layer was washed with water (100 ml) and brine (200 ml), and dried over anhydrous sodium sulfate. The solvent was removed under reduced pressure, the resultant solid was suspended in ethyl acetate (50 ml) and hexane (30 ml). The solid was collected by filtration and dried under aeration to provide the titled compound as a pale yellow solid (9.6 g, 70.6%).

$^1$H-NMR Spectrum (CDCl$_3$) δ (ppm): 3.95-4.10 (3H, m), 5.23 (2H, m), 6.84 (1H, m), 7.00 (1H, m), 7.11 (2H, m), 7.34-7.50 (5H, m), 7.56 (1H, m), 7.62 (1H, m), 8.59 (1H, m).

Production Example 24

4-(4-Benzyloxycarbonylamino-2-fluorophenoxy)pyridine-2-carboxylic acid 4-(4-Benzyloxycarbonylamino-2-fluorophenoxy)pyridine-2-carboxylic acid methyl ester (10.7 g) was dissolved in methanol (450 ml) and N,N-dimethylformamide (150 ml), and water (75 ml) and lithium hydroxide (1.36 g) were added thereto, followed by stirring at room temperature for 1 hr. 1N hydrochloric acid (100 ml) was added thereto, then the reaction mixture was concentrated under reduced pressure and liquid-liquid separation was carried out after addition of ethyl acetate (500 ml), and the precipitated solid was collected by filtration. The resultant solid was washed with water and hexane, and dried under aeration. The organic layer of the filtrate obtained above was washed with water (100 ml×2) and brine (200 ml) and dried over anhydrous sodium sulfate. The solvent was removed under reduced pressure, and the resultant solid was washed with water and hexane and dried under aeration. This solid was combined with the solid obtained above, and dried at 60° C. overnight to provide the titled compound as white powder (9.53 g, 92.3%).

$^1$H-NMR Spectrum (CDCl$_3$) δ (ppm): 3.32 (1H, brs), 5.19 (2H, s), 7.21 (1H, m), 7.25-7.58 (8H, m), 7.64 (1H, d, J=12.8 Hz), 8.59 (1H, d, J=5.6 Hz), 10.18 (1H, brs).

Production Example 25

[4-(4-Benzyloxycarbonylamino-2-fluorophenoxy)pyridin-2-yl]carbamic acid tert-butyl ester 4-(4-Benzyloxycarbonylamino-2-fluorophenoxy)pyridine-2-carboxylic acid (500 mg) was dissolved in tert-butyl alcohol (5 ml), and triethylamine (0.457 ml) and diphenylphosphoryl azide (0.310 ml) were added thereto under a nitrogen atmosphere at room temperature, followed by stirring for 1.5 hr. The reaction mixture was heated up to 30° C. and stirred for 1 hr and at 40° C. for 45 min. The reaction mixture was heated up to 50° C. and stirred for 30 min, then heated up to 60° C. and stirred for 30 min. The reaction mixture was heated up to 70° C. and stirred for 30 min and at 80° C. for 30 min. The reaction mixture was heated up to 90° C. and stirred for 1.5 hr, then allowed to cool down to room temperature and stirred for 15 hr. The reaction mixture was partitioned between ethyl acetate (50 ml) and a saturated aqueous solution of sodium hydrogencarbonate (30 ml). The organic layer was washed with water (30 ml) and brine (30 ml) in this order and dried over anhydrous sodium sulfate. The solvent was removed under reduced pressure, the resultant residue was purified by silica gel column chromatography (Fuji Silysia NH, eluent; heptane:ethyl acetate=3:2). Fractions containing the target compound were concentrated under reduced pressure to give a residue, which was suspended in diethyl ether (3 ml) and hexane (3 ml). The solid was collected by filtration and dried under aeration to provide the titled compound as a pale yellow solid (277 mg, 46.6%).

$^1$H-NMR Spectrum (CDCl$_3$) δ (ppm): 1.49 (9H, s), 5.22 (2H, s), 6.46 (1H, dd, J=2.0, 6.0 Hz), 6.77 (1H, brs), 6.99-7.14 (2H, m), 7.28-7.48 (7H, m), 7.52 (1H, m), 8.06 (1H, d, J=6.0 Hz).

ESI-MS (m/z): 476 [M+Na]$^+$.

Production Example 26

[4-(2-Aminopyridin-4-yloxy)-3-fluorophenyl]carbamic acid benzyl ester

To a 4N solution of hydrochloric acid in ethyl acetate (30 ml) was added [4-(4-benzyloxycarbonylamino-2-fluorophenoxy)pyridin-2-yl]carbamic acid tert-butyl ester (510 mg) while stirring in an ice water bath. The reaction mixture was allowed to warm up to room temperature, followed by stirring for 16 hr. To the reaction mixture were added diethyl ether (10 ml) and a 5N aqueous solution of sodium hydroxide (1 ml), followed by stirring for 30 min. The separated organic layer was washed with a saturated aqueous solution of sodium hydrogencarbonate (20 ml), water (20 ml) and brine (20 ml), and dried over anhydrous sodium sulfate. The solvent was removed under reduced pressure, the resultant residue was purified by silica gel column chromatography (Fuji Silysia NH, eluent; heptane:ethyl acetate=1:2) and fractions containing the target compound were concentrated under reduced pressure. To the resultant residue were added diethyl ether (4 ml) and hexane (6 ml) to suspend the precipitated solid. The solid was collected by filtration and dried under aeration to provide the titled compound as pale yellow powder (46.6 mg, 11.7%).

$^1$H-NMR Spectrum (CDCl$_3$) δ (ppm): 3.35 (2H, brs), 5.19 (2H, m), 6.14 (1H, brs), 6.69 (1H, m), 7.30-7.52 (6H, m), 7.66 (1H, m), 7.83 (1H, m), 7.97 (1H, m), 10.24 (1H, brs).

Production Example 27

{4-[4-(Benzyloxycarbonylamino)-2-fluorophenoxy] pyridin-2-yl}-N-(phenoxycarbonyl)carbamic acid phenyl ester To a solution of [4-(2-aminopyridin-4-yloxy)-3-fluorophenyl]carbamic acid benzyl ester (1.0 g) in tetrahydrofuran (25 ml) were added triethylamine (0.983 ml) and phenyl chloroformate (0.884 ml) in this order while stirring in an ice water bath. The reaction mixture was stirred at room temperature for 30 min. After the reaction mixture was diluted with ethyl acetate, a saturated aqueous solution of sodium hydrogencarbonate was added thereto, and the reaction mixture was stirred. The organic layer was separated, washed with a saturated aqueous solution of sodium hydrogencarbonate and brine in this order, and dried over anhydrous sodium sulfate. The solvent was concentrated under reduced pressure, and the residue was dried under reduced pressure to provide a crude product of the titled compound as a brown oil (1.945 g).

ESI-MS (m/z): 616 [M+Na]$^+$.

Production Example 28

[4-(4-Amino-2-fluorophenoxy)pyridin-2-yl]-N-(phenoxycarbonyl)carbamic acid phenyl ester To a solution of a crude product of {4-[4-(benzyloxycarbonylamino)-2-fluorophenoxy]pyridin-2-yl}-N-(phenoxycarbonyl)carbamic acid phenyl ester (1.945 g) in tetrahydrofuran (100 ml) was added 20% palladium hydroxide on carbon (792 mg), followed by stirring under a hydrogen atmosphere at room temperature for 3 hr. The catalyst was removed by filtration and washed with tetrahydrofuran. The filtrate was concentrated under reduced pressure, and the residue was dried under reduced pressure to provide a crude product of the titled compound as a brown oil (1.617 g).

ESI-MS (m/z): 482 [M+Na]$^+$, 941 [2M+Na]$^+$.

Production Example 29

[4-(2-Fluoro-4-{[1-(4-fluorophenylcarbamoyl)cyclopropanecarbonyl]amino}phenoxy)pyridin-2-yl]-N-(phenoxycarbonyl)carbamic acid phenyl ester A crude product of [4-(4-amino-2-fluorophenoxy)pyridin-2-yl]-N-(phenoxycarbonyl)carbamic acid phenyl ester (1.617 g) was dissolved in N,N-dimethylformamide (25 ml). 1-(4-Fluorophenylcarbamoyl)cyclopropanecarboxylic acid (1.26 g), triethylamine (0.786 ml) and benzotriazol-1-yloxy-tris(dimethylamino)phosphonium hexafluorophosphate (2.49 g) were added thereto under a nitrogen atmosphere at room temperature, followed by stirring overnight. Liquid-liquid separation was carried out after addition of ethyl acetate and water to the reaction mixture. The organic layer was washed with a saturated aqueous solution of sodium hydrogencarbonate (3 times) and brine in this order and dried over anhydrous sodium sulfate. The solvent was removed to give residue, which was purified by silica gel column chromatography (eluent; heptane:ethyl acetate=1:1) to provide the titled compound as white powder (1.007 g).

$^1$H-NMR Spectrum (CDCl$_3$) δ (ppm): 1.50-1.80 (4H, m), 6.89 (1H, dd, J=2.4, 5.6 Hz), 7.00-7.50 (17H, m), 7.75 (1H, dd, J=2.4, 12.0 Hz), 8.14 (1H, brs), 8.44 (1H, d, J=5.6 Hz), 10.05 (1H, brs).

ESI-MS (m/z): 687 [M+Na]$^+$.

Production Example 30

2-{[(4-(Dimethylaminomethyl)piperidin-1-yl)carbonylamino]-4-(2-fluoro-4-nitrophenoxy)pyridine 2-Amino-4-(2-fluoro-4-nitrophenoxy)pyridine (125 mg) was dissolved in tetrahydrofuran (2 ml) under a nitrogen atmosphere. While stirring in an ice water bath, triethylamine (0.210 ml) and phenyl chloroformate (0.189 ml) were added dropwise. After stirring at room temperature for 20 min, the solvent was removed under reduced pressure. To the resultant residue were added a solution of 4-(dimethylaminomethyl)piperidine dihydrochloride (648 mg) in N,N-dimethylformamide (5.0 ml) and triethylamine (0.985 ml) under a nitrogen atmosphere at room temperature, followed by stirring for 2.5 hr. The reaction mixture was partitioned between ethyl acetate and water. The organic layer was washed with a 1N aqueous solution of sodium hydroxide and brine, and dried over anhydrous sodium sulfate. The solvent was removed under reduced pressure, and the residue was purified by silica gel column chromatography (Fuji Silysia NH, eluent; ethyl acetate:heptane=2:1, then ethyl acetate) to provide the titled compound as pale yellow powder (183 mg, 87%).

$^1$H-NMR Spectrum (CDCl$_3$) δ (ppm): 1.10-1.30 (2H, m), 1.60-1.90 (3H, m), 2.10-2.20 (2H, m), 2.21 (6H, s), 2.80-3.00 (2H, m), 4.00-4.20 (2H, m), 6.64 (1H, dd, J=2.4, 5.6 Hz), 7.26-7.40 (2H, m), 7.72 (1H, d, J=2.4 Hz), 8.00-8.20 (3H, m).

Production Example 31

4-(4-Amino-2-fluorophenoxy)-2-{[4-(dimethylaminomethyl)piperidin-1-yl]carbonylamino}pyridine 2-{[4-(Dimethylaminomethyl)piperidin-1-yl]carbonylamino}-4-(2-fluoro-4-nitrophenoxy)pyridine (183 mg) was dissolved in tetrahydrofuran (20 ml). 20% palladium hydroxide on carbon (123 mg) was added thereto, followed by stirring under a hydrogen atmosphere overnight. The catalyst was removed by filtration and washed with tetrahydrofuran. The filtrate and the washing were combined and concentrated under reduced pressure, the resultant residue was dried under reduced pressure to provide the titled compound as pale yellow powder (167 mg, 98%).

ESI-MS (m/z): 388 [M+H]$^+$.

Production Example 32

2-Propyl 4-chloropyridine-2-carboxylate

To 4-chloropyridine-2-carboxylic acid (5.0 g) was added thionyl chloride (10 ml), followed by stirring at 100° C. for 3 hr. The reaction mixture was allowed to cool down to room temperature, and concentrated under reduced pressure. The residue was added to 2-propanol (50 ml) cooled in an ice water bath, and the reaction mixture was stirred overnight at room temperature. A saturated aqueous solution of sodium hydrogencarbonate was added to the reaction mixture, and extracted with ethyl acetate. The organic layer was washed with brine and dried over anhydrous sodium sulfate. The solvent was removed under reduced pressure and distilled azeotropically with toluene, and the resultant residue was dried under reduced pressure to provide the titled compound as a brown oil (6.1 g, 96%).

$^1$H-NMR Spectrum (CDCl$_3$) δ (ppm): 1.43 (6H, d, J=7.2 Hz), 5.35 (1H, m), 7.48 (1H, dd, J=2.4, 5.6 Hz), 8.12 (1H, d, J=2.4 Hz), 8.67 (1H, d, J=5.6 Hz).

Production Example 33

2-Propyl 4-(4-nitrophenoxy)pyridine-2-carboxylate

2-Propyl 4-chloropyridine-2-carboxylate (3.13 g) was dissolved in chlorobenzene (9.5 ml). 4-Nitrophenol (3.28 g) was added thereto, followed by stirring at 120° C. for 23 hr. 4-Nitrophenol (1.09 g) was added thereto, followed by stirring at 120° C. for 3 hr. The reaction mixture was allowed to cool down to room temperature. Ethyl acetate (50 ml) and a 1N aqueous solution of sodium hydroxide (50 ml) were added to the reaction mixture and stirred. Insoluble matter was precipitated, which was dissolved by addition of THF (50 ml). The organic layer was separated, washed with a 1N aqueous solution of sodium hydroxide (50 ml×3) and brine (50 ml) in this order, and dried over anhydrous sodium sulfate. The solvent was concentrated under reduced pressure. The resultant residue was purified by silica gel column chromatography (eluent; heptane:ethyl acetate=2:1 to 1:1). Fractions containing the target compound were concentrated under reduced pressure, and dried under reduced pressure to provide the titled compound as pale brown crystals (2.147 g, 45%).

$^1$H-NMR Spectrum (CDCl$_3$) δ (ppm): 1.43 (6H, d, J=7.2 Hz), 5.34 (1H, m), 7.10 (1H, dd, J=2.4, 5.6 Hz), 7.20-7.25 (2H, m), 7.75 (1H, d, J=2.4 Hz), 8.31-8.36 (2H, m), 8.72 (1H, d, J=5.6 Hz).

Production Example 34

4-[4-(Benzyloxycarbonylamino)phenoxy]pyridine-2-carboxylic acid

2-Propyl 4-(4-nitrophenoxy)pyridine-2-carboxylate (4.5 g) was dissolved in 2-propanol (100 ml)-tetrahydrofuran (50 ml). 20% palladium hydroxide on carbon (1.05 g) was added thereto, followed by stirring overnight under a hydrogen atmosphere. The catalyst was removed by filtration and washed with tetrahydrofuran and methanol in this order. To the filtrate was added 5N hydrochloric acid (7 ml), and concentrated under reduced pressure. The resultant residue was dissolved in acetone (100 ml)-water (50 ml). Sodium hydrogencarbonate (8.4 g) was added dropwise to the reaction mixture while stirring in an ice water bath. Then benzyl chloroformate (3.5 ml) was added dropwise. The reaction mixture was allowed to gradually warm up to room temperature and stirred for 2.5 hr. The reaction mixture was concentrated under reduced pressure. The residue containing crystals was diluted with water (100 ml). Ashen crystals were collected by filtration, washed with water (50 ml, 3 times) and hexane (50 ml, 4 times) in this order, and dried under aeration. Crude crystals (8.17 g) were suspended in ethanol (100 ml)-water (20 ml). Lithium hydroxide (718 mg) was added at room temperature, followed by stirring overnight. To the reaction mixture was added 1N hydrochloric acid (30 ml). The reaction mixture was concentrated under reduced pressure. The target compound which is insoluble was collected by filtration, washed with water, tetrahydrofuran and ethyl acetate in this order. The organic layer of the filtrate was separated and concentrated under reduced pressure. The resultant solid residue and the solid collected by previous filtration were combined, and suspended in ethyl acetate: hexane=1:1 (50 ml). The solid was collected by filtration, washed with water and diethyl ether:hexane=1:1. Drying under aeration for 1 hr, and hot-air drying at 60° C. for 48 hr provided the titled compound as pale brown powder (5.062 g, 93%).

ESI-MS (neg.) (m/z): 363 [M−H]$^-$.

Production Example 35

{4-[(4-Benzyloxycarbonylamino)phenoxy]pyridin-2-yl}carbamic acid tert-butyl ester 4-[4-(Benzyloxycarbonylamino)phenoxy]pyridine-2-carboxylic acid (5.03 g) was suspended in tert-butanol (50 ml), and triethylamine (4.81 ml) was added thereto at room temperature. Diphenylphosphoryl azide (3.5 ml) was added thereto at room temperature while stirring. The reaction mixture was stirred under a nitrogen atmosphere at room temperature for 30 min. The reaction mixture was stirred under a nitrogen atmosphere at 90° C. for 30 min and at 100° C. for 4 hr. The reaction mixture was allowed to cool down to room temperature while stirring. To the reaction mixture in which crystals were suspended, was added tert-butyl methyl ether (100 ml), followed by stirring overnight at room temperature. The crystals were collected by filtration and washed with diethyl ether to provide the titled compound as white crystals (4.609 g, 77%). The filtrate was concentrated under reduced pressure, and the resultant brown oil was dissolved in ethyl acetate (100 ml), washed with a 1N aqueous solution of sodium hydroxide (50 ml, twice) and brine (50 ml) and dried over anhydrous sodium sulfate. The solvent was concentrated under reduced pressure. Crystals (impurities) were precipitated by addition of ethyl acetate (15 ml) to the resultant residue (3.13 g). The crystals (impurities) were removed by filtration. The filtrate was concentrated under reduced pressure, and crystals were precipitated by addition of ethyl acetate (5 ml) to the resultant residue. The crystals were collected by filtration and washed with small quantity of diethyl ether to provide the titled compound as white crystals (493 mg, 8%).

$^1$H-NMR Spectrum (CDCl$_3$) δ (ppm): 1.49 (9H, s), 5.22 (2H, s), 6.45 (1H, dd, J=2.4, 5.6 Hz), 6.70 (1H, brs), 7.02-7.07 (2H, m), 7.30-7.45 (8H, m), 7.52 (1H, brs), 8.04 (1H, d, J=5.6 Hz).

Production Example 36

[4-(2-Aminopyridin-4-yloxy)phenyl]carbamic acid benzyl ester

To {4-[(4-benzyloxycarbonylamino)phenoxy]pyridin-2-yl}carbamic acid tert-butyl ester (5.087 g) was added a 4N solution of hydrochloric acid in ethyl acetate (75 ml) in an ice water bath, followed by stirring in an ice water bath for 10 min, then at room temperature for 24 hr. Hydrochloric acid was removed from the reaction mixture under reduced pressure. The residue was diluted with ethyl acetate and cooled in an ice water bath, and a 2N aqueous solution of sodium hydroxide (100 ml) was added thereto. The organic layer was separated, washed with brine and dried over anhydrous sodium sulfate. The solvent was concentrated under reduced pressure. Crystals were precipitated by addition of tert-butyl methyl ether (20 ml)-heptane (40 ml) to the residue. The crystals were collected by filtration and dried under aeration to provide the titled compound as white crystals (3.159 g, 81%).

$^1$H-NMR Spectrum (CDCl$_3$) δ (ppm): 4.38 (2H, brs), 5.22 (2H, s), 5.92 (1H, d, J=2.4 Hz), 6.27 (1H, dd, J=2.4, 5.6 Hz), 6.72 (1H, brs), 7.02-7.06 (2H, m), 7.30-7.50 (7H, m), 7.92 (1H, d, J=5.6 Hz).

Production Example 37

{4-[4-(Benzyloxycarbonylamino)phenoxy]pyridin-2-yl}-N-(phenoxycarbonyl)carbamic acid phenyl ester To a solution of [4-(2-aminopyridin-4-yloxy)phenyl]carbamic acid benzyl ester (500 mg) in tetrahydrofuran (15 ml) were added triethylamine (0.519 ml) and phenyl chloroformate (0.467 ml) while stirring in an ice water bath. The reaction mixture was stirred at room temperature for 30 min. The reaction mixture was partitioned between ethyl acetate (50 ml) and a saturated aqueous solution of sodium hydrogencarbonate (20 ml). The separated organic layer was washed with a saturated aqueous solution of sodium hydrogencarbonate (20 ml), water (20 ml) and brine (20 ml) in this order, and dried over anhydrous sodium sulfate. The solvent was concentrated under reduced pressure to provide a crude product of the titled compound as brown foam (935.6 mg).

ESI-MS (m/z): 598 [M+Na]$^+$.

Production Example 38

[4-(4-Aminophenoxy)pyridin-2-yl]-N-(phenoxycarbonyl)carbamic acid phenyl ester

To a crude product of {-[4-(benzyloxycarbonylamino)phenoxy]pyridin-2-yl}-N-(phenoxycarbonyl)carbamic acid phenyl ester (936 mg) dissolved in tetrahydrofuran (60 ml) was added 20% palladium hydroxide on carbon (209 mg), followed by stirring under a hydrogen atmosphere at room temperature for 5 hr. The catalyst was removed by filtration and washed with tetrahydrofuran. The solvent was removed under reduced pressure to provide a crude product of the titled compound as a brown oil (820 mg).

ESI-MS (m/z): 442 [M+Na]$^+$, 905 [2M+Na]$^+$.

Production Example 39

[4-(4-{[1-(4-Fluorophenylcarbamoyl)cyclopropanecarbonyl]amino}phenoxy)pyridin-2-yl]-N-(phenoxycarbonyl)carbamic acid phenyl ester A crude product of [4-(4-aminophenoxy)pyridin-2-yl]-N-(phenoxycarbonyl)carbamic acid phenyl ester (820 mg) was dissolved in N,N-dimethylformamide (15 ml). 1-(4-Fluorophenylcarbamoyl)cyclopropanecarboxylic acid (830 mg), triethylamine (0.519 ml) and benzotriazol-1-yloxytris(dimethylamino)phosphonium hexafluorophosphate (1.65 g) were added in this order under a nitrogen atmosphere at room temperature, followed by stirring for 15.5 hr. Liquid-liquid separation was carried out after addition of ethyl acetate and a saturated aqueous solution of sodium hydrogencarbonate to the reaction mixture. The resultant organic layer was washed with brine and dried over anhydrous sodium sulfate. The solvent was evaporated under reduced pressure to give residue, which was purified by silica gel column chromatography (eluent; heptane:ethyl acetate=2:3 to 1:1). Fractions containing the target compound were concentrated under reduced pressure to provide the titled compound as white foam (845.8 mg).

$^1$H-NMR Spectrum (CDCl$_3$) δ (ppm): 1.40-1.90 (4H, m), 6.89 (1H, dd, J=2.0, 5.6 Hz), 7.00-7.32 (11H, m), 7.32-7.42 (4H, m), 7.42-7.54 (2H, m), 7.61 (2H, m), 8.43 (1H, d, J=5.6 Hz), 8.61 (1H, brs), 9.39 (1H, brs).

ESI-MS (m/z): 669 [M+Na]$^+$.

Production Example 40

6-(2-Fluoro-4-nitrophenoxy)pyrimidin-4-ylamine

2-Fluoro-4-nitrophenol (1.736 g) was dissolved in dimethyl sulfoxide (10 ml), and sodium hydride (400 mg) was added thereto, followed by stirring for 20 min. Then, 4-Amino-6-chloropyrimidine (648 mg) was added thereto and stirred at 100° C. for 45 min. The reaction mixture was heated up to 120° C. and stirred for 1 hr 25 min. The reaction mixture was then heated up to 140° C. and stirred overnight. The reaction mixture was allowed to cool down to room temperature, a 1N aqueous solution of sodium hydroxide (10 ml) was added thereto and stirred, then extracted with ethyl acetate. The organic layer was washed with a 1N aqueous solution of sodium hydroxide, water and brine in this order, and dried over anhydrous sodium sulfate. The solvent was concentrated under reduced pressure to give residue, which was purified by silica gel column chromatography (eluent; hexane:ethyl acetate=1:2). The solvent was concentrated under reduced pressure, the resultant residue was suspended in diethyl ether (7 ml)-hexane (3.5 ml). The solid was collected by filtration and dried under aeration to provide the titled compound as pale brown powder (201 mg, 16.0%).

$^1$H-NMR Spectrum (DMSO-d$_6$) δ (ppm): 6.02 (1H, m), 7.06 (2H, brs), 7.60 (1H, dd, J=8.0, 8.8 Hz), 8.04 (1H, m), 8.10-8.19 (1H, m), 8.30 (1H, dd, J=2.0, 10.0 Hz).

Production Example 41

[6-(2-Fluoro-4-nitrophenoxy)pyrimidin-4-yl]carbamic acid phenyl ester 6-(2-Fluoro-4-nitrophenoxy)pyrimidin-4-ylamine (1 g) was dissolved in tetrahydrofuran (40 ml) under a nitrogen atmosphere, and triethylamine (1.67 ml) and phenyl chloroformate (1.51 ml) were added thereto in an ice water bath. The reaction mixture was allowed to warm up to room temperature, and stirred for 1 hr. The reaction mixture was partitioned between ethyl acetate (200 ml) and a saturated aqueous solution of sodium hydrogencarbonate (100 ml). The organic layer was washed with a saturated aqueous solution of sodium hydrogencarbonate (100 ml), water (100 ml) and brine (100 ml) in this order, and dried over anhydrous sodium sulfate. To the resultant residue was added tetrahydrofuran (40 ml), and a 1N aqueous solution of sodium hydroxide (4 ml) was added while stirring in an ice water bath, followed by stirring for 30 min. The reaction mixture was allowed to warm up to room temperature and stirred for 1 hr. After addition of 1N hydrochloric acid (4 ml), the reaction mixture was partitioned between tetrahydrofuran (100 ml) and a saturated aqueous solution of sodium hydrogencarbonate (50 ml). The organic layer was washed with water (50 ml) and brine (100 ml) in this order and dried over anhydrous sodium sulfate. The solvent was removed under reduced pressure to give residue (4.3 g), to which was added ethyl acetate (20 ml), and allowed to stand for 4 days. The precipitated solid was collected by filtration and dried under aeration to provide the titled compound as pale yellow powder (399 mg, 26.9%).

$^1$H-NMR Spectrum (CDCl$_3$) δ (ppm): 7.16-7.25 (2H, m), 7.25-7.35 (1H, m), 7.36-7.50 (3H, m), 7.72 (1H, m), 8.04-8.18 (2H, m), 8.50 (1H, m), 9.18 (1H, brs).

ESI-MS (neg.) (m/z): 369 [M−H]$^−$

Production Example 42

[6-(4-Amino-2-fluorophenoxy)pyrimidin-4-yl]carbamic acid phenyl ester

To a solution of 6-(2-fluoro-4-nitrophenoxy)pyrimidin-4-yl]carbamic acid phenyl ester (394 mg) in tetrahydrofuran (20 ml) was added 20% palladium hydroxide on carbon (149 mg), followed by stirring under a hydrogen atmosphere at room temperature for 15 hr. The catalyst was removed by filtration and washed with tetrahydrofuran. The solvent was removed under reduced pressure to provide a crude product of the titled compound as a white solid (303 mg).

ESI-MS (m/z): 341 [M+H]$^+$, 363 [M+Na]$^+$

Production Example 43

[6-(2-Fluoro-4-{[1-(4-fluorophenylcarbamoyl)cyclopropanecarbonyl]amino}phenoxy)pyrimidin-4-yl]carbamic acid phenyl ester A crude product of [6-(4-amino-2-fluorophenoxy)pyrimidin-4-yl]carbamic acid phenyl ester (303 mg) was dissolved in N,N-dimethylformamide (5 ml). 1-(4-Fluorophenylcarbamoyl)cyclopropanecarboxylic acid (497 mg), triethylamine (0.310 ml) and benzotriazol-1-yloxytris(dimethylamino)phosphonium hexafluorophosphate (984 mg) were added in this order under a nitrogen atmosphere at room temperature, followed by stirring for 5 hr. Liquid-liquid separation was carried out after addition of ethyl acetate and a saturated aqueous solution of sodium hydrogencarbonate to the reaction mixture. The resultant organic layer was washed with brine and dried over anhydrous sodium sulfate. The solvent was removed under reduced pressure to give residue, which was purified by silica gel column chromatography (eluent; heptane:ethyl acetate=2:3 to 1:1). Fractions containing the target compound were concentrated under reduced pressure, the resultant residue was purified again by silica gel column chromatography (eluent; heptane:ethyl acetate=2:3 to 1:1). Fractions containing the target compound were concentrated under reduced pressure to provide the titled compound as white powder (100.4 mg).

$^1$H-NMR Spectrum (CDCl$_3$) δ (ppm): 1.30-1.80 (4H, m), 7.00-7.10 (2H, m), 7.10-7.35 (5H, m), 7.35-7.52 (4H, m), 7.58 (1H, s), 7.70 (1H, dd, J=1.6, 12.0 Hz), 8.38 (1H, brs), 8.49 (1H, s), 8.69 (1H, brs), 9.57 (1H, brs).

ESI-MS (m/z): 568 [M+Na]$^+$.

Production Example 44

1-(Benzyloxycarbonyl)cyclopanecarboxylic acid 1,1-Cyclopropanedicarboxylic acid (5.02 g) was dissolved in tetrahydrofuran (50 ml) under a nitrogen atmosphere, and triethylamine (5.38 ml) was added dropwise thereto while stirring in an ice water bath. After stirring at the same temperature for 30 min, thionyl chloride (2.82 ml) was added dropwise while stirring in an ice water bath. After stirring at the same temperature for 30 min, a solution of benzyl alcohol (4.39 ml) in tetrahydrofuran (25 ml) was added while stirring in an ice water bath, and the reaction mixture was allowed to gradually warm up to room temperature, followed by stirring overnight. To the reaction mixture was added a 2N aqueous solution of sodium hydroxide (100 ml), and tetrahydrofuran was removed under reduced pressure. To the resultant aqueous solution was added tert-butyl methyl ether (25 ml) and stirred. The organic layer and the aqueous layer were separated. The aqueous layer was cooled in an ice water bath, and adjusted to pH 4 with 2N hydrochloric acid (50 ml). Ethyl acetate (150 ml) was added thereto and stirred for a while. The organic layer was separated, washed with brine, and dried over anhydrous sodium sulfate. The solvent was removed to give residue, which was dried under reduced pressure to provide the titled compound as a pale yellow oil (6.29 g, 74%).

$^1$H-NMR Spectrum (DMSO-d$_6$) δ (ppm): 1.30-1.40 (4H, m), 5.15 (2H, s), 7.30-7.38 (5H, m).

ESI-MS (m/z): 243 [M+Na]$^+$.

Production Example 45

[4-(4-{[1-(Benzyloxycarbonyl)cyclopropanecarbonyl]amino}phenoxy)-3-fluoropyridin-2-yl]-N-(phenoxycarbonyl)carbamic acid phenyl ester A crude product of [4-(4-amino-3-fluorophenoxy)pyridin-2-yl]-N-(phenoxycarbonyl)carbamic acid phenyl ester (678 mg) was dissolved in N,N-dimethylformamide (25 ml). 1-(benzyloxycarbonyl)cyclopropanecarboxylic acid (815 mg), triethylamine (0.516 ml) and benzotriazol-1-yloxytris(dimethylamino)phosphonium hexafluorophosphate (1.64 g) were added under a nitrogen atmosphere at room temperature, followed by stirring overnight. Liquid-liquid separation was carried out after addition of ethyl acetate and water to the reaction mixture. The organic layer was washed with a saturated aqueous solution of sodium hydrogencarbonate (3 times) and brine in this order, and dried over anhydrous sodium sulfate. The solvent was removed, and the resultant residue was purified by silica gel column chromatography (eluent; heptane:ethyl acetate=2:1) to provide the titled compound as a colorless oil (928 mg).

ESI-MS (m/z): 684 [M+Na]$^+$.

Production Example 46

1-(Benzyloxycarbonyl)-N-(2-fluoro-4-{2-[3-methyl-3-(1-methylpiperidin-4-yl)ureido]pyridin-4-yloxy}phenyl)cyclopropanecarboxamide To a solution of [4-(4-{[1-(benzyloxycarbonyl)cyclopropanecarbonyl]amino}phenoxy)-3-fluoropyridin-2-yl]-N-(phenoxycarbonyl)carbamic acid phenyl ester (928 mg) in N,N-dimethylformamide (20 ml) was added 1-methyl-4-methylaminopiperidine (0.814 ml) at room temperature, followed by stirring for 4 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of tert-butyl methyl ether:heptane=1:5 to the resultant residue. The solvent was removed under reduced pressure. The solid residue was dried under reduced pressure to provide the titled compound as white powder (516 mg, 64%).

ESI-MS (m/z): 576 [M+H]$^+$.

Production Example 47

1-(2-Fluoro-4-{2-[3-methyl-3-(1-methylpiperidin-4-yl)ureido]pyridin-4-yloxy}phenyl)carbamoylcyclopropanecarboxylic acid To a solution of 1-(benzyloxycarbonyl)-N-(2-fluoro-4-{2-[3-methyl-3-(1-methylpiperidin-4-yl)ureido]pyridin-4-yloxy}phenyl)cyclopropanecarboxamide (510 mg) in tetrahydrofuran (20 ml)-methanol (20 ml) was added 20% palladium hydroxide on carbon (377 mg), followed by stirring under a hydrogen atmosphere at room temperature for 24 hr. The catalyst was removed by filtration, and washed with tetrahydrofuran-methanol (1:1). The filtrate was concentrated under reduced pressure, and the residue was dried under reduced pressure to provide the titled compound as white crystals (358.7 mg, 83%).

ESI-MS (neg.) (m/z): 484 [M–H]$^-$.

Production Example 48

[4-(3-Fluoro-4-{[1-(phenylcarbamoyl)cyclopropanecarbonyl]amino}phenoxy)pyridin-2-yl]-N-(phenoxycarbonyl)carbamic acid phenyl ester A crude product of [4-(4-amino-3-fluorophenoxy)pyridin-2-yl]-N-(phenoxycarbonyl)carbamic acid phenyl ester (219 mg) was dissolved in N,N-dimethylformamide (5 ml). 1-(Phenylcarbomoyl)cyclopropanecarboxylic acid (196 mg), triethylamine (0.133 ml) and benzotriazol-1-yloxytris(dimethylamino)phosphonium hexafluorophosphate (422 mg) were added under a nitrogen atmosphere at room temperature, followed by stirring overnight. Liquid-liquid separation was carried out after addition of ethyl acetate and water to the reaction mixture. The organic layer was washed with a saturated aqueous solution of sodium hydrogencarbonate (3 times) and brine in this order, and dried over anhydrous sodium sulfate. The solvent was removed and the resultant residue was purified by silica gel column chromatography (eluent; heptane:ethyl acetate=3:2) to provide the titled compound as white powder (271 mg).

ESI-MS (m/z): 669 [M+Na]$^+$.

Production Example 49

1-(2,4-Difluorophenylcarbamoyl)cyclopropanecarboxylic acid 1,1-Cyclopropanedicarboxylic acid (2.5 g) was dissolved in tetrahydrofuran (25 ml) under a nitrogen atmosphere, and triethylamine (2.68 ml) was added dropwise thereto while stirring in an ice water bath. After stirring at the same temperature for 30 min, thionyl chloride (1.4 ml) was added dropwise while stirring in an ice water bath. After stirring at the same temperature for 30 min, a solution of 2,4-difluoroaniline (2.15 ml) in tetrahydrofuran (15 ml) was added while stirring in an ice water bath, and the reaction mixture was allowed to gradually warm up to room temperature and stirred overnight. After addition of a 2N aqueous solution of sodium hydroxide (75 ml) to the reaction mixture, tetrahydrofuran was removed under reduced pressure. To the resultant solution was added tert-butyl methyl ether (25 ml), followed by stirring. The organic layer and the aqueous layer were separated. The aqueous layer was cooled in an ice water bath, 5N hydrochloric acid (30 ml) was added and stirred. The precipitated solid was collected by filtration, and washed with water. Drying under aeration and hot-air drying at 60° C. for 8 hr provided the titled compound as white powder (2.918 g, 63%).

$^1$H-NMR Spectrum (CDCl$_3$) δ (ppm): 1.80-1.95 (4H, m), 6.80-6.95 (2H, m), 8.20 (1H, m), 10.69 (1H, brs).

ESI-MS (m/z): 264 [M+Na]$^+$.

Production Example 50

1-(2-Fluorophenylcarbamoyl)cyclopropanecarboxylic acid 1,1-Cyclopropanedicarboxylic acid (2.5 g) was dissolved in tetrahydrofuran (25 ml) under a nitrogen atmosphere, triethylamine (2.68 ml) was added dropwise thereto while stirring in an ice water bath. After stirring at the same temperature for 30 min, thionyl chloride (1.4 ml) was added dropwise while stirring in an ice water bath. After stirring at the same temperature for 30 min, a solution of 2-fluoroaniline (2.04 ml) in tetrahydrofuran (15 ml) was added while stirring in an ice water bath, and the reaction mixture was allowed to gradually warm up to room temperature and stirred overnight. To the reaction mixture was added a 2N aqueous solution of sodium hydroxide (75 ml), and tetrahydrofuran was removed under reduced pressure. To the resultant aqueous solution was added tert-butyl methyl ether (25 ml) and stirred. The organic layer and aqueous layer were separated. The aqueous layer was cooled in an ice water bath, 5N hydrochloric acid (30 ml) was added and stirred. The precipitated solid was collected by filtration and washed with water. Drying under aeration and hot-air drying at 60° C. for 8 hr provided the titled compound as white powder (2.294 g, 54%).

$^1$H-NMR Spectrum (CDCl$_3$) δ (ppm): 1.80-1.94 (4H, m), 7.00-7.15 (3H, m), 8.26 (1H, m), 10.74 (1H, brs).

ESI-MS (m/z): 246 [M+Na]$^+$.

Production Example 51

[4-(4-{[1-(2,4-Difluorophenylcarbamoyl)cyclopropanecarbonyl]amino}-3-fluorophenoxy)pyridin-2-yl]-N-(phenoxycarbonyl)carbamic acid phenyl ester A crude product of [4-(4-amino-3-fluorophenoxy)pyridin-2-yl]-N-(phenoxycarbonyl)carbamic acid phenyl ester (400 mg) was dissolved in N,N-dimethylformamide (5 ml). 1-(2,4-Difluorophenylcarbamoyl)cyclopropanecarboxylic acid (241 mg), triethylamine (0.139 ml) and benzotriazol-1-yloxytris(dimethylamino)phosphonium hexafluorophosphate (442 mg) were added under a nitrogen atmosphere at room temperature and stirred overnight. Liquid-liquid separation was carried out after addition of ethyl acetate and water to the reaction mixture. The organic layer was washed with a saturated aqueous solution of sodium hydrogencarbonate (3 times) and brine in this order, and dried over anhydrous sodium sulfate. The solvent was removed and the residue was purified by silica gel column chromatography (eluent; heptane:ethyl acetate=3:2 to 1:1) to provide the titled compound as white powder (116.2 mg).

ESI-MS (m/z): 705 [M+Na]$^+$.

Production Example 52

[4-(3-Fluoro-4-{[1-(2-fluorophenylcarbamoyl)cyclopropanecarbonyl]amino}phenoxy)pyridin-2-yl]-N-(phenoxycarbonyl)carbamic acid phenyl ester A crude product of [4-(4-amino-3-fluorophenoxy)pyridin-2-yl]-N-(phenoxycarbonyl)carbamic acid phenyl ester (410 mg) was dissolved in N,N-dimethylformamide (5 ml). 1-(2-Fluorophenylcarbamoyl)cyclopropanecarboxylic acid (223 mg), triethylamine (0.139 ml) and benzotriazol-1-yloxytris(dimethylamino)phosphonium hexafluorophosphate (442 mg) were added under a nitrogen atmosphere at room temperature and stirred overnight. Liquid-liquid separation was carried out after addition of ethyl acetate and water to the reaction mixture. The organic layer was washed with a saturated aqueous solution of sodium hydrogencarbonate (3 times) and brine in this order, and dried over anhydrous sodium sulfate. The solvent was removed and the resultant residue was purified by silica gel column chromatography (eluent; heptane:ethyl acetate=3:2 to 1:1) to provide the titled compound as white powder (90.6 mg).

ESI-MS (m/z): 687 [M+Na]$^+$.

Production Example 53

2-Amino-4-(4-nitrophenoxy)pyridine

2-Amino-4-chloropyridine (2.00 g) was dissolved in N-methylpyrrolidone (31.8 ml) under a nitrogen atmosphere, and 4-nitrophenol (6.51 g) and N,N-diisopropylethylamine (15.9 ml) were added, followed by stirring at 150° C. for 3 days. The reaction mixture was allowed to cool down to room temperature, and partitioned between ethyl acetate and a 1N aqueous solution of sodium hydroxide (32 ml). The organic layer was washed with water and brine in this order, and dried over anhydrous sodium sulfate. The solvent was concentrated under reduced pressure, and the resultant residue was purified by silica gel column chromatography (eluent; hexane:ethyl acetate=1:2 to 1:5). Fractions containing the target compound were concentrated under reduced pressure, and the residue was dried under reduced pressure to provide the titled compound as a brown solid (764 mg, 21.2%).

$^1$H-NMR Spectrum (CDCl$_3$) δ (ppm): 4.54 (2H, brs), 6.11 (1H, s), 6.35 (1H, m), 7.17 (2H, m), 8.05 (1H, d, J=5.6 Hz), 8.27 (2H, m).

Production Example 54

4-(Pyrrolidin-1-ylmethyl)piperidine-1-carboxylic acid [4-(4-aminophenoxy)pyridin-2-yl]amide After 2-amino-4-(4-nitrophenoxy)pyridine (160 mg) was dissolved in tetrahydrofuran (7 ml) under a nitrogen atmosphere, triethylamine (0.289 ml) and phenyl chloroformate (0.260 ml) were added while stirring in an ice water bath. The reaction mixture was allowed to warm up to room temperature and stirred for 1 hr. The reaction mixture was partitioned between ethyl acetate (200 ml) and a saturated aqueous solution of sodium hydrogencarbonate (50 ml). The separated organic layer was washed with a saturated aqueous solution of sodium hydrogencarbonate (50 ml), water (50 ml) and brine (100 ml) in this order, and dried over anhydrous sodium sulfate. The solvent was removed under reduced pressure, and to the resultant residue was added N,N-dimethylformamide (8 ml). 4-(Pyrrolidin-1-ylmethyl)piperidine dihydrochloride (668 mg) and triethylamine (0.772 ml) were added and stirred for 4 hr. The reaction mixture was partitioned between ethyl acetate (100 ml) and a saturated aqueous solution of ammonium chloride (50 ml). The separated organic layer was washed with a saturated aqueous solution of ammonium chloride (50 ml), water (50 ml) and brine (50 ml) in this order, and dried over anhydrous sodium sulfate. The solvent was removed under reduced pressure, and the resultant residue was purified by silica gel column chromatography (Fuji Silysia NH, eluent; heptane:ethyl acetate=1:1, then ethyl acetate). Fractions containing the target compound were concentrated under reduced pressure to provide a crude product of 4-(pyrrolidin-1-ylmethyl)piperidine-1-carboxylic acid [4-(4-nitrophenoxy)pyridin-2-yl]amide (295 mg) as a pale yellow oil. 4-(Pyrrolidin-1-ylmethyl)piperidine-1-carboxylic acid [4-(4-nitrophenoxy)pyridin-2-yl]amide (295 mg) was dissolved in tetrahydrofuran (7 ml) and methanol (7 ml) under a nitrogen atmosphere, 10% palladium on carbon (147 mg) was added and stirred under a hydrogen atmosphere for 10 hr. The atmosphere in the reaction vessel was replaced with nitrogen, and the catalyst was removed by filtration and washed with methanol. The filtrate was concentrated under reduced pressure. The resultant residue was purified by silica gel column chromatography (Fuji Silysia NH, eluent; ethyl acetate), and fractions containing the target compound were concentrated under reduced pressure to provide the titled compound as white foam (233.7 mg).

$^1$H-NMR Spectrum (CDCl$_3$) δ (ppm): 1.10-1.35 (2H, m), 1.60-1.90 (7H, m), 2.31 (2H, d, J=6.8 Hz), 2.40-2.50 (4H, m), 2.86 (2H, m), 3.64 (2H, brs), 4.00-4.10 (2H, m), 6.47 (1H, dd, J=2.4, 5.6 Hz), 6.70 (2H, d, J=8.8 Hz), 6.90 (2H, d, J=8.8 Hz), 7.18 (1H, brs), 7.58 (1H, d, J=2.4 Hz), 7.98 (1H, d, J=5.6 Hz).

Production Example 55

1-[4-(4-Amino-3-chlorophenoxy)pyridin-2-yl]-3-(3-diethylaminopropyl)urea 4-(4-Amino-3-chlorophenoxy)pyridin-2-ylamine (750 mg) was dissolved in tetrahydrofuran (30 ml), and triethylamine (0.444 ml) was added thereto. This was cooled in an ice bath, phenyl chloroformate (0.399 ml) were added dropwise, and stirred at room temperature for 5 hr. Triethylamine (0.222 ml) and phenyl chloroformate (0.200 ml) were further added and stirred for 40 min. Triethylamine (0.111 ml) and phenyl chloroformate (0.100 ml) were further added and stirred for 30 min. The reaction mixture was concentrated under reduced pressure, and to the residue were added N,N-dimethylformamide (10 ml) and 3-(diethylamino)propylamine (2.49 ml), followed by stirring at room temperature for 3 hr. Liquid-liquid separation was carried out after addition of ethyl acetate (50 ml), water (20 ml) and a saturated aqueous solution of sodium hydrogencarbonate to the reaction mixture. The organic layer was washed with brine, and dried over anhydrous sodium sulfate. The solvent was removed and the resultant residue was dried under reduced pressure to provide the titled compound as a pale yellow solid (645 mg, 51.8%).

$^1$H-NMR Spectrum (DMSO-d$_6$) δ (ppm): 0.93 (6H, t, J=7.2 Hz), 1.53 (2H, m), 2.38 (2H, t, J=7.2 Hz), 2.43 (4H, q, J=7.2 Hz), 3.14 (2H, m), 5.39 (2H, s), 6.47 (1H, dd, J=2.2, 6.0 Hz), 6.80 (1H, d, J=2.2 Hz), 6.84-6.89 (2H, m), 7.08 (1H, d, J=2.2 Hz), 8.00 (1H, d, J=6.0 Hz), 8.19 (1H, brs), 9.07 (1H, brs).

Production Example 56

1-(3-Diethylaminopropyl)-3-[4-(2-fluoro-4-nitrophenoxy)pyridin-2-yl]-1-methylurea To a solution of 4-(2-fluoro-4-nitrophenoxy)pyridin-2-ylamine (300 mg) and triethylamine (0.335 ml) in tetrahydrofuran (30 ml), was added dropwise phenyl chloroformate (0.226 ml) while stirring in an ice bath, followed by stirring for 0.5 hr. The reaction mixture was concentrated under reduced pressure, and to the residue were added N,N-dimethylformamide (6.0 ml) and N,N-diethyl-N'-methyl-1,3-propanediamine (606 mg), followed by stirring at room temperature for 4 hr 45 min. To the reaction mixture was added ethyl acetate (150 ml), washed with a saturated aqueous solution of sodium hydrogencarbonate, and dried over anhydrous sodium sulfate. The solvent was removed and the resultant residue was filtered with silica gel (Fuji Silysia NH, hexane:ethyl acetate=3:1 to 1:1) to provide the titled compound as a yellow oil (503 mg, 100%).

ESI-MS (m/z): 420 [M+H]$^+$.

Production Example 57

1-(3-Diethylaminopropyl)-3-[4-(4-amino-2-fluorophenoxy)pyridin-2-yl]-1-methylurea To a solution of 1-(3-diethylaminopropyl)-3-[4-(2-fluoro-4-nitrophenoxy)pyridin-2-yl]-1-methylurea (503 mg) in methanol (40 ml)-tetrahydrofuran (20 ml) was added 10% palladium on carbon (200 mg), followed by stirring under a hydrogen atmosphere at room temperature for 12 hr. The catalyst was removed by filtration and washed with methanol, and the filtrate was concentrated under reduced pressure. The residue was purified by silica gel column chromatography (Fuji Silysia NH, ethyl acetate, then ethyl acetate:methanol=10:1) to provide the titled compound as a yellow oil (467 mg, 85.6%).

$^1$H-NMR Spectrum (DMSO-d$_6$) δ (ppm): 0.97 (6H, t, J=7.2 Hz), 1.68 (2H, m), 2.36 (2H, m), 2.52 (4H, m), 2.80 (3H, s), 3.29 (2H, m), 5.43 (2H, m), 6.40 (1H, dd, J=2.4, 8.8 Hz), 6.47-6.51 (2H, m), 6.94 (1H, dd, J=8.8, 8.8 Hz), 7.29 (1H, d, J=2.4 Hz), 8.02 (1H, d, J=5.6 Hz), 9.33 (1H, s).

Production Example 58

4-(2-Methyl-4-nitrophenoxy)pyridin-2-ylamine

2-Amino-4-chloropyridine (5.0 g), N-methylpyrrolidone (40 ml), 2-hydroxy-5-nitrotoluene (11.9 g) and diisopropylethylamine (20.1 g) were placed in a reaction vessel, followed by stirring under a nitrogen atmosphere at 150° C. for 5 days. The reaction mixture was allowed to cool down to room temperature and concentrated under reduced pressure. To the residue was added a saturated aqueous solution of sodium hydrogencarbonate, followed by stirring overnight at room temperature. Liquid-liquid separation was carried out after addition of tetrahydrofuran (200 ml) to the reaction mixture. The aqueous layer was extracted with diethyl ether (100 ml). The organic layer was washed with brine, dried over anhydrous sodium sulfate and concentrated under reduced pressure. The precipitated solid was suspended in diethyl ether and collected by filtration. The solid was washed with diethyl ether:ethyl acetate=1:1 and dried under aeration to provide the titled compound as a yellow solid (4.36 g, 45.7%).

$^1$H-NMR Spectrum (DMSO-d$_6$) δ (ppm): 2.28 (3H, s), 5.89 (1H, d, J=2.0 Hz), 6.04 (2H, brs), 6.19 (1H, dd, J=2.4, 5.6 Hz), 7.23 (1H, d, J=8.8 Hz), 7.87 (1H, d, J=5.6 Hz), 8.14 (1H, dd, J=2.8, 8.8 Hz), 8.29 (1H, d, J=2.8 Hz).

ESI-MS (m/z): 246 [M+H]$^+$.

Production Example 59

1-(3-Diethylaminopropyl)-3-[4-(2-methyl-4-nitrophenoxy)pyridin-2-yl]urea

To a solution of 4-(2-methyl-4-nitrophenoxy)pyridin-2-ylamine (500 mg) and triethylamine (0.569 ml) in tetrahydrofuran (50 ml) was added dropwise phenyl chloroformate (0.384 ml) while cooling in an ice bath, followed by stirring for 0.5 hr. The reaction mixture was concentrated under reduced pressure, and to the residue were added N,N-dimethylformamide (20 ml) and N,N-diethyl-1,3-propanediamine (1.28 ml), followed by stirring at room temperature for 2 hr. The reaction mixture was partitioned between ethyl acetate and water. The organic layer was washed with brine, dried over anhydrous sodium sulfate and concentrated under reduced pressure. The residue was purified by silica gel column chromatography (Fuji Silysia NH, eluent; hexane:ethyl acetate=1:1, then ethyl acetate) to provide the titled compound as a pale yellow oil (794 mg, 96.9%).

ESI-MS (m/z): 402 [M+H]$^+$.

Production Example 60

1-[4-(4-Amino-2-methylphenoxy)pyridin-2-yl]-3-(3-diethylaminopropyl)urea

To a solution of 1-(3-diethylaminopropyl)-3-[4-(2-methyl-4-nitrophenoxy)pyridin-2-yl]urea (794 mg) in ethanol (50 ml) were added electrolytic iron powder (442 mg), ammonium chloride (847 mg) and water (10 ml), followed by stirring at 90° C. for 1 hr. The reaction mixture was allowed to cool down to room temperature, insoluble matter was removed by filtration, and the filtrate was concentrated under reduced pressure. To the residue was added ethyl acetate (100 ml), washed with a saturated aqueous solution of sodium hydrogencarbonate, and dried over anhydrous sodium sulfate. The solvent was removed and the resultant residue was purified by silica gel column chromatography (Fuji Silysia NH, eluent; hexane:ethyl acetate=1:1 to 1:2, ethyl acetate, then ethyl acetate:methanol=20:1 to 10:1) to provide the titled compound (110 mg, 15%).

$^1$H-NMR Spectrum (DMSO-d$_6$) δ (ppm): 0.93 (6H, t, J=7.2 Hz), 1.53 (2H, m), 1.93 (3H, s), 2.38 (2H, m), 2.43 (4H, q, J=7.2 Hz), 3.12 (2H, m), 5.03 (2H, m), 6.39 (1H, dd, J=2.4, 6.0 Hz), 6.44 (1H, dd, J=2.4, 8.4 Hz), 6.49 (1H, d, J=2.4 Hz), 6.72 (2H, m), 7.97 (1H, d, J=6.0 Hz), 8.22 (1H, brs), 9.04 (1H, s).

ESI-MS (m/z): 372 [M+H]$^+$.

Production Example 61

N-(1-Ethylpiperidin-4-yl)-N-methylamine

To a solution of 40% methylamine in methanol (1.26 g) were added acetonitrile (150 ml), 1-ethyl-4-piperidone (2.0 ml) and acetic acid (0.932 ml), followed by addition of sodium triacetoxyborohydride (6.59 g) and stirring for 1 hr. To the reaction mixture was added a saturated aqueous solution of sodium hydrogencarbonate (20 ml), and the reaction mixture was concentrated under reduced pressure. The resultant residue was suspended in methanol (20 ml), the solid was removed by filtration and washed with methanol (20 ml). The filtrate was concentrated under reduced pressure, the resultant residue was suspended in tetrahydrofuran (50 ml). The solid was removed by filtration and washed with tetrahydrofuran (100 ml). The filtrate was concentrated under reduced pressure to provide a crude product of the titled compound as a pale yellow oil (3.33 g).

ESI-MS (m/z): 143 [M+H]+.

Example 1

N-(3-Fluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide 3-[4-(4-Amino-2-fluorophenoxy)pyridin-2-yl]-1-methyl-1-(1-methylpiperidin-4-yl)urea (40.8 mg) was dissolved in N,N-dimethylformamide (1.0 ml). 1-(4-Fluorophenylcarbamoyl)cyclopropanecarboxylic acid (73 mg), triethylamine (0.0456 ml) and benzotriazol-1-yloxytris(dimethylamino) phosphonium hexafluorophosphate (145 mg) were added under a nitrogen atmosphere at room temperature and stirred for 3.5 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed and the resultant residue was purified by silica gel column chromatography (Fuji Silysia NH, eluent; ethyl acetate, then ethyl acetate:methanol=97:3) to provide the titled compound as white powder (26.3 mg, 42%).

$^1$H-NMR Spectrum (CDCl$_3$) δ (ppm): 1.50-1.80 (8H, m), 1.90-2.10 (2H, m), 2.26 (3H, s), 2.80-2.94 (5H, m), 4.11 (1H, m), 6.57 (1H, dd, J=2.4, 5.6 Hz), 7.00-7.30 (5H, m), 7.40-7.50 (2H, m), 7.63 (1H, d, J=2.4 Hz), 7.68 (1H, dd, J=2.4, 12.0 Hz), 8.06 (1H, d, J=5.6 Hz), 8.65 (1H, m), 9.59 (1H, brs).

ESI-MS (m/z): 579 [M+H]$^+$.

Example 2

N-[4-({2-[({4-[2-(Dimethylamino)ethyl]piperazin-1-yl}carbonyl)amino]pyridin-4-yl}oxy)-2-fluorophenyl]-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (1.0 ml) was added 1-(2-dimethylaminoethyl)piperazine (59.0 mg), followed by stirring at room temperature for 25 hr. The reaction mixture was partitioned between ethyl acetate and a 1N aqueous solution of sodium hydroxide. The organic layer was washed with brine, and dried over anhydrous sodium sulfate. The solvent was removed, the residue was purified by silica gel column chromatography (Fuji Silysia NH, heptane:ethyl acetate=1:2, ethyl acetate, then ethyl acetate:methanol=20:1). Fractions containing the target compound were concentrated. To the residue was added diethyl ether:hexane=1:3, and the precipitate was collected by filtration. This was washed with diethyl ether:hexane=1:3 and dried under aeration to provide the titled compound as white powder (31.7 mg, 69.6%).

$^1$H-NMR Spectrum (CDCl$_3$) δ (ppm): 1.68 (2H, m), 1.74 (2H, m), 2.26 (6H, m), 2.43-2.54 (8H, m), 3.45-3.53 (4H, m), 6.55 (1H, dd, J=2.4, 5.6 Hz), 6.91 (2H, m), 7.04 (2H, m), 7.24 (1H, s), 7.50 (2H, dd, J=4.8, 9.2 Hz), 7.63 (1H, d, J=2.4 Hz), 8.06 (1H, d, J=5.6 Hz), 8.19 (1H, m), 8.86 (1H, s), 9.20 (1H, s).

ESI-MS (m/z): 608 [M+H]$^+$.

Example 3

N-(2-Fluoro-4-{[2-({[methyl(1-methylpiperidin-4-yl)amino]carbonyl}amino)pyridin-4-yl]oxy}phenyl)-N'-(4-fluorophenyncyclopropane-1,1-dicarboxamide To a solution of phenyl N44-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (1.0 ml) was added 1-methyl-4-(methylamino)piperidine (0.0436 ml), followed by stirring at room temperature for 16 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, heptane:ethyl acetate=1:2, ethyl acetate, then ethyl acetate:methanol=50:1). Fractions containing the target compound were concentrated. To the residue was added diethyl ether:hexane=1:3, and the precipitate was collected by filtration. This was washed with diethyl ether:hexane=1:3 and dried under aeration to provide the titled compound as white powder (26.1 mg, 60.1%).

$^1$H-NMR Spectrum (CDCl$_3$) δ (ppm): 1.62-1.84 (8H, m), 2.07 (2H, m), 2.29 (3H, s), 2.89 (3H, s), 2.92 (2H, m), 4.15 (1H, m), 6.50 (1H, dd, J=2.4, 5.6 Hz), 6.91 (2H, m), 7.03 (2H, m), 7.21 (1H, s), 7.49 (2H, dd, J=4.8, 9.2 Hz), 7.68 (1H, d, J=2.4 Hz), 8.07 (1H, d, J=5.6 Hz), 8.18 (1H, m), 8.98 (1H, s), 9.19 (1H, s).

ESI-MS (m/z): 579 [M+H]$^+$, 601 [M+Na]$^+$.

Example 4

N-(4-Fluorophenyl)-N'-{2-fluoro-4-[(2-{[(4-pyrrolidin-1-ylpiperidin-1-yl)carbonyl]amino}pyridin-4-yl)oxy]phenyl}cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (1.0 ml) was added 4-(pyrrolidin-1-yl)piperidine (46.3 mg), followed by stirring at room temperature for 16 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, heptane:ethyl acetate=1:2, ethyl acetate, then ethyl acetate:methanol=20:1). Fractions containing the target compound were concentrated. To the residue was added diethyl ether:hexane=1:3, and the precipitate was collected by filtration. This was washed with diethyl ether:hexane=1:3 and dried under aeration to provide the titled compound as white powder (36.9 mg, 81.4%).

$^1$H-NMR Spectrum (CDCl$_3$) δ (ppm): 1.57 (4H, m), 1.66 (2H, m), 1.75 (2H, m), 1.85 (4H, m), 1.98 (2H, m), 2.33 (1H, m), 2.67 (2H, m), 2.96 (2H, m), 4.04 (2H, m), 6.55 (1H, dd, J=2.0, 5.6 Hz), 6.92 (2H, m), 7.04 (2H, m), 7.25 (1H, m), 7.50 (2H, dd, J=4.8, 9.2 Hz), 7.61 (1H, d, J=2.0 Hz), 8.06 (1H, d, J=5.6 Hz), 8.20 (1H, m), 8.78 (1H, s), 9.25 (1H, s).

ESI-MS (m/z): 605 [M+H]$^+$.

Example 5

N-[4-({2-[({4-[(Dimethylamino)methyl]piperidin-1-yl}carbonyl)amino]pyridin-4-yl}oxy)-3-fluorophenyl]-N'-(4-fluorophenyl)cyclopropane-1,1-dicarboxamide 4-(Dimethylaminomethyl)piperidine-1-carboxylic acid [4-(4-amino-2-fluorophenoxy)pyridin-2-yl]amide (88 mg) was dissolved in N,N-dimethylformamide (2.5 ml). 1-(4-Fluorophenylcarbamoyl)cyclopropanecarboxylic acid (101 mg), triethylamine (0.0633 ml) and benzotriazol-1-yloxytris(dimethylamino)phosphonium hexafluorophosphate (201 mg) were added under a nitrogen atmosphere at room temperature, followed by stirring overnight. Liquid-liquid separation was carried out after addition of ethyl acetate and water to the reaction mixture. The organic layer was washed with a 1N aqueous solution of sodium hydroxide and brine, and dried over anhydrous sodium sulfate. The solvent was removed and the resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of heptane to the resultant residue. The solid was collected by filtration, and dried under aeration to provide the titled compound as white powder (39.8 mg, 30%).

$^1$H-NMR Spectrum (CDCl$_3$) δ (ppm): 1.15-1.30 (2H, m), 1.60-1.85 (7H, m), 2.10-2.15 (2H, m), 2.64 (3H, s), 2.66 (3H, s), 2.87 (2H, m), 4.04 (2H, m), 6.56 (1H, dd, J=2.4, 5.6 Hz), 7.00-7.30 (5H, m), 7.40-7.50 (2H, m), 7.58 (1H, d, J=2.4 Hz), 7.68 (1H, dd, J=2.4, 12.0 Hz), 8.04 (1H, d, J=5.6 Hz), 8.73 (1H, brs), 9.57 (1H, brs).

ESI-MS (neg.) (m/z): 591[M−H]$^-$.

Example 6

N-[4-({2-[({4-[(Dimethylamino)methyl]piperidin-1-yl}carbonyl)amino]pyridin-4-yl}oxy)-3-fluorophenyl]-N'-(4-fluorophenyl)cyclobutane-1,1-dicarboxamide 4-(Dimethylaminomethyl)piperidine-1-carboxylic acid [4-(4-amino-2-fluorophenoxy)pyridin-2-yl]amide (114 mg) was dissolved in N,N-dimethylformamide (4.0 ml). 1-(4-Fluorophenylcarbamoyl)cyclobutanecarboxylic acid (279 mg), triethylamine (0.164 ml) and benzotriazol-1-yloxytris(dimethylamino)phosphonium hexafluorophosphate (520 mg) were added under a nitrogen atmosphere at room temperature and stirred overnight. Liquid-liquid separation was carried out after addition of ethyl acetate and water to the reaction mixture. The organic layer was washed with 0.5N hydrochloric acid (4 times), water, a saturated aqueous solution of sodium hydrogencarbonate (3 times) and brine in this order, and dried over anhydrous sodium sulfate. The solvent was removed and the resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of a mixture of diethyl ether and heptane (1:3) to the resultant residue. The solid was collected by filtration and dried under aeration to provide the titled compound as white powder (19.1 mg, 11%).

$^1$H-NMR Spectrum (CDCl$_3$) δ (ppm): 1.10-1.25 (2H, m), 1.50-1.85 (3H, m), 2.00-2.15 (4H, m), 2.21 (6H, s), 2.70-2.90 (6H, m), 4.00-4.10 (2H, m), 6.54 (1H, dd, J=2.4, 5.6 Hz), 7.00-7.20 (5H, m), 7.48-7.54 (2H, m), 7.57 (1H, d, J=2.4 Hz), 7.73 (1H, dd, J=2.4, 12.0 Hz), 7.78 (1H, brs), 8.03 (1H, d, J=5.6 Hz), 8.08 (1H, brs).

ESI-MS (m/z): 607 [M+H]$^+$.

Example 7

N-[4-({2-[({4-[2-(Dimethylamino)ethyl]piperazin-1-yl}carbonyl)amino]pyridin-4-yl}oxy)-3-fluorophenyl]-N'-(4-fluorophenyl)cyclopropane-1,1-dicarboxamide To [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (130 mg) was added a solution of 1-[2-(dimethylamino)ethyl]piperazine (123 mg) in N,N-dimethylformamide (2.5 ml) at room temperature, followed by stirring for 3.5 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solid was collected by filtration and dried under aeration to provide the titled compound as white powder (42.3 mg, 36%).

$^1$H-NMR Spectrum (CDCl$_3$) δ (ppm): 1.50-1.78 (4H, m), 2.25 (6H, s), 2.40-2.56 (8H, m), 3.46-3.54 (4H, m), 6.55 (1H, dd, J=2.4, 5.6 Hz), 7.00-7.30 (5H, m), 7.40-7.50 (2H, m), 7.58 (1H, d, J=2.4 Hz), 7.69 (1H, dd, J=2.4, 12.0 Hz), 8.04 (1H, d, J=5.6 Hz), 8.49 (1H, brs), 9.53 (1H, brs).

ESI-MS (m/z): 608 [M+H]$^+$.

Example 8

N-[4-({2-[({4-[(Dimethylamino)methyl]piperidin-1-yl}carbonyl)amino]pyridin-4-yl}oxy)-2-fluorophenyl]-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (1.0 ml) were added 4-(dimethylaminomethyl)piperidine dihydrochloride (67.0 mg), triethylamine (0.0523 ml) and water (0.050 ml), followed by stirring at room temperature for 10 hr. To the reaction mixture were added triethylamine (0.0523 ml) and water (0.050 ml), followed by further stirring at room temperature for 24 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added hexane, and the precipitate was collected by filtration. This was washed with hexane and dried under aeration to provide the titled compound as white powder (22.4 mg, 50.4%).

$^1$H-NMR Spectrum (CDCl$_3$) δ (ppm): 1.10-1.20 (2H, m), 1.65-1.99 (7H, m), 2.13 (2H, d, J=6.2 Hz), 2.21 (6H, s), 2.87 (2H, m), 4.06 (2H, m), 6.55 (1H, m), 6.90 (2H, m), 7.03 (2H, m), 7.32 (1H, brs), 7.49 (2H, dd, J=5.0, 9.0 Hz), 7.62 (1H, s), 8.06 (1H, m), 8.15 (1H, m), 8.99 (1H, s), 9.27 (1H, s).
ESI-MS (m/z): 593 [M+H]$^+$.

Example 9

N-{4-[(2-{[(4-Azetidin-1-ylpiperidin-1-yl)carbonyl]amino}pyridin-4-yl)oxy]-2-fluorophenyl}-N'-(4-fluorophenyncyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (1.0 ml) were added 4-(azetidin-1-yl)piperidine dihydrochloride (79.9 mg), triethylamine (0.105 ml) and water (0.050 ml), followed by stirring at room temperature for 24 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:3, and the precipitate was collected by filtration. This was washed with hexane and dried under aeration to provide the titled compound as white powder (22.9 mg, 51.7%).
$^1$H-NMR Spectrum (CDCl$_3$) δ (ppm): 1.22-1.33 (2H, m), 1.64-1.83 (6H, m), 2.06 (2H, m), 2.20 (1H, m), 3.03 (2H, m), 3.18 (4H, m), 3.89 (2H, m), 6.54 (1H, dd, J=2.0, 6.0 Hz), 6.91 (2H, m), 7.03 (2H, m), 7.28 (1H, s), 7.50 (2H, dd, J=4.8, 9.2 Hz), 7.61 (1H, d, J=2.0 Hz), 8.05 (1H, d, J=6.0 Hz), 8.17 (1H, m), 8.85 (1H, s), 9.28 (1H, s).
ESI-MS (m/z): 591 [M+H]$^+$.

Example 10

N-(4-Fluorophenyl)-N'-{3-fluoro-4-[(2-{[(4-pyrrolidin-1-ylpiperidin-1-yl)carbonyl]amino}pyridin-4-yl)oxy]phenyl}cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) was added 4-(pyrrolidin-1-yl)piperidine (61.3 mg) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solid was collected by filtration and dried under aeration to provide the titled compound as white powder (48.0 mg, 80%).
$^1$H-NMR Spectrum (CDCl$_3$) δ (ppm): 1.50-2.00 (12H, m), 2.20 (1H, m), 2.50-2.64 (4H, m), 2.96 (2H, m), 3.92-4.04 (2H, m), 6.56 (1H, dd, J=2.4, 5.6 Hz), 7.00-7.30 (5H, m), 7.40-7.50 (2H, m), 7.55 (1H, d, J=2.4 Hz), 7.68 (1H, dd, J=2.4, 12.0 Hz), 8.04 (1H, d, J=5.6 Hz), 8.70 (1H, brs), 9.48 (1H, brs).
ESI-MS (m/z): 605 [M+H]$^+$.

Example 11

N-{4-[(2-{[(4-Azetidin-1-ylpiperidin-1-yl)carbonyl]amino}pyridin-4-yl)oxy]-3-fluorophenyl}-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) were added 4-(azetidin-1-yl)piperidine dihydrochloride (85 mg) and triethylamine (0.112 ml) at room temperature, followed by stirring for 24 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solid was collected by filtration and dried under aeration to provide the titled compound as white powder (34.6 mg, 59%).
$^1$H-NMR Spectrum (CDCl$_3$) δ (ppm): 1.16-1.34 (4H, m), 1.50-1.72 (4H, m), 2.00-2.10 (2H, m), 2.19 (1H, m), 3.02 (2H, m), 3.10-3.24 (4H, m), 3.80-3.90 (2H, m), 6.56 (1H, dd, J=2.4, 5.6 Hz), 7.00-7.30 (5H, m), 7.40-7.50 (2H, m), 7.55 (1H, d, J=2.4 Hz), 7.68 (1H, dd, J=2.4, 12.0 Hz), 8.04 (1H, d, J=5.6 Hz), 8.67 (1H, brs), 9.47 (1H, brs).
ESI-MS (m/z): 591[M+H]$^+$.

Example 12

N-(4-Fluorophenyl)-N'-(4-{[2-({[methyl(1-methylpiperidin-4-yl)amino]carbonyl}amino)pyridin-4-yl]oxy}phenyl)cyclopropane-1,1-dicarboxamide

[4-(4-{[1-(4-Fluorophenylcarbamoyl)cyclopropanecarbonyl]amino}phenoxy)pyridin-2-yl]-N-(phenoxycarbonyl)carbamic acid phenyl ester (50 mg) was dissolved in N,N-dimethylformamide (1.0 ml), and methyl(1-methylpiperidin-4-yl)amine (0.045 ml) was added thereto, followed by stirring for 62 hr. The reaction mixture was partitioned between ethyl acetate (50 ml) and a saturated aqueous solution of sodium hydrogencarbonate (20 ml). The organic layer was washed with a saturated aqueous solution of sodium hydrogencarbonate (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; ethyl acetate, then ethyl acetate:methanol=95:5). Fractions containing the target compound were concentrated under reduced pressure, and the resultant residue was suspended in diethyl ether (2 ml) and hexane (4 ml). The solid was collected by filtration and dried under aeration to provide the titled compound as white powder (37.6 mg, 86.8%).
$^1$H-NMR Spectrum (CDCl$_3$) δ (ppm): 1.40-1.90 (8H, m), 2.08 (2H, m), 2.30 (3H, s), 2.88 (3H, s), 2.93 (2H, m), 4.15 (1H, m), 6.54 (1H, dd, J=2.0, 5.6 Hz), 6.90-7.14 (4H, m), 7.18 (1H, brs), 7.40-7.60 (4H, m), 7.64 (1H, d, J=2.0 Hz), 8.05 (1H, d, J=5.6 Hz), 8.95 (1H, brs), 9.09 (1H, brs).
ESI-MS (m/z): 583 [M+Na]$^+$.

Example 13

N-{4-[(2-{[(4-Azetidin-1-ylpiperidin-1-yl)carbonyl]amino}pyridin-4-yl)oxy]phenyl}-N'-(4-fluorophenyl)cyclopropane-1,1-dicarboxamide

[4-(4-{[1-(4-Fluorophenylcarbamoyl)cyclopropanecarbonyl]amino}phenoxy)pyridin-2-yl]-N-(phenoxycarbonyl)carbamic acid phenyl ester (50 mg) was dissolved in N,N-dimethylformamide (1.0 ml), and 4-(azetidin-1-yl)piperidine dihydrochloride (82.9 mg), triethylamine (0.0782 ml) and water (0.100 ml) were added thereto in this order, followed by stirring for 62 hr. The reaction mixture was partitioned between ethyl acetate (50 ml) and a saturated aqueous solution of sodium hydrogencarbonate (20 ml). The separated organic layer was washed with a saturated aqueous solution of sodium hydrogencarbonate (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; ethyl acetate, then ethyl acetate:methanol=95:5). Fractions containing the target compound were concentrated under reduced pressure, and the resultant residue was suspended in diethyl ether (2 ml) and hexane (4 ml). The solid was collected by filtration and dried under aeration to provide the titled compound as white powder (28.8 mg, 65.1%).

$^1$H-NMR Spectrum (CDCl$_3$) δ (ppm): 1.40-1.80 (8H, m), 2.06 (2H, m), 2.21 (1H, m), 3.02 (2H, m), 3.19 (4H, m), 3.80-4.00 (2H, m), 6.53 (1H, dd, J=2.0, 5.6 Hz), 6.94-7.14 (5H, m), 7.40-7.66 (5H, m), 8.03 (1H, d, J=5.6 Hz), 8.83 (1H, brs), 9.15 (1H, brs).

ESI-MS (m/z): 595 [M+Na]$^+$.

Example 14

N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) were added N,N-dimethyl-N-[1-(piperidin-4-yl)azetidin-3-yl]amine trihydrochloride (79.9 mg), triethylamine (0.105 ml) and water (0.050 ml), followed by stirring at room temperature for 12 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:3, and the precipitate was collected by filtration. This was washed with hexane and dried under aeration to provide the titled compound as white powder (30.8 mg, 64.8%).

$^1$H-NMR Spectrum (CDCl$_3$) δ (ppm): 1.31 (2H, m), 1.50-1.80 (6H, m), 2.14 (6H, s), 2.32 (1H, m), 2.90 (3H, m), 3.05 (2H, m), 3.53 (2H, m), 3.89 (2H, m), 6.54 (1H, dd, J=2.4, 5.6 Hz), 6.92 (2H, m), 7.04 (2H, m), 7.23 (1H, s), 7.50 (2H, dd, J=4.8, 9.2 Hz), 7.61 (1H, d, J=2.4 Hz), 8.06 (1H, d, J=5.6 Hz), 8.19 (1H, m), 8.77 (1H, s), 9.25 (1H, s).

ESI-MS (m/z): 634 [M+H]$^+$, 656 [M+Na]$^+$.

Example 15

N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide Method A To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) was added 1-methyl-4-(piperidin-4-yl)piperazine (68.7 mg), followed by stirring at room temperature for 12 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, ethyl acetate:methanol=20:1, then 10:1). Fractions containing the target compound were concentrated. To the residue was added diethyl ether:hexane=1:3, and the precipitate was collected by filtration. This was washed with hexane and dried under aeration to provide the titled compound as white powder (34.6 mg, 72.8%). The titled compound could be synthesized by the following method.

Method B

N-{4-[(2-Aminopyridin-4-yl)oxy]-2-fluorophenyl}-N'-(4-fluorophenyl)cyclopropane-1,1-dicarboxamide (1.137 g) and sodium hydrogencarbonate (1.35 g) were dissolved in ethyl acetate (20 ml) and water (10 ml), and phenyl chloroformate (0.841 ml) was added at room temperature, followed by stirring for 30 min. The reaction mixture was partitioned between ethyl acetate and water. The organic layer was washed with a saturated aqueous solution of sodium hydrogencarbonate (twice) and brine in this order, and dried over anhydrous sodium sulfate. The solvent was concentrated under reduced pressure. The residue was dissolved in N,N-dimethylformamide (15 ml), and 1-methyl-4-(piperidin-4-yl)piperazine (1.23 g) was added at room temperature, followed by stirring overnight. The reaction mixture was partitioned between ethyl acetate and water. The organic layer was washed with a saturated aqueous solution of ammonium chloride, water and brine in this order, and dried over anhydrous sodium sulfate. The solvent was removed, and the residue was purified by silica gel column chromatography (Fuji Silysia NH, eluent; heptane:ethyl acetate=1:4, ethyl acetate, ethyl acetate:methanol=95:5). Fractions containing the target compound were concentrated. To the resultant residue (836 mg) was added ethyl acetate:tert-butyl methyl ether=1:2 to suspend a solid. The solid was collected by filtration and washed with tert-butyl methyl ether. This was dried under aeration to provide the titled compound as white powder (584 mg, 34.4%).

$^1$H-NMR Spectrum (CDCl$_3$) δ (ppm): 1.44 (2H, m), 1.68 (2H, m), 1.75 (2H, m), 1.90 (2H, m), 2.32 (3H, s), 2.39-2.71 (9H, m), 2.90 (2H, m), 4.11 (2H, m), 6.55 (1H, dd, J=2.0, 5.6 Hz), 6.92 (2H, m), 7.04 (2H, m), 7.26 (1H, covered by CDCl$_3$), 7.50 (2H, dd, J=4.8, 9.2 Hz), 7.62 (1H, d, J=2.0 Hz), 8.06 (1H, d, J=5.6 Hz), 8.20 (1H, m), 8.84 (1H, s), 9.20 (1H, s).

ESI-MS (m/z): 634 [M+H]$^+$, 656 [M+Na]$^+$.

Example 16

N-(2-Fluoro-4-{[2-({[4-(1-methylpiperidin-4-yl)piperazin-1-yl]carbonyl}amino)pyridin-4-yl]oxy}phenyl)-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) was added 1-(N-methylpiperidin-4-yl)piperazine (68.7 mg), followed by stirring at room temperature for 12 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, ethyl acetate:methanol=20:1 then 10:1). Fractions containing the target compound were concentrated. To the residue was added diethyl ether:hexane=1:3, and the precipitate was collected by filtration. This was washed with hexane and dried under aeration to provide the titled compound as white powder (30.1 mg, 63.3%).

$^1$H-NMR Spectrum (CDCl$_3$) δ (ppm): 1.59-1.76 (8H, m), 1.96 (2H, m), 2.28 (4H, m), 2.57 (4H, m), 2.92 (2H, m), 3.50 (4H, m), 6.55 (1H, dd, J=2.0, 5.6 Hz), 6.91 (2H, m), 7.04 (2H, m), 7.24 (1H, s), 7.50 (2H, dd, J=4.8, 9.2 Hz), 7.62 (1H, d, J=2.0 Hz), 8.06 (1H, d, J=5.6 Hz), 8.19 (1H, m), 8.88 (1H, s), 9.20 (1H, s).

ESI-MS (m/z): 634 [M+H]$^+$, 656 [M+Na]$^+$.

Example 17

N-(2-Fluoro-4-{[2-({[4-(1-methylazetidin-3-yl)piperazin-1-yl]carbonyl}amino)pyridin-4-yl]oxy}phenyl)-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) were added 1-(1-methylazetidin-3-yl)piperazine trihydrochloride (79.4 mg), triethylamine (0.125 ml) and water (0.10 ml), followed by stirring at room temperature for 6 hr. To the reaction mixture were added 1-(1-methylazetidin-3-yl)piperazine trihydrochloride (19.9 mg) and triethylamine (0.032 ml), followed by stirring at room temperature for 2 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, ethyl acetate:methanol=20:1 then 10:1). Fractions containing the target compound were concentrated. To the residue was added diethyl ether:hexane=1:3, and the precipitate was collected by filtration. This was washed with hexane and dried under aeration to provide the titled compound as white powder (19.7 mg, 43.4%).

$^1$H-NMR Spectrum (CDCl$_3$) δ (ppm): 1.67 (2H, m), 1.73 (2H, m), 2.06 (3H, s), 2.31-2.36 (6H, m), 2.93 (3H, m), 3.51 (4H, m), 6.55 (1H, dd, J=2.0, 5.6 Hz), 6.88-6.93 (2H, m), 7.03 (2H, m), 7.25 (1H, s), 7.49 (2H, dd, J=4.8, 9.2 Hz), 7.62 (1H, d, J=2.0 Hz), 8.06 (1H, d, J=5.6 Hz), 8.19 (1H, m), 8.93 (1H, s), 9.19 (1H, s).

ESI-MS (m/z): 606 [M+H]$^+$, 628 [M+Na]$^+$.

Example 18

N-(4-{[2-({[4-(Dimethylamino)piperidin-1-yl]carbonyl}amino)pyridin-4-yl]oxy}-2-fluorophenyl)-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) were added N,N-dimethyl-N-(piperidin-4-yl)amine dihydrochloride (79.4 mg), triethylamine (0.157 ml) and water (0.10 ml), followed by stirring at room temperature for 10 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, ethyl acetate:methanol=20:1, then 10:1). Fractions containing the target compound were concentrated. To the residue was added diethyl ether:hexane=1:3, and the precipitate was collected by filtration. This was washed with hexane and dried under aeration to provide the titled compound as white powder (30.6 mg, 70.5%).

$^1$H-NMR Spectrum (CDCl$_3$) δ (ppm): 1.43-1.53 (2H, m), 1.66-1.77 (4H, m), 1.89 (2H, m), 2.30 (6H, m), 2.37 (1H, m), 2.91 (2H, m), 4.11 (2H, m), 6.56 (1H, dd, J=2.0, 5.6 Hz), 6.91-6.95 (2H, m), 7.05 (2H, m), 7.30 (1H, s), 7.51 (2H, dd, J=4.8, 9.2 Hz), 7.64 (1H, d, J=2.0 Hz), 8.08 (1H, d, J=5.6 Hz), 8.19 (1H, m), 8.89 (1H, s), 9.24 (1H, s).

ESI-MS (m/z): 579 [M+H]$^+$, 601 [M+Na]$^+$.

Example 19

N-(3-Fluoro-4-{[2-({[4-(1-methylpiperidin-4-yl)piperazin-1-yl]carbonyl}amino)pyridin-4-yl]oxy}phenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) was added 1-(1-methylpiperidin-4-yl)piperazine (73.3 mg) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solid was collected by filtration and dried under aeration to provide the titled compound as white powder (56.4 mg, 89%).

$^1$H-NMR Spectrum (CDCl$_3$) δ (ppm): 1.50-1.80 (8H, m), 1.93 (2H, m), 2.20-2.34 (4H, m), 2.50-2.60 (4H, m), 2.84-2.96 (2H, m), 3.40-3.56 (4H, m), 6.56 (1H, dd, J=2.4, 5.6 Hz), 7.00-7.30 (5H, m), 7.40-7.50 (2H, m), 7.56 (1H, d, J=2.4 Hz), 7.68 (1H, dd, J=2.4, 12.0 Hz), 8.05 (1H, d, J=5.6 Hz), 8.60 (1H, brs), 9.54 (1H, brs).

ESI-MS (m/z): 634 [M+H]$^+$.

Example 20

N-(3-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) was added 1-methyl-4-(piperidin-4-yl)piperazine (73.3 mg) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (60.1 mg, 95%).

$^1$H-NMR Spectrum (CDCl$_3$) δ (ppm): 1.40-2.00 (9H, m), 2.29 (3H, s), 2.35-2.70 (8H, m), 2.88 (2H, m), 4.00-4.10 (2H, m), 6.56 (1H, dd, J=2.4, 5.6 Hz), 7.00-7.30 (5H, m), 7.40-7.50 (2H, m), 7.56 (1H, d, J=2.4 Hz), 7.68 (1H, dd, J=2.4, 12.0 Hz), 8.05 (1H, d, J=5.6 Hz), 8.63 (1H, brs), 9.54 (1H, brs).

ESI-MS (m/z): 656 [M+Na]$^+$.

Example 21

N-[4-({2-[({4-[3-(Dimethylamino)azetidin-1-yl]piperidin-1-yl}carbonyl)amino]pyridin-4-yl}oxy)-3-fluorophenyl]-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) were added 4-(3-dimethylaminoazetidin-1-yl)piperidine trihydrochloride (116 mg) and triethylamine (0.168 ml) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (57.5 mg, 91%).

$^1$H-NMR Spectrum (CDCl$_3$) δ (ppm): 1.20-1.80 (8H, m), 2.11 (6H, s), 2.25 (1H, m), 2.74-2.90 (3H, m), 3.04 (2H, m), 3.40-3.50 (2H, m), 3.80-3.90 (2H, m), 6.56 (1H, dd, J=2.4, 5.6 Hz), 7.00-7.30 (5H, m), 7.40-7.50 (2H, m), 7.55 (1H, d, J=2.4 Hz), 7.68 (1H, dd, J=2.4, 12.0 Hz), 8.04 (1H, d, J=5.6 Hz), 8.66 (1H, brs), 9.48 (1H, brs).

ESI-MS (m/z): 634 [M+H]$^+$.

Example 22

N-(3-Fluoro-4-{[2-({[4-(1-methylazetidin-3-yl)piperazin-1-yl]carbonyl}amino)pyridin-4-yl]oxy}phenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) were added 1-(1-methylazetidin-3-yl)piperazine trihydrochloride (106 mg) and triethylamine (0.167 ml) at room temperature, followed by stirring for 25 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solid was collected by filtration and dried under aeration to provide the titled compound as white powder (20.2 mg, 33%).

$^1$H-NMR Spectrum (CDCl$_3$) δ (ppm): 1.60-1.80 (4H, m), 2.25-2.34 (4H, m), 2.35 (3H, s), 2.85-3.00 (3H, m), 3.45-3.55 (6H, m), 6.56 (1H, dd, J=2.4, 5.6 Hz), 7.00-7.30 (5H, m), 7.40-7.50 (2H, m), 7.55 (1H, d, J=2.4 Hz), 7.68 (1H, dd, J=2.4, 12.0 Hz), 8.05 (1H, d, J=5.6 Hz), 8.57 (1H, brs), 9.57 (1H, brs).

ESI-MS (m/z): 606 [M+H]$^+$.

Example 23

N-(4-{[2-({[4-(Dimethylamino)piperidin-1-yl]carbonyl}amino)pyridin-4-yl]oxy}-3-fluorophenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) were added 4-dimethylaminopiperidine dihydrochloride (80.5 mg) and triethylamine (0.112 ml) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (52.1 mg, 90%).

$^1$H-NMR Spectrum (CDCl$_3$) δ (ppm): 1.40-1.76 (6H, m), 1.80-1.90 (2H, m), 2.28 (6H, s), 2.35 (1H, m), 2.89 (2H, m), 4.02-4.12 (2H, m), 6.55 (1H, dd, J=2.4, 5.6 Hz), 7.00-7.30 (5H, m), 7.40-7.50 (2H, m), 7.57 (1H, d, J=2.4 Hz), 7.69 (1H, dd, J=2.4, 12.0 Hz), 8.05 (1H, d, J=5.6 Hz), 8.54 (1H, brs), 9.52 (1H, brs).

ESI-MS (m/z): 579 [M+H]$^+$.

Example 24

N-(4-{([2-({[(3S)-3-Dimethylamino)pyrrolidin-1-yl]carbonyl}amino)pyridin-4-yl]oxy}-3-fluorophenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (66 mg) in N,N-dimethylformamide (1.0 ml) was added (3S)-3-dimethylaminopyrrolidine (0.0508 ml) at room temperature, followed by stirring for 6 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (45.6 mg, 81%).

$^1$H-NMR Spectrum (CDCl$_3$) δ (ppm): 1.50-1.75 (4H, m), 1.87 (1H, m), 2.16 (1H, m), 2.27 (6H, s), 2.75 (1H, m), 3.21 (1H, m), 3.39 (1H, m), 3.64 (1H, m), 3.71 (1H, m), 6.58 (1H, dd, J=2.4, 5.6 Hz), 7.00-7.30 (5H, m), 7.40-7.50 (2H, m), 7.63 (1H, d, J=2.4 Hz), 7.69 (1H, dd, J=2.4, 12.0 Hz), 8.05 (1H, d, J=5.6 Hz), 8.61 (1H, brs), 9.50 (1H, brs).

ESI-MS (m/z): 587 [M+Na]$^+$.

Example 25

N-(4-{[2-({[{1-[2-(Dimethylamino)ethyl]piperidin-4-yl}(methyl)amino]carbonyl}amino)pyridin-4-yl]oxy}-2-fluorophenyl)-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) was added N-[1-(2-dimethylaminoethyl)piperidin-4-yl]-N-methylamine (69.5 mg), followed by stirring at room temperature for 22 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:3, and the precipitate was collected by filtration. This was washed with hexane and dried under aeration to provide the titled compound as white powder (31.4 mg, 65.9%).

$^1$H-NMR Spectrum (CDCl$_3$) δ (ppm): 1.60-1.83 (8H, m), 2.05-2.11 (2H, m), 2.24 (6H, s), 2.39-2.49 (4H, m), 2.88 (3H, s), 3.00 (2H, m), 4.13 (1H, m), 6.55 (1H, dd, J=2.4, 5.6 Hz), 6.91 (2H, m), 7.03 (2H, m), 7.21 (1H, s), 7.49 (2H, dd, J=4.8, 9.2 Hz), 7.68 (1H, d, J=2.4 Hz), 8.07 (1H, d, J=5.6 Hz), 8.18 (1H, m), 8.97 (1H, s), 9.21 (1H, s).

ESI-MS (m/z): 636 [M+H]+.

Example 26

N-(4-{[2-({[4-(Azetidin-1-ylmethyl)piperidin-1-yl]carbonyl}amino)pyridin-4-yl]oxy}-3-fluorophenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (50 mg) in N,N-dimethylformamide (1.0 ml) were added 4-(azetidin-1-ylmethyl)piperidine dihydrochloride (69 mg) and triethylamine (0.085 ml) at room temperature, followed by stirring for 3 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the titled compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (42.0 mg, 92%).

$^1$H-NMR Spectrum (CDCl$_3$) δ (ppm): 1.05-1.20 (2H, m), 1.45-1.80 (7H, m), 2.07 (2H, m), 2.28 (2H, d, J=6.8 Hz), 2.84 (2H, m), 3.10-3.25 (4H, m), 4.02 (2H, m), 6.55 (1H, dd, J=2.4, 5.6 Hz), 7.00-7.30 (5H, m), 7.40-7.50 (2H, m), 7.58 (1H, d, J=2.4 Hz), 7.68 (1H, dd, J=2.4, 12.0 Hz), 8.04 (1H, d, J=5.6 Hz), 8.55 (1H, brs), 9.49 (1H, brs).

ESI-MS (m/z): 605 [M+H]$^+$.

Example 27

N-(4-{[2-({[4-(Azetidin-1-ylmethyl)piperidin-1-yl]carbonyl}amino)pyridin-4-yl]oxy}phenyl)-N'-(4-fluorophenyl)cyclopropane-1,1-dicarboxamide

[4-(4-{[1-(4-Fluorophenylcarbamoyl)cyclopropanecarbonyl]amino}phenoxy)pyridin-2-yl]-N-(phenoxycarbonyl)carbamic acid phenyl ester (50 mg) was dissolved in N,N-dimethylformamide (1.0 ml), and 4-(azetidin-1-ylmethyl)piperidine dihydrochloride (70.2 mg), triethylamine (0.0862 ml) and water (0.100 ml) were added thereto in this order, followed by stirring for 62 hr. The reaction mixture was partitioned between ethyl acetate (50 ml) and a saturated aqueous solution of ammonium chloride (20 ml). The organic layer was washed with a saturated aqueous solution of ammonium chloride (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; ethyl acetate, then ethyl acetate:methanol=95:5). Fractions containing the target compound were concentrated under reduced pressure, and the resultant residue was suspended in diethyl ether (2 ml) and hexane (4 ml). The solid was collected by filtration and dried under aeration to provide the titled compound as white powder (35.8 mg, 78.9%).

$^1$H-NMR Spectrum (CDCl$_3$) δ (ppm): 1.06-1.30 (2H, m), 1.43-1.73 (5H, m), 1.75 (2H, m), 2.08 (2H, m), 2.31 (2H, m), 2.84 (2H, m), 3.20 (4H, m), 4.03 (2H, m), 6.53 (1H, dd, J=2.4, 6.0 Hz), 6.95-7.12 (4H, m), 7.43-7.65 (6H, m), 8.03 (1H, d, J=6.0 Hz), 8.87 (1H, brs), 9.14 (1H, brs).

ESI-MS (m/z): 587 [M+H]$^+$.

Example 28

N-(4-{[2-({[4-(2-Azetidin-1-ylethyl)piperazin-1-yl]carbonyl}amino)pyridin-4-yl]oxy}phenyl)-N'-(4-fluorophenyl)cyclopropane-1,1-dicarboxamide

[4-(4-{[1-(4-Fluorophenylcarbamoyl)cyclopropanecarbonyl]amino}phenoxy)pyridin-2-yl]-N-(phenoxycarbonyl)carbamic acid phenyl ester (50 mg) was dissolved in N,N-dimethylformamide (1.0 ml), and 1-[2-(azetidin-1-yl)ethyl]piperazine trihydrochloride (64.6 mg), triethylamine (0.129 ml) and water (0.100 ml) were added thereto in this order, followed by stirring for 20 hr. The reaction mixture was partitioned between ethyl acetate (50 ml) and a saturated aqueous solution of ammonium chloride (20 ml). The organic layer was washed with a saturated aqueous solution of ammonium chloride (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; ethyl acetate, then ethyl acetate:methanol=9:1). Fractions containing the target compound were concentrated under reduced pressure, and the resultant residue was suspended in diethyl ether (2 ml) and hexane (4 ml). The solid was collected by filtration and dried under aeration to provide the titled compound as white powder (23.8 mg, 51.2%).

¹H-NMR Spectrum (CDCl₃) δ (ppm): 1.50-1.90 (4H, m), 2.05-2.17 (2H, m), 2.33-2.42 (2H, m), 2.46 (4H, m), 2.50-2.65 (2H, m), 3.25 (4H, m), 3.49 (4H, m), 6.54 (1H, dd, J=2.4, 6.0 Hz), 6.94-7.16 (4H, m), 7.42-7.68 (6H, m), 8.03 (1H, d, J=6.0 Hz), 8.90 (1H, brs), 9.08 (1H, brs).

ESI-MS (m/z): 602 [M+H]⁺.

Example 29

N-(4-Fluorophenyl)-N'-(4-{[2-({[4-(pyrrolidin-1-ylmethyl)piperidin-1-yl]carbonyl}amino)pyridin-4-yl]oxy}phenyl)cyclopropane-1,1-dicarboxamide 4-(Pyrrolidin-1-ylmethyl)piperidine-1-carboxylic acid [4-(4-aminophenoxy)pyridin-2-yl]amide (125 mg) was dissolved in N,N-dimethylformamide (2 ml), and 1-(4-fluorophenylcarbamoyl)cyclopropanecarboxylic acid (176 mg), triethylamine (0.11 ml) and (1H-1,2,3-benzotriazol-1-yloxy)[tri(dimethylamino)]phosphonium hexafluorophosphate (349 mg) were added thereto in this order at room temperature, followed by stirring for 1 hr. Liquid-liquid separation was carried out after addition of ethyl acetate and a saturated aqueous solution of sodium hydrogencarbonate to the reaction mixture. The organic layer was washed with brine, and dried over anhydrous sodium sulfate. The solvent was concentrated under reduced pressure, and the resultant residue was purified by silica gel column chromatography (Fuji Silysia NH, eluent; heptane:ethyl acetate=1:5, then ethyl acetate). The solvent was concentrated under reduced pressure, and the resultant residue was suspended in diethyl ether (4 ml) and hexane (4 ml). The solid was collected by filtration and dried under aeration to provide the titled compound as white powder (121.2 mg, 63.8%).

¹H-NMR Spectrum (CDCl₃) δ (ppm): 1.10-1.35 (2H, m), 1.50-1.75 (5H, m), 1.75-1.90 (6H, m), 2.35 (2H, m), 2.45-2.58 (4H, m), 2.86 (2H, m), 4.05 (2H, m), 6.54 (1H, dd, J=2.4, 5.6 Hz), 6.90-7.14 (4H, m), 7.44-7.62 (6H, m), 8.03 (1H, d, J=5.6 Hz), 8.87 (1H, brs), 9.18 (1H, brs).

ESI-MS (m/z): 601 [M+H]⁺.

Example 30

N-[4-({2-[({4-[2-(Dimethylamino)ethyl]piperazin-1-yl}carbonyl)amino]pyridin-4-yl}oxy)phenyl]-N'-(4-fluorophenyl)cyclopropane-1,1-dicarboxamide To [4-(4-{[1-(4-fluorophenylcarbamoyl)cyclopropanecarbonyl]amino}phenoxy)pyridin-2-yl]-N-(phenoxycarbonyl)carbamic acid phenyl ester (50 mg) was added a solution of 1-[2-(dimethylamino)ethyl]piperazine (48.6 mg) in N,N-dimethylformamide (1.0 ml) at room temperature, followed by stirring for 5 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (34.7 mg, 76%).

¹H-NMR Spectrum (CDCl₃) δ (ppm): 1.50-1.74 (4H, m), 2.27 (6H, s), 2.40-2.56 (8H, m), 3.46-3.56 (4H, m), 6.53 (1H, dd, J=2.4, 5.6 Hz), 7.00-7.10 (4H, m), 7.17 (1H, brs), 7.44-7.62 (5H, m), 8.03 (1H, d, J=5.6 Hz), 8.85 (1H, brs), 9.01 (1H, brs).

ESI-MS (m/z): 590 [M+H]⁺.

Example 31

N-(4-Fluorophenyl)-N'-(4-{[2-({[4-(1-methylpiperidin-4-yl)piperazin-1-yl]carbonyl}amino)pyridin-4-yl]oxy}phenyl)cyclopropane-1,1-dicarboxamide To a solution of [4-(4-{[1-(4-fluorophenylcarbamoyl)cyclopropanecarbonyl]amino}phenoxy)pyridin-2-yl]-N-(phenoxycarbonyl)carbamic acid phenyl ester (50 mg) in N,N-dimethylformamide (1.0 ml) was added 1-(1-methylpiperidin-4-yl)piperazine (56.7 mg) at room temperature, followed by stirring for 5 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (40.1 mg, 84%).

¹H-NMR Spectrum (CDCl₃) δ (ppm): 1.40-1.82 (8H, m), 1.95 (2H, m), 2.24-2.34 (4H, m), 2.54-2.60 (4H, m), 2.92 (2H, m), 3.44-3.54 (4H, m), 6.53 (1H, dd, J=2.4, 5.6 Hz), 7.00-7.10 (4H, m), 7.17 (1H, brs), 7.44-7.62 (5H, m), 8.04 (1H, d, J=5.6 Hz), 8.85 (1H, brs), 9.01 (1H, brs).

ESI-MS (m/z): 616 [M+H]⁺.

Example 32

N-(4-Fluorophenyl)-N'-(4-{[2-({[4-(4-methylpiperazin-1-yl)piperidin-1-yl]carbonyl}amino)pyridin-4-yl]oxy}phenyl)cyclopropane-1,1-dicarboxamide To a solution of [4-(4-{[1-(4-fluorophenylcarbamoyl)cyclopropanecarbonyl]amino}phenoxy)pyridin-2-yl]-N-(phenoxycarbonyl)carbamic acid phenyl ester (50 mg) in N,N-dimethylformamide (1.0 ml) was added 1-methyl-4-(piperidin-4-yl)piperazine (56.7 mg) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (37.7 mg, 79%).

$^1$H-NMR Spectrum (CDCl$_3$) δ (ppm): 1.40-1.94 (9H, m), 2.28 (3H, s), 2.30-2.70 (8H, m), 2.88 (2H, m), 4.02-4.14 (2H, m), 6.54 (1H, dd, J=2.4, 5.6 Hz), 7.00-7.10 (4H, m), 7.23 (1H, brs), 7.45-7.60 (5H, m), 8.03 (1H, d, J=5.6 Hz), 8.89 (1H, brs), 9.12 (1H, brs).

ESI-MS (m/z): 616 [M+H]$^+$.

Example 33

N-(3-Fluoro-4-{[6-({[methyl(1-methylpiperidin-4-yl)amino]carbonyl}amino)pyrimidin-4-yl]oxy}phenyl)-N'-(4-fluorophenyl)cyclopropane-1,1-dicarboxamide

[6-(2-Fluoro-4-{[1-(4-fluorophenylcarbamoyl)cyclopropanecarbonyl]amino}phenoxy)pyrimidin-4-yl]carbamic acid phenyl ester (40 mg) was dissolved in N,N-dimethylformamide (1.0 ml), and 1-methyl-4-(methylamino)piperidine (0.045 ml) was added thereto, followed by stirring for 3 hr. The reaction mixture was partitioned between ethyl acetate (50 ml) and a saturated aqueous solution of ammonium chloride (20 ml). The organic layer was washed with a saturated aqueous solution of ammonium chloride (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; ethyl acetate, then ethyl acetate:methanol=95:5). Fractions containing the target compound were concentrated under reduced pressure, and the resultant residue was suspended in diethyl ether (2 ml) and hexane (4 ml). The solid was collected by filtration and dried under aeration to provide the titled compound as white powder (33.7 mg, 79.3%).

$^1$H-NMR Spectrum (CDCl$_3$) δ (ppm): 1.50-1.75 (6H, m), 1.75-1.90 (2H, m), 2.06-2.17 (2H, m), 2.30 (3H, s), 2.92 (3H, s), 2.96 (2H, m), 4.10-4.25 (1H, m), 7.05 (2H, m), 7.12-7.24 (2H, m), 7.31 (1H, brs), 7.40-7.50 (2H, m), 7.65 (1H, m), 7.68 (1H, dd, J=2.0, 12.0 Hz), 8.34 (1H, m), 8.49 (1H, brs), 9.48 (1H, brs).

ESI-MS (m/z): 602 [M+Na]$^+$.

Example 34

N-{4-[(6-{[(4-Azetidin-1-ylpiperidin-1-yl)carbonyl]amino}pyrimidin-4-yl)oxy]-3-fluorophenyl}-N'-(4-fluorophenyl)cyclopropane-1,1-dicarboxamide

[6-(2-Fluoro-4-{[1-(4-fluorophenylcarbamoyl)cyclopropanecarbonyl]amino}phenoxy)pyrimidin-4-yl]carbamic acid phenyl ester (35.5 mg) was dissolved in N,N-dimethylformamide (1.0 ml), and 4-(azetidin-1-yl)piperidine dihydrochloride (21 mg), triethylamine (0.0198 ml) and water (0.10 ml) were added thereto in this order, followed by stirring for 21 hr. The reaction mixture was partitioned between ethyl acetate (50 ml) and a saturated aqueous solution of ammonium chloride (20 ml). The organic layer was washed with a saturated aqueous solution of ammonium chloride (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; ethyl acetate, then ethyl acetate:methanol=95:5). Fractions containing the target compound were concentrated under reduced pressure, and the resultant residue was suspended in diethyl ether (2 ml) and hexane (4 ml). The solid was collected by filtration and dried under aeration to provide the titled compound as white powder (26.5 mg, 68.8%).

$^1$H-NMR Spectrum (CDCl$_3$) δ (ppm): 1.15-1.42 (4H, m), 1.45-1.90 (4H, m), 2.09 (2H, m), 2.28 (1H, m), 3.11 (2H, m), 3.16-3.35 (4H, m), 3.80-3.90 (2H, m), 7.00-7.12 (2H, m), 7.12-7.26 (2H, m), 7.37 (1H, brs), 7.41-7.52 (2H, m), 7.59 (1H, s), 7.63-7.76 (1H, m), 8.34 (1H, m), 8.53 (1H, brs), 9.42 (1H, brs).

ESI-MS (m/z): 614 [M+Na]$^+$.

Example 35

N-[3-Fluoro-4-({6-{(morpholin-4-ylcarbonyl)amino}pyrimidin-4-yl}oxy)phenyl]-N'-(4-fluorophenyl)cyclopropane-1,1-dicarboxamide

[6-(2-Fluoro-4-{[1-(4-fluorophenylcarbamoyl)cyclopropanecarbonyl]amino}phenoxy)pyrimidin-4-yl]carbamic acid phenyl ester (40 mg) was dissolved in N,N-dimethylformamide (1.0 ml), and morpholine (0.045 ml) was added thereto, followed by stirring for 26 hr. The reaction mixture was partitioned between ethyl acetate (50 ml) and a saturated aqueous solution of ammonium chloride (20 ml). The organic layer was washed with a saturated aqueous solution of ammonium chloride (20 ml), water (20 ml) and brine (20 ml) in this order, and dried over anhydrous sodium sulfate. The solvent was removed under reduced pressure, and the resultant residue was purified by silica gel column chromatography (Fuji Silysia NH, eluent; heptane:ethyl acetate=1:5, then ethyl acetate). Fractions containing the target compound were concentrated under reduced pressure, and the resultant residue was suspended in diethyl ether (2 ml) and hexane (4 ml). The solid was collected by filtration and dried under aeration to provide the titled compound as white powder (18.3 mg, 82.9%).

$^1$H-NMR Spectrum (CDCl$_3$) δ (ppm): 1.54-1.67 (2H, m), 1.68-1.78 (2H, m), 3.52 (4H, m), 3.75 (4H, m), 7.06 (2H, m), 7.12-7.25 (2H, m), 7.31-7.38 (1H, m), 7.45 (2H, m), 7.61 (1H, s), 7.69 (1H, dd, J=2.0, 11.2 Hz), 8.35 (1H, s), 8.42 (1H, brs), 9.52 (1H, brs).

ESI-MS (m/z): 561 [M+Na]$^+$.

Example 36

N-(4-{[2-({[(3R)-3-(Dimethylamino)pyrrolidin-1-yl]carbonyl}amino)pyridin-4-yl]oxy}-3-fluorophenyl)-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (50 mg) in N,N-dimethylformamide (1.0 ml) was added (3R)-3-dimethylaminopyrrolidine (0.050 ml) at room temperature, followed by stirring for 4 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:3 to the resultant residue. The solid was collected by filtration and dried under aeration to provide the titled compound as white powder (21.8 mg, 51%).

$^1$H-NMR Spectrum (CDCl$_3$) δ (ppm): 1.50-1.75 (4H, m), 1.87 (1H, m), 2.16 (1H, m), 2.27 (6H, s), 2.75 (1H, m), 3.21 (1H, m), 3.39 (1H, m), 3.64 (1H, m), 3.71 (1H, m), 6.58 (1H, dd, J=2.4, 5.6 Hz), 7.00-7.30 (5H, m), 7.40-7.50 (2H, m), 7.63 (1H, d, J=2.4 Hz), 7.69 (1H, dd, J=2.4, 12.0 Hz), 8.05 (1H, d, J=5.6 Hz), 8.61 (1H, brs), 9.50 (1H, brs)

ESI-MS (m/z): 587 [M+Na]$^+$.

Example 37

N-(4-{[2-({[4-(Azetidin-1-ylmethyl)piperidin-1-yl]carbonyl}amino)pyridin-4-yl]oxy}-2-fluorophenyl)-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) was added 4-(azetidin-1-ylmethyl)piperidine dihydrochloride (85.2 mg), followed by stirring at room temperature for 16 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:3, and the precipitate was collected by filtration. This was washed with hexane and dried under aeration to provide the titled compound as white powder (21.9 mg, 48.3%).

$^1$H-NMR Spectrum (CDCl$_3$) δ (ppm): 1.16 (2H, m), 1.66 (3H, m), 1.75 (4H, m), 2.08 (2H, m), 2.31 (2H, d, J=6.8 Hz), 2.85 (2H, m), 3.20 (4H, m), 4.04 (2H, m), 6.54 (1H, dd, J=2.4, 6.0 Hz), 6.91 (2H, m), 7.04 (2H, m), 7.24 (1H, brs), 7.50 (2H, dd, J=5.0, 9.0 Hz), 7.63 (1H, d, J=2.4 Hz), 8.06 (1H, d, J=6.0 Hz), 8.19 (1H, m), 8.80 (1H, s), 9.23 (1H, s).

ESI-MS (m/z): 605 [M+H]$^+$.

Example 38

N-[4-({2-[({4-[3-(Dimethylamino)azetidin-1-yl]piperidin-1-yl}carbonyl)amino]pyridin-4-yl}oxy)phenyl]-N'-(4-fluorophenyl)cyclopropane-1,1-dicarboxamide To a solution of phenyl N-[4-(4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) were added N,N-dimethyl-N-[1-(piperidin-4-yl)azetidin-3-yl]amine trihydrochloride (90.5 mg), triethylamine (0.129 ml) and water (0.10 ml), followed by stirring at room temperature for 12 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:3, and the precipitate was collected by filtration. This was washed with hexane and dried under aeration to provide the titled compound as white powder (11.8 mg, 24.8%).

$^1$H-NMR Spectrum (CDCl$_3$) δ (ppm): 1.31 (2H, m), 1.64-1.76 (6H, m), 2.14 (6H, s), 2.30 (1H, m), 2.90 (3H, m), 3.03 (2H, m), 3.52 (2H, m), 3.88 (2H, m), 6.53 (1H, dd, J=2.2, 6.0 Hz), 7.06 (2H, m), 7.08 (2H, d, J=8.8 Hz), 7.24 (1H, m), 7.49 (2H, dd, J=4.6, 9.0 Hz), 7.55 (3H, m), 8.02 (1H, d, J=6.0 Hz), 8.81 (1H, m), 9.10 (1H, m).

ESI-MS (m/z): 638 [M+Na]$^+$.

Example 39

N-(4-{[2-({[{1-[2-(Dimethylamino)ethyl]piperidin-4-yl}(methyl)amino]carbonyl}amino)pyridin-4-yl]oxy}phenyl)-N'-(4-fluorophenyl)cyclopropane-1,1-dicarboxamide To a solution of phenyl N-[4-(4-{[1-(4-fluorophenylcarbamoyl)cyclopropanecarbonyl]amino}phenoxy)pyridin-2-yl]-N-phenoxycarbonylcarbamate (50.0 mg) in N,N-dimethylformamide (2.0 ml) was added N-[1-(2-dimethylaminoethyl)piperidin-4-yl]-N-methylamine (69.5 mg), followed by stirring at room temperature for 12 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:3, and the precipitate was collected by filtration. This was washed with hexane and dried under aeration to provide the titled compound as white powder (15.8 mg, 33.1%).

$^1$H-NMR Spectrum (CDCl$_3$) δ (ppm): 1.57-1.83 (8H, m), 2.00 (2H, m), 2.23 (6H, s), 2.36-2.45 (4H, m), 2.87 (3H, s), 2.92 (2H, m), 4.08 (1H, m), 6.57 (1H, dd, J=2.4, 5.6 Hz), 7.02 (2H, m), 7.06 (2H, d, J=9.0 Hz), 7.22 (1H, brs), 7.49 (2H, dd, J=4.8, 9.2 Hz), 7.54 (2H, d, J=9.0 Hz), 7.62 (1H, d, 3=2.4 Hz), 8.05 (1H, d, J=5.6 Hz), 9.06 (1H, s), 9.32 (1H, s).

ESI-MS (m/z): 640 [M+Na]$^+$.

Example 40

N-(4-Fluorophenyl)-N'-(2-fluoro-4-{[2-({[4-(pyrrolidin-1-ylmethyl)piperidin-1-yl]carbonyl}amino)pyridin-4-yl]oxy}phenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (41.0 mg) in N,N-dimethylformamide (2.0 ml) were added 4-(pyrrolidin-1-ylmethyl)piperidine dihydrochloride (74.2 mg), triethylamine (0.0857 ml) and water (0.20 ml), followed by stirring at room temperature for 13 hr. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, heptane: ethyl acetate=1:2, ethyl acetate, then ethyl acetate:methanol=20:1). Fractions containing the target compound were concentrated. To the residue were added diethyl ether and hexane, and the precipitate was collected by filtration. This was washed with hexane and dried under aeration to provide the titled compound as white powder (10.5 mg, 28%).

$^1$H-NMR Spectrum (CDCl$_3$) δ (ppm): 1.21 (2H, m), 1.65-1.92 (11H, m), 2.46 (2H, m), 2.66 (4H, m), 2.88 (2H, m), 4.08 (2H, m), 6.55 (1H, dd, J=2.4, 5.6 Hz), 6.91 (2H, m), 7.04 (2H, m), 7.29 (1H, brs), 7.50 (2H, dd, J=4.6, 9.0 Hz), 7.62 (1H, d, J=2.4 Hz), 8.06 (1H, d, J=5.6 Hz), 8.18 (1H, m), 8.85 (1H, s), 9.25 (1H, s).

ESI-MS (m/z): 619 [M+H]$^+$.

Example 41

N-(4-{[2-({[(3S)-3-(Dimethylamino)pyrrolidin-1-yl]carbonyl}amino)pyridin-4-yl]oxy}phenyl)-N'-(4-fluorophenyncyclopropane-1,1-dicarboxamide To a solution of [4-(4-{[1-(4-fluorophenylcarbamoyl)cyclopropanecarbonyl]amino}phenoxy)pyridin-2-yl]-N-(phenoxycarbonyl)carbamic acid phenyl ester (50 mg) in N,N-dimethylformamide (1.0 ml) was added (3S)-3-dimethylaminopyrrolidine (0.050 ml) at room temperature, followed by stirring for 3 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:3 to the resultant residue. The solid was collected by filtration and dried under aeration to provide the titled compound as white powder (23.0 mg, 54%).

$^1$H-NMR Spectrum (CDCl$_3$) δ (ppm): 1.50-1.75 (4H, m), 1.89 (1H, m), 2.17 (1H, m), 2.29 (6H, s), 2.75 (1H, m), 3.23 (1H, m), 3.41 (1H, m), 3.65 (1H, m), 3.73 (1H, m), 6.54 (1H, dd, J=2.4, 5.6 Hz), 6.99-7.14 (5H, m), 7.44-7.58 (4H, m), 7.66 (1H, d, J=2.4 Hz), 8.03 (1H, d, J=5.6 Hz), 8.81 (1H, brs), 9.01 (1H, brs).

ESI-MS (m/z): 547 [M+H]$^+$.

Example 42

N-(4-{[2-({[(3R)-3-Dimethylamino)pyrrolidin-1-yl]carbonyl}amino)pyridin-4-yl]oxy}phenyl)-N'-(4-fluorophenyl)cyclopropane-1,1-dicarboxamide To a solution of [4-(4-{[1-(4-fluorophenylcarbamoyl)cyclopropanecarbonyl]amino}phenoxy)pyridin-2-yl]-N-(phenoxycarbonyl)carbamic acid phenyl ester (50 mg) in N,N-dimethylformamide (1.0 ml) was added (3R)-3-dimethylaminopyrrolidine (0.050 ml) at room temperature, followed by stirring for 3 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of ethyl acetate:heptane=1:5 to the resultant residue. The solid was collected by filtration and dried under aeration to provide the titled compound as white powder (16.3 mg, 39%).

$^1$H-NMR Spectrum (CDCl$_3$) δ (ppm): 1.50-1.75 (4H, m), 1.89 (1H, m), 2.17 (1H, m), 2.29 (6H, s), 2.75 (1H, m), 3.23 (1H, m), 3.41 (1H, m), 3.65 (1H, m), 3.73 (1H, m), 6.54 (1H, dd, J=2.4, 5.6 Hz), 6.99-7.14 (5H, m), 7.44-7.58 (4H, m), 7.66 (1H, d, J=2.4 Hz), 8.03 (1H, d, J=5.6 Hz), 8.81 (1H, brs), 9.01 (1H, brs).

ESI-MS (m/z): 547 [M+H]$^+$.

Example 43

N-[2-Chloro-4-({21({[3-(diethylamino)propyl]amino}carbonyl)amino]pyridin-4-yl}oxy)phenyl]-N'-(4-fluorophenyl)cyclopropane-1,1-dicarboxamide To a solution of 1-[(4-amino-3-chlorophenoxy)pyridin-2-yl]-3-(3-dimethylaminopropyl)urea (67.0 mg) in N,N-dimethylformamide (2.0 ml) were added 1-(4-fluorophenylcarbamoyl)cyclopropanecarboxylic acid (115 mg), benzotriazol-1-yltris(dimethylamino)phosphonium hexafluorophosphate (227 mg) and triethylamine (0.0681 ml), followed by stirring at room temperature for 2 days. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. The residue was purified by LC-MS. Fractions containing the target compound were concentrated, the residue was partitioned between ethyl acetate and saturated sodium hydrogencarbonate. The organic layer was washed with brine, and dried over anhydrous sodium sulfate. The solvent was removed to provide the titled compound as colorless powder (9.0 mg, 8.8%).

$^1$H-NMR Spectrum (CDCl$_3$) δ (ppm): 1.10 (6H, t, J=7.0 Hz), 1.68-1.83 (6H, m), 2.70 (6H, m), 3.36 (2H, m), 6.31 (1H, m), 6.49 (1H, m), 7.04 (3H, m), 7.17 (1H, m), 7.52 (2H, dd, J=4.4, 8.4 Hz), 7.90 (1H, m), 8.02 (1H, d, J=6.0 Hz), 8.31 (1H, d, J=8.8 Hz), 9.32 (3H, m).

ESI-MS (neg.) (m/z): 595 [M−H]$^-$.

Example 44

N-(4-{[2-({[[3-Diethylamino)propyl](methyl)amino]carbonyl}amino)pyridin-4-yl]oxy}-3-fluorophenyl)-N'-(4-fluorophenyl)cyclopropane-1,1-dicarboxamide To a solution of 1-[(4-amino-2-fluorophenoxy)pyridin-2-yl]-3-(3-dimethylaminopropyl)-3-methylurea (50.0 mg) in N,N-dimethylformamide (2.0 ml) were added 1-(4-fluorophenylcarbamoyl)cyclopropanecarboxylic acid (85.7 mg), benzotriazol-1-yltris(dimethylamino)phosphonium hexafluorophosphate (170 mg) and triethylamine (0.0510 ml), followed by stirring at room temperature for 2 days. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, hexane:ethyl acetate=1:2, ethyl acetate, then ethyl acetate:methanol=20:1). Fractions containing the target compound were concentrated to provide the titled compound as colorless powder (30.0 mg, 39.4%).

$^1$H-NMR Spectrum (CDCl$_3$) δ (ppm): 1.05 (6H, t, J=7.2 Hz), 1.76 (4H, m), 2.45 (2H, m), 2.64 (6H, m), 2.80 (3H, s), 3.37 (2H, m), 6.57 (1H, dd, J=2.4, 5.6 Hz), 6.98 (2H, m), 7.05 (1H, m), 7.19 (2H, m), 7.44-7.51 (3H, m), 7.63 (1H, dd, J=2.2, 8.2 Hz), 8.07 (1H, d, J=2.4 Hz), 9.46 (1H, s), 9.62 (1H, s).

ESI-MS (neg.) (m/z): 593 [M−H]$^-$.

Example 45

N-[4-({2-[({[3-(Diethylamino)propyl]amino}carbonyl)amino]pyridin-4-yl}oxy)-3-methylphenyl]-N'-(4-fluorophenyl)cyclopropane-1,1-dicarboxamide To a solution of 1-[(4-amino-2-methylphenoxy)pyridin-2-yl]-3-(3-dimethylaminopropyl)urea (50.0 mg) in N,N-dimethylformamide (2.0 ml) were added 1-(4-fluorophenylcarbamoyl)cyclopropanecarboxylic acid (90.4 mg), benzotriazol-1-yltris(dimethylamino)phosphonium hexafluorophosphate (179 mg) and triethylamine (0.0538 ml), followed by stirring at room temperature for 2 days. The reaction mixture was partitioned between ethyl acetate and a 1N aqueous solution of sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. The residue was purified by LC-MS. Fractions containing the target compound were concentrated, and the residue was partitioned between ethyl acetate and saturated sodium hydrogencarbonate. The organic layer was washed with brine, and dried over anhydrous sodium sulfate. The solvent was removed to provide the titled compound as colorless powder (22.6 mg, 29.0%).

$^1$H-NMR Spectrum (CDCl$_3$) δ (ppm): 1.05 (6H, t, J=7.0 Hz), 1.63-1.79 (6H, m), 2.13 (3H, s), 2.56-2.63 (6H, m), 3.33 (2H, m), 6.14 (1H, m), 6.43 (1H, dd, J=2.4, 6.0 Hz), 6.96 (1H, d, J=8.8 Hz), 7.03 (2H, m), 7.40 (1H, dd, J=2.4, 8.8 Hz), 7.47-7.51 (3H, m), 7.81 (1H, m), 7.95 (1H, d, J=6.0 Hz), 9.12 (1H, brs), 9.25 (1H, brs), 9.28 (1H, brs).

ESI-MS (m/z): 577 [M+H]$^+$.

Example 46

N-(4-{[2-({[(3S)-3-(Dimethylamino)pyrrolidin-1-yl]carbonyl}amino)pyridin-4-yl]oxy}-2-fluorophenyl)-N'-(4-fluorophenyncyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (60.8 mg) in N,N-dimethylformamide (1.0 ml) was added (3S)-(−)-3-dimethylaminopyrrolidine (41.7 mg), followed by stirring at room temperature for 7 hr. The reaction mixture was partitioned between ethyl acetate and 1N sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:2, and the precipitated solid was collected by filtration. This was dried under aeration to provide the titled compound as white powder (18.5 mg, 35.8%).

$^1$H-NMR Spectrum (CDCl$_3$) δ (ppm): 1.64-1.76 (4H, m), 1.86 (1H, m), 2.17 (1H, m), 2.27 (6H, s), 2.74 (1H, m), 3.21 (1H, m), 3.41 (1H, m), 3.65 (1H, m), 3.72 (1H, m), 6.56 (1H, dd, J=2.4, 5.6 Hz), 6.91 (2H, d, J=9.2 Hz), 7.03 (2H, m), 7.07 (1H, brs), 7.50 (2H, m), 7.68 (1H, d, J=2.4 Hz), 8.06 (1H, d, J=5.6 Hz), 8.18 (1H, m), 8.88 (1H, m), 9.27 (1H, s).

ESI-MS (m/z): 587 [M+Na]$^+$.

Example 47

N-(4-{[2-({[(3R)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide To a solution of phenyl N-[4-(3-fluoro-4-{[1-(4-fluorophenylcarbamoyl)cyclopropanecarbonyl]amino}phenoxy)pyridin-2-yl]-N-phenoxycarbonylcarbamate (60.8 mg) in N,N-dimethylformamide (1.0 ml) was added (3R)-(+)-3-dimethylaminopyrrolidine (41.7 mg), followed by stirring at room temperature for 7 hr. The reaction mixture was partitioned between ethyl acetate and 1N sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=20:1). Fractions containing the target compound were concentrated. To the residue was added diethyl ether:hexane=1:2, and the precipitated solid was collected by filtration. This was dried under aeration to provide the titled compound as white powder (18.3 mg). This was purified again by silica gel column chromatography (Fuji Silysia NH, hexane:ethyl acetate=1:2, ethyl acetate, then ethyl acetate:methanol=20:1). Fractions containing the target compound were concentrated. To the residue was added diethyl ether:hexane=1:2, and the precipitated solid was collected by filtration. This was dried under aeration to provide the titled compound as white powder (12.3 mg, 23.8%).

$^1$H-NMR Spectrum (CDCl$_3$) δ (ppm): 1.64-1.76 (4H, m), 1.87 (1H, m), 2.17 (1H, m), 2.27 (6H, s), 2.74 (1H, m), 3.21 (1H, m), 3.41 (1H, m), 3.65 (1H, m), 3.72 (1H, m), 6.56 (1H, dd, J=2.4, 5.6 Hz), 6.91 (2H, m), 7.03 (2H, m), 7.09 (1H, brs), 7.50 (2H, m), 7.69 (1H, d, J=2.4 Hz), 8.06 (1H, d, J=5.6 Hz), 8.18 (1H, m), 8.87 (1H, m), 9.26 (1H, s).

ESI-MS (m/z): 587 [M+Na]$^+$.

Example 48

N-(2-Fluoro-4-{[2-([methyl(1-methylpiperidin-4-yl)amino]carbonyl}amino)pyridin-4-yl]oxy}phenyl)-N'-phenylcyclopropane-1,1-dicarboxamide To a solution of 1-(2-fluoro-4-{2-[3-methyl-3-(1-methylpiperidin-4-yl)ureido]pyridin-4-yloxy}phenyl)carbamoylcyclopropanecarboxylic acid (40 mg) in N,N-dimethylformamide (1.0 ml) were added aniline (0.015 ml), triethylamine (0.023 ml) and benzotriazol-1-yloxytris(dimethylamino)phosphonium hexafluorophosphate (72.9 mg) at room temperature, followed by stirring for 5 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed, and the resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (24.5 mg, 53%).
$^1$H-NMR Spectrum (CDCl$_3$) δ (ppm): 1.50-1.85 (8H, m), 2.00-2.15 (2H, m), 2.30 (3H, s), 2.85-3.00 (5H, m), 4.17 (1H, m), 6.54 (1H, dd, J=2.4, 5.6 Hz), 6.90-6.93 (2H, m), 7.15 (1H, m), 7.21 (1H, brs), 7.33-7.38 (2H, m), 7.50-7.55 (2H, m), 7.69 (1H, d, J=2.4 Hz), 8.07 (1H, d, J=5.6 Hz), 8.22 (1H, m), 8.91 (1H, brs), 9.16 (1H, brs).
ESI-MS (m/z): 583 [M+Na]$^+$.

Example 49

N-Benzyl-N'-(2-fluoro-4-{[2-({[methyl(1-methylpiperidin-4-yl)amino]carbonyl}amino)pyridin-4-yl]oxy}phenyl)cyclopropane-1,1-dicarboxamide To a solution of 1-(2-fluoro-4-{2-[3-methyl-3-(1-methylpiperidin-4-yl)ureido]pyridin-4-yloxy}phenyl)carbamoylcyclopropanecarboxylic acid (40 mg) in N,N-dimethylformamide (1.0 ml) were added benzylamine (0.018 ml), triethylamine (0.023 ml) and benzotriazol-1-yloxytris(dimethylamino)phosphonium hexafluorophosphate (72.9 mg) at room temperature, followed by stirring for 32 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed, and the resultant residue was purified by silica gel column chromatography (Fuji Silysia NH, eluent; ethyl acetate, then ethyl acetate:methanol=97:3). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (27.1 mg, 57%).
$^1$H-NMR Spectrum (CDCl$_3$) δ (ppm): 1.50-1.85 (8H, m), 2.00-2.15 (2H, m), 2.29 (3H, s), 2.80-3.00 (5H, m), 4.18 (1H, m), 4.49 (2H, d, J=5.6 Hz), 6.22 (1H, m), 6.52 (1H, dd, J=2.4, 5.6 Hz), 6.85-6.95 (2H, m), 7.17 (1H, brs), 7.20-7.40 (5H, m), 7.69 (1H, d, J=2.4 Hz), 8.05 (1H, d, J=5.6 Hz), 8.27 (1H, m), 10.72 (1H, brs).
ESI-MS (m/z): 575 [M+H]$^+$.

Example 50

N-(2-Fluoro-4-{[2-({[methyl(1-methylpiperidin-4-yl)amino]carbonyl}amino)pyridin-4-yl]oxy}phenyl)-N'-(1-methylpiperidin-4-yl)cyclopropane-1,1-dicarboxamide To a solution of 1-(2-fluoro-4-{2-[3-methyl-3-(1-methylpiperidin-4-yl)ureido]pyridin-4-yloxy}phenyl)carbamoylcyclopropanecarboxylic acid (40 mg) in N,N-dimethylformamide (1.0 ml) were added 4-amino-1-methylpiperidine (18.8 mg), triethylamine (0.023 ml) and benzotriazol-1-yloxytris(dimethylamino)phosphonium hexafluorophosphate (72.9 mg) at room temperature, followed by stirring for 8 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed, and the resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (20.0 mg, 42%).
$^1$H-NMR Spectrum (CDCl$_3$) δ (ppm): 1.40-2.20 (16H, m), 2.29 (6H, s), 2.70-3.00 (7H, m), 3.83 (1H, m), 4.17 (1H, m), 5.85 (1H, m), 6.52 (1H, dd, J=2.4, 5.6 Hz), 6.85-6.95 (2H, m), 7.20 (1H, brs), 7.69 (1H, d, J=2.4 Hz), 8.05 (1H, d, J=5.6 Hz), 8.27 (1H, m), 10.68 (1H, brs).
ESI-MS (m/z): 582 [M+H]$^+$.

Example 51

N-(2-Fluoro-4-{[2-({[methyl(1-methylpiperidin-4-yl)amino]carbonyl}amino)pyridin-4-yl]oxy}phenyl)-N'-pyridin-3-ylcyclopropane-1,1-dicarboxamide To a solution of 1-(2-fluoro-4-{2-[3-methyl-3-(1-methylpiperidin-4-yl)ureido]pyridin-4-yloxy}phenyl)carbamoylcyclopropanecarboxylic acid (40 mg) in N,N-dimethylformamide (1.0 ml) were added 3-aminopyridine (15.5 mg), triethylamine (0.023 ml) and benzotriazol-1-yloxytris(dimethylamino)phosphonium hexafluorophosphate (72.9 mg) at room temperature, followed by stirring for 30 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed, and the resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (14.7 mg, 32%).
$^1$H-NMR Spectrum (CDCl$_3$) δ (ppm): 1.50-1.85 (8H, m), 2.00-2.15 (2H, m), 2.30 (3H, s), 2.85-3.00 (5H, m), 4.17 (1H, m), 6.56 (1H, dd, J=2.4, 5.6 Hz), 6.90-6.95 (2H, m), 7.10-7.30 (2H, m), 7.69 (1H, d, J=2.4 Hz), 8.08 (1H, d, J=5.6 Hz), 8.13

(1H, m), 8.18 (1H, m), 8.30 (1H, brs), 8.38 (1H, dd, J=1.6, 4.8 Hz), 8.66 (1H, d, J=2.4 Hz), 9.87 (1H, brs).
ESI-MS (neg.) (m/z): 560 [M–H]⁻.

Example 52

N-Cyclopentyl-N'-(2-fluoro-4-{[2-({[methyl(1-methylpiperidin-4-yl)amino]carbonyl}amino)pyridin-4-yl]oxy}phenyl)cyclopropane-1,1-dicarboxamide To a solution of 1-(2-fluoro-4-{2-[3-methyl-3-(1-methylpiperidin-4-yl)ureido]pyridin-4-yloxy}phenyl)carbamoyl-cyclopropanecarboxylic acid (40 mg) in N,N-dimethylformamide (1.0 ml) were added cyclopentylamine (0.0163 ml), triethylamine (0.023 ml) and benzotriazol-1-yloxytris(dimethylamino)phosphonium hexafluorophosphate (72.9 mg) at room temperature, followed by stirring for 25 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed, and the resultant residue was purified by silica gel column chromatography (Fuji Silysia NH, eluent; ethyl acetate, then ethyl acetate:methanol=97:3). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (23.2 mg, 51%).
¹H-NMR Spectrum (CDCl₃) δ (ppm): 1.25-1.90 (15H, m), 2.00-2.20 (4H, m), 2.30 (3H, s), 2.85-3.00 (5H, m), 4.18 (1H, m), 5.82 (1H, m), 6.52 (1H, dd, J=2.4, 5.6 Hz), 6.85-6.92 (2H, m), 7.16 (1H, brs), 7.69 (1H, d, J=2.4 Hz), 8.05 (1H, d, J=5.6 Hz), 8.27 (1H, m), 10.74 (1H, brs).
ESI-MS (m/z): 553 [M+H]⁺.

Example 53

N-(2,2-Dimethylpropyl)-N'-(2-fluoro-4-{[2-({[methyl(1-methylpiperidin-4-yl)amino]carbonyl}amino)pyridin-4-yl]oxy}phenyl)cyclopropane-1,1-dicarboxamide To a solution of 1-(2-fluoro-4-{2-[3-methyl-3-(1-methylpiperidin-4-yl)ureido]pyridin-4-yloxy}phenyl)carbamoyl-cyclopropanecarboxylic acid (40 mg) in N,N-dimethylformamide (1.0 ml) were added neopentylamine (0.0194 ml), triethylamine (0.023 ml) and benzotriazol-1-yloxytris(dimethylamino)phosphonium hexafluorophosphate (72.9 mg) at room temperature, followed by stirring for 22 hr. Liquid-liquid separation was carried out after addition of ethyl acetate and water to the reaction mixture. The organic layer was washed with a saturated aqueous solution of sodium hydrogencarbonate and brine, and dried over anhydrous sodium sulfate. The solvent was removed, and the resultant residue was purified by silica gel column chromatography (Fuji Silysia NH, eluent; ethyl acetate, then ethyl acetate:methanol=97:3). Fractions containing the target compound were concentrated under reduced pressure. A solid was precipitated by addition of diethyl ether:heptane=1:3 to the resultant residue. The solvent was removed under reduced pressure. The solid residue was dried under reduced pressure to provide the titled compound as white powder (23.2 mg, 51%).
¹H-NMR Spectrum (CDCl₃) δ (ppm): 0.93 (9H, s), 1.50-1.90 (8H, m), 2.00-2.20 (2H, m), 2.30 (3H, s), 2.85-3.00 (5H, m), 3.13 (2H, d, J=6.0 Hz), 4.18 (1H, m), 6.07 (1H, m), 6.52 (1H, dd, J=2.4, 5.6 Hz), 6.85-6.95 (2H, m), 7.17 (1H, brs), 7.69 (1H, d, J=2.4 Hz), 8.05 (1H, d, J=5.6 Hz), 8.28 (1H, m), 10.60 (1H, brs).
ESI-MS (m/z): 577 [M+Na]⁺.

Example 54

N-(2-Fluoro-4-{[2-({[4-(4-methylpiperazin-1-yl)piperidin-1-yl]carbonyl}amino)pyridin-4-yl]oxy}phenyl)-N'-phenylcyclopropane-1,1-dicarboxamide To a solution of [4-(3-fluoro-4-{[1-(phenylcarbamoyl)cyclopropanecarbonyl]amino}phenoxy)pyridin-2-yl]-N-(phenoxycarbonyl)carbamic acid phenyl ester (100 mg) in N,N-dimethylformamide (2.0 ml) was added 1-methyl-4-(piperidin-4-yl)piperazine (114 mg) at room temperature, followed by stirring for 5 hr. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether to the resultant residue. The solid was collected by filtration. The solid was dried under aeration to provide the titled compound as white powder (28.3 mg, 30%).
¹H-NMR Spectrum (CDCl₃) δ (ppm): 1.40-2.00 (9H, m), 2.29 (3H, s), 2.35-2.70 (8H, m), 2.89 (2H, m), 4.05-4.15 (2H, m), 6.53 (1H, dd, J=2.4, 5.6 Hz), 6.90-6.95 (2H, m), 7.15 (1H, m), 7.24 (1H, brs), 7.33-7.40 (2H, m), 7.50-7.55 (2H, m), 7.63 (1H, d, J=2.4 Hz), 8.05 (1H, d, J=5.6 Hz), 8.22 (1H, m), 8.94 (1H, brs), 9.09 (1H, brs).
ESI-MS (m/z): 638 [M+Na]⁺.

Example 55

N-[4-({2-[({4-[3-(Dimethylamino)azetidin-1-yl]piperidin-1-yl}carbonyl)amino]pyridin-4-yl}oxy)-2-fluorophenyl]-N'-phenylcyclopropane-1,1-dicarboxamide To a solution of [4-(3-fluoro-4-{[1-(phenylcarbamoyl)cyclopropanecarbonyl]amino}phenoxy)pyridin-2-yl]-N-(phenoxycarbonyl)carbamic acid phenyl ester (100 mg) in N,N-dimethylformamide (2.0 ml) were added 4-(3-dimethylaminoazetidin-1-yl)piperidine trihydrochloride (181 mg) and triethylamine (0.259 ml) at room temperature, followed by stirring for 5 days. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. A solid was precipitated by addition of diethyl ether to the resultant residue. The solid was collected by filtration. The solid was dried under aeration to provide the titled compound as white powder (24.0 mg, 25%).

¹H-NMR Spectrum (CDCl₃) δ (ppm): 1.20-1.80 (8H, m), 2.12 (6H, s), 2.27 (1H, m), 2.74-2.90 (3H, m), 3.05 (2H, m), 3.44-3.54 (2H, m), 3.80-3.94 (2H, m), 6.53 (1H, dd, J=2.4, 5.6 Hz), 6.86-6.96 (2H, m), 7.14 (1H, m), 7.22 (1H, brs), 7.32-7.40 (2H, m), 7.50-7.55 (2H, m), 7.62 (1H, d, J=2.4 Hz), 8.05 (1H, d, J=5.6 Hz), 8.21 (1H, m), 8.99 (1H, brs), 9.03 (1H, brs).

ESI-MS (m/z): 616 [M+H]⁺.

Example 56

N-(2,4-Difluorophenyl)-N'-(2-fluoro-4-{[2-({[methyl(1-methylpiperidin-4-yl)amino]carbonyl}amino) pyridin-4-yl]oxy}phenyl)cyclopropane-1,1-dicarboxamide To a solution of [4-(4-{[1-(2,4-Difluorophenylcarbamoyl)cyclopropanecarbonyl]amino}-3-fluorophenoxy)pyridin-2-yl]-N-(phenoxycarbonyl)carbamic acid phenyl ester (116 mg) in N,N-dimethylformamide (2.0 ml) was added 1-methyl-4-(methylamino)piperidine (0.150 ml) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:1 to the resultant residue. The solid was collected by filtration. The solid was dried under aeration to provide the titled compound as white powder (14.0 mg, 14%).

¹H-NMR Spectrum (CDCl₃) δ (ppm): 1.50-1.85 (8H, m), 2.00-2.15 (2H, m), 2.30 (3H, s), 2.85-3.00 (5H, m), 4.17 (1H, m), 6.54 (1H, dd, J=2.4, 5.6 Hz), 6.80-7.30 (5H, m), 7.69 (1H, d, J=2.4 Hz), 8.07 (1H, d, J=5.6 Hz), 8.18 (1H, m), 8.24 (1H, m), 9.02 (1H, brs), 9.18 (1H, brs).

ESI-MS (neg.) (m/z): 595 [M–H]⁻.

Example 57

N-(2-Fluoro-4-{[2-({[methyl(1-methylpiperidin-4-yl)amino]carbonyl}amino)pyridin-4-yl]oxy}phenyl)-N'-(2-fluorophenyn)cyclopropane-1,1-dicarboxamide To a solution of [4-(3-fluoro-4-{[1-(2-fluorophenylcarbamoyl)cyclopropanecarbonyl]amino}phenoxy)pyridin-2-yl]-N-(phenoxycarbonyl)carbamic acid phenyl ester (90.6 mg) in N,N-dimethylformamide (2.0 ml) was added 1-methyl-4-(methylamino)piperidine (0.120 ml) at room temperature, followed by stirring overnight. The reaction mixture was partitioned between ethyl acetate and water. The organic layer was washed with a saturated aqueous solution of ammonium chloride and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=98:2). Fractions containing the target compound were concentrated under reduced pressure. A solid was precipitated by addition of diethyl ether:heptane=1:1 to the resultant residue. The solid was collected by filtration. The solid was dried under aeration to provide the titled compound as white powder (30.2 mg, 38%).

¹H-NMR Spectrum (CDCl₃) δ (ppm): 1.50-1.85 (8H, m), 2.00-2.15 (2H, m), 2.29 (3H, s), 2.85-3.00 (5H, m), 4.17 (1H, m), 6.54 (1H, dd, J=2.4, 5.6 Hz), 6.80-7.30 (6H, m), 7.69 (1H, d, J=2.4 Hz), 8.07 (1H, d, J=5.6 Hz), 8.20-8.30 (2H, m), 8.97 (1H, brs), 9.35 (1H, brs).

ESI-MS (neg.) (m/z): 577 [M–H]⁻.

Example 58

N-(4-{[2-({[(3S)-3-(Dimethylamino)pyrrolidin-1-yl] carbonyl}amino)pyridin-4-yl]oxy}-2-fluorophenyl)-N'-phenylcyclopropane-1,1-dicarboxamide To a solution of phenyl N-[4-(3-fluoro-4-{[1-(phenylcarbamoyl)cyclopropanecarbonyl]amino}phenoxy)pyridin-2-yl]-N-phenoxycarbonylcarbamate (50.0 mg) in N,N-dimethylformamide (1.0 ml) was added (3S)-(−)-3-dimethylaminopyrrolidine (44 mg), followed by stirring at room temperature for 3.5 hr. The reaction mixture was partitioned between ethyl acetate and 1N sodium hydroxide. The organic layer was washed with brine, and dried over anhydrous sodium sulfate.

The solvent was removed, and the residue was purified by silica gel column chromatography (Fuji Silysia NH, ethyl acetate:methanol=98:2). Fractions containing the target compound were concentrated. A solid was precipitated by addition of diethyl ether:hexane=1:2 to the residue. The solvent was removed, and the residue was dried under reduced pressure to provide the titled compound as white powder (36.1 mg, 85%).

¹H-NMR Spectrum (CDCl₃) δ (ppm): 1.64-1.76 (4H, m), 1.87 (1H, m), 2.17 (1H, m), 2.27 (6H, s), 2.75 (1H, m), 3.22 (1H, m), 3.41 (1H, m), 3.66 (1H, m), 3.73 (1H, m), 6.55 (1H, dd, J=2.4, 5.6 Hz), 6.88-6.96 (2H, m), 7.03 (1H, brs), 7.14 (1H, m), 7.32-7.40 (2H, m), 7.50-7.56 (2H, m), 7.70 (1H, d, J=2.4 Hz), 8.05 (1H, d, J=5.6 Hz), 8.23 (1H, m), 8.98 (1H, brs), 9.04 (1H, brs).

ESI-MS (m/z): 569 [M+Na]⁺.

Example 59

N-(4-{[2-({[(3R)-3-(Dimethylamino)pyrrolidin-1-yl] carbonyl}amino)pyridin-4-yl]oxy}-2-fluorophenyl)-N'-phenylcyclopropane-1,1-dicarboxamide To a solution of phenyl N-[4-(3-fluoro-4-{[1-phenylcarbamoyl)cyclopropanecarbonyl]amino}phenoxy)pyridin-2-yl]-N-phenoxycarbonylcarbamate (50.0 mg) in N,N-dimethylformamide (1.0 ml) was added (3R)-(+)-3-dimethylaminopyrrolidine (44 mg), followed by stirring at room temperature for 3.5 hr. The reaction mixture was partitioned between ethyl acetate and 1N sodium hydroxide. The organic layer was washed with brine, and dried over anhydrous sodium sulfate. The solvent was removed, and the residue was purified by silica gel column chromatography (Fuji Silysia NH, ethyl acetate:methanol=98:2). Fractions containing the target compound were concentrated. A solid was precipitated by addition of diethyl ether:hexane=1:2 to the residue. The solvent was removed, and the residue was dried under reduced pressure to provide the titled compound as white powder (33.2 mg, 79%).

¹H-NMR Spectrum (CDCl₃) δ (ppm): 1.64-1.76 (4H, m), 1.87 (1H, m), 2.17 (1H, m), 2.27 (6H, s), 2.75 (1H, m), 3.22 (1H, m), 3.41 (1H, m), 3.66 (1H, m), 3.73 (1H, m), 6.55 (1H, dd, J=2.4, 5.6 Hz), 6.88-6.96 (2H, m), 7.03 (1H, brs), 7.14

(1H, m), 7.32-7.40 (2H, m), 7.50-7.56 (2H, m), 7.70 (1H, d, J=2.4 Hz), 8.05 (1H, d, J=5.6 Hz), 8.23 (1H, m), 8.98 (1H, brs), 9.04 (1H, brs).

ESI-MS (m/z): 569 [M+Na]$^+$.

Example 60

N-(4-{[2-({[(1-Ethylpiperidin-4-yl)(methyl)amino]carbonyl}amino)pyridin-4-yl]oxy}-2-fluorophenyl)-N'-phenylcyclopropane-1,1-dicarboxamide To phenyl N-[4-(3-fluoro-4-{[1-(phenylcarbamoyl)cyclopropanecarbonyl]amino}phenoxy)pyridin-2-yl]-N-phenoxycarbonylcarbamate (50.0 mg) was added a solution of N-(1-ethylpiperidin-4-yl)-N-methylamine (66 mg) in N,N-dimethylformamide (1.0 ml), followed by stirring at room temperature for 9 hr. The reaction mixture was partitioned between ethyl acetate and 1N sodium hydroxide. The organic layer was washed with brine, and dried over anhydrous sodium sulfate. The solvent was removed, and the residue was purified by silica gel column chromatography (Fuji Silysia NH, ethyl acetate, then ethyl acetate:methanol=98:2). Fractions containing the target compound were concentrated. A solid was precipitated by addition of diethyl ether:hexane=1:2 to the residue. The solid was collected by filtration and dried under aeration to provide the titled compound as white powder (25.8 mg, 58%).

$^1$H-NMR Spectrum (CDCl$_3$) δ (ppm): 1.08 (3H, t, J=7.2 Hz), 1.60-1.85 (8H, m), 2.03 (2H, m), 2.41 (2H, q, J=7.2 Hz), 2.89 (3H, s), 3.02 (2H, m), 4.17 (1H, m), 6.54 (1H, dd, J=2.4, 5.6 Hz), 6.86-6.94 (2H, m), 7.15 (1H, m), 7.17 (1H, brs), 7.30-7.38 (2H, m), 7.50-7.56 (2H, m), 7.70 (1H, d, J=2.4 Hz), 8.06 (1H, d, J=5.6 Hz), 8.22 (1H, m), 8.92 (1H, brs), 9.13 (1H, brs).

ESI-MS (m/z): 575 [M+H]$^-$.

Production Example 62

4-(4-Amino-2-fluorophenoxy)pyridine-2-carboxamide

4-Amino-2-fluorophenol (9.63 g) was dissolved in dimethyl sulfoxide (100 ml) under a nitrogen atmosphere. Potassium tert-butoxide (9.07 g) was added at room temperature, followed by stirring for 15 min. 4-Chloropyridine-2-carboxamide (7.9 g) was added thereto, followed by stirring at 80° C. under a nitrogen atmosphere for 1 hr. The reaction mixture was allowed to cool down to room temperature. To the reaction mixture was added a 1N aqueous solution of sodium hydroxide (100 ml), then water (100 ml), followed by stirring for 5 hr. The precipitated solid was collected by filtration with suction, and washed with water (50 ml, 4 times). The resultant solid was hot air-dried at 60° C. for 2 days to provide the titled compound as pale brown powder (10.39 g, 83%).

$^1$H-NMR Spectrum (DMSO-d$_6$) δ (ppm): 5.51 (2H, m), 6.44 (1H, dd, J=2.4, 8.8 Hz), 6.53 (1H, dd, J=2.4, 13.2 Hz), 7.03 (1H, m), 7.14 (1H, dd, J=2.8, 5.6 Hz), 7.34 (1H, d, J=2.4 Hz), 7.71 (1H, brs), 8.11 (1H, brs), 8.49 (1H, d, J=5.6 Hz).

Production Example 63

4-(2-Fluoro-4-{[1-(4-fluorophenylcarbamoyl)cyclopropanecarbonyl]amino}phenoxy)pyridine-2-carboxamide To a solution of 1-(4-fluorophenylaminocarbonyl)cyclopropanecarboxylic acid (5.58 g) in tetrahydrofuran (60 ml) was added dropwise triethylamine (4.18 ml) while cooling in an ice water bath under a nitrogen atmosphere, followed by stirring for 15 min. To the reaction mixture, was then added thionyl chloride (2.0 ml), followed by stirring at the same temperature for 60 min. To the reaction mixture was added a suspension of 4-(4-amino-2-fluorophenoxy)pyridine-2-carboxamide (4.945 g) and triethylamine (4.18 ml) in tetrahydrofuran (50 ml) while cooling in an ice water bath under a nitrogen atmosphere, followed by stirring for 2 hr. The reaction was allowed to warm up to room temperature, followed by stirring overnight. The reaction mixture was partitioned after addition of ethyl acetate (100 ml) and a 1N aqueous solution of sodium hydroxide (100 ml). The organic layer was washed with a 2N aqueous solution of sodium hydroxide (100 ml, 3 times), 1N hydrochloric acid (100 ml, twice) and brine (100 ml) in this order, and dried over anhydrous sodium sulfate. The organic layer was filtered and the filtrate was concentrated under reduced pressure. To the resultant residue (8.3 g) were added ethyl acetate (20 ml) and heptane (5 ml) to precipitate a solid. After diluting with addition of ethyl acetate (20 ml), the solid was collected by filtration with suction, washed with ethyl acetate-heptane (16 ml-2 ml). Drying under aeration with suction on a paper filter provided the titled compound as pale brown powder (3.73 g, 41%). The filtrate was concentrated under reduced pressure, and ethyl acetate (20 ml) and heptane (4 ml) were again added to the residue (3.6 g) to precipitate a solid. The solid was collected by filtration with suction. Drying under aeration with suction on a paper filter provided the titled compound as pale brown powder (216 mg, 2.4%). The filtrate was further concentrated under reduced pressure, and the residue (3.06 g) was purified by silica gel column chromatography (Fuji Silysia NH, eluent; ethyl acetate). Fractions containing the target compound were concentrated under reduced pressure to provide the titled compound as pale brown powder (885 mg, 9.8%).

$^1$H-NMR Spectrum (CDCl$_3$) δ (ppm): 1.60-1.90 (4H, m), 5.78 (1H, m), 6.95-7.30 (5H, m), 7.40-7.50 (2H, m), 7.64 (1H, d, J=2.4 Hz), 7.74 (1H, dd, J=2.4, 12.0 Hz), 7.88 (1H, m), 8.33 (1H, brs), 8.44 (1H, d, J=5.6 Hz), 9.87 (1H, brs).

ESI-MS (m/z): 475 [M+Na]$^+$.

Production Example 64

N-{4-[(2-Aminopyridin-4-yl)oxy]-3-fluorophenyl}-N'-(4-fluorophenyl)cyclopropane-1,1-dicarboxamide 4-(2-Fluoro-4-{[1-(4-fluorophenylcarbamoyl)cyclopropanecarbonyl]amino}phenoxy)pyridine-2-carboxamide (4.81 g) was dissolved in N,N-dimethylformamide (50 ml) under a nitrogen atmosphere, and water (0.5 ml), [bis(trifluoroacetoxy)iodo]benzene (5.17 g) and pyridine (2.57 ml) were added in this order at room temperature, followed by stirring overnight. Water (0.5 ml), [bis(trifluoroacetoxy)iodo]benzene (5.17 g) and pyridine (2.57 ml) were added in this order at room temperature, followed by further stirring for 1 hr. The reaction mixture was partitioned between ethyl acetate (200 ml) and water (100 ml). The organic layer was separated, washed with brine, and dried over anhydrous sodium sulfate. The solvent was concentrated under reduced pressure and the residue was purified by silica gel column chromatography (Fuji Silysia NH, eluent; ethyl acetate). Fractions containing the target compound were concentrated under reduced pressure and the residue was dried under reduced pressure to provide the titled compound as pale brown foam (2.878 g, 64%).

$^1$H-NMR Spectrum (CDCl$_3$) δ (ppm): 1.60-1.80 (4H, m), 4.84 (2H, brs), 5.94 (1H, d, J=2.4 Hz), 6.31 (1H, dd, J=2.4, 5.6

Hz), 7.00-7.50 (6H, m), 7.69 (1H, dd, J=2.4, 12.4 Hz), 7.89 (1H, d, J=5.6 Hz), 8.20 (1H, brs), 9.92 (1H, brs).
ESI-MS (m/z): 425 [M+H]$^+$.

Production Example 65

N-(4-Fluorophenyl)-N'-(2-fluoro-4-hydroxyphenyl)cyclopropane-1,1-dicarboxamide

To a solution of 1-(4-fluorophenylcarbamoyl)cyclopropanecarboxylic acid (1.02 g) in N,N-dimethylformamide (5.0 ml) were added triethylamine (1.28 ml) and benzotriazol-1-yloxytris(dimethylamino)phosphonium hexafluorophosphate (2.03 g), followed by stirring at room temperature for 5 min. To this was added 4-amino-3-fluorophenol hydrochloride (500 mg), followed by stirring at room temperature for 3 days. The reaction mixture was partitioned between ethyl acetate and a 1N aqueous solution of sodium hydroxide. The organic layer was washed with a 1N aqueous solution of sodium hydroxide. To the aqueous layer was added 5N hydrochloric acid to make it acidic, this was extracted with ethyl acetate. The organic layer was washed with brine and dried over anhydrous sodium sulfate. The solvent was removed and the residue was purified by silica gel column chromatography (eluent; heptane:ethyl acetate=2:3 to 1:2). Fractions containing the target compound were concentrated under reduced pressure to provide the titled compound as a pale red solid (395 mg, 39%).
$^1$H-NMR Spectrum (CDCl$_3$) δ (ppm): 1.50-1.80 (4H, m), 4.99 (1H, brs), 6.60-6.70 (2H, m), 6.90-7.10 (2H, m), 7.45-7.55 (2H, m), 7.98 (1H, m), 8.23 (1H, brs), 9.58 (1H, brs).
ESI-MS (m/z): 355 [M+Na]$^+$.

Production Example 66

4-(4-Amino-3-fluorophenoxy)pyridine-2-carboxamide

4-Amino-3-fluorophenol (5.7 g) was dissolved in dimethyl sulfoxide (57 ml) under a nitrogen atmosphere, and potassium tert-butoxide (5.6 g) was added at room temperature, followed by stirring for 15 min. To the reaction mixture was added 4-chloropicolylamide (5.0 g), followed by stirring in an oil bath at an external temperature of 80° C. under a nitrogen atmosphere for 50 min. The reaction mixture was allowed to cool down to room temperature. To the reaction mixture was added a 1N aqueous solution of sodium hydroxide (85.5 ml), followed by stirring. The precipitated solid was collected by filtration, and washed with water. The solid was dried under aeration, then hot air-dried at 100° C. to provide the titled compound as pale brown powder (5.88 g, 74.3%).
$^1$H-NMR Spectrum (DMSO-d$_6$) δ (ppm): 5.18-5.30 (2H, m), 6.80 (1H, dd, J=2.4, 8.4 Hz), 6.81-6.90 (1H, m), 7.02 (1H, dd, J=2.4, 11.6 Hz), 6.99-7.14 (1H, m), 7.32-7.39 (1H, m), 7.69 (1H, brs), 8.10 (1H, brs), 8.48 (1H, m).

Production Example 67

4-(3-Fluoro-4-{[1-(4-fluorophenylcarbamoyl)cyclopropanecarbonyl]amino}phenoxy)pyridine-2-carboxamide N-(4-Fluorophenyl)-N'-(2-fluoro-4-hydroxyphenyl)cyclopropane-1,1-dicarboxamide (665 mg) was dissolved in N-methylpyrrolidone (10 ml) under a nitrogen atmosphere, and potassium tert-butoxide (247 mg) was added at room temperature, followed by stirring for 1.5 hr. After 4-chloropicolylamide (313 mg) was added, the reaction mixture was stirred under a nitrogen atmosphere at 110° C. overnight, then at 120° C. for 8 hr. The reaction mixture was allowed to cool down to room temperature. The reaction mixture was partitioned between ethyl acetate and water. The organic layer was washed with a saturated aqueous solution of sodium hydrogencarbonate (twice) and brine, and dried over anhydrous sodium sulfate. The solvent was concentrated under reduced pressure, and the residue was purified by silica gel column chromatography (eluent; heptane:ethyl acetate=1:2, 1:3, then 1:4). Fractions containing the target compound were concentrated under reduced pressure. After ethyl acetate (3 ml)-heptane (6 ml) was added, crystals were allowed to precipitate under sonication. The solvent was removed and the crystals were dried under reduced pressure to provide the titled compound as pale brown crystals (261 mg, 29%).
$^1$H-NMR Spectrum (CDCl$_3$) δ (ppm): 1.40-1.80 (4H, m), 5.54 (1H, brs), 6.90-7.30 (7H, m), 7.71 (1H, m), 7.86 (1H, brs), 8.28 (1H, m), 8.45 (1H, d, J=5.6 Hz), 8.94 (1H, brs), 9.14 (1H, brs).
ESI-MS (m/z): 475 [M+Na]$^+$.

Alternative Method A for Synthesis of 4-(3-Fluoro-4-{[1-(4-fluorophenylcarbamoyl)cyclopropanecarbonyl]amino}phenoxy)pyridine-2-carboxamide To a solution of 1-(4-fluorophenylaminocarbonyl)cyclopropanecarboxylic acid (1.45 g) in tetrahydrofuran (14.5 ml) was added dropwise triethylamine (1.13 ml) under a nitrogen atmosphere while cooling in an ice water bath, followed by stirring for 15 min. To the reaction mixture was added thionyl chloride (0.473 ml), followed by stirring at the same temperature for 1.5 hr. To the reaction mixture were added a solution of 4-(4-amino-3-fluorophenoxy)pyridine-2-carboxamide (1.0 g) in tetrahydrofuran (10.5 ml) and triethylamine (1.13 ml) in this order at the same temperature under a nitrogen atmosphere, followed by stirring. The reaction mixture was allowed to warm up to room temperature and stirred overnight. The reaction mixture was partitioned after addition of ethyl acetate (50 ml) and a 2N aqueous solution of sodium hydroxide (10 ml). The organic layer was washed with a 2N aqueous solution of sodium hydroxide (10 ml, twice), 1N hydrochloric acid (10 ml, three times) and a saturated aqueous solution of sodium hydrogencarbonate (30 ml), and dried over anhydrous sodium sulfate. The solvent was concentrated under reduced pressure, and the residue was filtered (eluent; ethyl acetate) through silica gel column (Fuji Silysia NH). The filtrate was concentrated under reduced pressure, and to the resultant residue (1.28 g) were added ethyl acetate (4 ml) and heptane (4 ml) to suspend. The solid was collected by filtration and dried under aeration to provide the titled compound as a pale pink solid (991.1 mg, 54.1%). The residue obtained by concentrating the filtrate under reduced pressure was purified by silica gel column chromatography (Fuji Silysia NH, eluent; ethyl acetate:heptane=3:1). Fractions containing the target compound were concentrated under reduced pressure to provide the titled compound as a white solid (24.3 mg, 1.33%).

Alternative Method B for Synthesis of 4-(3-Fluoro-4-{[1-(4-fluorophenylcarbamoyl)cyclopropanecarbonyl]amino}phenoxy)pyridine-2-carboxamide To a solution of 1,1-cyclopropanedicarboxylic acid (3.12 g) in tetrahydrofuran (90 ml) was added dropwise triethylamine (2.43 g) while cooling in an ice water bath under a nitrogen atmosphere for 1.5 hr. To the reaction mixture, was then added thionyl chloride (1.75 ml), followed by stirring at the same temperature for 30 min. To the reaction mixture were added 4-(4-amino-3-fluorophenoxy)pyridine-2-carboxamide (2.97 g) and triethylamine (2.43 g) in this order while cooling in an ice water bath under a nitrogen atmosphere, followed by stirring for 70 min. The reaction mixture was partitioned after addition of tert-butyl methyl ether (30 ml) and a 1N aqueous solution of sodium hydroxide (90 ml). The aqueous layer was partitioned with tert-butyl methyl ether (30 ml) again, and the separated aqueous layer was treated with 1N hydrochloric acid to precipitate a solid. The solid was collected by suction filtration and washed with water (10 ml, four times). Drying under reduced pressure at 50° C. provided 1-[4-(2-carbamoylpyridin-4-yl)oxy-2-fluorophenylaminocarbonyl]cyclopropanecarboxylic acid as a pale purple solid (1.90 g, 44%). After the filtrate was stood overnight, further precipitated solid was collected by suction filtration and washed with water (10 ml, twice). Drying under reduced pressure provided additional 1-[4-(2-carbamoylpyridin-4-yl)oxy-2-fluorophenylaminocarbonyl]cyclopropanecarboxylic acid as a pale purple solid (758 mg, 18%).

$^1$H-NMR Spectrum (DMSO-$d_6$) δ (ppm): 1.50-1.60 (4H, m), 7.07 (1H, dd, J=2.4, 8.8 Hz), 7.19 (1H, dd, J=2.4, 5.6 Hz), 7.35 (1H, m), 7.42 (1H, d, J=2.4 Hz), 7.72 (1H, m), 8.12 (1H, m), 8.24 (1H, m), 8.53 (1H, d, J=5.6 Hz), 10.14 (1H, brs).

ESI-MS (neg.)(m/z): 358 [M−H]$^−$.

To a suspension of 1-[4-(2-carbamoylpyridin-4-yl)oxy-2-fluorophenylaminocarbonyl]cyclopropanecarboxylic acid (743 mg) and 4-fluoroaniline (459 mg) in tetrahydrofuran (30 ml) was added 4-(4,6-dimethoxy[1.3.5]triazin-2-yl)-4-methylmorpholinium chloride hydrate (1.22 g), followed by stirring at room temperature for 7.5 hr. The reaction mixture was partitioned between ethyl acetate and an aqueous solution of sodium hydrogencarbonate. The organic layer was washed with water and dried over anhydrous magnesium sulfate. The solvent was concentrated under reduced pressure, and the resultant residue was suspended by addition of tert-butyl methyl ether—ethyl acetate (1:1, 20 ml). The solid was collected by filtration and dried under aeration to provide the titled compound as a white solid (815 mg, 87%).

Production Example 68

N-{4-[(2-Aminopyridin-4-yl)oxy]-2-fluorophenyl}-N'-(4-fluorophenyl)cyclopropane-1,1-dicarboxamide 4-(3-Fluoro-4-{[1-(4-fluorophenylcarbamoyl)cyclopropanecarbonyl]amino}phenoxy)pyridine-2-carboxamide (101 mg) was dissolved in N,N-dimethylformamide (1.0 ml) under a nitrogen atmosphere, and water (0.01 ml), [bis(trifluoroacetoxy)iodo]benzene (109 mg) and pyridine (0.0541 ml) were added at room temperature in this order, followed by stirring overnight. Water (0.01 ml), [bis(trifluoroacetoxy)iodo]benzene (109 mg) and pyridine (0.0541 ml) were added at room temperature in this order, followed by further stirring for 24 hr. The reaction mixture was partitioned between ethyl acetate and a 1N aqueous solution of sodium hydroxide. The organic layer was separated, washed with brine, and dried over anhydrous sodium sulfate. The solvent was concentrated under reduced pressure, and the residue was purified by silica gel column chromatography (Fuji Silysia NH, eluent; ethyl acetate). Fractions containing the target compound were concentrated under reduced pressure, and the residue was dried under reduced pressure to provide the titled compound as white foam (62.2 mg, 66%).

$^1$H-NMR Spectrum (CDCl$_3$) δ (ppm): 1.50-1.90 (4H, m), 4.90 (2H, brs), 5.98 (1H, d, J=2.4 Hz), 6.33 (1H, dd, J=2.4, 5.6 Hz), 6.85-7.55 (6H, m), 7.90 (1H, d, J=5.6 Hz), 8.20 (1H, m), 8.84 (1H, brs), 9.26 (1H, brs).

ESI-MS (m/z): 447 [M+Na]$^+$.

Production Example 69

N-{4-[(2-Aminopyridin-4-yl)oxy]-2-fluorophenyl}-N'-(4-fluorophenyl)cyclopropane-1,1-dicarboxamide monohydrochloride 4-(3-Fluoro-4-{[1-(4-fluorophenylcarbamoyl)cyclopropanecarbonyl]amino}phenoxy)pyridine-2-carboxamide (1.0 g) was dissolved in N,N-dimethylformamide (10 ml) under a nitrogen atmosphere, and water (0.199 ml), [bis(trifluoroacetoxy)iodo]benzene (1.96 g) and pyridine (1.07 ml) were added at room temperature in this order, followed by stirring for 33 hr. The reaction mixture was partitioned after addition of ethyl acetate (30 ml) and a 1N aqueous solution of sodium hydroxide (10 ml). The organic layer was washed with a 1N aqueous solution of sodium hydroxide (10 ml, twice) and brine (30 ml) in this order, and dried over anhydrous sodium sulfate. The solvent was removed under reduced pressure. The resultant residue was dissolved in ethyl acetate (10 ml), 5N hydrochloric acid (0.486 ml, 1.1 equivalents) was added under sonication. The precipitated solid was collected by filtration, washed with ethyl acetate, and dried under aeration for 1 hr. The solid was hot air-dried at 80° C. overnight to provide the titled compound as pale brown powder (559.3 mg, 54.9%).

$^1$H-NMR Spectrum (DMSO-$d_6$) δ (ppm): 1.45-1.80 (4H, m), 6.14 (1H, d, J=2.4 Hz), 6.65 (1H, dd, J=2.4, 6.8 Hz), 7.10-7.23 (3H, m), 7.42 (1H, dd, J=2.4, 11.6 Hz), 7.55-7.64 (2H, m), 7.77 (1H, m), 7.96 (1H, d, J=6.8 Hz), 7.99-8.10 (1H, m), 9.88 (1H, brs), 10.79 (1H, brs).

Production Example 70

Morpholine-4-carboxylic acid [4-(4-nitrophenoxy)pyridin-2-yl]amide 4-(4-Nitrophenoxy)pyridin-2-ylamine (100 mg) was dissolved in tetrahydrofuran (5 ml) under a nitrogen atmosphere, and triethylamine (0.181 ml) and phenyl chloroformate (0.163 ml) were added while stirring and cooling in an ice water bath. The reaction mixture was allowed to warm up to room temperature, followed by stirring for 30 min. The reaction mixture was partitioned between ethyl acetate (50 ml) and a saturated aqueous solution of sodium hydrogencarbonate (30 ml). The separated organic layer was washed with water (30 ml) and brine (30 ml) in this order, and dried over anhydrous sodium sulfate. The solvent was removed under reduced pressure. To the residue was added N,N-dimethylformamide (5 ml), then morpholine (0.189 ml) was added, followed by stirring for 3 hr. The reaction mixture was concentrated under reduced pressure, and the resultant residue was partitioned after addition of ethyl acetate (50 ml) and a saturated aqueous solution of ammonium chloride (30 ml). The separated organic layer was washed with a saturated aqueous solution of ammonium chloride (30 ml), water (30 ml) and brine (30 ml), and dried over anhydrous sodium sulfate. The solvent was removed under reduced pressure, and the residue was purified by silica gel column chromatography (eluent; heptane:ethyl acetate=1:3, then ethyl acetate). Fractions containing the target compound were concentrated under reduced pressure to provide roughly-purified titled compound as a pale yellow solid (128.8 mg).

$^1$H-NMR Spectrum (CDCl$_3$) δ (ppm): 3.52 (4H, m), 3.74 (4H, m), 6.68 (1H, dd, J=2.0, 5.6 Hz), 7.17-7.26 (2H, m), 7.67 (1H, m), 7.79 (1H, brs), 8.15 (1H, d, J=5.6 Hz), 8.20-8.40 (2H, m).

Production Example 71

Morpholine-4-carboxylic acid
[4-(4-aminophenoxy)pyridin-2-yl]amide

Morpholine-4-carboxylic acid [4-(4-nitrophenoxy)pyridin-2-yl]amide (128 mg) was dissolved in tetrahydrofuran (3 ml), and 20% palladium hydroxide on carbon (26.3 mg) was added at room temperature under a nitrogen atmosphere, followed by stirring under a hydrogen atmosphere for 7 hr. The atmosphere in the reaction vessel was replaced with nitrogen, and the catalyst was removed by filtration and washed with tetrahydrofuran. The solvent was removed under reduced pressure to provide the titled compound as a pale yellow solid (121 mg).

ESI-MS (m/z): 337 [M+Na]$^+$.

Production Example 72

Pyrrolidine-1-carboxylic acid
[4-(4-nitrophenoxy)pyridin-2-yl]amide 4-(4-Nitrophenoxy)pyridin-2-ylamine (100 mg) was dissolved in tetrahydrofuran (5 ml) under a nitrogen atmosphere, triethylamine (0.181 ml) and phenyl chloroformate (0.163 ml) were added while stirring and cooling in an ice water bath. The reaction mixture was allowed to warm up to room temperature and stirred for 30 min. The reaction mixture was partitioned between ethyl acetate (50 ml) and a saturated aqueous solution of sodium hydrogencarbonate (30 ml). The separated organic layer was washed with water (30 ml) and brine (30 ml) in this order, and dried over anhydrous sodium sulfate. The solvent was removed under reduced pressure. To the residue was added N,N-dimethylformamide (5 ml), and pyrrolidine (0.181 ml) was added, followed by stirring for 2 hr. The reaction mixture was concentrated under reduced pressure, and the resultant residue was partitioned after addition of ethyl acetate (50 ml) and a saturated aqueous solution of ammonium chloride (30 ml). The separated organic layer was washed with a saturated aqueous solution of ammonium chloride (30 ml), water (30 ml) and brine (30 ml), and dried over anhydrous sodium sulfate. The solvent was removed under reduced pressure, and the residue was purified by silica gel column chromatography (eluent; heptane:ethyl acetate=1:3, then ethyl acetate). Fractions containing the target compound were concentrated under reduced pressure to provide the roughly-purified titled compound as a pale yellow solid (116.8 mg).

$^1$H-NMR Spectrum (CDCl$_3$) δ (ppm): 1.98 (4H, m), 3.48 (4H, m), 6.67 (1H, dd, J=2.4, 6.0 Hz), 7.18-7.34 (2H, m), 7.46 (1H, m), 7.88 (1H, dd, J=2.4 Hz), 8.14 (1H, d, J=6.0 Hz), 8.25-8.35 (2H, m).

Production Example 73

Pyrrolidine-1-carboxylic acid
[4-(4-aminophenoxy)pyridin-2-yl]amide

Pyrrolidine-1-carboxylic acid [4-(4-nitrophenoxy)pyridin-2-yl]amide (116.8 mg) was dissolved in tetrahydrofuran (3 ml), 20% palladium hydroxide on carbon (25.0 mg) was added under a nitrogen atmosphere at room temperature while stirring, followed by stirring under a hydrogen atmosphere for 7 hr. The atmosphere in the reaction vessel was replaced with nitrogen, and the catalyst was removed by filtration and washed with tetrahydrofuran. The solvent was removed under reduced pressure to provide the titled compound as a pale yellow solid (112 mg).

ESI-MS (m/z): 321 [M+Na]$^+$.

Production Example 74

Azetidine-1-carboxylic acid
[4-(4-nitrophenoxy)pyridin-2-yl]amide 4-(4-Nitrophenoxy)pyridin-2-ylamine (100 mg) was dissolved in tetrahydrofuran (5 ml) under a nitrogen atmosphere, triethylamine (0.181 ml) and phenyl chloroformate (0.163 ml) were added while stirring and cooling in an ice water bath. The reaction mixture was allowed to warm up to room temperature and stirred for 30 min. The reaction mixture was partitioned between ethyl acetate (50 ml) and a saturated aqueous solution of sodium hydrogencarbonate (30 ml). The separated organic layer was washed with water (30 ml) and brine (30 ml) in this order, and dried over anhydrous sodium sulfate. The solvent was removed under reduced pressure. To the residue was added N,N-dimethylformamide (5 ml), and azetidine monohydrochloride (203 mg) and triethylamine (0.483 ml) were added, followed by stirring overnight. The reaction mixture was concentrated under reduced pressure, the resultant residue was partitioned after addition of ethyl acetate (50 ml) and a saturated aqueous solution of ammonium chloride (30 ml). The separated organic layer was washed with a saturated aqueous solution of ammonium chloride (30 ml), water (30 ml) and brine (30 ml), and dried over anhydrous sodium sulfate. The solvent was removed under reduced pressure, and the residue was purified by silica gel column chromatography (eluent; heptane:ethyl acetate=1:3, then ethyl acetate). Fractions containing the target compound were concentrated under reduced pressure to provide the roughly-purified titled compound as a pale yellow solid (118.7 mg).

$^1$H-NMR Spectrum (CDCl$_3$) δ (ppm): 2.33 (2H, m), 4.11 (4H, m), 6.66 (1H, dd, J=2.4, 6.0 Hz), 7.15-7.25 (3H, m), 7.83 (1H, d, J=2.4 Hz), 8.13 (1H, d, J=6.0 Hz), 8.25-8.34 (2H, m).

Production Example 75

Azetidine-1-carboxylic acid
[4-(4-aminophenoxy)pyridin-2-yl]amide

Azetidine-1-carboxylic acid [4-(4-nitrophenoxy)pyridin-2-yl]amide (118.7 mg) was dissolved in tetrahydrofuran (6 ml), and 20% palladium hydroxide on carbon (26.6 mg) was added under a nitrogen atmosphere at room temperature while stirring, followed by stirring under a hydrogen atmosphere for 7 hr. The atmosphere in the reaction vessel was replaced with nitrogen, and the catalyst was removed by filtration and washed with tetrahydrofuran. The solvent was removed under reduced pressure to provide the titled compound as a pale yellow solid (110 mg).

ESI-MS (m/z): 307 [M+Na]$^+$.

Production Example 76

Benzyl 4-(1-tert-butoxycarbonylpiperidin-4-yl)piperazine-1-carboxylate

Benzyl 1-piperazinecarboxylate (5.00 g) and tert-butyl 4-oxopiperidine-1-carboxylate (4.52 g) were dissolved in methanol (100 ml), and acetic acid (2.34 ml) and 10% palladium on carbon (1.55 g) were added thereto, followed by stirring under a hydrogen atmosphere for 4 days. The catalyst was removed by filtration, and the filtrate was concentrated. To the residue were added acetone (50 ml) and water (50 ml) to dissolve, and sodium hydrogencarbonate (6.67 g) was added and stirred while cooling in an ice bath. Benzyl chloroformate (3.89 ml) was added thereto, followed by stirring in an ice bath for 3.5 hr. Part of the reaction mixture was concentrated, and ethyl acetate:tetrahydrofuran=1:1 (200 ml) and water (100 ml) were added thereto, followed by stirring at room temperature for 10 min. The organic layer was separated. The organic layer was washed with brine, and dried over anhydrous sodium sulfate. This was concentrated, and the residue was purified by silica gel column chromatography (eluent; ethyl acetate, then ethyl acetate:methanol=50:1). Fractions containing the target compound were concentrated to provide the titled compound as a pale yellow oil (2.71 g, 29.6%).

$^1$H-NMR Spectrum (CDCl$_3$) δ (ppm): 1.40 (2H, m), 1.45 (9H, s), 1.77 (2H, m), 2.40 (1H, m), 2.52 (4H, m), 2.69 (2H, m), 3.51 (4H, m), 4.13 (2H, m), 5.13 (2H, s), 7.30-7.39 (5H, m).

ESI-MS (m/z): 426 [M+Na]$^+$.

Production Example 77

Benzyl 4-(piperidin-4-yl)piperazine-1-carboxylate

To benzyl 4-(1-t-butoxycarbonylpiperidin-4-yl)piperazine-1-carboxylate (2.31 g) was added trifluoroacetic acid (10 ml) while cooling in an ice bath, followed by stirring at room temperature for 3 hr. The reaction mixture was poured into ice water, and a 5N aqueous solution of sodium hydroxide (26 ml) was added thereto. This was extracted with ethyl acetate: tetrahydrofuran=1:1. The organic layer was washed with brine, and dried over anhydrous sodium sulfate. The solvent was removed to provide the crude product of the titled compound as a pale yellow oil (1.93 g).

$^1$H-NMR Spectrum (CDCl$_3$) δ (ppm): 1.57-1.66 (2H, m), 1.87 (2H, m), 2.00-3.62 (14H, m), 5.14 (2H, m), 7.27-7.40 (5H, m).

ESI-MS (m/z): 304 [M+H]$^+$.

Production Example 78

1-Benzhydrylazetidin-3-one

To a mixture of 1-benzhydrylazetidin-3-ol hydrochloride (5.52 g) and triethylamine (27.9 ml) was added dropwise a solution of pyridine sulfur trioxide complex (19.7 g) in dimethyl sulfoxide (80 ml) at room temperature. The reaction mixture was stirred at 50° C. for 30 min. The reaction was allowed to cool down to room temperature. This was poured into ice water. This was extracted with ethyl acetate, and the organic layer was washed with brine. Activated carbon (5 g) was added to the organic layer, followed by stirring at room temperature for 3 days. Activated carbon was removed by filtration and the filtrate was concentrated. The residue was dissolved in methanol (200 ml), and activated carbon (10 g) was added thereto, followed by stirring at room temperature for 3 days. Activated carbon was removed by filtration, and the filtrate was concentrated. The residue was purified by silica gel column chromatography (eluent; heptane:ethyl acetate=4:1, then 2:1). Fractions containing the target compound were concentrated to provide the target compound as a pale yellow oil (3.21 g). Hexane was added thereto to precipitate crystals, which were collected by filtration. Drying under aeration provided the titled compound (1.11 g, 23.4%). To the residue obtained by concentrating the filtrate was added hexane, and allowed to stand at room temperature. After crystals precipitated, supernatant was removed by a pipette. This was dried under reduced pressure to provide the titled compound as pale yellow crystals (940 mg, 19.8%).

$^1$H-NMR Spectrum (CDCl$_3$) δ (ppm): 4.01 (4H, s), 4.60 (1H, s), 7.22 (2H, m), 7.30 (4H, m), 7.48 (4H, m).

Production Example 79

3-(Azetidin-1-yl)-1-benzhydrylazetidine

To a solution of 1-benzhydrylazetidin-3-one (750 mg) in dichloromethane (12 ml) was added azetidine hydrochloride (326 mg), followed by stirring at room temperature. Sodium triacetoxy borohydride (1.01 g) was added thereto, followed by stirring at room temperature for 25 hr. To the reaction mixture were added sodium carbonate (until bubbling stopped), water (50 ml) and ethyl acetate (100 ml). The organic layer was separated. This was washed with brine, and dried over anhydrous sodium sulfate. The organic layer after drying was concentrated under reduced pressure. The residue was purified by silica gel column chromatography (Fuji Silysia NH, eluent; heptane:ethyl acetate=1:1, 1:2, then ethyl acetate) to provide the titled compound as a pale yellow solid (643 mg, 73.1%).

$^1$H-NMR Spectrum (CDCl$_3$) δ (ppm): 2.06 (2H, m), 2.91 (2H, m), 3.16-3.24 (7H, m), 4.35 (1H, s), 7.15 (2H, m), 7.25 (4H, m), 7.40 (4H, d, J=7.6 Hz).

ESI-MS (m/z): 279 [M+H]$^+$.

Production Example 80

3-(Azetidin-1-yl)azetidine dihydrochloride

To a solution of 3-(azetidin-1-yl)-1-benzhydrylazetidine (643 mg) in ethyl acetate was added a 4N solution of hydrochloric acid in ethyl acetate (1.16 ml), followed by concentration. The resultant residue was dissolved in methanol (65 ml), and 20% palladium hydroxide (811 mg) was added thereto. This was stirred at room temperature under a pressurized hydrogen atmosphere (0.3 to 0.4 MPa) for 4 hr. The catalyst was removed by filtration, and the filtrate was concentrated. Hexane was added to the residue to suspend a solid. The residue after removing a supernatant by a pipette was concentrated under reduced pressure to provide a crude product of the titled compound as a pale yellow oil (471.2 mg).

ESI-MS (m/z): 113 [M+H]$^+$.

Production Example 81

1-Benzhydryl-3-(methanesulfonyloxy)azetidine

A suspension of 1-benzhydrylazetidin-3-ol (15.0 g) in pyridine (100 ml) was cooled to −20° C. under a nitrogen atmosphere, and methanesulfonyl chloride (6.33 ml) was added dropwise thereto. The reaction mixture was stirred under a nitrogen atmosphere at −20° C. for 1 hr, then in a water bath for 2.5 days. The reaction mixture was partitioned after addition of water and ethyl acetate. The organic layer was washed with a saturated aqueous solution of sodium hydrogencarbonate, water and brine, and dried over anhydrous sodium sulfate. The solvent was concentrated under reduced pressure. To the residue were added ethanol (10 ml) and hexane (50 ml) to suspend precipitated crystals. The crystals were collected by filtration and washed with hexane. This was dried under aeration at room temperature to provide the titled compound as pale yellow crystals (5.943 g, 44.8%). The filtrate was concentrated, and the residue was purified by silica gel column chromatography (eluent; heptane:ethyl acetate=2:1, 1:1, then heptane:ethyl acetate:methanol=50:50:1, 40:60:1, then ethyl acetate:methanol=100:1). Fractions containing the target compound were concentrated to provide the titled compound as pale yellow crystals (1.58 g, 11.9%).

$^1$H-NMR Spectrum (CDCl$_3$) δ (ppm): 2.99 (3H, s), 3.18-3.21 (2H, m), 3.62-3.66 (2H, m), 4.40 (1H, s), 5.11 (1H, m), 7.18-7.22 (2H, m), 7.26-7.31 (4H, m), 7.39 (4H, d, J=7.2 Hz).

Production Example 82

1-Benzhydryl-3-cyanoazetidine

To a solution of 1-benzhydryl-3-(methanesulfonyloxy)azetidine (7.52 g) in N,N-dimethylformamide (60 ml) were added water (7.2 ml) and sodium cyanide (3.48 g), followed by stirring at 65° C. for 9 hr. To the reaction mixture were added water, sodium carbonate and ethyl acetate, and this was partitioned. The aqueous layer was extracted with ethyl acetate. The organic layer was combined, washed with brine, and dried over anhydrous sodium sulfate. This was concentrated under reduced pressure, and the resultant crystals were suspended by addition of diethyl ether (10 ml). The crystals were collected by filtration and washed with diethyl ether. This was dried under aeration to provide the titled compound as pale yellow crystals (5.43 g, 92.3%).

$^1$H-NMR Spectrum (CDCl$_3$) δ (ppm): 3.20-3.31 (3H, m), 3.47 (2H, m), 4.36 (1H, s), 7.19-7.23 (2H, m), 7.26-7.30 (4H, m), 7.39 (4H, m).

Production Example 83

1-Benzhydrylazetidine-3-carboxylic acid

To a solution of 1-benzhydryl-3-cyanoazetidine (5.43 g) in methoxyethanol (54 ml) were added potassium hydroxide (6.48 g) and water (3.25 ml), followed by stirring at 100° C. for 4 hr. The reaction mixture was allowed to cool down to room temperature. The reaction mixture was poured into ice. After adjusting this to pH 5 with 1N hydrochloric acid, sodium chloride was added thereto. This was extracted with a mixed solvent of ethyl acetate and tetrahydrofuran. The organic layer was washed with brine, and dried over anhydrous sodium sulfate. The organic layer after drying was concentrated under reduced pressure to provide a crude product of the titled compound as pale yellow crystals. The crystals were suspended by addition of diethyl ether (15 ml). The crystals were collected by filtration and washed with diethyl ether. This was dried under aeration to provide the titled compound as pale yellow crystals (4.20 g, 71.7%).

$^1$H-NMR Spectrum (CDCl$_3$) δ (ppm): 3.00-3.90 (5H, m), 4.95 (1H, s), 7.25-7.28 (2H, m), 7.33 (4H, m), 7.53 (4H, m).

Production Example 84

Methyl 1-benzhydrylazetidine-3-carboxylate

A solution of 1-benzhydrylazetidine-3-carboxylic acid (4.20 g) in N,N-dimethylformamide (45 ml) were added potassium carbonate (6.53 g) and iodomethane (0.976 ml), followed by stirring at room temperature for 20.5 hr. The reaction mixture was poured into ice water, and extracted with ethyl acetate. The organic layer was washed with brine, and dried over anhydrous sodium sulfate. The solvent was removed, and the residue was purified by silica gel column chromatography (eluent; heptane:ethyl acetate=5:1, then 3:1). Fractions containing the target compound were concentrated to provide the titled compound as yellow crystals (3.57 g, 80.8%).

$^1$H-NMR Spectrum (CDCl$_3$) δ (ppm): 3.26 (2H, m), 3.31 (1H, m), 3.44 (2H, m), 3.69 (3H, s), 4.38 (1H, s), 7.16-7.20 (2H, m), 7.25-7.28 (4H, m), 7.39-7.41 (4H, m).

ESI-MS (m/z): 282 [M+H]$^+$.

Production Example 85

Methyl azetidine-3-carboxylate hydrochloride

A solution of methyl 1-benzhydrylazetidine-3-carboxylate (3.57 g) in methanol (360 ml) were added a 4N solution of hydrochloric acid in ethyl acetate (12.7 ml) and 20% palladium hydroxide (3.57 g), followed by stirring at room temperature under a pressurized hydrogen atmosphere (0.4 MPa) for 11 hr. The catalyst was removed by filtration and washed with methanol and water. The filtrate was concentrated to provide a crude product of the target compound as a pale yellow oil. The reaction was assessed as quantitative and the product obtained was assessed as 1.93 g, which were used for the subsequent reaction.

ESI-MS (m/z): 116 [M+H]$^+$.

Production Example 86

Methyl 1-tert-butoxycarbonylazetidine-3-carboxylate

A crude product of methyl azetidine-3-carboxylate hydrochloride (assessed as 1.93 g of a pure product) was dissolved in water (26 ml), and sodium hydrogencarbonate (3.2 g) and a solution of di-t-butyl dicarbonate (2.91 g) in tetrahydrofuran (13 ml) were added while stirring and cooling in an ice bath, followed by stirring at the same temperature for 0.5 hr. The reaction mixture was stirred at room temperature for 19.5 hr. Tetrahydrofuran in the reaction mixture was removed, and extracted with ethyl acetate. The organic layer was washed with brine (70 ml), and dried over anhydrous sodium sulfate. The concentrated organic layer and the aqueous layer were combined, and tetrahydrofuran (50 ml) was added. This was stirred while cooling in an ice bath, and sodium hydrogencarbonate (3.2 g), and di-t-butyl dicarbonate (2.91 g) were again added thereto. After stirring at the same temperature for 0.5 hr, stirring was carried out at room temperature for 2.5 days. The reaction mixture was partitioned, and the aqueous layer was extracted with ethyl acetate. The organic layer was combined and dried over anhydrous sodium sulfate. The solvent was removed, and the residue was purified by silica gel column chromatography (eluent; heptane:ethyl acetate=2:1, 1:1, ethyl acetate, then ethyl acetate:methanol=10:1). Fractions containing the target compound were concentrated to provide the titled compound as a colorless oil (370 mg, 13.5%).

$^1$H-NMR Spectrum (CDCl$_3$) δ (ppm): 1.44 (9H, s), 3.35 (1H, m), 3.75 (3H, s), 4.10 (4H, d, J=7.6 Hz).

Production Example 87 tert-Butyl 3-(hydroxymethyl)azetidine-1-carboxylate

Lithium aluminum hydride (128 mg) was placed in a round-bottomed flask and suspended in tetrahydrofuran (30 ml). This was cooled in an ice bath, and a solution of methyl 1-tert-butoxycarbonylazetidine-3-carboxylate (970 mg) in tetrahydrofuran (10 ml) was gradually added thereto, followed by stirring under a nitrogen atmosphere at the same temperature for 1 hr. To the reaction mixture were added water (0.13 ml) and a 5N aqueous solution of sodium hydroxide (0.13 ml) and water (0.39 ml) while cooling in an ice bath, followed by stirring at the same temperature for 1 hr. Insoluble matter in the reaction mixture was removed by filtration. The filtrate was concentrated to provide the titled compound as a colorless oil(805 mg, 95.3%).

$^1$H-NMR Spectrum (CDCl$_3$) δ (ppm): 1.44 (9H, s), 2.71 (1H, m), 3.69 (2H, dd, J=5.2, 8.4 Hz), 3.79 (2H, d, J=6.8 Hz), 4.00 (2H, m).

Production Example 88

3-(Hydroxymethyl)azetidine trifluoroacetate

To tert-butyl 3-(hydroxymethyl)azetidine-1-carboxylate (125 mg) was added trifluoroacetic acid (0.413 ml) while cooling in an ice bath, followed by stirring at the same temperature for 30 min. Then, the reaction mixture was stirred at room temperature for 1.5 hr. The reaction mixture was concentrated to provide a crude product of the titled compound as a yellow oil (209.8 mg).

ESI-MS (m/z): 88 [M+H]$^+$.

Production Example 89 tert-Butyl 3-[(methanesulfonyloxy)methyl]azetidine-1-carboxylate

To a solution of tert-butyl 3-(hydroxymethyl)azetidine-1-carboxylate (806 mg) in tetrahydrofuran (25 ml) was added triethylamine (1.80 ml). This was cooled in an ice bath under a nitrogen atmosphere, and methanesulfonyl chloride (0.499 ml) was added dropwise, followed by stirring at the same temperature for 30 min. The reaction mixture was partitioned after addition of ethyl acetate (100 ml) and water (70 ml). The aqueous layer was extracted with ethyl acetate. The combined organic layer was washed with brine, and dried over anhydrous sodium sulfate. The solvent was removed, and the residue was purified by silica gel column chromatography (eluent; ethyl acetate). Fractions containing the target compound were concentrated to provide the titled compound as a colorless oil (1.05 g, 92.0%).

$^1$H-NMR Spectrum (CDCl$_3$) δ (ppm): 1.44 (9H, s), 2.93 (1H, m), 3.05 (3H, s), 3.72 (2H, dd, J=5.0, 9.0 Hz), 4.06 (2H, m), 4.35 (2H, d, J=6.8 Hz).

ESI-MS (m/z): 288 [M+Na]$^+$.

Production Example 90 tert-Butyl 3-(dimethylaminomethyl)azetidine-1-carboxylate

To a solution of tert-butyl 3-[(methanesulfonyloxy)methyl]azetidine-1-carboxylate (1.05 g) in methanol (20 ml) was added a 2M solution of dimethylamine in tetrahydrofuran (20 ml), followed by heating in a sealed tube at 70° C. for 40 hr. The reaction mixture was allowed to cool down to room temperature. The reaction mixture was concentrated, and partitioned between ethyl acetate and a saturated aqueous solution of sodium hydrogencarbonate. The organic layer was washed with brine, and dried over anhydrous sodium sulfate. The solvent was removed to provide the titled compound as a yellow oil (678 mg, 79.9%).

$^1$H-NMR Spectrum (CDCl$_3$) δ (ppm): 1.43 (9H, s), 2.22 (6H, s), 2.50 (2H, d, J=7.6 Hz), 2.69 (1H, m), 3.59 (2H, dd, J=5.2, 8.4 Hz), 4.16 (2H, m).

ESI-MS (m/z): 215 [M+H]$^+$, 269 [M+Na+MeOH]$^+$.

Production Example 91

3-(Dimethylaminomethyl)azetidine ditrifluoroacetate

To tert-butyl 3-(dimethylaminomethyl)azetidine-1-carboxylate (678 mg) was added trifluoroacetic acid (1.95 ml) while cooling in an ice bath, followed by stirring at the same temperature for 30 min. Then, the reaction mixture was stirred at room temperature for 1.5 hr. The reaction mixture was concentrated, then azeotropically distilled after addition of toluene to provide a crude product of the titled compound as a yellow oil (1.79 g).

ESI-MS (m/z): 115 [M+Na]$^+$.

Production Example 92 tert-Butyl 3-methoxyazetidine-1-carboxylate

A suspension of sodium hydride (2.89 g) in tetrahydrofuran (50 ml) was stirred while cooling in an ice bath. A solution of tert-butyl 3-hydroxyazetidine-1-carboxylate (5.00 g) in tetrahydrofuran (50 ml) was gradually added thereto, followed by stirring at the same temperature for 30 min. Then, the reaction mixture was stirred at room temperature for 30 min. The reaction mixture was again stirred while cooling in an ice bath for 15 min. To the reaction mixture was added dropwise iodomethane (3.09 ml), followed by stirring for 2 hr. Water was gradually added to the reaction mixture. When bubbling stopped, the organic layer was separated. The aqueous layer was extracted with ethyl acetate. The organic layer was combined, washed with brine, and dried over anhydrous sodium sulfate. The solvent was removed, and the residue was purified by silica gel column chromatography (eluent; heptane:ethyl acetate=3:1, 2:1, 1:1, then ethyl acetate). Fractions containing the target compound were concentrated to provide the titled compound as a colorless oil (1.80 g, 33.3%). Fractions containing the starting material were concentrated for recovery (2.10 g, 42.0%).

$^1$H-NMR Spectrum (CDCl$_3$) δ (ppm): 1.44 (9H, s), 3.28 (3H, s), 3.82 (2H, m), 4.06 (2H, m), 4.14 (1H, m).

Production Example 93

3-Methoxyazetidine trifluoroacetate tert-Butyl 3-methoxyazetidine-1-carboxylate (125 mg) was dissolved in dichloromethane (0.618 ml), and trifluoroacetic acid (0.618 ml) was added thereto, followed by stirring at room temperature for 3.5 hr. The reaction mixture was concentrated to provide a crude product of the target compound as a yellow oil (232 mg).

ESI-MS (m/z): 88 [M+H]$^+$.

Production Example 94

1-(Benzyloxy)-2,5-difluoro-4-nitrobenzene

To a solution of 2,4,5-trifluoronitrobenzene (9.48 g) and benzyl alcohol (5.54 ml) in N,N-dimethylformamide (40 ml) was added potassium carbonate (11.1 g), followed by stirring at room temperature for 60 hr. To the reaction mixture was added water (120 ml) at 0° C., followed by stirring at 4° C. for 24 hr. The precipitated crystals were collected by filtration and washed with water. These crystals were dried under reduced pressure to provide the titled compound as pale yellow crystals (11.5 g, 81%).

$^1$H-NMR Spectrum (DMSO-d$_6$) δ (ppm): 5.35 (2H, s), 7.40-7.50 (5H, m), 7.64 (1H, dd, J=7.2, 13.2 Hz), 8.20 (1H, dd, J=7.2, 10.8 Hz).

Production Example 95

4-Amino-2,5-difluorophenol

To a solution of 1-(benzyloxy)-2,5-difluoro-4-nitrobenzene (9.21 g) in methanol (300 ml) was added 10% palladium on carbon (921 mg), followed by stirring under a hydrogen atmosphere at room temperature for 24 hr and 20 min. The atmosphere in the reaction vessel was replaced with nitrogen to stop the reaction, and the catalyst was filtered through Celite. The filtrate was removed under reduced pressure to provide the titled compound as a brown solid (4.96 g, 99%).

$^1$H-NMR Spectrum (DMSO-d$_6$) δ (ppm): 4.67 (1H, s), 6.53-6.64 (1H, m), 9.03 (1H, s).

Production Example 96

4-(4-Amino-2,5-difluorophenoxy)pyridine-2-carboxamide

4-Amino-2,5-difluorophenol (4.95 g) was dissolved in dimethyl sulfoxide (50 ml) under a nitrogen flow, and potassium tert-butoxide (4.05 g) was added at room temperature, followed by stirring for 25 min. 4-Chloropyridine-2-carboxamide (2.70 g) was added thereto, followed by stirring at 80° C. for 2.5 hr. The reaction mixture was allowed to cool down to room temperature, and a 1N aqueous solution of sodium hydroxide (74.25 ml) was added, followed by stirring for 10 hr. The precipitated solid was collected by filtration, and the resultant solid was washed with water. This solid was dried under hot air at 100° C. for 24 hr to provide the titled compound as purple powder (3.38 g, 74%).

$^1$H-NMR Spectrum (DMSO-d$_6$) δ (ppm): 5.57 (2H, d, J=6.0 Hz), 6.75-6.80 (1H, m), 7.17-7.20 (1H, m), 7.26 (1H, dd, J=7.2, 10.8 Hz), 7.38 (1H, m), 7.73 (1H, s), 8.14 (1H, s), 8.52 (1H, d, J=5.6 Hz).

ESI-MS (m/z): 288 [M+Na]$^+$.

Production Example 97

N-(4-{[2-(Aminocarbonyl)pyridin-4-yl]oxy}-2,5-difluorophenyl)-N'-(4-fluorophenyl)cyclopropane-1,1-dicarboxamide 1-(4-Fluorophenylaminocarbonyl)cyclopropanecarboxylic acid (1.35 g) was dissolved in tetrahydrofuran (25.0 ml) under a nitrogen atmosphere, and triethylamine (1.06 ml) was added dropwise while cooling in an ice water bath, followed by stirring for 15 min. Then thionyl chloride (0.439 ml) was added at the same temperature, followed by stirring for 1.5 hr. To the reaction mixture was added dropwise at the same temperature a mixture of 4-(4-amino-2,5-difluorophenoxy)pyridine-2-carboxamide (1.0 g), tetrahydrofuran (12 ml) and triethylamine (1.06 ml), followed by stirring at 0° C. for 24 hr and 45 min. The reaction mixture was partitioned between ethyl acetate (70 ml) and a 2N aqueous solution of sodium hydroxide (15 ml). The organic layer was washed with a 2N aqueous solution of sodium hydroxide (15 ml) twice, 1N hydrochloric acid (15 ml) three times and a saturated aqueous solution of sodium hydrogencarbonate (10 ml) in this order, and dried over anhydrous sodium sulfate. The solvent was removed under reduced pressure. The resultant residue was purified by silica gel column chromatography (Fuji Silysia NH, eluent; heptane:ethyl acetate=1:1, 1:2, then ethyl acetate), and fractions containing the target compound were concentrated under reduced pressure. The residue was dried under reduced pressure to provide the titled compound as a white solid (372.8 mg, 21%).

$^1$H-NMR Spectrum (DMSO-d$_6$) δ (ppm): 1.28-1.33 (4H, m), 7.12-7.22 (2H, m), 7.22-7.28 (1H, m), 7.41 (1H, d, J=2.4 Hz), 7.59-7.67 (3H, m), 7.75 (1H, m), 8.10-8.17 (2H, m), 8.56 (1H, d, J=5.6 Hz), 9.80 (1H, m), 11.02 (1H, m).

Alternative Method for Synthesis of N-(4-{([2-(Aminocarbonyl)pyridin-4-yl]oxy}-2,5-difluorophenyl)-N'-(4-fluorophenyl)cyclopropane-1,1-carboxamide To a solution of 1,1-cyclopropanedicarboxylic acid (492 mg) in tetrahydrofuran (15 ml) was added dropwise 4-methylmorpholine (0.416 ml) while cooling in an ice water bath under a nitrogen atmosphere, followed by stirring for 15 min. To the reaction mixture, was then added thionyl chloride (0.276 ml), followed by stirring at the same temperature for 30 min. To the reaction mixture were added 4-(4-amino-2,5-difluorophenoxy)pyridine-2-carboxamide (500 mg) and 4-methylmorpholine (0.416 ml) in this order while cooling in an ice water bath under a nitrogen atmosphere. The reaction mixture was allowed to warm to room temperature and stirred overnight. The reaction mixture was partitioned after addition of a 1N aqueous solution of sodium hydroxide (15 ml) and tent-butyl methyl ether (30 ml). The separated aqueous layer was treated with 1N hydrochloric acid (15 ml) to precipitate a solid. The solid was collected by suction filtration and washed with water (10 ml, three times). Hot air drying at 60° C. provided 1-[4-(2-carbamoylpyridin-4-yl)oxy-2,5-difluorophenylaminocarbonyl]cyclopropanecarboxylic acid as a pale purple solid (674 mg, 95%).

$^1$H-NMR Spectrum (DMSO-d$_6$) δ (ppm): 1.53-1.65 (4H, m), 7.25 (1H, dd, J=2.4, 5.6 Hz), 7.44 (1H, d, J=2.4 Hz), 7.65-7.70 (1H, m), 7.75 (1H, brs), 8.15 (1H, brs), 8.26-8.31 (1H, m), 8.55 (1H, d, J=5.6 Hz), 11.48 (1H, brs).

ESI-MS (neg.)(m/z): 376 [M–H]$^-$.

To a suspension of 144-(2-carbamoylpyridin-4-yl)oxy-2,5-difluorophenylaminocarbonyl]cyclopropanecarboxylic acid (100 mg) and 4-fluoroaniline (0.051 ml) in tetrahydrofuran (4 ml) was added 4-(4,6-dimethoxy[1.3.5]triazin-2-yl)-4-methylmorpholinium chloride hydrate (157 mg), followed by stirring at room temperature 23 hr. The reaction mixture was partitioned between ethyl acetate and an aqueous solution of sodium hydrogencarbonate. The organic layer was washed with water and brine, dried over anhydrous magnesium sulfate. The solvent was concentrated under reduced pressure. The resultant residue was purified by silica gel column chromatography (Fuji Silysia NH, eluent; heptane:ethyl acetate=1:2, ethyl acetate, then ethyl acetate:methanol=10:1), and fractions containing the target compound were concentrated under reduced pressure. The residue was dried under reduced pressure to provide the titled compound as a white solid (133.5 mg, quant.).

ESI-MS (m/z): 493 [M+Na]$^+$.

Production Example 98

N-(4-{[2-(Aminopyridin-4-yl)oxy]-2,5-difluorophenyl}-N'-(4-fluorophenyl)cyclopropane-1,1-dicarboxamide N-(4-{[2-(Aminocarbonyl)pyridin-4-yl]oxy}-2,5-difluorophenyl)-N'-(4-fluorophenyl)cyclopropane-1,1-dicarboxamide (372.8 mg) was dissolved in N,N-dimethylformamide (5.0 ml). Water (0.0713 ml), [bis(trifluoroacetoxy)iodo]benzene (679 mg) and pyridine (0.384 ml) were added thereto at room temperature in this order, followed by stirring for 3 hr. The reaction mixture was partitioned between ethyl acetate (30 ml) and a 1N aqueous solution of sodium hydroxide (9 ml). The organic layer was separated, washed with brine, and dried over anhydrous sodium sulfate. The solvent was concentrated under reduced pressure, and the residue was purified by silica gel column chromatography (Fuji Silysia NH, eluent; heptane:ethyl acetate=1:3, then ethyl acetate). Fractions containing the target compound were concentrated under reduced pressure, and the residue was dried under reduced pressure to provide the titled compound as white powder (301.0 mg, 86%).

$^1$H-NMR Spectrum (DMSO-d$_6$) δ (ppm): 1.54-1.68 (4H, m), 5.83 (1H, d, J=2.4 Hz), 5.99 (2H, d, J=5.2 Hz), 6.17 (1H, dd, J=2.4, 5.6 Hz), 7.16-7.20 (2H, m), 7.47-7.53 (1H, m), 7.57-7.62 (2H, m), 7.81 (1H, d, J=5.6 Hz), 8.02-8.10 (1H, m), 9.77 (1H, m), 10.99 (1H, m).

ESI-MS (m/z): 443 [M+H]$^+$.

Production Example 99

3-(Azetidin-1-ylcarbonyl)-1-benzhydrylazetidine

1-Benzhydrylazetidine-3-carboxylic acid (1.52 g) was dissolved in N,N-dimethylformamide (30 ml) at room temperature under a nitrogen atmosphere. Triethylamine (3.17 ml), BOP reagent (5.03 g), and azetidine hydrochloride (1.06 g) were added in this order, followed by stirring for 24 hr. To the reaction mixture was added a 1N aqueous solution of sodium hydroxide (50 ml), followed by stirring. The liquid-liquid separation was carried out after addition of ethyl acetate (100 ml). The separated organic layer was washed with a 1N aqueous solution of sodium hydroxide, water and brine in this order, and dried over anhydrous sodium sulfate. To the residue (1.83 g) obtained by removing the solvent were added ethyl acetate (2 ml) and tert-butyl methyl ether (10 ml) to precipitate crystals. The crystals were collected by filtration and dried under aeration to provide the titled compound as pale yellow crystals (1.14 g, 65%).

$^1$H-NMR Spectrum (CDCl$_3$) δ (ppm): 2.15-2.30 (2H, m), 3.20-3.50 (5H, m), 3.90-4.10 (4H, m), 4.45 (1H, s), 7.15-7.45 (10H, m).

ESI-MS (m/z): 307 [M+H]$^+$.

Production Example 100

3-(Azetidin-1-ylmethyl)-1-benzhydrylazetidine

Lithium aluminum hydride (300 mg) was suspended in tetrahydrofuran (10 ml) under a nitrogen atmosphere at room temperature, and a solution of 3-(azetidin-1-ylcarbonyl)-1-benzhydrylazetidine (1.14 g) in tetrahydrofuran (30 ml) was added dropwise. After the dropwise addition, the reaction mixture was stirred at 60° C. for 2 hr. The reaction mixture was cooled in an ice water bath, and water (0.3 ml), a 5N aqueous solution of sodium hydroxide (0.3 ml) and water (0.9 ml) were added, followed by stirring overnight. Insoluble matter was removed by filtration and washed with ethyl acetate (100 ml). The filtrate was concentrated under reduced pressure to provide the titled compound as a pale brown oil (1.115 g, quantitative).

$^1$H-NMR Spectrum (CDCl$_3$) δ (ppm): 2.07 (2H, m), 2.40-2.60 (3H, m), 2.74 (2H, m), 3.11-3.15 (4H, m), 3.32 (2H, m), 4.29 (1H, s), 7.14-7.40 (10H, m).

ESI-MS (m/z): 293 [M+H]$^+$.

Production Example 101

3-(Azetidin-1-ylmethyl)azetidine dihydrochloride 3-(Azetidin-1-ylmethyl)-1-benzhydrylazetidine (1.115 g) was dissolved in methanol (25 ml). Then, 10% palladium on carbon (1.1 g) wad added under a nitrogen atmosphere, followed by stirring under a pressurized hydrogen atmosphere (0.4 MPa) for 12 hr. The atmosphere in the reaction vessel was replaced with nitrogen, and the catalyst was removed by filtration and washed with methanol. To the filtrate was added a 4N solution of hydrochloric acid in ethyl acetate (4 ml), followed by concentration under reduced pressure. To the residue was added heptane (25 ml), and the supernatant was removed. This operation was repeated once more. The resultant residue was dried under reduced pressure for 2 days to provide the titled compound as a pale brown oil (680 mg, 90%).

ESI-MS (m/z): 127 [M+H]$^+$.

Production Example 102

1-Benzhydryl-3-(hydroxymethyl)azetidine

1-Benzhydryl-3-azetidinecarboxylic acid (3.12 g) was suspended in tetrahydrofuran (60 ml) and cooled under a nitrogen atmosphere in an ice-ethanol bath. Triethylamine (1.96 ml) was added dropwise, and a solution of ethyl chlorocarbonate (1.34 ml) in tetrahydrofuran (5 ml) was added dropwise over 20 min. After the dropwise addition, stirring was carried out at the same temperature for 30 min. The reaction mixture was filtered and washed with tetrahydrofuran (30 ml). The filtrate was added dropwise over 15 min to an aqueous (15 ml) solution of sodium borohydride (1.33 g) cooled in an ice water bath. Upon completion of the dropwise addition, the reaction mixture was stirred at room temperature. To the reaction mixture was gradually added 1N hydrochloric acid (35 ml) to decompose excess sodium borohydride, and a 1N aqueous solution of sodium hydroxide (35 ml) was added. This was extracted with ethyl acetate (100 ml). The organic layer was washed with brine, and dried over anhydrous sodium sulfate. The solvent was concentrated, and the residue was dried under reduced pressure to provide the titled compound as a pale brown solid (1.59 g, 54%).

$^1$H-NMR Spectrum (CDCl$_3$) δ (ppm): 2.57 (1H, m), 3.03 (2H, m), 3.24 (2H, m), 3.80 (2H, d, J=5.2 Hz), 4.33 (1H, s), 7.15-7.45 (10H, m).

ESI-MS (m/z): 254 [M+H]$^+$.

Production Example 103

3-(Hydroxymethyl)azetidine hydrochloride

1-Benzhydryl-3-(hydroxymethyl)azetidine (1.59 g) was dissolved in methanol (30 ml), and palladium hydroxide on carbon (1.0 g) was added under a nitrogen atmosphere, followed by stirring under a pressurized hydrogen atmosphere (0.4 MPa). The atmosphere in the reaction vessel was replaced with nitrogen, and the catalyst was filtered and washed with methanol. After addition of a 4N solution of hydrochloric acid in ethyl acetate (2 ml), concentration under reduced pressure was carried out. To the residue was added heptane (15 ml), and the supernatant was removed. This operation was repeated. The residue was dried under reduced pressure overnight to provide a crude product of the titled compound as a pale yellow oil (832 mg).

ESI-MS (m/z): 88 [M+H]$^+$.

Production Example 104

Benzyl (2,5-difluoro-4-hydroxyphenyl)carbamate 1-(Benzyloxy)-2,5-difluoro-4-nitrobenzene (5.3 g) was dissolved in methanol (100 ml)—tetrahydrofuran (100 ml). 20% palladium hydroxide on carbon (2.81 g) was added thereto, followed by stirring under a hydrogen atmosphere at room temperature for 8 hr. The catalyst was removed by filtration and washed with methanol. The filtrate was concentrated under reduced pressure. The resultant residue (3.06 g) was dissolved in acetone (100 ml)—water (50 ml). Sodium carbonate (2.02 g) and benzyl chloroformate (3.43 ml) were added thereto while stirring and cooling in an ice water bath, followed by stirring at room temperature for 1 hr. The reaction mixture was concentrated under reduced pressure. The residue was partitioned between ethyl acetate and brine. The organic layer was separated and concentrated under reduced pressure. The resultant residue was purified by silica gel column chromatography (eluent; heptane:ethyl acetate=2:1). Fractions containing the target compound were concentrated under reduced pressure and the residue was dried under reduced pressure to provide the titled compound as a brown solid (4.90 g, 88%).

ESI-MS (neg.) (m/z): 278 [M−H]⁻.

Production Example 105

Benzyl[4-(4-chloropyrimidin-6-yloxy)-2,5-difluorophenyl]carbamate

Benzyl(2,5-difluoro-4-hydroxyphenyl)carbamate (4.90 g) was dissolved in N,N-dimethylformamide (30 ml), then 4,6-dichloropyrimidine (2.61 g) and potassium carbonate (3.63 g) were added thereto at room temperature, followed by stirring for 2 hr. Water (90 ml) was added to the reaction mixture to precipitate crystals. The crystals were collected by filtration and washed with water (30 ml, 6 times). The crystals were hot air-dried at 60° C. for 2 days to provide the titled compound as pale brown crystals (6.108 g, 89%).

¹H-NMR Spectrum (CDCl₃) δ (ppm): 5.25 (2H, s), 6.95 (1H, brs), 7.01 (1H, m), 7.04 (1H, d, J=0.8 Hz), 7.30-7.50 (5H, m), 8.16 (1H, m), 8.56 (1H, d, J=0.8 Hz).

ESI-MS (neg.) (m/z): 390 [M−H]⁻.

Production Example 106

Benzyl[4-(4-aminopyrimidin-6-yloxy)-2,5-difluorophenyl]carbamate

A mixture of benzyl[4-(4-chloropyrimidin-6-yloxy)-2,5-difluorophenyl]carbamate (3.92 g) and 2M ammonia-isopropanol (50 ml) was heated at 120° C. for 2 days in a sealed tube. The reaction mixture was allowed to cool to room temperature, then concentrated under reduced pressure. The resultant residue was partitioned between ethyl acetate and a 10% aqueous solution of potassium bisulfate. The organic layer was washed with brine, dried over anhydrous sodium sulfate. The solvent was concentrated under reduced pressure and the resultant residue was purified by silica gel column chromatography (Fuji Silysia NH, eluent; heptane:ethyl acetate=1:2). Fractions containing the target compound were concentrated under reduced pressure and the residue was dried under reduced pressure to provide the titled compound as pale yellow crystals (561 mg, 15%).

¹H-NMR Spectrum (CDCl₃) δ (ppm): 4.94 (2H, br), 5.23 (2H, s), 5.97 (1H, d, J=0.8 Hz), 6.91 (1H, brs), 6.99 (1H, m), 7.30-7.50 (5H, m), 8.10 (1H, m), 8.24 (1H, d, J=0.8 Hz).

ESI-MS (m/z): 395 [M+Na]⁺.

Production Example 107

Benzyl[4-(4-azidopyrimidin-6-yloxy)-2,5-difluorophenyl]carbamate

Benzyl[4-(4-chloropyrimidin-6-yloxy)-2,5-difluorophenyl]carbamate (1.96 g) was dissolved in N,N-dimethylformamide (20 ml). Sodium azide (650 mg) was added thereto, followed by stirring at 60° C. for 2 hr. The reaction mixture was allowed to cool to room temperature, then partitioned between ethyl acetate and water. The organic layer was washed with brine, dried over anhydrous sodium sulfate. The solvent was concentrated under reduced pressure and the resultant residue was purified by silica gel column chromatography (eluent; heptane:ethyl acetate=3:1). Fractions containing the target compound were concentrated under reduced pressure and the residue was dried under reduced pressure to provide the titled compound as white crystals (685 mg, 34%).

¹H-NMR Spectrum (CDCl₃) δ (ppm): 5.24 (2H, s), 6.40 (1H, d, J=0.8 Hz), 6.93 (1H, brs), 6.99 (1H, dd, J=7.2, 10.0 Hz), 7.30-7.50 (5H, m), 8.13 (1H, m), 8.51 (1H, d, J=0.8 Hz).

Production Example 108

4-Amino-6-(4-amino-2,5-difluorophenoxy)pyrimidine

Production Method—1

4-Amino-2,5-difluorophenol (2.15 g) was dissolved in dimethyl sulfoxide (12.5 ml) at room temperature under a nitrogen flow. Potassium tert-butoxide (1.66 g) was added thereto, followed by stirring at room temperature for 5 min. 4-Amino-6-chloropyrimidine (1.55 g) was added, and the resultant mixture was stirred at 100° C. for 18.5 hr under a nitrogen flow. The reaction mixture was allowed to cool to room temperature, then partitioned between ethyl acetate (100 ml) and a 1N aqueous solution of sodium hydroxide (50 ml). The organic layer was washed with a 2N aqueous solution of sodium hydroxide (50 ml, 3 times) and brine (50 ml). The solvent was concentrated under reduced pressure and the resultant residue was purified by silica gel column chromatography (Fuji Silysia NH, eluent; heptane:ethyl acetate=1:2). Fractions containing the target compound were concentrated under reduced pressure and the residue was dried under reduced pressure to provide the titled compound as pale yellow powder (271 mg, 9.5%).

¹H-NMR Spectrum (CDCl₃) δ (ppm): 3.76 (2H, br), 4.97 (2H, br), 5.94 (1H, d, J=0.8 Hz), 6.60 (1H, dd, J=8.0, 11.2 Hz), 6.87 (1H, dd, J=7.2, 11.2 Hz), 8.26 (1H, d, J=0.8 Hz).

ESI-MS (m/z): 239 [M+H]⁺.

Production Method—2

Benzyl[4-(4-aminopyrimidin-6-yloxy)-2,5-difluorophenyl]carbamate (561 mg) was dissolved in methanol (30 ml). 10% palladium on carbon (321 mg) was added, followed by stirring under a hydrogen atmosphere for 4 hr. The catalyst was filtered off and washed with methanol. The filtrate was concentrated under reduced pressure and the residue was dried under reduced pressure to provide the titled compound as pale yellow powder (360 mg, quantitative).

Production Method—3

Benzyl[4-(4-azidopyrimidin-6-yloxy)-2,5-difluorophenyl]carbamate (684 mg) was dissolved in methanol (20 ml)— tetrahydrofuran (20 ml). 10% palladium on carbon (366 mg) was added, followed by stirring under a hydrogen atmosphere for 5 hr. The catalyst was filtered off and washed with methanol. The filtrate was concentrated under reduced pressure and the residue was dried under reduced pressure to provide the titled compound as pale yellow powder (373 mg, 91%).

Production Example 109

N-{4-[(4-Aminopyrimidin-6-yl)oxy]-2,5-difluorophenyl}-N'-(4-fluorophenyl)cyclopropane-1,1-dicarboxamide To a solution of 1-(4-fluorophenylaminocarbonyl)cyclopropanecarboxylic acid (378 mg) in N,N-dimethylformamide (3 ml) were added triethylamine (0.236 ml) and HATU (644 mg) at room temperature under a nitrogen atmosphere, followed by stirring for 30 min. To the resultant mixture was added 4-amino-6-(4-amino-2,5-difluorophenoxy)pyrimidine (270 mg) in N,N-dimethylformamide (3 ml) at room temperature, followed by stirring for 6 hr. Triethylamine (0.079 ml) and HATU (215 mg) were added again and the resultant mixture was stirred overnight. The reaction mixture was partitioned between ethyl acetate (20 ml) and a 1N aqueous solution of sodium hydroxide (10 ml). The organic layer was washed with a 1N aqueous solution of sodium hydroxide (10 ml, twice) and brine (10 ml), dried over anhydrous sodium sulfate. The solvent was concentrated under reduced pressure and the resultant residue was purified by silica gel column chromatography (Fuji Silysia NH, eluent; heptane:ethyl acetate=1:2 to 1:4). Fractions containing the target compound were concentrated under reduced pressure and the residue was dried under reduced pressure to provide the titled compound as pale brown powder (199 mg, 40%).
$^1$H-NMR Spectrum (CDCl$_3$) δ (ppm): 1.60-1.80 (4H, m), 4.99 (2H, br), 6.00 (1H, s), 7.00-7.50 (5H, m), 8.24 (1H, s), 8.26 (1H, m), 8.59 (1H, brs), 9.54 (1H, brs).
ESI-MS (m/z): 466 [M+Na]$^+$.

Production Example 110

1-(Benzyloxy)-2,3-difluoro-4-nitrobenzene

To a solution of 1,2,3-trifluoro-4-nitrobenzene (5.0 g) and benzyl alcohol (2.92 ml) in N,N-dimethylformamide (20 ml) was added potassium carbonate (5.85 g), followed by stirring at room temperature for 62 hr and 45 min. To the reaction mixture was added water (80 ml) at 0° C., followed by stirring at 4° C. for 28 hr. The precipitated crystals were collected by filtration and washed with water. These crystals were dried under reduced pressure to provide the titled compound as pale yellow crystals (6.54 g) which was a mixture of 2-(benzyloxy)-3,4-difluoro-1-nitrobenzene.

Production Example 111

4-Amino-2,3-difluorophenol

To a solution of a mixture of 1-(benzyloxy)-2,3-difluoro-4-nitrobenzene and 2-(benzyloxy)-3,4-difluoro-1-nitrobenzene (6.54 g) in methanol (200 ml) was added 10% palladium on carbon (654 mg), followed by stirring under a hydrogen atmosphere at room temperature for 26 hr and 50 min. The atmosphere in the reaction vessel was replaced with nitrogen to stop the reaction, and the catalyst was filtered off through Celite. The filtrate was concentrated under reduced pressure to provide the titled compound as a black solid (3.52 g) which was a mixture of 6-amino-2,3-difluorophenol.
ESI-MS (m/z): 144 [M−H]$^-$.

Production Example 112

4-(4-Amino-2,3-diflurophenoxy)pyridine-2-carboxamide

The mixture of 4-amino-2,3-difluorophenol and 6-amino-2,3-difluorophenol (3.52 g) was dissolved in dimethyl sulfoxide (30 ml) under a nitrogen flow, and potassium tert-butoxide (1.49 g) was added at room temperature, followed by stirring for 30 min. 4-Chloropyridine-2-carboxamide (947 mg) was added thereto, followed by stirring at 80° C. for 6 hr. Then the reaction mixture was stirred at 100° C. for 14 hr. The reaction mixture was allowed to cool down to room temperature, and a 1N aqueous solution of sodium hydroxide (52.8 ml) was added, followed by stirring for 9 hr and 15 min. The reaction mixture was partitioned between ethyl acetate (300 ml) and water (300 ml). The aqueous layer was extracted with ethyl acetate (200 ml, twice), then the combined organic layer was dried over anhydrous sodium sulfate. The solvent was removed under reduced pressure. The resultant residue was purified by silica gel column chromatography (Fuji Silysia NH, eluent; heptane:ethyl acetate=1:3) and fractions containing the target compound were concentrated under reduced pressure. The residue was dried under reduced pressure to provide the titled compound as a pale brown solid (532 mg) which was a mixture of 4-(6-amino-2,3-diflurophenoxy)pyridine-2-carboxamide.
ESI-MS (m/z): 264 [M−H]$^-$.

Production Example 113

N-(4-{[2-(Aminocarbonyl)pyridin-4-yl]oxy}-2,3-difluorophenyl)-N'-(4-fluorophenyl)cyclopropane-1,1-dicarboxyamide 1-(4-Fluorophenylaminocarbonyl)cyclopropanecarboxylic acid (1.12 g) was dissolved in tetrahydrofuran (11 ml) under a nitrogen atmosphere, and N-methylmorpholine (1.21 ml) was added dropwise while cooling in an ice water bath, followed by stirring for 15 min. Then thionyl chloride (0.803 ml) was added at the same temperature, followed by stirring for 35 min. The solvent was removed under reduced pressure, the residue was azeotroped with toluene and dried under reduced pressure. The resultant residue and the mixture of 4-(4-amino-2,3-diflurophenoxy)pyridine-2-carboxamide and 4-(6-amino-2,3-diflurophenoxy)pyridine-2-carboxamide (532 mg) were dissolved in tetrahydrofuran (12 ml) under a nitrogen atmosphere. Then N-methylmorpholine (1.21 ml) was added at room temperature, followed by stirring for 28 hr and 20 min. The reaction was stopped by adding a 1N aqueous solution of sodium hydroxide (10 ml), and the reaction mixture was partitioned between ethyl acetate (100 ml) and water (20 ml). The organic layer was washed with water (100 ml) and brine (50 ml), dried over anhydrous sodium sulfate. The solvent was removed under reduced pressure. The resultant residue was purified by silica gel column chromatography (Fuji Silysia NH, eluent; heptane:ethyl acetate=1:1, 1:2, then ethyl acetate), and fractions containing the target compound were concentrated under reduced pressure. The residue was dried under reduced pressure to provide the titled compound as a pale brown solid (294.7 mg).
1H-NMR Spectrum (CDCl$_3$) δ (ppm): 1.63-1.82 (4H, m), 5.53-5.56 (2H, m), 7.03-7.08 (3H, m), 7.46-7.49 (2H, m), 7.66 (1H, d, J=2.8 Hz), 7.80-7.88 (1H, m), 8.03-8.08 (1H, m), 8.46 (1H, d, J=5.2 Hz), 8.48 (1H, brs), 9.78-9.81 (1H, m).

ESI-MS (m/z): 493 [M+Na]$^+$

Production Example 114

N-{4-[(2-Aminopyridin-4-yl)oxy]-2,3-difluorophenyl}-N'-(4-fluorophenyl)cyclopropane-1,1-dicarboxamide N-(4-{[2-(Aminocarbonyl)pyridin-4-yl]oxy}-2,3-difluorophenyl)-N'-(4-fluorophenyl)cyclopropane-1,1-dicarboxamide (295 mg) was dissolved in N,N-dimethylformamide (4 ml). Water (0.0563 ml), [bis(trifluoroacetoxy)iodo]benzene (536 mg) and pyridine (0.303 ml) were added thereto at room temperature in this order, followed by stirring for 25 hr and 10 min. The reaction was stopped by adding a 1N aqueous solution of sodium hydroxide (9 ml), and the reaction mixture was partitioned between ethyl acetate (30 ml) and water (10 ml). The organic layer was washed with water (30 ml) in twice, brine and dried over anhydrous sodium sulfate. The solvent was removed under reduced pressure. The resultant residue was purified by silica gel column chromatography (Fuji Silysia NH, eluent; heptane:ethyl acetate=1:3), and fractions containing the target compound were concentrated under reduced pressure. The residue was dried under reduced pressure to provide the titled compound as a pale yellow solid (168.4 mg, 61%).

1H-NMR Spectrum (CDCl$_3$) δ (ppm): 1.67-1.80 (4H, m), 3.74 (2H, m), 4.54 (2H, brs), 5.96 (1H, d, J=2.4 Hz), 6.28 (1H, dd, J=2.4, 5.6 Hz), 6.92-7.02 (1H, m), 7.02-7.10 (2H, m), 7.45-7.50 (1H, m), 7.96 (1H, d, J=5.6 Hz), 8.42 (1H, brs), 9.75 (1H, brs).

ESI-MS (m/z): 443[M+H]$^+$.

Example 61

N-[4-({2-[(Azetidin-1-ylcarbonyl)amino]pyridin-4-yl}oxy)-2-fluorophenyl]-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (1.5 g) was dissolved in tetrahydrofuran (15 ml) under a nitrogen atmosphere, and triethylamine (0.987 ml) and phenyl chloroformate (0.978 ml) were added dropwise at room temperature in this order, followed by stirring for 30 min. The reaction mixture was stirred after addition of ethyl acetate and a saturated aqueous solution of sodium hydrogencarbonate. The organic layer was separated, washed with brine, and dried over anhydrous sodium sulfate. The solvent was concentrated under reduced pressure. The residue was dissolved in N,N-dimethylformamide (7.5 ml). Triethylamine (4.92 ml) and azetidine hydrochloride (1.33 g) were added at room temperature, followed by stirring for 7.5 hr. The reaction mixture was partitioned between ethyl acetate and a saturated aqueous solution of sodium hydrogencarbonate. The organic layer was washed with water (three times) and brine in this order, and dried over anhydrous sodium sulfate. The solvent was concentrated under reduced pressure. To the resultant residue were added ethyl acetate (5 ml) and heptane (5 ml) to precipitate a solid. The solid was collected by filtration and dried under aeration to provide the titled compound as white powder (1.29 g, 72%).

1H-NMR Spectrum (CDCl$_3$) δ (ppm): 1.60-1.80 (4H, m), 2.31 (2H, m), 4.11 (4H, m), 6.60 (1H, dd, J=2.4, 5.6 Hz), 6.91-7.52 (7H, m), 7.74 (1H, d, J=2.4 Hz), 8.01 (1H, d, J=5.6 Hz), 8.24 (1H, m), 8.96 (1H, brs), 9.12 (1H, brs).

ESI-MS (m/z): 530 [M+Na]$^+$.

Example 62

N-(4-Fluorophenyl)-N'-[2-fluoro-4-({2-[(pyrrolidin-1-ylcarbonyl)amino]pyridin-4-yl}oxy)phenyl]cyclopropane-1,1-dicarboxamide To a solution of roughly purified [4-(3-fluoro-4-{[1-(4-fluorophenylcarbamoyl)cyclopropanecarbonyl]amino}phenoxy)pyridin-2-yl]-N-(phenoxycarbonyl)carbamic acid phenyl ester (150 mg) in N,N-dimethylformamide (1.5 ml) was added pyrrolidine (0.100 ml) at room temperature, followed by stirring overnight. The reaction mixture was partitioned between ethyl acetate and water. The organic layer was washed with a saturated aqueous solution of sodium hydrogencarbonate and brine in this order, and dried over anhydrous sodium sulfate. The solvent was concentrated under reduced pressure. The resultant residue was purified by silica gel column chromatography (eluent; ethyl acetate, then ethyl acetate:methanol=95:5). Fractions containing the target compound were concentrated under reduced pressure. To the resultant residue was added diethyl ether:heptane=1:2 to precipitate a solid. The solvent was concentrated under reduced pressure, and the residue was dried under reduced pressure to provide the titled compound as white powder (17.4 mg).

$^1$H-NMR Spectrum (CDCl$_3$) δ (ppm): 1.60-1.80 (4H, m), 1.90-2.04 (4H, m), 3.44-3.60 (4H, m), 6.63 (1H, dd, J=2.4, 5.6 Hz), 6.90-7.55 (7H, m), 7.88 (1H, m), 8.00 (1H, d, J=5.6 Hz), 8.28 (1H, m), 9.00-9.10 (2H, m).

ESI-MS (m/z): 544 [M+Na]$^+$.

Example 63

N-[2-Fluoro-4-{2-[(morpholin-4-ylcarbonyl)amino]pyridin-4-yl}oxy)phenyl]-N'-(4-fluorophenyl)cyclopropane-1,1-dicarboxamide To a solution of roughly purified [4-(3-fluoro-4-{[1-(4-fluorophenylcarbamoyl)cyclopropanecarbonyl]amino}phenoxy)pyridin-2-yl]-N-(phenoxycarbonyl)carbamic acid phenyl ester (150 mg) in N,N-dimethylformamide (1.5 ml) was added morpholine (0.100 ml) at room temperature, followed by stirring overnight. The reaction mixture was partitioned between ethyl acetate and water. The organic layer was washed with a saturated aqueous solution of sodium hydrogencarbonate and brine in this order, and dried over anhydrous sodium sulfate. The solvent was concentrated under reduced pressure. The resultant residue was purified by silica gel column chromatography (eluent; ethyl acetate, then ethyl acetate:methanol=95:5). Fractions containing the target compound were concentrated under reduced pressure. To the resultant residue was added diethyl ether:heptane=1:2 to precipitate a solid. The solvent was concentrated under reduced pressure, and the residue was dried under reduced pressure to provide the titled compound as white powder (12.2 mg).

$^1$H-NMR Spectrum (CDCl$_3$) δ (ppm): 1.60-1.80 (4H, m), 3.60-3.80 (8H, m), 6.78 (1H, dd, J=2.4, 5.6 Hz), 6.90-7.55 (7H, m), 7.91 (1H, d, J=5.6 Hz), 8.06 (1H, m), 8.40 (1H, m), 8.51 (1H, brs), 9.70 (1H, brs).

ESI-MS (m/z): 560 [M+Na]$^+$.

Example 64

N-{2-Fluoro-4-[(2-{[(1-methylpiperazin-4-yl)carbonyl]amino}pyridin-4-yl)oxy]phenyl}-N'-(4-fluorophenyl)cyclopropane-1,1-dicarboxamide To a solution of roughly purified [4-(3-fluoro-4-{[1-(4-fluorophenylcarbamoyl)cyclopropanecarbonyl]amino}phenoxy)pyridin-2-yl]-N-(phenoxycarbonyl)carbamic acid phenyl ester (200 mg) in N,N-dimethylformamide (2.0 ml) was added 1-methylpiperazine (0.170 ml) at room temperature, followed by stirring overnight. The reaction mixture was partitioned between ethyl acetate and water. The organic layer was washed with a saturated aqueous solution of sodium hydrogencarbonate and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. To the resultant residue was added diethyl ether:heptane=1:2 to precipitate a solid. The solvent was concentrated under reduced pressure, and the residue was dried under reduced pressure to provide the titled compound as white powder (27.0 mg).

$^1$H-NMR Spectrum (CDCl$_3$) δ (ppm): 1.60-1.80 (4H, m), 2.65 (3H, brs), 2.80-3.00 (4H, m), 3.80-4.00 (4H, m), 6.65 (1H, m), 6.90-7.55 (7H, m), 7.68 (1H, m), 8.00 (1H, m), 8.29 (1H, m), 8.79 (1H, brs), 9.35 (1H, brs).
ESI-MS (m/z): 573 [M+Na]$^+$.

Example 65

N-[4-({2-[(Azetidin-1-ylcarbonyl)amino]pyridin-4-yl}oxy)-3-fluorophenyl]-N'-(4-fluorophenyl)cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (80 mg) in N,N-dimethylformamide (1.0 ml) were added triethylamine (0.130 ml) and azetidine hydrochloride (60 mg) at room temperature, followed by stirring for 3 hr. The reaction mixture was partitioned between ethyl acetate and water. The organic layer was washed with a saturated aqueous solution of sodium hydrogencarbonate and brine in this order, and dried over anhydrous sodium sulfate. The solvent was concentrated under reduced pressure. The resultant residue was purified by silica gel column chromatography (eluent; ethyl acetate). Fractions containing the target compound were concentrated under reduced pressure. To the resultant residue was added diethyl ether:heptane=1:2 to precipitate a solid. The solvent was concentrated under reduced pressure, and residue was dried under reduced pressure to provide the titled compound as white powder (41.7 mg, 69%).

$^1$H-NMR Spectrum (CDCl$_3$) δ (ppm): 1.60-1.80 (4H, m), 2.30 (2H, m), 4.10 (4H, m), 6.63 (1H, dd, J=2.4, 5.6 Hz), 7.00-7.50 (7H, m), 7.67 (1H, m), 7.70 (1H, dd, J=2.4, 12.0 Hz), 8.01 (1H, d, J=5.6 Hz), 8.60 (1H, brs), 9.64 (1H, brs).
ESI-MS (m/z): 530 [M+Na]$^+$.

Example 66

N-(4-Fluorophenyl)-N'-[3-fluoro-4-({2-[(pyrrolidin-1-ylcarbonyl)amino]pyridin-4-yl}oxy)phenyl]cyclopropane-1,1-dicarboxamide To a solution of [4-(2-fluoro-4-[1-(4-fluorophenylcarbamoyl)cyclopropanecarbonyl]amino}phenoxy)pyridin-2-yl]-N-(phenoxycarbonyl)carbamic acid phenyl ester (80 mg) in N,N-dimethylformamide (1.0 ml) was added pyrrolidine (0.050 ml) at room temperature, followed by stirring for 3 hr. The reaction mixture was partitioned between ethyl acetate and water. The organic layer was washed with a saturated aqueous solution of sodium hydrogencarbonate and brine in this order, and dried over anhydrous sodium sulfate. The solvent was concentrated under reduced pressure. The resultant residue was purified by silica gel column chromatography (eluent; ethyl acetate). Fractions containing the target compound were concentrated under reduced pressure. To the resultant residue was added diethyl ether:heptane=1:2 to precipitate a solid. The solvent was concentrated under reduced pressure, and the residue was dried under reduced pressure to provide the titled compound as white powder (45.9 mg, 73%).

$^1$H-NMR Spectrum (CDCl$_3$) δ (ppm): 1.60-1.80 (4H, m), 1.86-2.04 (4H, m), 3.40-3.52 (4H, m), 6.63 (1H, dd, J=2.4, 5.6 Hz), 7.00-7.50 (7H, m), 7.65-7.75 (2H, m), 8.01 (1H, d, J=5.6 Hz), 8.68 (1H, brs), 9.62 (1H, brs).
ESI-MS (m/z): 544 [M+Na]$^+$.

Example 67

N-[3-Fluoro-4-({2-[(morpholin-4-ylcarbonyl)amino]pyridin-4-yl}oxy)phenyl]-N'-(4-fluorophenyl)-cyclopropane-1,1-dicarboxamide To a solution of [4-(2-fluoro-4-{[1-(4-fluorophenylcarbamoyl)cyclopropanecarbonyl]amino}phenoxy)pyridin-2-yl]-N-(phenoxycarbonyl)carbamic acid phenyl ester (80 mg) in N,N-dimethylformamide (1.0 ml) was added morpholine (0.055 ml) at room temperature, followed by stirring overnight. The reaction mixture was partitioned between ethyl acetate and water. The organic layer was washed with a saturated aqueous solution of sodium hydrogencarbonate and brine in this order, and dried over anhydrous sodium sulfate. The solvent was concentrated under reduced pressure. The resultant residue was purified by silica gel column chromatography (eluent; ethyl acetate). Fractions containing the target compound were concentrated under reduced pressure. To the resultant residue was added diethyl ether:heptane=1:2 to precipitate a solid. The solvent was concentrated under reduced pressure to provide the titled compound as white powder (52.3 mg, 81%).

$^1$H-NMR Spectrum (CDCl$_3$) δ (ppm): 1.60-1.80 (4H, m), 3.44-3.54 (4H, m), 3.66-3.76 (4H, m), 6.58 (1H, dd, J=2.4, 5.6 Hz), 7.00-7.50 (7H, m), 7.58 (1H, m), 7.69 (1H, m), 8.03 (1H, d, J=5.6 Hz), 8.51 (1H, brs), 9.64 (1H, brs).
ESI-MS (m/z): 560 [M+Na]$^+$.

Example 68

N-(4-Fluorophenyl)-N'-[4-({2-[(morpholin-4-ylcarbonyl)amino]pyridin-4-yl}oxy)phenyl]cyclopropane-1,1-dicarboxamide Morpholine-4-carboxylic acid [4-(4-aminophenoxy)pyridin-2-yl]amide (121 mg) and 1-(4-fluorophenylcarbamoyl)cyclopropanecarboxylic acid (92.0 mg) were dissolved in N,N-dimethylformamide (4 ml), and diisopropylethylamine (0.358 ml) and HBTU (O-benzotriazol-1-yl-N,N,N',N'-tetramethyluronium hexafluorophosphate; 213 mg) were added under a nitrogen atmosphere at room temperature, followed by stirring for 4 hr. The reaction mixture was partitioned after addition of ethyl acetate (50 ml) and a saturated aqueous solution of sodium hydrogencarbonate (20 ml). The separated organic layer was washed with a saturated aqueous solution of sodium hydrogencarbonate (30 ml) and brine (30 ml), and dried over anhydrous sodium sulfate. The solvent was removed under reduced pressure, and the resultant residue was purified by silica gel column chromatography (eluent; heptane:ethyl acetate=1:7, then ethyl acetate). Fractions containing the target compound were concentrated under reduced pressure, and to the residue (131.9 mg) were added tert-butyl methyl ether (4 ml) and heptane (4 ml) to suspend a solid. The solid was collected by filtration, and dried under aeration to provide a titled compound as pale yellow powder (107.1 mg, 55.1%).

$^1$H-NMR Spectrum (CDCl$_3$) δ (ppm): 1.44-2.04 (4H, m), 3.53 (4H, m), 3.72 (4H, m), 6.63 (1H, m), 7.00-7.15 (5H, m), 7.40-7.53 (2H, m), 7.53-7.62 (3H, m), 7.99 (1H, m), 8.94 (1H, brs), 9.07 (1H, brs).

ESI-MS (m/z): 542 [M+Na]$^+$.

Example 69

N-(4-Fluorophenyl)-N'-[4-({2-[(pyrrolidin-1-ylcarbonyl)amino]pyridin-4-yl}oxy)phenyl]cyclopropane-1,1-dicarboxamide Pyrrolidine-1-carboxylic acid [4-(4-aminophenoxy)pyridin-2-yl]amide (112 mg) and 1-(4-fluorophenylcarbamoyl)cyclopropanecarboxylic acid (87.4 mg) were dissolved in N,N-dimethylformamide (4 ml), and diisopropylethylamine (0.341 ml) and HBTU (203 mg) were added under a nitrogen atmosphere at room temperature, followed by stirring for 3 hr. The reaction mixture was partitioned after addition of ethyl acetate (50 ml) and a saturated aqueous solution of sodium hydrogencarbonate (20 ml). The separated organic layer was washed with a saturated aqueous solution of sodium hydrogencarbonate (30 ml) and brine (30 ml), and dried over anhydrous sodium sulfate. The solvent was removed under reduced pressure. The resultant residue was purified by silica gel column chromatography (eluent; heptane:ethyl acetate=1:7, then ethyl acetate). Fractions containing the target compound were concentrated under reduced pressure, and to the residue (133.0 mg) were added tert-butyl methyl ether (4 ml) and heptane (4 ml) to suspend a solid. The solid was collected by filtration and dried under aeration to provide the titled compound as pale yellow powder (111.1 mg, 62.0%).

$^1$H-NMR Spectrum (CDCl$_3$) δ (ppm): 1.78-1.84 (4H, m), 1.95 (4H, m), 3.47 (4H, m), 6.63 (1H, m), 6.95-7.10 (5H, m), 7.40-7.53 (2H, m), 7.57 (2H, m), 7.66 (1H, brs), 7.98 (1H, m), 8.98 (1H, brs), 9.11 (1H, brs).

ESI-MS (m/z): 526 [M+Na]$^+$.

Example 70

N-[4-({2-[(Azetidin-1-ylcarbonyl)amino]pyridin-4-yl}oxy)phenyl]-N'-(4-fluorophenyl)cyclopropane-1,1-dicarboxamide Azetidine-1-carboxylic acid [4-(4-aminophenoxy)pyridin-2-yl]amide (108 mg) and 1-(4-fluorophenylcarbamoyl)cyclopropanecarboxylic acid (93.1 mg) were dissolved in N,N-dimethylformamide (4 ml), and diisopropylethylamine (0.363 ml) and HBTU (216 mg) were added under a nitrogen atmosphere at room temperature, followed by 3 hr. The reaction mixture was partitioned after addition of ethyl acetate (50 ml) and a saturated aqueous solution of sodium hydrogencarbonate (20 ml). The separated organic layer was washed with a saturated aqueous solution of sodium hydrogencarbonate (30 ml) and brine (30 ml), and dried over anhydrous sodium sulfate. The solvent was removed under reduced pressure, and the resultant residue was purified by silica gel column chromatography (eluent; heptane:ethyl acetate=1:7, then ethyl acetate). Fractions containing the target compound were concentrated under reduced pressure, and to the residue (106.2 mg) were added tert-butyl methyl ether (4 ml) and heptane (4 ml) to suspend a solid. The solid was collected by filtration, and dried under aeration to provide the roughly purified titled compound as pale yellow powder (87.5 mg). This was purified by silica gel column chromatography (eluent; heptane:ethyl acetate 1:7, then ethyl acetate). Fractions containing the target compound were concentrated under reduced pressure, and to the residue were added tert-butyl methyl ether (4 ml) and heptane (2 ml) to suspend a solid. The solid was collected by filtration, and dried under aeration to provide white powder. The powder obtained by filtration and the filtrate were combined, and purified by LC-MS. The solution containing TFA, acetonitrile and water was concentrated under reduced pressure, and to the residue was added a saturated aqueous solution of sodium hydrogencarbonate (50 ml), followed by stirring. The solvent was removed under reduced pressure, and the residue was partitioned after addition of ethyl acetate (100 ml). The organic layer was washed with a saturated aqueous solution of sodium hydrogencarbonate (50 ml) and brine (50 ml) in this order, and dried over anhydrous sodium sulfate. The solvent was removed under reduced pressure, and to the residue were added tert-butyl methyl ether and heptane to suspend a solid. The solid was collected by filtration, and derided under aeration to provide the titled compound as a white powder (16.3 mg, 8.79%)

$^1$H-NMR Spectrum (CDCl$_3$) δ (ppm): 1.30-1.80 (4H, m), 2.30 (2H, m), 4.12 (4H, m), 6.62 (1H, m), 6.95-7.14 (5H, m), 7.48 (2H, m), 7.59 (2H, m), 7.73 (1H, brs), 7.96 (1H, m), 8.98 (1H, brs), 9.07 (1H, brs).

ESI-MS (m/z): 512 [M+Na]$^+$.

Example 71

N-(4-Fluorophenyl)-N'-{2-fluoro-4-[(2-{[(4-piperazin-1-ylpiperidin-1-yl)carbonyl]amino}pyridin-4-yl)oxy]phenyl}cyclopropane-1,1-dicarboxamide To a solution of a crude product of [4-(3-fluoro-4-{[1-(4-fluorophenylcarbamoyl)cyclopropanecarbonyl]amino}phenoxy)pyridin-2-yl]-N-(phenoxycarbonyl)carbamic acid phenyl ester (300 mg) in N,N-dimethylformamide (4.5 ml) were added benzyl 4-(piperidin-4-yl)piperazine-1-carboxylate (684 mg) and triethylamine (0.629 ml), followed by stirring at room temperature for 20.5 hr. The reaction mixture was partitioned between ethyl acetate and water. The organic layer was washed with brine, and dried over anhydrous sodium sulfate. The solvent was removed to provide a crude product of benzyl 4-{1-[4-(3-fluoro-4-{[1-(4-fluorophenylcarbamoyl)cyclopropanecarbonyl]amino}phenoxy)pyridin-2-ylcarbamoyl]piperidin-4-yl}piperazine-1-carboxylate as a pale yellow oil (501 mg). This was dissolved in ethanol(10 ml) and N,N-dimethylformamide (5.0 ml). 1,4-cyclohexadiene (0.633 ml) and 10% palladium on carbon (144 mg) were added thereto, followed by stirring at 65° C. for 1.5 hr. The reaction mixture was allowed to cool down to room temperature. The catalyst was removed by filtration, and the filtrate was concentrated. The residue was purified by silica gel column chromatography (Fuji Silysia NH, eluent; ethyl acetate, ethyl acetate:methanol=10:1, then 5:1). Fractions containing the target compound were concentrated to give the residue (56.3 mg). The residue was purified by LC-MS. Fractions containing the target compound were concentrated, which were partitioned between ethyl acetate and a saturated aqueous solution of sodium hydrogencarbonate. The organic layer was dried over anhydrous sodium sulfate. The solvent was removed, and to the residue was added diethyl ether to suspend a solid. This was collected by filtration, and dried under aeration to provide the titled compound as pale yellow powder (12.7 mg).

$^1$H-NMR Spectrum (CDCl$_3$) δ (ppm): 1.48 (2H, m), 1.66-1.75 (4H, m), 1.85 (2H, m), 2.47-3.16 (12H, m), 4.13 (2H, m), 6.56 (1H, m), 6.91 (2H, m), 7.04 (2H, m), 7.40 (1H, m), 7.50 (2H, dd, J=4.8, 8.8 Hz), 7.60 (1H, s), 8.06 (1H, d, J=5.6 Hz), 8.19 (1H, m), 8.98 (1H, s), 9.16 (1H, s).

ESI-MS (m/z): 620 [M+H]$^+$.

Example 72

N-{2-Fluoro-4-[(2-{1(3-hydroxyazetidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (250 mg) was dissolved in tetrahydrofuran (6.0 ml) under a nitrogen atmosphere, and triethylamine (0.247 ml) and phenyl chloroformate (0.163 ml) were added dropwise at room temperature in this order, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (6.0 ml). This solution was added to a mixture of 3-hydroxyazetidine hydrochloride (259 mg) and triethylamine (0.822 ml), followed by stirring at room temperature for 14.25 hr. The reaction mixture was partitioned between ethyl acetate and water. The organic layer was washed with a 1N aqueous solution of sodium hydroxide, water and brine in this order, and dried over anhydrous sodium sulfate. The solvent was removed and the residue was purified by silica gel column chromatography (Fuji Silysia NH, eluent; heptane:ethyl acetate=1:2, ethyl acetate, ethyl acetate:methanol=30:1, then 10:1). Fractions containing the target compound were concentrated. To the resultant residue was added diethyl ether:heptane=1:2 to suspend a solid. The solid was collected by filtration and washed with heptane. This was dried under aeration to provide white powder (198 mg). This was suspended in 2-propanol (2 ml). Insoluble matter was removed by filtration and washed with 2-propanol. This was dried under aeration to provide white powder (178 mg). This was again suspended in 2-propanol (2 ml). This was collected by filtration, washed with 2-propanol, and dried under aeration to provide the titled compound as white powder (144.2 mg, 46.7%).

$^1$H-NMR Spectrum (CDCl$_3$) δ (ppm): 1.64-1.76 (4H, m), 2.27 (1H, m), 3.92 (2H, dd, J=4.2, 9.8 Hz), 4.28 (2H, dd, J=6.6, 9.8 Hz), 4.69 (1H, m), 6.57 (1H, dd, J=2.0, 5.6 Hz), 6.79 (1H, s), 6.91 (2H, m), 7.04 (2H, m), 7.50 (2H, dd, J=4.8, 9.2 Hz), 7.64 (1H, d, J=2.0 Hz), 8.06 (1H, d, J=5.6 Hz), 8.19 (1H, m), 8.82 (1H, s), 9.26 (1H, s).

ESI-MS (m/z): 524 [M+H]$^+$, 546 [M+Na]$^+$.

Example 73

N-[4-({2-[(1,3'-Biazetidin-1'-ylcarbonyl)amino]pyridin-4-yl}oxy)-2-fluorophenyl]-N'-(4-fluorophenyl)cyclopropane-1,1-dicarboxamide To a suspension of 3-(azetidin-1-yl)azetidine dihydrochloride (111 mg) in N,N-dimethylformamide (1.5 ml) was added triethylamine (0.167 ml), followed by stirring at room temperature for 15 min. A crude product of [4-(3-fluoro-4-{[1-(4-fluorophenylcarbamoyl)cyclopropanecarbonyl]amino}phenoxy)pyridin-2-yl]-N-(phenoxycarbonyl) carbamic acid phenyl ester (100 mg) was added thereto, followed by stirring at room temperature for 25 hr. The reaction mixture was partitioned between ethyl acetate and water. The organic layer was washed with brine, and dried over anhydrous sodium sulfate. This was concentrated and the residue was purified by LC-MS. Fractions containing the target compound were concentrated, and the residue was partitioned between ethyl acetate and a saturated aqueous solution of sodium hydrogencarbonate. The organic layer was washed with brine, and dried over anhydrous sodium sulfate. The solvent was removed, and to the resultant solid (31.5 mg) was added diethyl ether (2 ml) to suspend. This was collected by filtration and washed with diethyl ether. This was dried under aeration to provide the titled compound as colorless powder (5.0 mg).

$^1$H-NMR Spectrum (CDCl$_3$) δ (ppm): 1.65-1.75 (4H, m), 2.17 (2H, m), 3.33 (4H, m), 3.48 (1H, m), 3.88 (2H, m), 4.06 (2H, m), 6.58 (1H, m), 6.92 (2H, m), 7.04 (2H, m), 7.11 (1H, m), 7.51 (2H, dd, J=4.8, 9.2 Hz), 7.66 (1H, s), 8.05 (1H, d, J=6.0 Hz), 8.22 (1H, m), 8.84 (1H, s), 9.22 (1H, s).

ESI-MS (m/z): 585 [M+Na]$^+$.

Example 75

N-(2-Fluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (75 mg) was dissolved in tetrahydrofuran (1.8 ml) under a nitrogen atmosphere, and triethylamine (0.074 ml) and phenyl chloroformate (0.0488 ml) were added dropwise in this order at room temperature, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (1.8 ml). This solution was added to a mixture of a crude product of 3-(hydroxymethyl)azetidine trifluoroacetate (209.8 mg, corresponds to 0.671 mmol) and triethylamine (0.658 ml), followed by stirring at room temperature for 12 hr. The reaction mixture was partitioned between ethyl acetate and water. The organic layer was washed with a 1N aqueous solution of sodium hydroxide, water and brine in this order, and dried over anhydrous sodium sulfate. The solvent was removed and the residue was purified by silica gel column chromatography (eluent; ethyl acetate, ethyl acetate:methanol=50:1, 20:1, then 10:1). Fractions containing the target compound were concentrated. To the resultant residue (36.9 mg) was added diethyl ether:heptane=1:2 to suspend a solid. The solid was collected by filtration and washed with heptane. This was dried under aeration to provide the titled compound as white powder (22.0 mg, 23.1%).

$^1$H-NMR Spectrum (CDCl$_3$) δ (ppm): 1.64-1.75 (4H, m), 2.82 (1H, m), 3.80 (2H, d, J=6.0 Hz), 3.85 (2H, dd, J=5.6, 8.0 Hz), 4.11 (2H, m), 6.57 (1H, dd, J=2.4, 6.0 Hz), 6.89-7.00 (2H, m), 7.03 (2H, m), 7.12 (1H, m), 7.47-7.52 (2H, m), 7.65 (1H, d, J=2.4 Hz), 8.04 (1H, d, J=6.0 Hz), 8.17 (1H, m), 8.91 (1H, s), 9.27 (1H, s).

ESI-MS (m/z): 560 [M+Na]$^+$.

Example 76

N-(4-{[2-{[3-(Dimethylamino)azetidin-1-yl]
carbonyl}amino)pyridin-4-yl]oxy}-2-fluorophenyl)-
N'-(4-fluorophenyl)cyclopropane-1,1-dicarboxamide N-{4-[(2-Aminopyridin-4-yl)oxy]-2-fluorophenyl}-N'-
(4-fluorophenyl)cyclopropane-1,1-dicarboxamide (100 mg) was dissolved in tetrahydrofuran (2.4 ml) under a nitrogen atmosphere, and triethylamine (0.0987 ml) and phenyl chloroformate (0.0651 ml) were added dropwise at room temperature in this order, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (2.4 ml). This solution was added to a mixture of a crude product of 3-(dimethylamino)azetidine ditrifluoroacetate (592 mg, corresponds to 0.944 mmol) and triethylamine (0.658 ml), followed by stirring at room temperature for 12 hr. The reaction mixture was partitioned between ethyl acetate and water. The organic layer was washed with a 1N aqueous solution of sodium hydroxide, water and brine in this order, and dried over anhydrous sodium sulfate. The solvent was removed and the residue was purified by silica gel column chromatography (Fuji Silysia NH, eluent; ethyl acetate=1:2, ethyl acetate, then ethyl acetate:methanol=30:1). Fractions containing the target compound were concentrated. To the resultant residue (71.3 mg) was added diethyl ether:heptane=1:2 to suspend a solid. The solid was collected by filtration and washed with heptane. This was dried under aeration to provide the titled compound as white powder (52.4 mg, 40.3%).

$^{1}$H-NMR Spectrum (CDCl$_3$) δ (ppm): 1.64-1.76 (4H, m), 2.18 (6H, s), 3.13 (1H, m), 3.90 (2H, m), 4.04 (2H, m), 6.56 (1H, m), 6.86 (1H, brs), 6.91 (2H, m), 7.04 (2H, m), 7.49-7.52 (2H, dd, J=4.8, 8.8 Hz), 7.65 (1H, d, J=2.0 Hz), 8.05 (1H, d, J=5.6 Hz), 8.20 (1H, m), 8.81 (1H, s), 9.26 (1H, s).

ESI-MS (m/z): 573 [M+Na]$^{+}$.

Example 77

N-[4-({2-[({3-[(Dimethylamino)methyl]azetidin-1-
yl}carbonyl)amino]pyridin-4-yl}oxy)-2-fluorophenyl]-N'-(4-fluorophenyl)cyclopropane-1,1-dicarboxamide N-{4-[(2-Aminopyridin-4-yl)oxy]-2-fluorophenyl}-N'-
(4-fluorophenyl)cyclopropane-1,1-dicarboxamide (100 mg) was dissolved in tetrahydrofuran (2.4 ml) under a nitrogen atmosphere, and triethylamine (0.0987 ml) and phenyl chloroformate (0.0651 ml) were added dropwise at room temperature in this order, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (2.4 ml). This solution was added to a mixture of a crude product of 3-(dimethylaminomethyl)azetidine ditrifluoroacetate (469 mg, corresponds to 0.826 mmol), and triethylamine (0.658 ml), followed by stirring at room temperature for 17.5 hr. The reaction mixture was partitioned between ethyl acetate and water. The organic layer was washed with a 1N aqueous solution of sodium hydroxide, water and brine in this order, and dried over anhydrous sodium sulfate. The solvent was removed, and the residue was purified by silica gel column chromatography (Fuji Silysia NH, eluent; heptane:ethyl acetate=1:2, ethyl acetate, ethyl acetate:methanol=30:1, then 10:1). Fractions containing the target compound were concentrated. To the resultant residue (77.9 mg) were added diethyl ether:heptane=1:2 to suspend a solid. The solid was collected by filtration and washed with heptane. This was dried under aeration to provide the titled compound as white powder (70.9 mg, 53.2%).

$^{1}$H-NMR Spectrum (CDCl$_3$) δ (ppm): 1.64-1.75 (4H, m), 2.22 (6H, s), 2.53 (2H, d, J=7.2 Hz), 2.80 (1H, m), 3.71 (2H, m), 4.13 (2H, m), 6.56 (1H, m), 6.79 (1H, s), 6.91 (2H, m), 7.03 (2H, m), 7.50 (2H, dd, J=4.8, 9.2 Hz), 7.65 (1H, m), 8.06 (1H, d, J=5.6 Hz), 8.20 (1H, m), 8.82 (1H, s), 9.25 (1H, s).

ESI-MS (m/z): 565 [M+H]$^{+}$.

Example 78

N-{2-Fluoro-4-[(2-{[(3-methoxyazetidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-2-fluorophenyl}-N'-
(4-fluorophenyl)cyclopropane-1,1-dicarboxamide (75 mg) was dissolved in tetrahydrofuran (1.8 ml) under a nitrogen atmosphere, and triethylamine (0.074 ml) and phenyl chloroformate (0.0488 ml) were added dropwise in this order at room temperature, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (1.8 ml). This solution was added to a mixture of a crude product of 3-methoxyazetidine trifluoroacetate (209.8 mg, corresponds to 0.671 mmol) and triethylamine (0.450 ml), followed by stirring at room temperature for 13 hr. The reaction mixture was partitioned between ethyl acetate and water. The organic layer was washed with a 1N aqueous solution of sodium hydroxide, water and brine in this order, and dried over anhydrous sodium sulfate. The solvent was removed, and the residue was purified by silica gel column chromatography (eluent; heptane:ethyl acetate=1:2, ethyl acetate, ethyl acetate:methanol=50:1, then 20:1). Fractions containing the target compound were concentrated. To the resultant residue was added diethyl ether:heptane=1:2 to suspend a solid. The solid was collected by filtration and washed with heptane. This was dried under aeration to provide the titled compound as white powder (46.5 mg, 48.9%).

$^{1}$H-NMR Spectrum (CDCl$_3$) δ (ppm): 1.64-1.76 (4H, m), 3.31 (3H, s), 3.94 (2H, m), 4.20 (3H, m), 6.56 (1H, dd, J=2.4, 5.6 Hz), 6.91 (3H, m), 7.03 (2H, m), 7.50 (2H, m), 7.64 (1H, d, J=2.4 Hz), 8.05 (1H, d, J=5.6 Hz), 8.19 (1H, m), 8.90 (1H, s), 9.25 (1H, s).

ESI-MS (m/z): 560 [M+Na]$^{+}$.

Example 79

N-{3-Fluoro-4-[(2-{[(3-methoxyazetidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-3-fluorophenyl}-N'-
(4-fluorophenyl)cyclopropane-1,1-dicarboxamide (75 mg) was dissolved in tetrahydrofuran (1.8 ml) under a nitrogen atmosphere, and triethylamine (0.074 ml) and phenyl chloroformate (0.0488 ml) were added dropwise at room temperature in this order, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (1.8 ml). This solution was added to a mixture of a crude product of 3-methoxyazetidine trifluoroacetate (corresponds to 0.671 mmol) and triethylamine (0.247 ml), followed by stirring at room temperature overnight (for 11 hr). The reaction mixture was partitioned between ethyl acetate and water. The organic layer was washed with a 1N aqueous solution of sodium hydroxide, water and brine in this order, and dried over anhydrous sodium sulfate. The solvent was removed, and the residue was purified by silica gel column chromatography (eluent; heptane:ethyl acetate=1:2, ethyl acetate, then ethyl acetate:methanol=50:1). Fractions containing the target compound were concentrated. To the resultant residue (64.2 mg) was added diethyl ether:heptane=1:2 to suspend a solid. The solid was collected by filtration and washed with heptane. This was dried under aeration provide the titled compound as white powder (54.6 mg, 57.4%).

$^1$H-NMR Spectrum (CDCl$_3$) δ (ppm): 1.63-1.73 (4H, m), 3.30 (3H, s), 3.92 (2H, m), 4.20 (3H, m), 6.59 (1H, dd, J=2.4, 5.6 Hz), 6.86 (1H, brs), 7.04 (2H, m), 7.11 (1H, m), 7.19 (1H, m), 7.47 (2H, dd, J=4.8, 9.2 Hz), 7.59 (1H, d, J=2.4 Hz), 7.68 (1H, dd, J=2.8, 8.0 Hz), 8.04 (1H, d, J=5.6 Hz), 8.62 (1H, s), 9.53 (1H, s).

ESI-MS (m/z): 560 [M+H]$^+$.

Example 80

N-{3-Fluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-3-fluorophenyl}-N'-(4-fluorophenyl)cyclopropane-1,1-dicarboxamide (250 mg) was dissolved in tetrahydrofuran (6.0 ml) under a nitrogen atmosphere, and triethylamine (0.247 ml) and phenyl chloroformate (0.163 ml) were added dropwise in this order at room temperature, followed by stirring for 30 min. The reaction mixture was stirred after addition of ethyl acetate and water. The organic layer was separated, washed with a 1N aqueous solution of sodium hydroxide, water and brine in this order, and dried over anhydrous sodium sulfate. The solvent was concentrated under reduced pressure. The residue was dissolved in N,N-dimethylformamide (6.0 ml). Triethylamine (0.822 ml) and 3-hydroxyazetidine hydrochloride (259 mg) were added at room temperature, followed by stirring overnight. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The resultant residue was purified by silica gel column chromatography (eluent; ethyl acetate, ethyl acetate:methanol=95:5, 9:1). Fractions containing the target compound were concentrated under reduced pressure. To the resultant residue was added tert-butyl methyl ether:heptane=1:2 to precipitate a solid. The solid was collected by filtration and dried under aeration to provide the titled compound as white powder (173.7 mg, 56%).

$^1$H-NMR Spectrum (CDCl$_3$) δ (ppm): 1.60-1.80 (4H, m), 3.96 (2H, dd, J=4.0, 9.2 Hz), 4.30 (2H, dd, J=6.8, 9.2 Hz), 4.67 (1H, m), 6.66 (1H, dd, J=2.4, 5.6 Hz), 7.00-7.50 (7H, m), 7.66 (1H, brs), 7.71 (1H, dd, J=2.4, 12.0 Hz), 8.00 (1H, d, J=5.6 Hz), 8.61 (1H, brs), 9.66 (1H, brs).

ESI-MS (m/z): 546 [M+Na]$^+$.

Example 81

N-(3-Fluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-3-fluorophenyl}-N'-(4-fluorophenyl)cyclopropane-1,1-dicarboxamide (297 mg) was dissolved in tetrahydrofuran (8.0 ml) under a nitrogen atmosphere, and triethylamine (0.293 ml) and phenyl chloroformate (0.193 ml) were added dropwise at room temperature in this order, followed by stirring for 1 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The residue was dissolved in N,N-dimethylformamide (8.0 ml). This solution was added to a mixture of a crude product of 3-(hydroxymethyl)azetidine trifluoroacetate (corresponds to 2.58 mmol) and triethylamine (2.0 ml), followed by stirring at room temperature for 11 hr. The reaction mixture was partitioned between ethyl acetate and water. The organic layer was washed with a 1N aqueous solution of sodium hydroxide, water and brine in this order, and dried over anhydrous sodium sulfate. The solvent was removed, and the residue was purified by silica gel column chromatography (eluent; heptane:ethyl acetate=1:2, ethyl acetate, ethyl acetate:methanol=50:1, then 20:1). Fractions containing the target compound were concentrated. To the resultant residue (159.4 mg) was added diethyl ether:heptane=1:2 to suspend a solid. The solid was collected by filtration and washed with heptane. This was dried under aeration to provide the titled compound as white powder (143.2 mg, 38.1%).

$^1$H-NMR Spectrum (CDCl$_3$) δ (ppm): 1.59-1.67 (4H, m), 2.77 (1H, m), 3.74 (2H, d, J=5.6 Hz), 3.84 (2H, dd, J=5.2, 8.0 Hz), 4.05 (2H, m), 6.70 (1H, dd, J=2.0, 5.6 Hz), 6.98-7.06 (4H, m), 7.18 (1H, m), 7.46-7.94 (2H, m), 7.55 (1H, d, J=2.0 Hz), 7.64 (1H, dd, J=2.4, 8.4 Hz), 8.06 (1H, d, J=5.6 Hz), 9.21 (1H, s), 9.65 (1H, s).

ESI-MS (m/z): 560 [M+Na]$^+$.

Example 82

N-{2-Fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (100 mg) was dissolved in tetrahydrofuran (1 ml) under a nitrogen atmosphere, and triethylamine (0.0658 ml) and phenyl chloroformate (0.0652 ml) were added while stirring and cooling in an ice water bath, followed by stirring at the same temperature for 1 hr. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure. To the residue was added N,N-dimethylformamide (2.5 ml), and 4-hydroxypiperidine (95.5 mg) and triethylamine (0.132 ml) were added thereto, followed by stirring at room temperature overnight. The reaction mixture was partitioned after addition of ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure, and the residue was purified by silica gel column chromatography (Fuji Silysia NH, eluent; heptane:ethyl acetate=1:5, ethyl acetate, then ethyl acetate:methanol=95:5). Crude fractions containing the target compound were concentrated under reduced pressure, and the residue was purified by silica gel column chromatography (eluent; heptane:ethyl acetate=1:5, ethyl acetate, then ethyl acetate:methanol=95:5). Fractions containing the target compound were concentrated under reduced pressure, and to the residue were added tert-butyl methyl ether (2 ml) and heptane (4 ml) to suspend a solid. The solid was collected by filtration and dried under aeration to provide the titled compound as white powder (113.6 mg, 87.3%).

$^1$H-NMR Spectrum (CDCl$_3$) δ (ppm): 1.35-1.82 (7H, m), 1.82-2.00 (2H, m), 3.28 (2H, m), 3.76-3.90 (2H, m), 3.94 (1H, m), 6.59 (1H, m), 6.93 (2H, m), 7.04 (2H, m), 7.26 (1H, m), 7.40-7.60 (2H, m), 7.70 (1H, brs), 8.03 (1H, d, J=6.0 Hz), 8.23 (1H, m), 9.01 (1H, brs), 9.09 (1H, brs).

ESI-MS (m/z): 574 [M+Na]$^+$.

Example 83

N-(2-Fluoro-4-{[2-({[4-(hydroxymethyl)piperidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (100 mg) was dissolved in tetrahydrofuran (1 ml) under a nitrogen atmosphere, and triethylamine (0.0724 ml) and phenyl chloroformate (0.0652 ml) were added while stirring and cooling in an ice water bath, followed by stirring at the same temperature for 1 hr. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure. To the residue was added N,N-dimethylformamide (2.5 ml), and 4-piperidinemethanol (109 mg) and triethylamine (0.132 ml) were added, followed by stirring at room temperature overnight. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure, and the residue was purified by silica gel column chromatography (Fuji Silysia NH, eluent; heptane: ethyl acetate=1:5, ethyl acetate, then ethyl acetate:methanol=95:5). Crude fractions containing the target compound were concentrated under reduced pressure, and the residue was purified by silica gel column chromatography (eluent; heptane:ethyl acetate=1:5, ethyl acetate, then ethyl acetate:methanol=95:5). Fractions containing the target compound were concentrated under reduced pressure, and to the residue were added tert-butyl methyl ether (2 ml) and heptane (4 ml) to suspend a solid. The solid was collected by filtration and dried under aeration to provide the titled compound as white powder (98.1 mg, 73.5%).

$^1$H-NMR Spectrum (CDCl$_3$) δ (ppm): 1.40-1.77 (8H, m), 1.82 (2H, m), 2.90 (2H, m), 3.52 (2H, m), 4.19 (2H, m), 6.59 (1H, dd, J=2.4, 6.0 Hz), 6.93 (2H, m), 7.04 (2H, m), 7.26 (1H, m), 7.50 (2H, m), 7.73 (1H, brs), 8.02 (1H, d, J=6.0 Hz), 8.23 (1H, m), 9.01 (1H, brs), 9.09 (1H, brs).

ESI-MS (m/z): 588 [M+Na]$^+$.

Example 84

N-{3-Fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-3-fluorophenyl}-N'-(4-fluorophenyl)cyclopropane-1,1-dicarboxamide (150 mg) was dissolved in tetrahydrofuran (4.0 ml) under a nitrogen atmosphere, and triethylamine (0.148 ml) and phenyl chloroformate (0.098 ml) were added dropwise in this order at room temperature, followed by stirring for 10 min. The reaction mixture was stirred after addition of ethyl acetate and water. The organic layer was separated, washed with a 1N aqueous solution of sodium hydroxide, water and brine, and dried over anhydrous sodium sulfate. The solvent was concentrated under reduced pressure. The residue was dissolved in N,N-dimethylformamide (4.0 ml). 4-Hydroxypiperidine (146 mg) was added at room temperature, followed by stirring for 2 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The resultant residue was purified by silica gel column chromatography (eluent; ethyl acetate, then ethyl acetate:methanol=95:5). Fractions containing the target compound were concentrated under reduced pressure. To the resultant residue was added tert-butyl methyl ether:heptane=1:2 to precipitate a solid. The solid was collected by filtration and dried under aeration to provide the titled compound as white powder (138.0 mg, 71%).

$^1$H-NMR Spectrum (CDCl$_3$) δ (ppm): 1.40-2.00 (8H, m), 3.25 (2H, m), 3.80-4.00 (3H, m), 6.60 (1H, dd, J=2.4, 5.6 Hz), 7.00-7.50 (7H, m), 7.64 (1H, brs), 7.71 (1H, dd, J=2.4, 12.0 Hz), 8.01 (1H, brs), 8.53 (1H, m), 9.65 (1H, brs).

ESI-MS (m/z): 552 [M+H]$^+$.

Example 85

N-(3-Fluoro-4-{[2-({[4-(hydroxymethyl)piperidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-3-fluorophenyl}-N'-(4-fluorophenyl)cyclopropane-1,1-dicarboxamide (150 mg) was dissolved in tetrahydrofuran (4.0 ml) under a nitrogen atmosphere, and triethylamine (0.148 ml) and phenyl chloroformate (0.098 ml) were added dropwise at room temperature in this order, followed by stirring for 10 min. The reaction mixture was stirred after addition of ethyl acetate and water. The organic layer was separated, washed with a 1N aqueous solution of sodium hydroxide, water and brine, and dried over anhydrous sodium sulfate. The solvent was concentrated under reduced pressure. The residue was dissolved in N,N-dimethylformamide (4.0 ml). 4-Piperidinemethanol (163 mg) was added at room temperature, followed by stirring for 2 hr. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The resultant residue was purified by silica gel column chromatography (eluent; ethyl acetate, then ethyl acetate:methanol=95:5). Fractions containing the target compound were concentrated. To the resultant residue was added tert-butyl methyl ether:heptane=1:2 to precipitate a solid. The solid was collected by filtration and dried under aeration to provide the titled compound as white powder (143.7 mg, 72%).

¹H-NMR Spectrum (CDCl₃) δ (ppm): 1.40-2.00 (9H, m), 2.89 (2H, m), 3.51 (2H, m), 4.18 (2H, m), 6.62 (1H, dd, J=2.4, 5.6 Hz), 7.00-7.50 (7H, m), 7.60-7.80 (2H, m), 8.01 (1H, d, J=5.6 Hz), 8.49 (1H, brs), 9.69 (1H, brs).

ESI-MS (m/z): 566 [M+H]⁺.

Example 86

N-(3-Fluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-3-fluorophenyl}-N'-(4-fluorophenyl)cyclopropane-1,1-dicarboxamide (150 mg) was dissolved in tetrahydrofuran (1.5 ml) under a nitrogen atmosphere, and triethylamine (0.181 ml) and phenyl chloroformate (0.163 ml) were added while stirring and cooling in an ice water bath, followed by stirring at the same temperature for 15 min. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure. To the residue was added N,N-dimethylformamide (1.5 ml), and (R)-(−)-3-pyrrolidinol hydrochloride (175 mg) and triethylamine (0.198 ml) were added, followed by stirring at room temperature for 5 hr. The reaction mixture was partitioned after addition of ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure, and the residue was purified by silica gel column chromatography (eluent; heptane:ethyl acetate=1:5, ethyl acetate, then ethyl acetate:methanol=95:5). Fractions containing the target compound were concentrated under reduced pressure, and to the residue (130 mg) were added tert-butyl methyl ether (2 ml) and heptane (2 ml) to suspend a solid. The solid was collected by filtration and dried under aeration to provide the titled compound as white powder (123.6 mg, 65.0%).

¹H-NMR Spectrum (CDCl₃) δ (ppm): 1.30-2.00 (7H, m), 3.45-3.80 (4H, m), 4.50 (1H, m), 6.67 (1H, dd, J=2.4, 6.0 Hz), 6.90-7.15 (4H, m), 7.20 (1H, m), 7.40-7.60 (2H, m), 7.60-7.80 (2H, m), 8.04 (1H, d, J=6.0 Hz), 8.95 (1H, brs), 9.66 (1H, brs).

ESI-MS (m/z):538 [M+H]⁺, 560[M+Na]⁺.

Example 87

N-(2-Fluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (150 mg) was dissolved in tetrahydrofuran (1.5 ml) under a nitrogen atmosphere, and triethylamine (0.181 ml) and phenyl chloroformate (0.163 ml) were added while stirring and cooling in an ice water bath, followed by stirring at the same temperature for 15 min. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure. To the residue was added N,N-dimethylformamide (1.5 ml), and then (R)-(−)-3-pyrrolidinol hydrochloride (175 mg) and triethylamine (0.198 ml) were added, followed by stirring at room temperature for 5 hr. The reaction mixture was partitioned after addition of ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure, and the residue was purified by silica gel column chromatography (eluent; heptane:ethyl acetate=1:5, ethyl acetate, then ethyl acetate:methanol=95:5). Fractions containing the target compound were concentrated under reduced pressure, and to the residue (150 mg) were added tert-butyl methyl ether (2 ml) and heptane (2 ml) to suspend a solid. The solid was collected by filtration, and dried under aeration to provide the titled compound as white powder (141.6 mg, 74.4%).

¹H-NMR Spectrum (CDCl₃) δ (ppm): 1.40-2.00 (7H, m), 3.50-3.70 (4H, m), 4.55 (1H, m), 6.60 (1H, dd, J=2.4, 6.0 Hz), 6.92 (2H, m), 7.04 (2H, m), 7.26 (1H, m), 7.50 (2H, m), 7.75 (1H, m), 8.03 (1H, d, J=6.0 Hz), 8.21 (1H, m), 8.96 (1H, brs), 9.19 (1H, brs).

ESI-MS (m/z): 538 [M+H]⁺, 560 [M+Na]⁺.

Example 88

N-(3-Fluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-3-fluorophenyl}-N'-(4-fluorophenyl)cyclopropane-1,1-dicarboxamide (150 mg) was dissolved in tetrahydrofuran (1.5 ml) under a nitrogen atmosphere, and triethylamine (0.181 ml) and phenyl chloroformate (0.163 ml) were added while stirring and cooling in an ice water bath, followed by stirring at the same temperature for 15 min. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure. To the residue was added N,N-dimethylformamide (1.5 ml), and (S)-3-pyrrolidinol (123 mg) was added, followed by stirring at room temperature for 3 hr. The reaction mixture was partitioned after addition of ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure, and the residue was purified by silica gel column chromatography (eluent; heptane:ethyl acetate=1:5, ethyl acetate, then ethyl acetate:methanol=95:5). Fractions containing the target compound were concentrated under reduced pressure, and to the residue (158 mg) were added tert-butyl methyl ether (2 ml) and heptane (4 ml) to suspend a solid. The solid was collected by filtration and dried under aeration to provide the titled compound as white powder (146.1 mg, 76.8%).

¹H-NMR Spectrum (CDCl₃) δ (ppm): 1.30-2.00 (7H, m), 3.40-3.80 (4H, m), 4.50 (1H, m), 6.67 (1H, dd, J=2.4, 6.0 Hz), 7.03 (2H, m), 7.12 (2H, m), 7.20 (1H, m), 7.40-7.60 (2H, m), 7.60-7.80 (2H, m), 8.04 (1H, d, J=6.0 Hz), 8.95 (1H, brs), 9.66 (1H, brs).

ESI-MS (m/z): 560 [M+Na]⁺.

Example 89

N-(2-Fluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2-fluorophenyl}-N'-(4-fluorophenyl)cyclopropane-1,1-dicarboxamide (150 mg)

was dissolved in tetrahydrofuran (1.5 ml) under a nitrogen atmosphere, triethylamine (0.181 ml) and phenyl chloroformate (0.163 ml) were added while stirring and cooling in an ice water bath, followed by stirring at the same temperature for 15 min. The reaction mixture was partitioned between ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure. To the residue was added N,N-dimethylformamide (1.5 ml), and (S)-3-pyrrolidinol (123 mg) was added, followed by stirring at room temperature for 3 hr. The reaction mixture was partitioned after addition of ethyl acetate (30 ml) and a saturated aqueous solution of sodium hydrogencarbonate (20 ml). The separated organic layer was washed with brine (30 ml), and dried over anhydrous sodium sulfate. The solvent was removed under reduced pressure, and the residue was purified by silica gel column chromatography (eluent; heptane:ethyl acetate=1:5, ethyl acetate, then ethyl acetate:methanol=95:5). Fractions containing the target compound were concentrated under reduced pressure, and to the residue (169 mg) were added tert-butyl methyl ether (2 ml) and heptane (2 ml) to suspend a solid. The solid was collected by filtration and dried under aeration to provide the titled compound as white powder (151.9 mg, 79.8%).

$^1$H-NMR Spectrum (CDCl$_3$) δ (ppm): 1.30-2.00 (7H, m), 3.45-3.80 (4H, m), 4.55 (1H, m), 6.60 (1H, dd, J=2.4, 6.0 Hz), 6.92 (2H, m), 7.04 (2H, m), 7.26 (1H, m), 7.50 (2H, m), 7.75 (1H, m), 8.03 (1H, d, J=6.0 Hz), 8.21 (1H, m), 8.96 (1H, brs), 9.19 (1H, brs).

ESI-MS (m/z): 560 [M+Na]$^+$.

Example 90

N-[4-({2-[(Azetidin-1-ylcarbonyl)amino]pyridin-4-yl}oxy)-2,5-difluorophenyl]-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (1 ml) under a nitrogen atmosphere, and triethylamine (0.0630 ml) and phenyl chloroformate (0.0624 ml) were added dropwise at 0° C. in this order, followed by stirring for 30 min. The reaction mixture was stirred after addition of ethyl acetate (5 ml) and a saturated aqueous solution of sodium hydrogencarbonate (5 ml). The organic layer was separated, washed with brine, and dried over anhydrous sodium sulfate. The solvent was concentrated under reduced pressure. The residue was dissolved in N,N-dimethylformamide (1.0 ml). Triethylamine(0.315 ml) and azetidine hydrochloride (84.6 mg) were added at room temperature, followed by stirring for 16.5 hr. The reaction mixture was partitioned between ethyl acetate (10 ml) and a saturated aqueous solution of sodium hydrogencarbonate (5 ml). The organic layer was washed with brine, and dried over anhydrous sodium sulfate. The solvent was concentrated under reduced pressure. To the residue were added ethyl acetate (3 ml) and heptane (3 ml) to precipitate a solid. The solid was collected by filtration. The resultant solid was washed with heptane:ethyl acetate=1:1, dried under hot air at 60° C. for 4 hr to provide the titled compound as white powder (94.0 mg, 79%).

$^1$H-NMR Spectrum (DMSO-d$_6$) δ (ppm): 1.56-1.66 (4H, m), 2.09-2.16 (2H, m), 3.92-3.95 (4H, m), 6.63 (1H, dd, J=2.4, 5.6 Hz), 7.15-7.20 (2H, m), 7.51 (1H, d, J=2.4 Hz), 7.54 (1H, dd, J=6.8, 11.2 Hz), 7.58-7.62 (2H, m), 8.06-8.13 (1H, m), 8.13 (1H, d, J=5.6 Hz), 9.13 (1H, s), 9.81 (1H, d, J=4.4 Hz), 11.0 (1H, m).

ESI-MS (m/z): 526 [M+H]$^+$.

Example 91

N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (1 ml) under a nitrogen atmosphere, and triethylamine (0.0630 ml) and phenyl chloroformate (0.0624 ml) were added dropwise at 0° C. in this order, followed by stirring for 30 min. The reaction mixture was stirred after addition of ethyl acetate (5 ml) and a saturated aqueous solution of sodium hydrogencarbonate (5 ml). The organic layer was separated, washed with brine, and dried over anhydrous sodium sulfate. The solvent was concentrated under reduced pressure. The residue was dissolved in N,N-dimethylformamide (1.0 ml). 3-Hydroxyazetidine hydrochloride (99.0 mg) and triethylamine (0.315 ml) were added at room temperature, followed by stirring for 22 hr and 5 min. The reaction mixture was partitioned between ethyl acetate (10 ml) and a saturated aqueous solution of sodium hydrogencarbonate (5 ml). The organic layer was washed with brine, and dried over anhydrous sodium sulfate. The solvent was concentrated under reduced pressure. To the resultant residue were added ethyl acetate (1 ml) and heptane (1 ml) to precipitate a solid. The solid was collected by filtration. The resultant solid was purified by silica gel column chromatography (Fuji Silysia NH, eluent; ethyl acetate, then ethyl acetate:methanol=10:1), and fractions containing the target compound were concentrated under reduced pressure to provide the titled compound as white powder (71.1 mg, 58%).

$^1$H-NMR Spectrum (DMSO-d$_6$) δ (ppm): 1.55-1.68 (4H, m), 3.68 (2H, dd, J=4.4, 8.4 Hz), 4.10-4.14 (2H, m), 4.34-4.40 (1H, m), 5.60 (1H, d, J=6.4 Hz), 6.64 (1H, dd, J=2.4, 5.6 Hz), 7.15-7.20 (2H, m), 7.50 (1H, d, J=2.4 Hz), 7.52-7.62 (3H, m), 8.05-8.14 (1H, m), 8.13 (1H, d, J=5.6 Hz), 9.20 (1H, s), 9.81 (1H, m), 10.99 (1H, m).

ESI-MS (neg.) (m/z): 540 [M−H]$^-$.

Example 92

N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (104.0 mg) was dissolved in tetrahydrofuran (1 ml) under a nitrogen atmosphere, and triethylamine (0.0653 ml) and phenyl chloroformate (0.0646 ml) were added dropwise at 0° C. in this order, followed by stirring for 30 min. The reaction mixture was stirred after addition of ethyl acetate (5 ml) and a saturated aqueous solution of sodium hydrogencarbonate (5 ml). The organic layer was separated, washed with brine, and dried over anhydrous sodium sulfate. The solvent was concentrated under reduced pressure. The residue was dissolved in N,N-dimethylformamide (1.0 ml). 1-Methyl-4-(piperidin-4-yl)piperazine (172.0 mg) was added at room temperature, followed by stirring at 20 hr and 40 min. The reaction mixture was partitioned between ethyl acetate (10 ml) and a saturated aqueous solution of sodium hydrogencarbonate (5 ml). The organic layer was washed with brine, and dried over anhydrous sodium sulfate. The solvent was concentrated under reduced pressure. To the resultant residue were added ethyl acetate (5 ml) and heptane (5 ml) to precipitate a solid. The solid was collected by filtration. The resultant solid was washed with heptane:ethyl acetate=1:1, and dried under aeration to provide the titled compound as white powder (89.2 mg, 59%).

$^1$H-NMR Spectrum (DMSO-$d_6$) δ (ppm): 1.12-1.32 (2H, m), 1.55-1.67 (4H, m), 1.67-1.74 (2H, m), 2.12 (3H, s), 2.20-2.65 (7H, m), 2.65-2.80 (4H, m), 4.05-4.15 (2H, m), 6.63 (1H, dd, J=2.4, 5.6 Hz), 7.18 (2H, m), 7.39 (1H, d, J=2.4 Hz), 7.52-7.62 (3H, m), 8.05-8.15 (1H, m), 8.13 (1H, d, J=5.6 Hz), 9.24 (1H, s), 9.80 (1H, m), 10.99 (1H, m).

ESI-MS (m/z): 652 [M+H]$^+$.

Example 93

N-[2,5-Difluoro-4-({2-[({3-[(dimethylamino)methyl]azetidin-1-yl}carbonyl)amino]pyridin-4-yl}oxy)phenyl]-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (93.9 mg) was dissolved in tetrahydrofuran (1 ml) under a nitrogen atmosphere, and triethylamine (0.0592 ml) and phenyl chloroformate (0.0586 ml) were added dropwise at 0° C. in this order, followed by stirring for 25 min. The reaction mixture was stirred after addition of ethyl acetate (5 ml) and a saturated aqueous solution of sodium hydrogencarbonate (5 ml). The organic layer was separated, washed with brine, and dried over anhydrous sodium sulfate. The solvent was concentrated under reduced pressure. The residue was dissolved in N,N-dimethylformamide (1.0 ml). 3-(Dimethylaminomethyl)azetidine ditrifluoroacetate (363.0 mg) and triethylamine (0.591 ml) were added at room temperature, followed by stirring for 19 hr and 45 min. The reaction mixture was partitioned between ethyl acetate (10 ml) and a saturated aqueous solution of sodium hydrogencarbonate (5 ml). The organic layer was washed with water (10 ml) twice and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (92.3 mg, 73%).

$^1$H-NMR Spectrum (DMSO-$d_6$) δ (ppm): 1.55-1.68 (4H, m), 2.10 (6H, s), 2.40 (2H, d, J=7.2 Hz), 2.62-2.73 (1H, m), 3.54-3.62 (2H, m), 3.96-4.05 (2H, m), 6.64 (1H, dd, J=2.4, 5.6 Hz), 7.15-7.20 (2H, m), 7.50 (1H, d, J=2.4 Hz), 7.50-7.61 (3H, m), 8.05-8.13 (1H, m), 8.13 (1H, d, J=5.6 Hz), 9.16 (1H, s), 9.82 (1H, m), 10.99 (1H, m).

ESI-MS (m/z): 583 [M+H]$^+$.

Example 94

N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (94.0 mg) was dissolved in tetrahydrofuran (1 ml) under a nitrogen atmosphere, and triethylamine (0.0593 ml) and phenyl chloroformate (0.0587 ml) were added dropwise at 0° C. in this order, followed by stirring for 25 min. The reaction mixture was stirred after addition of ethyl acetate (5 ml) and a saturated aqueous solution of sodium hydrogencarbonate (5 ml). The organic layer was separated, washed with brine, and dried over anhydrous sodium sulfate. The solvent was concentrated under reduced pressure. The residue was dissolved in N,N-dimethylformamide (1.0 ml). 1-Methyl-4-(methylamino)piperidine (0.123 ml) was added at room temperature, followed by stirring for 18 hr and 35 min. The reaction mixture was partitioned between ethyl acetate (10 ml) and a saturated aqueous solution of sodium hydrogencarbonate (5 ml). The organic layer was washed with water (10 ml) twice and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (96.8 mg, 75%).

$^1$H-NMR Spectrum (CDCl$_3$) δ (ppm): 1.61-1.83 (8H, m), 2.03-2.10 (2H, m), 2.28 (3H, s), 2.88 (3H, s), 2.90-2.94 (2H, m), 4.10-4.20 (1H, m), 6.55 (1H, dd, J=2.4, 5.6 Hz), 6.98-7.08 (3H, m), 7.15 (1H, s), 7.46-7.50 (2H, m), 7.67 (1H, d, J=2.4 Hz), 8.08 (1H, d, J=5.6 Hz), 8.29 (1H, dd, J=7.2, 12.0 Hz), 8.57 (1H, s), 9.59 (1H, s).

ESI-MS (m/z): 597 [M+H]$^+$.

Example 95

N-{4-[(2-{[3-(Azetidin-1-ylmethyl)azetidin-1-ylcarbonyl]amino}pyridin-4-yl)oxy]-2,5-difluorophenyl}-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (94.7 mg) was dissolved in tetrahydrofuran (2.5 ml) under a nitrogen atmosphere, and triethylamine (0.100 ml) and phenyl chloroformate (0.070 ml) were added dropwise at room temperature in this order, followed by stirring for 15 min. The reaction mixture was stirred after addition of ethyl acetate and water. The organic layer was separated, washed with a 1N aqueous solution of sodium hydroxide, water and brine, dried over anhydrous sodium sulfate. The solvent was concentrated under reduced pressure. The residue was dissolved in N,N-dimethylformamide (2.5 ml). Triethylamine (0.315 ml) and 3-(azetidin-1-ylmethyl)azetidine dihydrochloride (180 mg) were added at room temperature, followed by stirring overnight. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5). Fractions containing the target compound were concentrated under reduced pressure. To the resultant residue was added tert-butyl methyl ether:heptane=1:2 to precipitate a solid. The solid was collected by filtration and dried under aeration to provide the titled compound as white powder (50.0 mg, 39%).

$^1$H-NMR Spectrum (CDCl$_3$) δ (ppm): 1.55-1.80 (4H, m), 2.10 (2H, m), 2.55-2.70 (3H, m), 3.10-3.30 (4H, m), 3.71 (2H, m), 4.10 (2H, m), 6.57 (1H, dd, J=2.4, 5.6 Hz), 6.78 (1H, brs), 6.95-7.10 (3H, m), 7.40-7.55 (2H, m), 7.62 (1H, d, J=2.4 Hz), 8.05 (1H, d, J=5.6 Hz), 8.29 (1H, m), 8.66 (1H, brs), 9.51 (1H, brs).

ESI-MS (m/z): 595 [M+H]$^+$.

Example 96

N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (108.2 mg) was dissolved in tetrahydrofuran (2.5 ml) under a nitrogen atmosphere, and triethylamine (0.100 ml) and phenyl chloroformate (0.080 ml) were added dropwise at room temperature in this order, followed by stirring for 15 min. The reaction mixture was stirred after addition of ethyl acetate and water. The organic layer was separated, washed with a 1N aqueous solution of sodium hydroxide, water and brine, dried over anhydrous sodium sulfate. The solvent was concentrated under reduced pressure. The residue was dissolved in N,N-dimethylformamide (2.5 ml). Triethylamine (0.256 ml) and 3-(hydroxymethyl)azetidine hydrochloride (182 mg) were added at room temperature, followed by stirring overnight. The reaction mixture was partitioned between ethyl acetate and water. The organic layer was washed with a 1N aqueous solution of sodium hydroxide, water and brine in this order, and dried over anhydrous sodium sulfate. The solvent was concentrated under reduced pressure. The resultant residue was purified by silica gel column chromatography (eluent; ethyl acetate, then ethyl acetate:methanol=95:5). Fractions containing the target compound were concentrated under reduced pressure. To the resultant residue was added tert-butyl methyl ether:heptane=1:2 to precipitate a solid. The solid was collected by filtration and dried under aeration to provide the titled compound as white powder (38.1 mg, 28%).

$^1$H-NMR Spectrum (CDCl$_3$) δ (ppm): 1.50-1.80 (4H, m), 2.83 (1H, m), 3.80 (2H, d, J=6.0 Hz), 3.93 (2H, m), 4.18 (2H, m), 6.57 (1H, dd, J=2.4, 5.6 Hz), 6.95-7.10 (4H, m), 7.40-7.55 (2H, m), 7.78 (1H, d, J=2.4 Hz), 7.99 (1H, d, J=5.6 Hz), 8.33 (1H, m), 8.48 (1H, brs), 9.79 (1H, brs).

ESI-MS (m/z): 578 [M+Na]$^+$.

Example 97

N-{2,5-Difluoro-4-[(4-{[(3-hydroxyazetidin-1-yl)carbonyl]amino}pyrimidin-6-yl)oxy]phenyl}-N'-(4-fluorophenyl)cyclopropane-1,1-dicarboxamide N-{4-[(4-Aminopyrimidin-6-yl)oxy]-2,5-difluorophenyl}-N'-(4-fluorophenyl)cyclopropane-1,1-dicarboxamide (100 mg) was dissolved in tetrahydrofuran (5 ml) under a nitrogen atmosphere, triethylamine (0.080 ml) and phenyl chloroformate (0.070 ml) were added dropwise at room temperature, followed by stirring for 10 min. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The residue was dissolved in N,N-dimethylformamide (2.5 ml). To the solution were added 3-hydroxyazetidine hydrochloride (150 mg) and triethylamine (0.250 ml) at room temperature, followed by stirring for 63 hr. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5), and fractions containing the target compound were concentrated under reduced pressure. To the resultant residue was added diethyl ether:heptane=1:2 to precipitate a solid. The solid was collected by filtration and dried under aeration to provide the titled compound as white powder (57.3 mg, 47%).

$^1$H-NMR Spectrum (CDCl$_3$) δ (ppm): 1.60-1.80 (4H, m), 2.27 (1H, m), 4.00 (2H, m), 4.37 (2H, m), 4.75 (1H, m), 6.90-7.10 (4H, m), 7.40-7.55 (2H, m), 7.66 (1H, s), 8.28 (1H, dd, J=7.2, 12.0 Hz), 8.34 (1H, s), 8.66 (1H, brs), 9.50 (1H, brs).

ESI-MS (m/z): 565 [M+Na]$^+$.

Example 98

N-[4-({4-[({3-[(Dimethylamino)methyl]azetidin-1-yl}carbonyl)amino]pyrimidin-6-yl}oxy)-2,5-difluorophenyl]-N'-(4-fluorophenyl)cyclopropane-1,1-dicarboxamide N-{4-[(4-Aminopyrimidin-6-yl)oxy]-2,5-difluorophenyl}-N'-(4-fluorophenyl)cyclopropane-1,1-dicarboxamide (99.0 mg) was dissolved in tetrahydrofuran (10 ml) under a nitrogen atmosphere, triethylamine (0.0622 ml) and phenyl chloroformate (0.0615 ml) were added dropwise at 0° C., followed by stirring for 40 min., then stirred for 20 min. at room temperature. Triethylamine (0.0622 ml) and phenyl chloroformate (0.0615 ml) were added again at room temperature, followed by stirring for 1 hr. The reaction mixture was stirred after addition of ethyl acetate (5 ml) and a saturated aqueous solution of sodium hydrogencarbonate (5 ml). The organic layer was separated, washed with brine, dried over anhydrous sodium sulfate and filtered. The solvent was concentrated under reduced pressure. The residue was dissolved in N,N-dimethylformamide (2.0 ml). This was added to 3-(dimethylaminomethyl)azetidine ditrifluoroacetate (227 mg) at room temperature under a nitrogen atmosphere, then triethylamine (0.623 ml) was added thereto, followed by stirring for 13 hr and 30 min. The reaction mixture was partitioned between ethyl acetate (10 ml) and a saturated aqueous solution of sodium hydrogencarbonate (5 ml). The organic layer was separated, washed with twice in water (10 ml) and brine in this order, and dried over anhydrous sodium sulfate. The solvent was concentrated under reduced pressure. To the resultant residue was added ethyl acetate:heptane=1:4 to precipitate the solid. The solid was collected by filtration. This was dissolved in ethanol (4 ml), and a 1N aqueous solution of sodium hydroxide (0.233 ml) was added at room temperature, followed by stirring for 1.5 hr. After the reaction was quenched by addition of 1N hydrochloric acid (0.223 ml) at room temperature, ethyl acetate (30 ml) and water (20 ml) were added to the reaction mixture. The separated organic layer was washed with brine, dried over anhydrous sodium sulfate and filtrated. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (60.8 mg, 47%).

$^1$H-NMR Spectrum (CDCl$_3$) δ (ppm): 1.66-1.71 (4H, m), 2.24 (6H, s), 2.55 (2H, d, J=7.6 Hz), 2.80-2.90 (1H, m), 3.77 (2H, dd, J=5.6, 8.4 Hz), 4.19 (2H, t, J=8.4 Hz), 6.93 (1H, brs), 7.01-7.10 (3H, m), 7.45-7.50 (2H, m), 7.66 (1H, s), 8.27 (1H, dd, J=7.2, 11.6 Hz), 8.33-8.35 (1H, m), 8.68 (1H, brs), 9.45-9.49 (1H, m).

ESI-MS (m/z): 584 [M+H]+.

Example 99

N-(2,5-Difluoro-4-{[4-({[3-(hydroxymethyl)azetidin-1-yl]carbonyl}amino)pyrimidin-6-yl]oxy}phenyl)-N'-(4-fluorophenyl)cyclopropane-1,1-dicarboxamide N-{4-[(4-Aminopyrimidin-6-yl)oxy]-2,5-difluorophenyl}-N'-(4-fluorophenyl)cyclopropane-1,1-dicarboxamide (100 mg) was dissolved in tetrahydrofuran (7.5 ml) under a nitrogen atmosphere, triethylamine (0.180 ml) and phenyl chloroformate (0.150 ml) were added dropwise at room temperature, followed by stirring for 50 min. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The residue was dissolved in N,N-dimethylformamide (2.5 ml). To the solution were added triethylamine (0.400 ml) and 3-(hydroxymethyl)azetidine hydrochloride (280 mg) at room temperature, followed by stirring overnight. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The resultant residue was purified by silica gel column chromatography (eluent; ethyl acetate, then ethyl acetate:methanol=95:5), and fractions containing the target compound were concentrated under reduced pressure. To the resultant residue was added tert-butyl methyl ether:heptane=1:2 to precipitate a solid. The solid was collected by filtration and dried under aeration to provide the titled compound as white powder (15.6 mg, 12%).

$^1$H-NMR Spectrum (CDCl$_3$) δ (ppm): 1.60-1.80 (4H, m), 2.83 (1H, m), 3.82 (2H, d, J=6.0 Hz), 3.93 (2H, m), 4.16 (2H, m), 6.90-7.15 (4H, m), 7.40-7.55 (2H, m), 7.66 (1H, s), 8.22 (1H, dd, J=7.2, 12.0 Hz), 8.33 (1H, s), 8.73 (1H, brs), 9.60 (1H, brs).

ESI-MS (m/z): 579 [M+Na]+.

Example 100

N-(2,5-Difluoro-4-{[4-({[methyl(1-methylpiperidin-4-yl)amino]carbonyl}amino)pyrimidin-6-yl]oxy}phenyl)-N'-(4-fluorophenyl)cyclopropane-1,1-dicarboxamide N-{4-[(4-Aminopyrimidin-6-yl)oxy]-2,5-difluorophenyl}-N'-(4-fluorophenyl)cyclopropane-1,1-dicarboxamide (100 mg) was dissolved in tetrahydrofuran (7.5 ml) under a nitrogen atmosphere, triethylamine (0.180 ml) and phenyl chloroformate (0.150 ml) were added dropwise at room temperature, followed by stirring for 50 min. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The residue was dissolved in N,N-dimethylformamide (2.5 ml). To the solution was added 1-methyl-4-(methylamino)piperidine (0.330 ml) at room temperature, followed by stirring overnight. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5), and fractions containing the target compound were concentrated under reduced pressure. To the resultant residue was added tert-butyl methyl ether:heptane=1:2 to precipitate a solid. The solid was collected by filtration and dried under aeration to provide the titled compound as white powder (19.5 mg, 14%).

$^1$H-NMR Spectrum (CDCl$_3$) δ (ppm): 1.60-1.80 (8H, m), 2.20-2.60 (2H, m), 2.96 (3H, s), 3.00-3.30 (2H, m), 3.22 (3H, s), 4.33 (1H, m), 6.90-7.15 (4H, m), 7.40-7.55 (2H, m), 7.66 (1H, s), 8.27 (1H, dd, J=7.2, 12.0 Hz), 8.35 (1H, s), 8.62 (1H, brs), 9.53 (1H, brs).

ESI-MS (m/z): 620 [M+Na]+.

Example 101

N-(2,5-Difluoro-4-{[4-({[4-(4-methylpiperazin-1-yl)piperidin-1-yl]carbonyl}amino)pyrimidin-6-yl]oxy}phenyl)-N'-(4-fluorophenyl)cyclopropane-1,1-dicarboxamide N-{4-[(4-Aminopyrimidin-6-yl)oxy]-2,5-difluorophenyl}-N'-(4-fluorophenyl)cyclopropane-1,1-dicarboxamide (100 mg) was dissolved in tetrahydrofuran (5 ml) under a nitrogen atmosphere, N,N-diisopropylethylamine (0.100 ml) and phenyl chloroformate (0.070 ml) were added dropwise at room temperature, followed by stirring for 15 min. The reaction mixture was partitioned between ethyl acetate and water. The organic layer was separated, washed with a saturated aqueous solution of sodium hydrogencarbonate and brine, dried over anhydrous sodium sulfate. The solvent was concentrated under reduced pressure. The residue was dissolved in N,N-dimethylformamide (2.5 ml). To the solution was added 1-methyl-4-(piperidin-4-yl)piperazine (250 mg) at room temperature, followed by stirring for 25 hr. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The resultant residue was purified by silica gel column chromatography (Fuji Silysia NH, eluent; ethyl acetate, then ethyl acetate:methanol=95:5), and fractions containing the target compound were concentrated under reduced pressure. To the resultant residue was added diethyl ether:heptane=1:2 to precipitate a solid. The solid was collected by filtration and dried under aeration to provide the titled compound as white powder (93.4 mg, 63%).

$^1$H-NMR Spectrum (CDCl$_3$) δ (ppm): 1.45-1.60 (2H, m), 1.66-1.76 (4H, m), 1.90-1.98 (2H, m), 2.34 (3H, s), 2.42-2.72 (9H, m), 2.95 (2H, m), 4.12 (2H, m), 7.00-7.10 (3H, m), 7.38 (1H, brs), 7.44-7.55 (2H, m), 7.62 (1H, s), 8.27 (1H, dd, J=6.8, 12.0 Hz), 8.33 (1H, s), 8.67 (1H, brs), 9.47 (1H, brs).

ESI-MS (m/z): 653 [M+H]+.

Example 102

N-(4-{[4-({[4-(Dimethylamino)piperidin-1-yl]carbonyl}amino)pyrimidin-6-yl]oxy}-2,5-difluorophenyl)-N'-(4-fluorophenyl)cyclopropane-1,1-dicarboxamide N-{4-[(4-Aminopyrimidin-6-yl)oxy]-2,5-difluorophenyl}-N'-(4-fluorophenyl)cyclopropane-1,1-dicarboxamide (100 mg) was dissolved in tetrahydrofuran (5 ml) under a nitrogen atmosphere, N,N-diisopropylethylamine (0.100 ml) and phenyl chloroformate (0.070 ml) were added dropwise at room temperature, followed by stirring for 15 min. The reaction mixture was partitioned between ethyl acetate and water. The organic layer was separated, washed with a saturated aqueous solution of sodium hydrogencarbonate and brine, dried over anhydrous sodium sulfate. The solvent was concentrated under reduced pressure. The residue was dissolved in N,N-dimethylformamide (2.5 ml). To the solution were added 4-dimethylaminopiperidine dihydrochloride (250 mg) and triethylamine (0.400 ml) at room temperature, followed by stirring for 25 hr. The reaction mixture was partitioned between ethyl acetate and water. The organic layer was separated, washed with a 1N aqueous solution of sodium hydroxide and brine, dried over anhydrous sodium sulfate. The solvent was concentrated under reduced pressure. The resultant residue was purified by silica gel column chromatography (Fuji Silysia NH, eluent; ethyl acetate, then ethyl acetate: methanol=95:5), and fractions containing the target compound were concentrated under reduced pressure. To the resultant residue was added diethyl ether:heptane=1:2 to precipitate a solid. The solid was collected by filtration and dried under aeration to provide the titled compound as white powder (100.3 mg, 74%).

$^1$H-NMR Spectrum (CDCl$_3$) δ (ppm): 1.46-1.56 (2H, m), 1.66-1.76 (4H, m), 1.86-1.96 (2H, m), 2.31 (6H, s), 2.38 (1H, m), 2.97 (2H, m), 4.06-4.16 (2H, m), 7.00-7.10 (3H, m), 7.39 (1H, brs), 7.44-7.54 (2H, m), 7.63 (1H, s), 8.27 (1H, dd, J=7.2, 12.0 Hz), 8.34 (1H, s), 8.68 (1H, brs), 9.47 (1H, brs).

ESI-MS (m/z): 598 [M+H]$^+$.

Example 103

N-(4-{[2-({[4-(Dimethylamino)piperidin-1-yl]carbonyl}amino)pyridin-4-yl]oxy}-2,5-difluorophenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (1 ml) under a nitrogen atmosphere, triethylamine (0.0631 ml) and phenyl chloroformate (0.0624 ml) were added dropwise at 0° C., followed by stirring for 20 min. The reaction mixture was stirred after addition of ethyl acetate (5 ml) and a saturated aqueous solution of sodium hydrogencarbonate (5 ml). The organic layer was separated, washed with brine, dried over anhydrous sodium sulfate and filtrated. The solvent was concentrated under reduced pressure. The residue was dissolved in N,N-dimethylformamide (3.0 ml). 4-dimethylaminopiperidine dihydrochloride (227 mg) and triethylamine (0.631 ml) were added at room temperature under a nitrogen atmosphere, followed by stirring for 18 hr and 30 min. The reaction mixture was partitioned between ethyl acetate (10 ml) and a saturated aqueous solution of sodium hydrogencarbonate (5 ml). The organic layer was separated, washed with water (10 ml, twice) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (107.5 mg, 78%).

$^1$H-NMR Spectrum (DMSO-d$_6$) δ (ppm): 1.20-1.30 (4H, m), 1.55-1.74 (6H, m), 2.15 (6H, s), 2.71-2.80 (1H, s), 4.06-4.12 (2H, m), 6.63 (1H, dd, J=2.4, 5.6 Hz), 7.15-7.2 (2H, m), 7.39-7.41 (1H, m), 7.51-7.63 (3H, m), 8.05-8.1 (1H, m), 8.13 (1H, d, J=5.6 Hz), 9.23-9.26 (1H, m), 9.78-9.85 (1H, m), 10.98-11.01 (1H, m).

ESI-MS (m/z): 597 [M+H]$^+$.

Example 104

N-{2,5-Difluoro-4-[(2-{[(4-methylpiperazin-1-yl)carbonyl]amino}pyridin-4-yl]oxy}phenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (1 ml) under a nitrogen atmosphere, triethylamine (0.0631 ml) and phenyl chloroformate (0.0624 ml) were added dropwise at 0° C., followed by stirring for 20 min. The reaction mixture was stirred after addition of ethyl acetate (5 ml) and a saturated aqueous solution of sodium hydrogencarbonate (5 ml). The organic layer was separated, washed with brine, dried over anhydrous sodium sulfate and filtrated. The solvent was concentrated under reduced pressure. The residue was dissolved in N,N-dimethylformamide (2.0 ml). 1-Methylpiperazine (0.100 ml) was added at room temperature under a nitrogen atmosphere, followed by stirring for 18 hr and 15 min. The reaction mixture was partitioned between ethyl acetate (10 ml) and a saturated aqueous solution of sodium hydrogencarbonate (5 ml). The organic layer was separated, washed with water (10 ml, twice) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (113.1 mg, 87%).

$^1$H-NMR Spectrum (DMSO-d$_6$) δ (ppm): 1.56-1.67 (4H, m), 2.17 (3H, m), 2.24-2.28 (4H, m), 3.38-3.43 (4H, m), 6.62-6.65 (1H, m), 7.15-7.20 (2H, m), 7.39-7.40 (1H, m), 7.52-7.63 (3H, m), 8.06-8.16 (1H, m), 8.14 (1H, d, J=6.4 Hz), 9.27-9.28 (1H, m), 9.79-9.81 (1H, m), 10.98-11.00 (1H, m).

ESI-MS (m/z): 591 [M+Na]$^+$.

Example 105

N-{2,5-Difluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (129.0 mg) was dissolved in tetrahydrofuran (2 ml) under a nitrogen atmosphere, triethylamine (0.0812 ml) and phenyl chloroformate (0.0803 ml) were added dropwise at 0° C., followed by stirring for 25 min. The reaction mixture was stirred after addition of ethyl acetate (5 ml) and a saturated aqueous solution of sodium hydrogencarbonate (5 ml). The organic layer was separated, washed with brine, dried over anhydrous sodium sulfate and filtrated. The solvent was concentrated under reduced pressure. The residue was dissolved in N,N-dimethylformamide (2.0 ml). A solution of 4-hydroxypiperidine (118 mg) in N,N-dimethylformamide (2 ml) was added at room temperature under a nitrogen atmosphere, followed by stirring for 17 hr and 15 min. The reaction mixture was partitioned between ethyl acetate (10 ml) and a saturated aqueous solution of sodium hydrogencarbonate (5 ml). The organic layer was separated, washed with twice in water (10 ml) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (158.4 mg, 92%).

$^1$H-NMR Spectrum (DMSO-d$_6$) δ (ppm): 1.22-1.33 (2H, m), 1.55-1.73 (6H, m), 3.00-3.07 (2H, m), 3.59-3.67 (1H, m), 3.74-3.82 (2H, m), 4.67 (1H, d, J=4.4 Hz), 6.62 (1H, dd, J=2.4, 5.6 Hz), 7.15-7.21 (2H, m), 7.40 (1H, d, J=2.4 Hz), 7.54 (1H, dd, J=7.2, 10.4 Hz), 7.57-7.63 (2H, m), 8.05-8.15 (1H, m), 8.13 (1H, d, J=5.6 Hz), 9.23 (1H, brs), 9.80-9.83 (1H, m), 10.97-11.01 (1H, m).

ESI-MS (m/z): 592 [M+Na]$^+$.

Example 106

N-{2,3-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide N-{4-[(2-Aminopyridin-4-yl)oxy]-2,3-difluorophenyl}-N'-(4-fluorophenyl)cyclopropane-1,1-dicarboxamide (84.0 mg) was dissolved in tetrahydrofuran (1 ml) under a nitrogen atmosphere, triethylamine (0.0530 ml) and phenyl chloroformate (0.0524 ml) were added dropwise at 0° C., followed by stirring for 20 min. The reaction mixture was stirred after addition of ethyl acetate (5 ml) and a saturated aqueous solution of sodium hydrogencarbonate (5 ml). The organic layer was separated, washed with brine, dried over anhydrous sodium sulfate and filtrated. The solvent was concentrated under reduced pressure. The residue was dissolved in N,N-dimethylformamide (2.0 ml). 3-hydroxyazetidine hydrochloride (83.3 mg) and triethylamine (0.265 ml) were added at room temperature under a nitrogen atmosphere, followed by stirring for 12 hr and 25 min. The reaction mixture was partitioned between ethyl acetate (10 ml) and a saturated aqueous solution of sodium hydrogencarbonate (5 ml). The organic layer was separated, washed with twice in water (10 ml) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (80.3 mg, 78%).

$^1$H-NMR Spectrum (DMSO-d$_6$) δ (ppm): 1.53-1.62 (4H, m), 3.66-3.72 (2H, m), 4.10-4.15 (2H, m), 4.34-4.40 (1H, m), 5.60 (1H, d, J=6.0 Hz), 6.66 (1H, dd, J=2.4, 5.6 Hz), 7.15-7.25 (3H, m), 7.52 (1H, d, J=2.4 Hz), 7.60-7.65 (2H, m), 7.70-7.78 (1H, m), 8.14 (1H, d, J=5.6 Hz), 9.22 (1H, brs), 9.95-9.99 (1H, m), 10.68-10.71 (1H, m).

ESI-MS (m/z): 564 [M+Na]$^+$.

Example 107

N-[4-({2-[({3-[(Dimethylamino)methyl]azetidine-1-yl}carbonyl)amino]pyridin-4-yl}oxy)-2,3-difluorophenyl]-N'-(4-fluorophenyl)cyclopropane-1,1-dicarboxamide N-{4-[(2-Aminopyridin-4-yl)oxy]-2,3-difluorophenyl}-N'-(4-fluorophenyl)cyclopropane-1,1-dicarboxamide (79.2 mg) was dissolved in tetrahydrofuran (2 ml) under a nitrogen atmosphere, triethylamine (0.0500 ml) and phenyl chloroformate (0.0494 ml) were added dropwise at 0° C., followed by stirring for 20 min. The reaction mixture was stirred after addition of ethyl acetate (5 ml) and a saturated aqueous solution of sodium hydrogencarbonate (5 ml). The organic layer was separated, washed with brine, dried over anhydrous sodium sulfate. After filtering the desiccant off, the filtrate was moved to a flask with 3-(dimethylaminomethyl)azetidine ditrifluoroacetate (434 mg). The solvent was concentrated under reduced pressure. The residue was dissolved in N,N-dimethylformamide (5.0 ml). Triethylamine (0.750 ml) was added at room temperature under a nitrogen atmosphere, followed by stirring for 13 hr. The reaction mixture was partitioned between ethyl acetate (10 ml) and a saturated aqueous solution of sodium hydrogencarbonate (5 ml). The organic layer was separated, washed with twice in water (10 ml) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure to provide the titled compound as white powder (83.0 mg, 80%).

$^1$H-NMR Spectrum (DMSO-d$_6$) δ (ppm): 1.53-1.62 (4H, m), 2.10 (6H, s), 2.39 (2H, d, J=7.6 Hz), 2.65-2.68 (1H, m), 3.53-3.60 (2H, m), 3.95-4.04 (2H, m), 6.95-6.98 (1H, m), 7.14-7.25 (4H, m), 7.52 (1H, d, J=2.4 Hz), 7.60-7.66 (2H, m), 7.70-7.78 (1H, m), 8.14 (1H, d, J=5.6 Hz), 9.17 (1H, brs), 9.95-9.98 (1H, m), 10.66-10.71 (1H, m).

ESI-MS (m/z): 583 [M+H]$^+$.

Example 108

N-{4-[(2-{[(4-Azetidin-1-ylpiperidin-1-yl)carbonyl]amino}pyridin-4-yl)oxy]oxy}-2,5-difluorophenyl-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (2.0 ml) under a nitrogen atmosphere, triethylamine (0.0631 ml) and phenyl chloroformate (0.0624 ml) were added dropwise at 0° C., followed by stirring for 1 hr. Then triethylamine (0.0631 ml) and phenyl chloroformate (0.0624 ml) were added dropwise at 0° C., followed by stirring for 20 min. The reaction mixture was stirred after addition of ethyl acetate (5 ml) and saturated sodium hydrogencarbonate (5 ml). The organic layer was separated, washed with brine, dried over anhydrous sodium sulfate and filtrated. The solvent was concentrated under reduced pressure. The residue was dissolved in N,N-dimethylformamide (2.0 ml). 4-(Azetidin-1-yl)piperidine dihydrochloride (227.0 mg) and triethylamine (0.631 ml) were added at room temperature under a nitrogen atmosphere, followed by stirring for 16 hr and 30 min. The reaction mixture was partitioned between ethyl acetate (10 ml) and saturated sodium hydrogencarbonate (5 ml). The organic layer was separated, washed with twice in water (10 ml) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure. To the resultant residue was added heptane:ethyl acetate=10:1 to suspend a solid. The solid was collected by filtration. This solid was purified by preparative TLC (Fuji Silysia NH TLC plate, eluent; ethyl acetate), and following short column chromatography (Fuji Silysia NH, eluent; ethyl acetate). Fractions containing the target compound were concentrated under reduced pressure. To the resultant residue was added heptane: ethyl acetate=10:1 to suspend a solid. The solid was collected by filtration to provide the titled compound as white powder (24.0 mg, 17%).

$^1$H-NMR Spectrum (CDCl$_3$) δ (ppm): 1.20-1.33 (4H, m), 1.67-1.75 (4H, m), 2.01-2.09 (2H, m), 2.13-2.23 (1H, m), 2.99-3.08 (2H, m), 3.15-3.20 (4H, m), 3.85-3.92 (2H, m), 6.55 (1H, dd, J=2.4, 5.6 Hz), 6.98-7.07 (3H, m), 7.46-7.50 (2H, m), 7.60 (1H, d, J=2.4 Hz), 8.06 (1H, d, J=5.6 Hz), 8.28 (1H, dd, J=7.2, 11.6 Hz), 8.66 (1H, brs), 9.49 (1H, brs).

ESI-MS (m/z): 609 [M+H]$^+$.

Example 109

N-(2,5-Difluoro-4-{[2-({[3-(2-dimethylaminoacetoxy)azetidin-1-yl]carbonyl}amino)pyridin-4-yl]oxy}phenyl)-N'-(4-fluorophenyl)cyclopropane-1,1-dicarboxamide N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide (38.9 mg) was dissolved in N,N-dimethylformamide (1.0 ml) under a nitrogen atmosphere, and N,N-dimethylglycine hydrochloride (20 mg), triethylamine (0.050 ml) and BOP reagent (63.5 mg) were added at room temperature, followed by stirring overnight. N,N-Dimethylglycine hydrochloride (20 mg), triethylamine (0.050 ml) and BOP reagent (63.5 mg) were added again at room temperature, and the reaction mixture was stirred for 5 hr. The reaction mixture was partitioned between ethyl acetate and water. The organic layer was separated, washed with a saturated aqueous solution of sodium hydrogencarbonate (twice) and brine, dried over anhydrous sodium sulfate. The solvent was concentrated under reduced pressure. The resultant residue was purified by silica gel column chromatography (Fuji Silysia NH, eluent; ethyl acetate), and fractions containing the target compound were concentrated under reduced pressure. To the resultant residue was added tert-butyl methyl ether (1 ml)—heptane (2 ml) to precipitate a solid. The solid was collected by filtration and dried under aeration to provide the titled compound as white powder (21.1 mg, 47%).

$^1$H-NMR Spectrum (CDCl$_3$) δ (ppm): 1.60-1.80 (4H, m), 2.38 (6H, s), 3.24 (2H, s), 4.05 (2H, m), 4.39 (2H, m), 5.28 (1H, m), 6.59 (1H, dd, J=2.4, 5.6 Hz), 6.90-7.15 (4H, m), 7.40-7.55 (2H, m), 7.62 (1H, d, J=2.4 Hz), 8.05 (1H, d, J=5.6 Hz), 8.29 (1H, dd, J=7.2, 12.0 Hz), 8.56 (1H, brs), 9.65 (1H, brs).

ESI-MS (m/z): 649 [M+Na]$^+$.

Example 110

N-(2,5-Difluoro-4-{[2-({[3S)-3-hydroxypyrrolidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (2.0 ml) under a nitrogen atmosphere, triethylamine (0.0630 ml) and phenyl chloroformate (0.0624 ml) were added dropwise at 0° C., followed by stirring for 30 min. The reaction mixture was stirred after addition of ethyl acetate (5 ml) and saturated sodium hydrogencarbonate (5 ml). The organic layer was separated, washed with brine, dried over anhydrous sodium sulfate and filtered it. The solvent was concentrated under reduced pressure. The residue was dissolved in N,N-dimethylformamide (2.0 ml). (S)-3-Hydroxypyrrolidine was added at room temperature under a nitrogen atmosphere, followed by stirring 22 hr. The reaction mixture was partitioned between ethyl acetate (10 ml) and saturated sodium hydrogencarbonate (5 ml). The organic layer was separated, washed with twice in water (10 ml) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure. To the resultant residue was added heptane: ethyl acetate=10:1 to suspend a solid. The solid was collected by filtration to provide the titled compound as white powder (63.7 mg, 51%).

$^1$H-NMR Spectrum (CDCl$_3$) δ (ppm): 1.60-1.80 (5H, m), 2.00-2.14 (2H, m), 3.47-3.67 (4H, m), 4.51-4.60 (1H, m), 6.58 (1H, dd, J=2.4, 5.6 Hz), 6.98-7.12 (3H, m), 7.45-7.52 (2H, m), 7.67 (1H, d, J=2.4 Hz), 8.07 (1H, d, J=5.6 Hz), 8.25-8.30 (1H, m), 8.68 (1H, brs), 9.50-9.57 (1H, m).

ESI-MS (neg.)(m/z): 554 [M−H]$^-$.

Example 111

N-(2,5-Difluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide N-{4-[(2-Aminopyridin-4-yl)oxy]-2,5-difluorophenyl}-N'-(4-fluorophenyl)cyclopropane-1,1-dicarboxamide (100.0 mg) was dissolved in tetrahydrofuran (2.0 ml) under a nitrogen atmosphere, triethylamine (0.0630 ml) and phenyl chloroformate (0.0624 ml) were added dropwise at 0° C., followed by stirring for 30 min. The reaction mixture was stirred after addition of ethyl acetate (5 ml) and saturated sodium hydrogencarbonate (5 ml). The organic layer was separated, washed with brine, dried over anhydrous sodium sulfate and filtered it. The solvent was concentrated under reduced pressure. The residue was dissolved in N,N-dimethylformamide (2.0 ml). (R)-(−)-3-Pyrrolidinol hydrochloride (112.0 mg) and triethylamine (0.315 ml) were added at room temperature under a nitrogen atmosphere, followed by stirring 22 hr and 15 min. The reaction mixture was partitioned between ethyl acetate (10 ml) and saturated sodium hydrogencarbonate (5 ml). The organic layer was separated, washed with twice in water (10 ml) and brine in this order, and dried over anhydrous sodium sulfate. The solvent was concentrated under reduced pressure. The resultant residue was purified by silica gel column chromatography (Fuji Silysia NH, eluent; ethyl acetate, then ethyl acetate:methanol=10:1), and fractions containing the target compound were concentrated under reduced pressure. To the resultant residue was added heptane: ethyl acetate=10:1 to suspend a solid. The solid was collected by filtration to provide the titled compound as white powder (76.4 mg, 61%).

$^1$H-NMR Spectrum (CDCl$_3$) δ (ppm): 1.65-1.70 (5H, m), 2.00-2.17 (2H, m), 3.46-3.68 (4H, m), 4.52-4.59 (1H, m), 6.57 (1H, dd, J=2.4, 5.6 Hz), 6.97-7.11 (3H, m), 7.46-7.50 (2H, m), 7.67 (1H, d, J=2.4 Hz), 8.07 (1H, d, J=5.6 Hz), 8.27 (1H, dd, J=7.2, 11.6 Hz), 8.68 (1H, brs), 9.54 (1H, brs).

ESI-MS (neg.)(m/z): 554 [M−H]$^-$.

Example 112

N-[4-({2-[(Azetidin-1-ylcarbonyl)amino]pyridin-4-yl}oxy)-2-fluorophenyl]-N'-(4-fluorophenyl)cyclopropane-1,1-dicarboxamide hydrochloride N-[4-({2-[(Azetidin-1-ylcarbonyl)amino]pyridin-4-yl}oxy)-2-fluorophenyl]-N'-(4-fluorophenyl)cyclopropane-1,1-dicarboxamide (25.4 mg) was suspended in acetone (0.254 ml). To this was added a 5M hydrochloric acid (0.010 ml) at room temperature, followed by stirring for 3 hr. After adding of acetone (0.127 ml), insoluble matter was collected by filtration and washed with acetone (0.127 ml, twice). This was dried under aeration at room temperature, then hot air-dried at 60° C. to provide the titled compound as white powder (26.5 mg, 97%).
$^1$H-NMR Spectrum (DMSO-$d_6$) δ (ppm): 1.52-1.70 (4H, m), 2.22 (2H, m), 3.96-4.12 (4H, m), 7.00-7.10 (2H, m), 7.14-7.24 (3H, m), 7.42 (1H, m), 7.55-7.65 (2H, m), 8.07 (1H, m), 8.25 (1H, d, J=7.2 Hz), 9.90 (1H, brs), 10.38 (1H, br), 10.80 (1H, brs).

Example 113

N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide hydrochloride N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide (31.7 mg) was suspended in acetone (0.317 ml). To this was added a 5M hydrochloric acid (0.010 ml) and water (0.0059 ml) at room temperature, followed by stirring for 5 hr. After adding of acetone (0.317 ml), insoluble matter was collected by filtration and washed with acetone (0.159 ml, twice). This was dried under aeration at room temperature, then hot air-dried at 60° C. to provide the titled compound as white powder (32.1 mg, 96%).
$^1$H-NMR Spectrum (DMSO-$d_6$) δ (ppm): 1.47 (2H, m), 1.58 (2H, m), 1.64 (2H, m), 1.97 (2H, m), 2.71 (6H, s), 2.96 (2H, m), 3.50-4.40 (6H, m), 4.59 (2H, m), 7.01 (1H, m), 7.10-7.25 (4H, m), 7.41 (1H, m), 7.55-7.65 (2H, m), 8.06 (1H, m), 8.27 (1H, d, J=6.8 Hz), 9.92 (1H, brs), 10.61 (1H, br), 10.80 (1H, brs), 12.30 (1H, br).

Example 114

N-(2-Fluoro-4-{[2-({[methyl(1-methylpiperidin-4-yl)amino]carbonyl}amino)pyridin-4-yl]oxy}phenyl)-N'-phenylcyclopropane-1,1-dicarboxamide ½ sulfate N-(2-Fluoro-4-{[2-({[methyl(1-methylpiperidin-4-yl)amino]carbonyl}amino)pyridin-4-yl]oxy}phenyl)-N'-phenylcyclopropane-1,1-dicarboxamide (28.0 mg) was suspended in acetone (0.280 ml). To this was added a 2.5M sulfuric acid (0.010 ml) and water (0.004 ml) at room temperature, followed by stirring overnight. After adding of acetone (0.140 ml), insoluble matter was collected by filtration and washed with acetone (0.140 ml, twice). This was dried under aeration at room temperature, then hot air-dried at 60° C. to provide the titled compound as white powder (28.2 mg, 93%).
$^1$H-NMR Spectrum (DMSO-$d_6$) δ (ppm): 1.50-1.70 (4H, m), 1.70-1.80 (2H, m), 1.85-2.00 (2H, m), 2.77 (3H, s), 2.81 (3H, s), 3.00-3.15 (2H, m), 3.40-3.50 (2H, m), 4.27 (1H, m), 6.81 (1H, m), 7.00-7.20 (2H, m), 7.22-7.40 (4H, m), 7.50-7.65 (2H, m), 7.99 (1H, m), 8.20 (1H, d, J=6.0 Hz), 9.20 (1H, br), 9.90 (1H, brs), 10.66 (1H, brs).

Example 115

N-[4-({2-[(Azetidin-1-ylcarbonyl)amino]pyridin-4-yl}oxy)-3-fluorophenyl]-N'-(4-fluorophenyl)cyclopropane-1,1-dicarboxamide ½ sulfate N-[4-({2-[(Azetidin-1-ylcarbonyl)amino]pyridin-4-yl}oxy)-3-fluorophenyl]-N'-(4-fluorophenyl)cyclopropane-1,1-dicarboxamide (25.4 mg) was suspended in acetone (0.254 ml). To this was added a 2.5M sulfuric acid (0.010 ml) at room temperature, followed by stirring for 3.5 hr. After adding of acetone (0.127 ml), insoluble matter was collected by filtration and washed with acetone (0.127 ml, twice). This was dried under aeration at room temperature, then hot air-dried at 60° C. to provide the titled compound as white powder (23.5 mg, 85%).
$^1$H-NMR Spectrum (DMSO-d6) δ (ppm): 1.40-1.56 (4H, m), 2.23 (2H, m), 3.96-4.14 (4H, m), 6.88 (1H, m), 7.05-7.20 (3H, m), 7.44 (1H, m), 7.54 (1H, m), 7.60-7.70 (2H, m), 7.92 (1H, dd, J=2.4, 13.2 Hz), 8.27 (1H, d, J=6.8 Hz), 9.96 (1H, brs), 10.27 (1H, br), 10.46 (1H, brs).

Example 116

N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide L-tartarate N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide (63.4 mg) was suspended in ethanol (1.168 ml). To this was added a 1M solution of L-(+)-tartaric acid in ethanol (0.100 ml), followed by heating at 50° C. Water (0.1268 ml) was added thereto to dissolve completely. The reaction mixture was stirred at 50° C. for 1 hr and 45 min, then stirred overnight while allowing it to gradually cool down to room temperature. Insoluble matter was collected by filtration and washed with ethanol (0.200 ml). This was dried under aeration at room temperature to provide the titled compound as colorless crystals (66.7 mg, 85.1%).
$^1$H-NMR Spectrum (DMSO-$d_6$) δ (ppm): 1.29 (2H, m), 1.68 (4H, m), 1.74 (2H, m), 2.35 (3H, s), 2.40-2.70 (9H, m), 2.77 (2H, m), 4.07 (2H, s), 4.12 (2H, m), 6.61 (1H, dd, J=2.4, 6.0 Hz), 7.01 (1H, m), 7.17 (2H, m), 7.23 (1H, m), 7.40 (1H, d, J=2.4 Hz), 7.59-7.63 (2H, m), 7.92 (1H, m), 8.14 (1H, d, J=6.0 Hz), 9.24 (1H, s), 9.96 (1H, m), 10.56 (1H, s).

Pharmacological Test Examples

The biological activity and pharmaceutical effect (inhibitory activity for hepatocyte growth factor receptor, anti-tumor activity, inhibitory activity for angiogenesis, and inhibitory activity for cancer metastasis) of the compound according to the present invention were evaluated by methods described below.

Abbreviations and terms used in the following Pharmacological Test Examples are listed as follows:
(Abbreviation List)
HGFR (Hepatocyte growth factor receptor)
DNA (Deoxyribonucleic acid)
Human placenta PCR (Polymerase chain reaction)
VEGFR2 (Vascular endothelial growth factor receptor 2)
FGFR1 (Fibroblast growth factor receptor 1)
PDGFRβ (Platelet derived growth factor receptor β)
EGFR (Epidermal growth factor receptor)
FBS (Fetal bovine serum)
PBS (Phosphate buffered saline)
Tris (Tris(hydroxymethyl)aminomethane, Tris(buffer))
PMSF (Phenylmethylsulfonyl fluoride)
NP-40 (Nonidet P-40)
EGTA (O,O-Bis(2-aminoethyleneglycol)-N,N,N',N'-tetraacetic acid)
SDS (Sodium dodecyl sulfate)
BSA (Bovine serum albumin)
Hepes (N-[2-hydroxyethyl]piperazine-N'-[2-ethanesulfonic acid], Hepes(buffer))
ATP (Adenosine 5'-triphosphate)
EDTA (Ethylenediamine tetraacetic acid)
HTRF (Homogenous Time-Resolved Fluorescence)
HRP (Horseradish peroxidase)
ELISA (Enzyme-linked immunosorbent assay)
HGF (Hepatocyte growth factor)
HBSS (Hank's Balanced Salt solution)
MTT (3-[4,5-dimethylthiazol-2-yl]-2,5-diphenyltetrazolium bromide; Thiazolyl blue)
EGM-2 (Endothelial Cell Growth Medium-2)

Pharmacological Test Example 1

Inhibitory Activity Against Receptor Tyrosine Kinase Activity

1. Cloning of Receptor Tyrosine Kinases, and Preparation of the Recombinant Baculovirus Solutions The cytoplasmic domain of HGFR (Genbank Accession No. J02958) is a 1.3 kb DNA fragment beginning with Lys974 and including a stop codon, and described by Park et al. (Proc. Natl. Acad. Sci. U.S.A. 84(18), 6379-6383, 1987). The DNA fragment was isolated from the human placental cDNA library (purchased from Clontech) by PCR (TaKaRa Ex Tae™ Kit, purchased from TaKaRa) using two kinds of primers (SEQ ID NO: 1,5'-CCGGCCGGATCCAAAAA-GAGAAAGCAAATTAAA-3' and SEQ ID NO: 2,5'-TTAAT-TCTGCAGCTATGATGTCTCCCAGAAGGA-3', purchased from Invitrogen). The DNA fragment was cloned into a baculovirus transplace vector (pFastBac™-HT (purchased from GIBCO BRL)) to produce a recombinant construct. The construct was transfected into insect cells (Spodoptera frugiperda 9 (Sf9)) to produce a solution of HGFR transfected baculovirus (preparation of a recombinant baculovirus can be found in the standard text (Bac-to-Bac Baculovirus Expression System (GIBCO BRL)). The cloning of the other receptor tyrosine kinases and preparation of the recombinant baculovirus solutions were prepared using a cytoplasmic fragment starting from Lys791 (VEGFR2, Genbank Accession No. L04947), a cytoplasmic fragment starting from Lys398 (FGFR1, Genbank Accession No. X52833) and a cytoplasmic fragment starting from Lys558 (PDGFRβ, Genbank Accession No. M21616) in stead of HGFR in the above method. EGFR was purchased from Sigma (Production No. E-2645).

2. Expression and Purification of Receptor Tyrosine Kinases

To the suspension of Sf9 cells ($3 \times 10^8$ cells) in SF-900II medium (purchased from Invitrogen) containing 2% FBS was added a solution of HGFR transfected baculovirus above (4 ml), followed by a shaking culture at 27° C. for 48 hrs. The cells infected with the HGFR transfected baculovirus were centrifuged at 1,000 rpm, 4° C. for 5 min to remove the supernatant. The precipitated infected cells were suspended in 80 ml of ice-cold PBS, and centrifuged at 1,000 rpm, 4° C. for 5 min to remove the supernatant. The precipitated infected cells were suspended in 40 ml of ice-cold Lysis Buffer (50 mM Tris-HCl (pH 8.5), 5 mM 2-mercaptoethanol, 100 mM KCl, 1 mM PMSF and 1% (v/v) NP-40). The suspension was centrifuged at 12,000 rpm, 4° C. for 30 min to provide a supernatant.

The supernatant was loaded onto an Ni-NTA agarose column (3 ml, purchased from Qiagen) equilibrated with 30 ml of Buffer A (20 mM Tris-HCl (pH 8.5), 5 mM 2-mercaptoethanol, 500 mM KCl, 20 mM imidazole and 10% (v/v) glycerol). The column was washed with 30 ml of Buffer A, 6 ml of Buffer B (20 mM Tris-HCl (pH 8.5), 5 mM 2-mercaptoethanol, 1 M KCl, and 10% (v/v) glycerol) and 6 ml of Buffer A in this order. Then, the column was eluted with 6 ml of Buffer C (20 mM Tris-HCl (pH 8.5), 5 mM 2-mercaptoethanol, 100 mM KCl, 100 mM imidazole, and 10% (v/v) glycerol) to provide a fraction. The fraction was entrapped in a dialysis membrane (purchased from Spectrum Laboratories), dialyzed at 4° C. overnight with 1 L of dialysis buffer (20 mM Tris-HCl (pH 7.5), 10% (v/v) glycerol, 1 mM dithiothreitol, 0.1 mM $Na_3VO_4$ and 0.1 mM EGTA), and stored at −80° C. until used. An aliquot of the dialyzed fraction was subjected to SDS electrophoresis, and then a recombinant protein (His6-HGFR, the HGFR cytoplasmic domain fused with six histidine at the N terminus) detected at a molecular weight of about 60 kDa when stained with Coomassie Brilliant Blue, was determined with regard to protein content using BSA (purchased from Sigma) as a standard. The VEGFR2 cytoplasmic domain, the FGFR1 cytoplasmic domain, and the PDGFRβ cytoplasmic domain were fused with six histidine at the N terminus by the similar method to produce respective recombinant proteins (His6-VEGFR2, His6-FGFR1, and His6-PDGFRβ).

3. Assay for the Inhibitory Activity Against HGFR Tyrosine Kinase Activity

To each well of a 96-well round plate (purchased from NUNC, Production No. 163320) were added 10 µl of a solution for kinase reaction (200 mM Hepes (pH 7.4), 80 mM $MgCl_2$, 16 mM $MnCl_2$ and 2 mM $Na_3VO_4$), 250 ng of biotinylated poly(Glu4: Tyr1) (biotin-poly(GT), purchased from Japan Schering) (6 µl, 15-fold diluted with distilled water), 30 ng of His6-HGFR (10 µl, 60-fold diluted with 0.4% BSA) and a test substance dissolved in dimethylsulfoxide (4 µl, 100-fold diluted with 0.1% BSA) to mess up to 30 µl. To the well was added 10 µl of 4 µM ATP (purchased from Sigma) diluted with distilled water to incubate at 30° C. for 10 min, followed by adding 10 µl of 500 mM EDTA (pH 8.0) (purchased from Wako Pure Chemicals) to provide a kinase reaction solution.

The tyrosine-phosphorylated biotin-poly(GT) was detected using the Homogenous Time-Resolved Fluorescence (HTRF) method (Analytical Biochemistry, 269, 94-104, 1999). That is, to each well of a 96-well half-area black plate (purchased from COSTAR, Production No. 3694) were added 20 µl of the above kinase reaction solution and 30 µl of a dilution solution (50 mM Hepes (pH 7.4), 20 mM $MgCl_2$, 4 mM $MnCl_2$, 0.5 mM $Na_3VO_4$, 0.1% BSA and 100 mM EDTA). To the well was added 7.5 ng of an europium cryptate-labelled anti-phosphotyrosine antibody (Eu(K)-PY20, purchased from Japan Schering) (25 µl, 250-fold diluted with 20 mM Hepes (pH 7.0), 0.5 M KF and 0.1% BSA) and 250 ng of XL665-labelled streptavidin (XL665-SA, purchased from Japan Schering) (25 µl, 62.5-fold diluted with 20 mM Hepes (pH 7.0), 0.5 M KF and 0.1% BSA), and using a discovery HTRF microplate analyzer (Packard), the well was instantly irradiated at an excitation wavelength of 337 nm to determine fluorescence intensities at 665 nm and 620 nm. The tyrosine phosphorylation rate of a biotin-poly (GT) was calculated using a delta F % value described in the text of a HTRF standard experiment method by Japan Schering. While defining the delta F % value of a well added with His6-HGFR and no test substance as 100% and the delta F % value of a well added with no His6-HGFR and no test substance as 0%, ratio (%) of the delta F % value of each well added with the test substance was calculated. The ratio (%) was used to calculate the concentration ($IC_{50}$) of the test substance necessary to inhibit HGFR kinase activity by 50%. The results are shown in Table 1.

TABLE 1

| Example | IC50 (µM) |
|---|---|
| 1 | 0.066 |
| 2 | 0.055 |
| 3 | 0.039 |
| 4 | 0.045 |
| 5 | 0.06 |
| 6 | 0.64 |
| 7 | 0.051 |
| 8 | 0.048 |
| 9 | 0.053 |
| 10 | 0.054 |
| 11 | 0.046 |
| 12 | 0.037 |
| 13 | 0.055 |
| 14 | 0.06 |
| 15 | 0.053 |
| 16 | 0.064 |
| 17 | 0.048 |
| 18 | 0.053 |
| 19 | 0.061 |
| 20 | 0.059 |
| 21 | 0.062 |
| 22 | 0.05 |
| 23 | 0.045 |
| 24 | 0.048 |
| 25 | 0.085 |
| 26 | 0.058 |
| 27 | 0.059 |
| 28 | 0.072 |
| 29 | 0.063 |
| 30 | 0.044 |
| 31 | 0.062 |
| 32 | 0.05 |
| 33 | 0.026 |
| 34 | 0.073 |
| 35 | 0.029 |
| 36 | 0.046 |
| 37 | 0.053 |
| 38 | 0.052 |
| 39 | 0.1 |
| 40 | 0.055 |
| 41 | 0.044 |
| 42 | 0.057 |
| 43 | 0.18 |
| 44 | 0.091 |
| 45 | 0.24 |
| 46 | 0.064 |
| 47 | 0.083 |
| 48 | 0.063 |
| 49 | 0.18 |
| 50 | 0.25 |
| 51 | 0.25 |
| 52 | 0.16 |
| 53 | 0.27 |
| 54 | 0.064 |
| 55 | 0.12 |
| 56 | 0.11 |
| 57 | 0.18 |
| 58 | 0.085 |
| 59 | 0.075 |

TABLE 1-continued

| Example | IC50 (µM) |
|---|---|
| 60 | 0.082 |
| 61 | 0.015 |
| 62 | 0.02 |
| 63 | 0.014 |
| 64 | 0.058 |
| 65 | 0.015 |
| 66 | 0.02 |
| 67 | 0.017 |
| 68 | 0.023 |
| 69 | 0.031 |
| 70 | 0.019 |
| 71 | 0.121 |
| 72 | 0.01 |
| 73 | 0.105 |
| 75 | 0.01 |
| 76 | 0.045 |
| 77 | 0.058 |
| 78 | 0.014 |
| 79 | 0.014 |
| 80 | 0.018 |
| 81 | 0.019 |
| 82 | 0.016 |
| 83 | 0.017 |
| 84 | 0.009 |
| 85 | 0.015 |
| 86 | 0.012 |
| 87 | 0.009 |
| 88 | 0.016 |
| 89 | 0.013 |
| 90 | 0.012 |
| 91 | 0.004 |
| 92 | 0.047 |
| 93 | 0.042 |
| 94 | 0.049 |
| 95 | 0.05 |
| 96 | 0.017 |
| 97 | 0.021 |
| 98 | 0.067 |
| 99 | 0.033 |
| 100 | 0.085 |
| 101 | 0.072 |
| 102 | 0.072 |
| 103 | 0.057 |
| 104 | 0.071 |
| 105 | 0.015 |
| 106 | 0.016 |
| 107 | 0.061 |

4. Assay for the Inhibitory Activity Against Receptor Tyrosine Kinase Activities Other than HGFR The inhibitory activity against tyrosine kinase activities of VEGFR2, FGFR1, and EGFR were determined by the similar manner as in the assay for the inhibitory activity against HGFR tyrosine kinase activity described above, using 15 ng of His6-VEGFR2, 15 ng of His6-FGFR1 or 23 ng of EGFR, respectively instead of HGFR.

The inhibitory activity against PDGFRβ tyrosine kinase activity was evaluated by obtaining a kinase reaction solution by the above method using 50 ng of His6-PDGFRβ, followed by detecting the tyrosine phosphorylated biotin-poly(GT) by a method described below.

To each well of a 96-well streptavidin-coated plate (purchased from PIERCE, Production No. 15129) were added 34 µl of the kinase reaction solution and 16 µl of a dilution solution, followed by incubation at room temperature for 30 min. Then, the well was washed three times with 150 µl of a washing solution (20 mM Tris-HCl (pH 7.6), 137 mM NaCl, 0.05% Tween-20 and 0.1% BSA), and to the well was added 70 µl of anti-phosphotyrosine (PY20)-HRP conjugate (purchased from Transduction Laboratories, Production No. P-11625) (2,000-fold diluted with 20 mM Tris-HCl (pH 7.6), 137 mM NaCl, 0.05% Tween-20 and 1% BSA), followed by incubation at room temperature for 1 hr. Then, each well was washed three times with 150 µl of the washing solution, and supplied with 100 µl of TMB Membrane Peroxidase Substrate (purchased from Funakoshi, Production No. 50-5077-03). After incubating the same at room temperature for 10 min, 100 µl of 1 M phosphoric acid was added to each well, and using a Plate Reader MTP-500 (Corona Electric), the absorbance of the well was instantly determined at 450 nm. While defining the absorbance of a well supplied with His6-PDGFRβ and no test substance as 100% and the absorbance of a well supplied with no His6-PDGFRβ and no test substance as 0%, the absorbance ratio (%) of each well supplied with the test substance was calculated. The absorbance ratio (%) was used to calculate the concentration ($IC_{50}$) of the test substance necessary to inhibit PDGFRβ kinase activity by 50%.

Pharmacological Test Example 2

Inhibitory Activity Against the Proliferation of Human Gastric Cancer Cells (MKN-45)

Human gastric cancer cells (MKN-45) were suspended in a 1% FBS-containing RPMI1640 medium (purchased from Sigma). The cell suspension ($1 \times 10^4$ cells/ml) was added in a 96-well plate for cell culture (purchased from NUNC, Production No. 167008) at 0.1 ml/well, and then cultured in a 5% $CO_2$ incubator (37° C.) overnight. After the culture, each well was supplied with 0.1 ml of a test substance diluted with a 1% FBS-containing RPMI1640 medium, followed by culturing in a 5% $CO_2$ incubator (37° C.) for 3 days. After the culture, each well was supplied with 10 µl of Cell Counting Kit-8 (purchased from DOJINDO, Production No. 343-07623), followed by incubation in a 5% $CO_2$ incubator (37° C.) for about 1.5 hrs. After the incubation, using the Plate Reader MTP-500 (Corona Electric), the absorbance of each well was determined at a measurement wavelength of 450 nm and a reference wavelength of 660 nm. The ratio (%) of absorbance of each well supplied with a test substance to absorbance of the well supplied with no test substance was calculated, and the ratio was used to calculate the concentration ($IC_{50}$) of the test substance necessary to inhibit the cell proliferation by 50%. The results are shown in Table 2.

TABLE 2

| Example | IC50 (µM) |
| --- | --- |
| 1 | 0.013 |
| 2 | 0.018 |
| 3 | 0.015 |
| 4 | 0.021 |
| 5 | 0.019 |
| 7 | 0.018 |
| 8 | 0.02 |
| 9 | 0.026 |
| 10 | 0.042 |
| 11 | 0.034 |
| 12 | 0.031 |
| 13 | 0.076 |
| 14 | 0.017 |
| 15 | 0.017 |
| 16 | 0.017 |
| 17 | 0.014 |
| 18 | 0.033 |
| 19 | 0.012 |
| 20 | 0.015 |
| 21 | 0.027 |
| 22 | 0.013 |
| 23 | 0.036 |
| 24 | 0.017 |
| 25 | 0.019 |
| 26 | 0.019 |
| 27 | 0.048 |
| 28 | 0.054 |
| 29 | 0.05 |
| 30 | 0.039 |
| 31 | 0.031 |
| 32 | 0.027 |
| 33 | 0.055 |
| 34 | 0.19 |
| 35 | 0.23 |
| 36 | 0.022 |
| 37 | 0.014 |
| 38 | 0.052 |
| 39 | 0.038 |
| 40 | 0.017 |
| 41 | 0.042 |
| 42 | 0.06 |
| 43 | 0.28 |
| 44 | 0.054 |
| 45 | 0.5 |
| 46 | 0.014 |
| 47 | 0.027 |
| 48 | 0.017 |
| 54 | 0.02 |
| 55 | 0.043 |
| 56 | 0.053 |
| 57 | 0.15 |
| 58 | 0.025 |
| 59 | 0.044 |
| 60 | 0.015 |
| 61 | 0.015 |
| 62 | 0.025 |
| 63 | 0.054 |
| 64 | 0.057 |
| 65 | 0.023 |
| 66 | 0.031 |
| 67 | 0.052 |
| 68 | 0.134 |
| 69 | 0.077 |
| 70 | 0.054 |
| 71 | 0.061 |
| 72 | 0.022 |
| 73 | 0.05 |
| 75 | 0.019 |
| 76 | 0.019 |
| 77 | 0.019 |
| 78 | 0.012 |
| 79 | 0.015 |
| 80 | 0.018 |
| 81 | 0.017 |
| 82 | 0.021 |
| 83 | 0.016 |
| 84 | 0.019 |
| 85 | 0.015 |
| 86 | 0.015 |
| 87 | 0.014 |
| 88 | 0.018 |
| 89 | 0.018 |
| 90 | 0.005 |
| 91 | 0.005 |
| 92 | 0.0049 |
| 93 | 0.0052 |
| 94 | 0.0049 |
| 95 | 0.0054 |
| 96 | 0.0038 |
| 97 | 0.038 |
| 98 | 0.023 |
| 99 | 0.018 |
| 100 | 0.016 |
| 101 | 0.016 |
| 102 | 0.04 |
| 103 | 0.0058 |
| 104 | 0.0068 |
| 105 | 0.0041 |
| 106 | 0.046 |
| 107 | 0.021 |

Pharmacological Test Example 3

Inhibitory Activity Against the HGFR Autophosphorylation Using ELISA

1. Preparation of Cell Extract

Human gastric cancer cells (MKN-45) were suspended in a 1% FBS-containing RPMI1640 medium (purchased from Sigma). The cell suspension ($1\times10^5$ cells/ml) was put in a 96-well plate for cell culture (purchased from NUNC, Production No. 167008) at 0.1 ml/well, and then cultured in a 5% $CO_2$ incubator (37° C.) overnight. After the culture, from each well was removed the supernatant, followed by adding 0.05 ml of a 1 FBS-containing RPMI1640 medium. Then, the well was supplied with 0.05 ml of the test substance dissolved in dimethyl sulfoxide (diluted with a 1% FBS-containing RPMI1640 medium), followed by culturing in a 5% $CO_2$ incubator (37° C.) for 1 hr. From each well was removed the supernatant, and each well was washed with 150 µl of PBS, followed by adding 100 µl of a lysis buffer (50 mM Hepes (pH 7.4), 150 mM NaCl, 10% (v/v) glycerol, 1% Triton X-100, 1.5 mM $MgCl_2$, 1 mM EDTA (pH 8.0), 100 mM NaF, 1 mM PMSF, 10 µg/ml Aprotinin, 50 Leupeptin, 1 µg/ml Pepstatin A and 1 mM $Na_3VO_4$). The plate was shaken at 4° C. for 1 hr to prepare the cell extract.

2. Preparation of an Anti-Phosphotyrosine Antibody-Immobilized Plate

To a 96-well plate for ELISA (purchased from COSTAR, Production No. 3369) was added 50 µl of 60 mM bicarbonate buffer (pH 9.6) containing 50 µg/ml of an anti-phosphotyrosine antibody (PY20, purchased from Transduction Laboratory, Production No. P-11120). The plate was incubated at 4° C. overnight.

3. Assay for Inhibitory Activity Against HGFR Autophosphorylation

Each well of the plate prepared in 2. was washed three times with 200 µl of PBS, and supplied with 150 µl of 3% BSA/PBS, followed by incubating at room temperature for 2 hrs. Each well was washed three times with 200 µl of PBS, and supplied with 50 µl of the above cell extract, followed by incubating at 4° C. overnight. After the incubation, each well was washed three times with 250 µl of a washing solution (0.1% BSA, 20 mM Tris-HCl (pH 7.6), 137 mM NaCl, and 0.05% Tween-20), and supplied with 70 µl of anti-HGFR antibody (h-Met(C-12), purchased from Santa Cruz, Production No. sc-10) 2,000-fold diluted with a reaction solution (1% BSA, 20 mM Tris-HCl (pH 7.6), 137 mM NaCl and 0.05% Tween-20), followed by incubating at room temperature for 1 hr. The well was washed three times with 250 µl of the washing solution, and supplied with 70 µl of peroxidase-labelled anti-rabbit IgG antibody (purchased from Cell Signaling, Production No. 7074) 2,000-fold diluted with the reaction solution, followed by incubating at room temperature for 1 hr. Each well was washed three times with 250 µl of the washing solution, and supplied with 70 µl of TMB Membrane Peroxidase Substrate (purchased from Funakoshi, Production No. 50-5077-03), followed by incubating at room temperature for 10 min. Each well was supplied with 70 µl of 1 M phosphoric acid, and using the Plate Reader MTP-500 (Corona Electric), the absorbance of the well was instantly determined at a measurement wavelength of 450 nm. While defining the absorbance of a well supplied with the cell extract having no test substance as 100% HGFR autophosphorylation activity, and the absorbance of a well supplied with 50 µl of the lysis buffer as 0% HGFR autophosphorylation activity, the HGFR autophosphorylation activity (%) was calculated for each well. The concentration of the test substance was changed by several levels to calculate HGFR autophosphorylation activities (%) in respective cases, and to calculate the concentration ($IC_{50}$) of the test substance necessary to inhibit HGFR autophosphorylation activity by 50%. The results are shown in Table 3.

TABLE 3

| Example | IC50 (µM) |
|---|---|
| 1 | 0.018 |
| 2 | 0.021 |
| 3 | 0.019 |
| 4 | 0.014 |
| 5 | 0.022 |
| 7 | 0.035 |
| 8 | 0.014 |
| 9 | 0.011 |
| 10 | 0.021 |
| 11 | 0.013 |
| 12 | 0.04 |
| 13 | 0.037 |
| 14 | 0.019 |
| 15 | 0.016 |
| 16 | 0.018 |
| 17 | 0.015 |
| 18 | 0.039 |
| 19 | 0.023 |
| 20 | 0.022 |
| 21 | 0.011 |
| 22 | 0.021 |
| 23 | 0.017 |
| 24 | 0.027 |
| 25 | 0.0046 |
| 26 | 0.0084 |
| 27 | 0.032 |
| 28 | 0.043 |
| 29 | 0.03 |
| 30 | 0.012 |
| 31 | 0.03 |
| 32 | 0.015 |
| 33 | 0.025 |
| 34 | 0.081 |
| 35 | 0.12 |
| 36 | 0.015 |
| 37 | 0.0066 |
| 38 | 0.018 |
| 39 | 0.016 |
| 40 | 0.008 |
| 41 | 0.016 |
| 42 | 0.042 |
| 43 | 0.33 |
| 44 | 0.08 |
| 45 | 0.44 |
| 46 | 0.019 |
| 47 | 0.03 |
| 48 | 0.012 |
| 49 | 0.26 |
| 51 | 0.38 |
| 52 | 0.17 |
| 53 | 0.37 |
| 54 | 0.024 |
| 55 | 0.016 |
| 56 | 0.041 |
| 57 | 0.082 |
| 58 | 0.017 |
| 59 | 0.016 |
| 60 | 0.008 |
| 61 | 0.008 |
| 62 | 0.011 |
| 63 | 0.021 |
| 64 | 0.02 |
| 65 | 0.01 |
| 66 | 0.013 |
| 67 | 0.01 |
| 68 | 0.071 |
| 69 | 0.037 |
| 70 | 0.027 |
| 71 | 0.011 |
| 72 | 0.01 |

TABLE 3-continued

| Example | IC50 (µM) |
|---|---|
| 73 | 0.008 |
| 75 | 0.013 |
| 76 | 0.03 |
| 77 | 0.013 |
| 78 | 0.015 |
| 79 | 0.016 |
| 80 | 0.014 |
| 81 | 0.007 |
| 82 | 0.022 |
| 83 | 0.018 |
| 84 | 0.017 |
| 85 | 0.014 |
| 86 | 0.011 |
| 87 | 0.012 |
| 88 | 0.02 |
| 89 | 0.017 |
| 90 | 0.011 |
| 91 | 0.0084 |
| 92 | 0.013 |
| 93 | 0.007 |
| 94 | 0.011 |
| 95 | 0.013 |
| 96 | 0.0042 |
| 97 | 0.014 |
| 98 | 0.017 |
| 99 | 0.014 |
| 100 | 0.0094 |
| 101 | 0.015 |
| 102 | 0.041 |
| 103 | 0.012 |
| 104 | 0.015 |
| 105 | 0.0086 |
| 106 | 0.039 |
| 107 | 0.036 |

Pharmacological Test Example 4

Inhibitory Activity Against Migration of Human Pancreatic Cancer Cells (SUIT-2)

Human pancreatic cancer cells (SUIT-2) were suspended in a 1% FBS-containing RPMI1640 medium (purchased from Sigma) to prepare a cell suspension ($8 \times 10^5$ cells/ml). To the lower compartment of Transwell (purchased from COSTAR, Production No. 3422) was added 600 µl of a 1% FBS-containing RPMI1640 medium. To the upper compartment were added 50 µl of the above cell suspension and 25 µl of the test substance dissolved in dimethyl sulfoxide (diluted with the 1% FBS-containing RPMI1640 medium), followed by culturing in a 5% $CO_2$ incubator (37° C.) for 1 hr. After the culture, to the upper compartment of each Transwell was added 25 µl of human recombinant hepatocyte growth factor (HGF, purchased from Wako Pure Chemical Industry, Production No. 22949) diluted to 280 ng/ml with a 1% FBS-containing RPMI1640 medium, followed by culturing in a 5% $CO_2$ incubator (37° C.) for 24 hrs. The cells adhering to the lower compartment of each well were counted in five fields by a phase contrast microscope (200×) to calculate an average adhering cell number. While defining the average adhering cell number of a well supplied with HGF and no test substance as 100% cell migration activity and the average adhering cell number of a well supplied with no HGF and no test substance as 0% cell migration activity, the cell migration activity percent (%) was calculated for each well. The concentration of the test substance was varied at several levels to calculate the cell migration activity percent (%) for respective cases, and to calculate the concentration of the test substance necessary to inhibit the cell migration activity by 50% ($IC_{50}$).

Pharmacological Test Example 5

Inhibitory Activity Against the Tumor Growth of Human Gastric Cancer Cells (MKN-45)

Human gastric cancer cells (MNK-45) were suspended in HBSS (purchased from GIBCO BRL). The cell suspension ($5 \times 10^7$ cells/ml) was transplanted under the right flank skin of seven-week-old female BALB/c (nu/nu) mice at a volume of 0.1 ml. When tumor volume of the site transplanted with MNK-45 cells grew to 100-200 $mm^3$, mice were grouped so that the groups might be equalized in average tumor volume. The test substance was suspended in 0.5% methylcellulose, a mixed solution of hydrochloric acid and glucose (0.1N hydrochloric acid:5% glucose=1:9) or a mixed solution of dimethyl sulfoxide-Tween-glucose (dimethyl sulfoxide:Tween 80:5% glucose (containing equimolar hydrochloric acid to the test substance)=7:13:80), were administered orally to the mice twice every day. The tumor volumes were determined at the fifth day after the initiation of the administration of the test substances. The major axis and the minor axis of tumor were measured by a caliper to calculate ½×(major axis×minor axis×minor axis) for the tumor volume. The experiment was conducted using 10 mice in the control group (solvent-administered group) and 5 mice in test substance-administered group. The ratio in tumor volume of the group for administrating the test substance relative to that of the control group was defined as a tumor proliferation rate (%). The results are shown in Table 4.

TABLE 4

| Example | Dose (mg/kg/time) | Tumor proliferation rate (%) |
|---|---|---|
| 2 | 30 | 73.3 |
| 2 | 100 | 27.5 |
| 8 | 30 | 53 |
| 8 | 100 | 23.3 |
| 12 | 30 | 73.9 |
| 12 | 100 | 27.6 |

Pharmacological Test Example 6

Inhibitory Activity Against Sandwich Tube Formation by Vascular Endothelial Cells Stimulated with Hepatocyte Growth Factor Human umbilical vein endothelial cells (HUVECs) were isolated according to the reported method (Shin Seikagaku Jikken Koza, "Cell culturing techniques", p 197-202), and then cultured in a 5% $CO_2$ incubator (37° C.) using EGM-2 medium (purchased from Clonetics) until the cells reached confluency.

To each well of a 24-well plate was added 0.4 ml of an ice-cold mixture of collagen: 5×RPMI1640:reconstitution buffer (all purchased from Nitta Gelatin, Inc.) at 7:2:1, followed by incubating in a 5% $CO_2$ incubator (37° C.) for 40 min to allow the solution to gell. Then, each well was supplied with 1 ml of the cell suspension of HUVEC (1-1.2×$10^5$ cells were used, though the cell number varied slightly depending on the lot of the HUVEC to be used) diluted with a serum free medium for endothelial cell culture (SFM, purchased from GIBCO RBL) supplemented with 10 ng/ml of EGF, followed by culturing in a 5% $CO_2$ incubator (37° C.) overnight. The supernatant was removed from each well, and then 0.4 ml of an ice-cold mixture of collagen:5×RPMI1640:reconstitution buffer (all purchased from Nitta Gelatin, Inc.) at 7:2:1 was layered on each well, followed by incubating in a 5% $CO_2$ incubator (37° C.) for 4 hours to allow the solution to gell. To the upper compartment was added 1.5 ml of a SFM solution containing 30 ng/ml of HGF (purchased from R&D), an angiogenic factor, and a diluted test substance, followed by culturing in a 5% $CO_2$ incubator (37° C.). On the fourth day after the addition of the test substance, the supernatant was removed from each well, and 0.4 ml of a 3.3 mg/ml solution of MTT (purchased from Sigma) in PBS was added to each well, followed by culturing in a 5% $CO_2$ incubator (37° C.) for about 2 hours. The tube formed in the collagen gel of each well was stained with MTT, and then the tube image was loaded in a computer (Macintosh) to determine the total length of the tube by an image analysis software "Angiogenesis quantification software" (purchased from Kurabo). The ratio of the total length of a tube formed in a well supplied with the test substance relative to a tube formed in a well supplied with no test substance was expressed as a percentage. The value of the ratio was used to provide the concentration ($IC_{50}$) of the test substance necessary to inhibit the tube formation by 50%.

Pharmacological Test Example 7

Inhibitory Activity Against the Growth of Vascular Endothelial Cells by Stimulated with Hepatocyte Growth Factor Human umbilical vein endothelial cells (HUVECs) were isolated according to the reported method (Shin Seikagaku Jikken Koza, "Cell culturing techniques", p 197-202), and then cultured in a 5% $CO_2$ incubator (37° C.) using EGM-2 medium (purchased from Clonetics) until the cells reached confluency.

HUVECs were suspended in a serum-free medium for endothelial cell culture (SFM, purchased from GIBCO RBL) containing 2% FBS. The cell suspension ($2\times10^4$ cells/ml) was put in a cell culturing 96-well plate (purchased from NUNC, Production No. 167008) at 0.1 ml/well, and then cultured in a 5% $CO_2$ incubator (37° C.) overnight. After the culture, each well was supplied with 50 µl of the test substance diluted with a 2% FBS-containing serum-free medium for endothelial cell culture and 50 µl of HGF (purchased from R&D) diluted at a concentration of 120 ng/ml with a 2% FBS-containing serum-free medium for endothelial cell culture, followed by culturing in a 5% $CO_2$ incubator (37° C.). On the third day after the addition of the test substance, each well was supplied with 10 µl of Cell Counting Kit-8 (purchased from DOJINDO, Production No. 343-07623), and then the plate was incubated in a 5% $CO_2$ incubator (37° C.) for about 2 hours. After the incubation, using a Plate Reader MTP-500 (Corona Electric), the absorbance of each well was determined at a measurement wavelength of 450 nm and a reference wavelength of 660 nm. While defining the absorbance of a well supplied with HGF and no test substance as 100% cell proliferation activity and the absorbance of the well supplied with no test substance and no HGF as 0% cell proliferation activity, the cell proliferation activity ratio (%) was calculated for each cell. The concentration of the test substance was changed at several levels to calculate the cell proliferation activity ratio (%) in respective cases, and to calculate the concentration ($IC_{50}$) of the test substance necessary to inhibit cell proliferation activity by 50%. The results are shown in Table 5.

TABLE 5

| Example | IC50 (µM) |
|---------|-----------|
| 1 | 0.0046 |
| 2 | 0.018 |
| 3 | 0.013 |
| 7 | 0.018 |
| 9 | 0.025 |
| 11 | 0.033 |
| 12 | 0.023 |
| 14 | 0.023 |
| 15 | 0.015 |
| 17 | 0.017 |
| 21 | 0.024 |

Chemical formulas of the compounds provided in Production Examples and Examples described above and Illustrative Examples are shown in Table 6 to Table 18 below.

TABLE 6

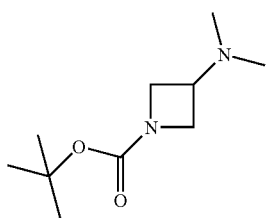

Pro. Ex. 1

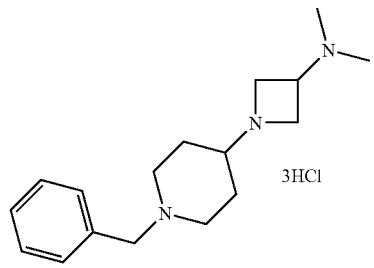

Pro. Ex. 2

TABLE 6-continued
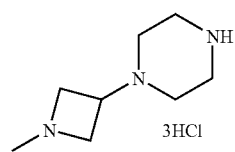
Pro. Ex. 3
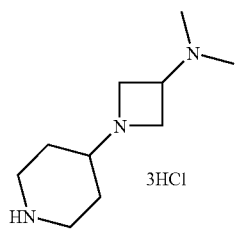
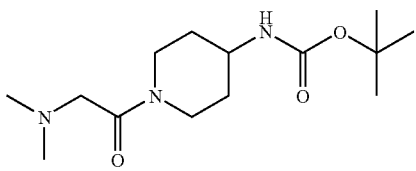
Pro. Ex. 5
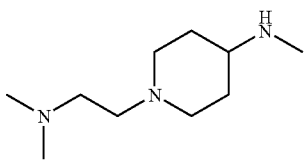
Pro. Ex. 6
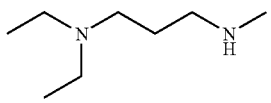
Pro. Ex. 7
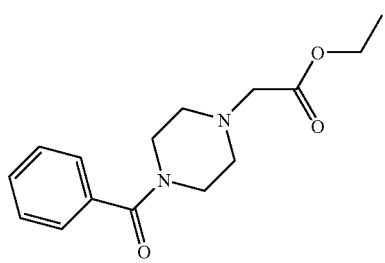
Pro. Ex. 8
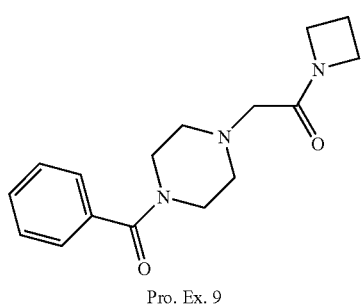
Pro. Ex. 9

TABLE 6-continued
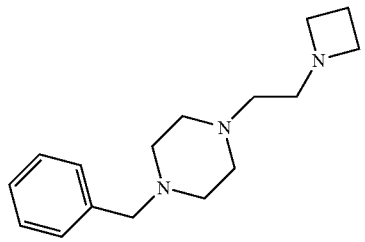
Pro. Ex. 10
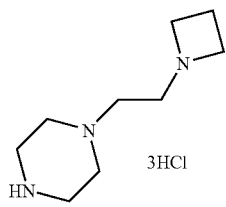
3HCl
Pro. Ex. 11
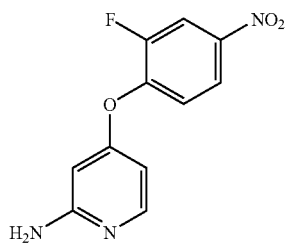
Pro. Ex. 12
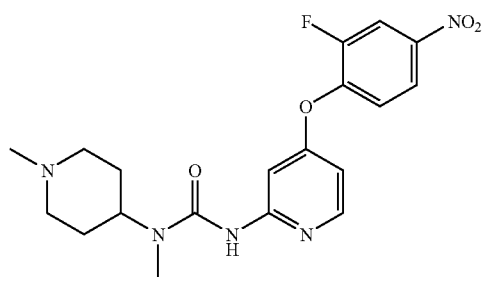
Pro. Ex. 13
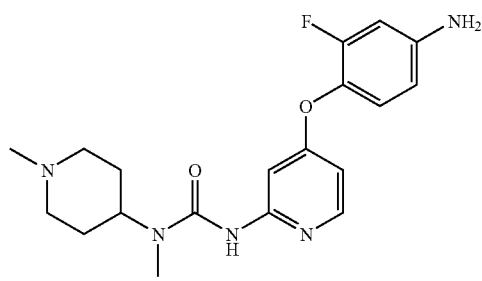
Pro. Ex. 14

TABLE 6-continued
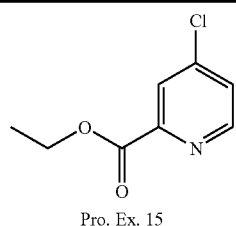
Pro. Ex. 15
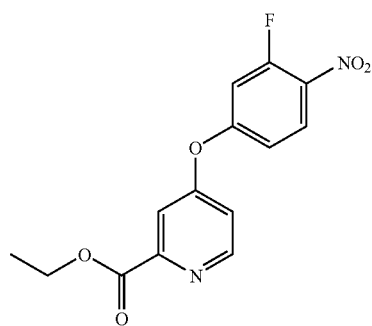
Pro. Ex. 16
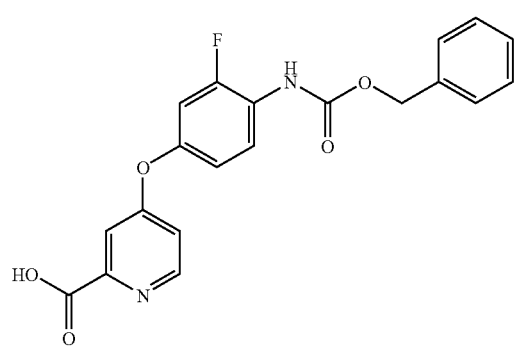
Pro. Ex. 17
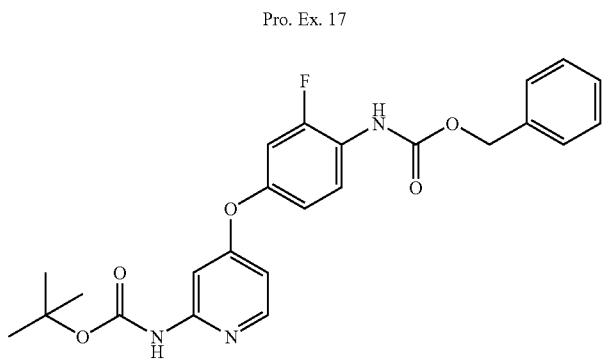
Pro. Ex. 18
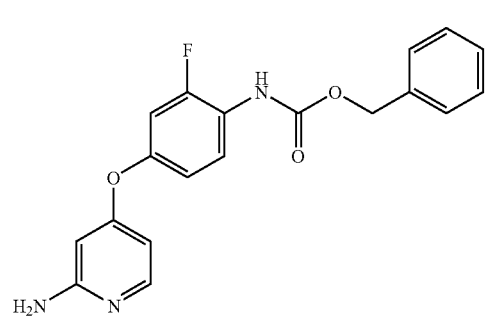
Pro. Ex. 19

TABLE 6-continued
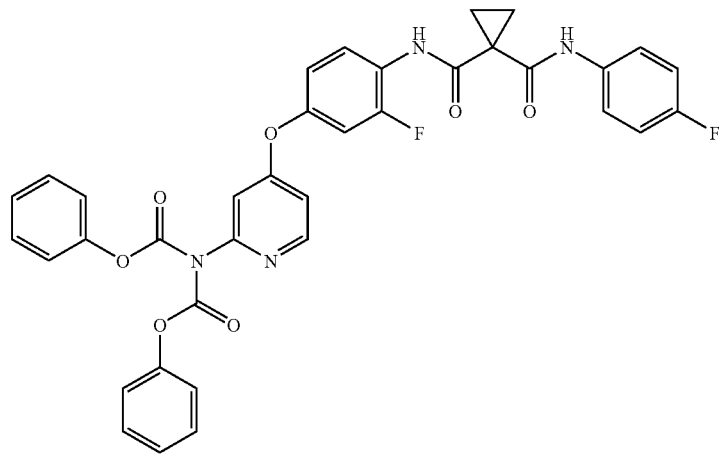
Pro. Ex. 20
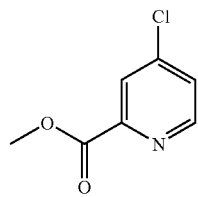
Pro. Ex. 21
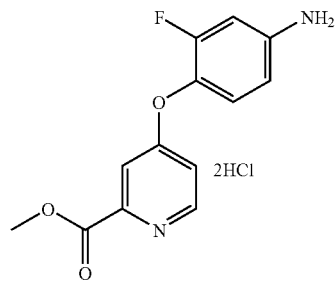
2HCl
Pro. Ex. 22
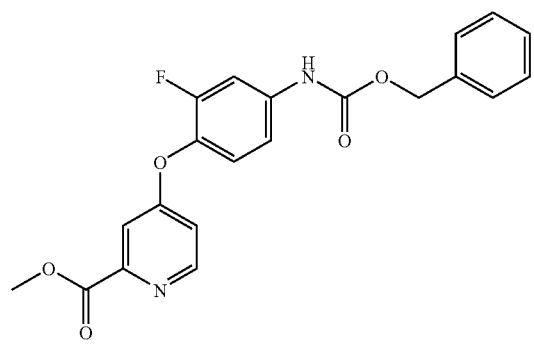
Pro. Ex. 23

TABLE 6-continued
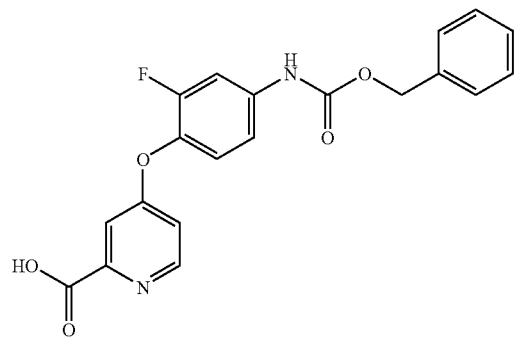
Pro. Ex. 24
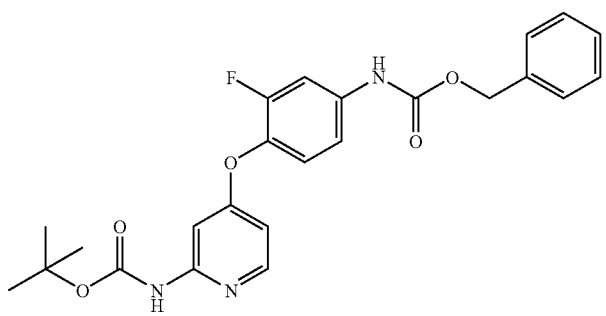
Pro. Ex. 25
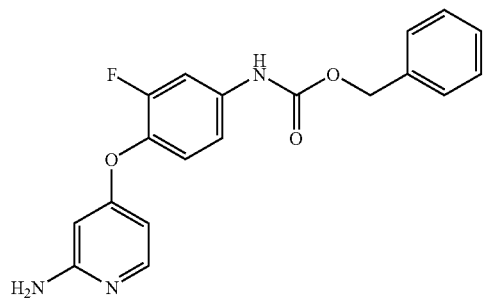
Pro. Ex. 26
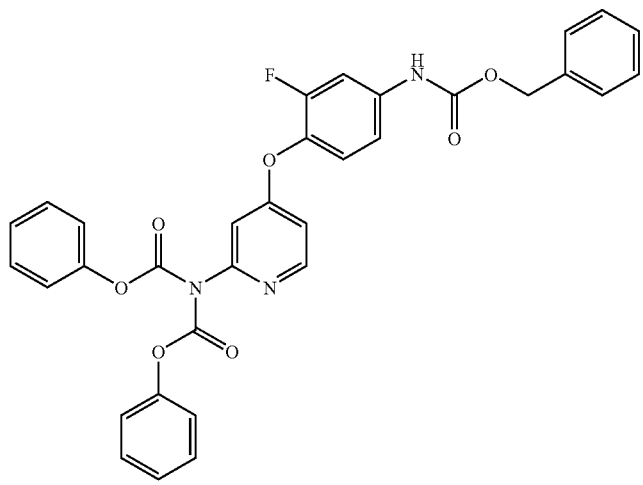
Pro. Ex. 27

TABLE 6-continued
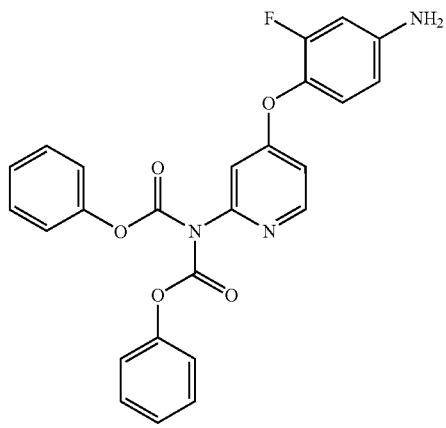
Pro. Ex. 28
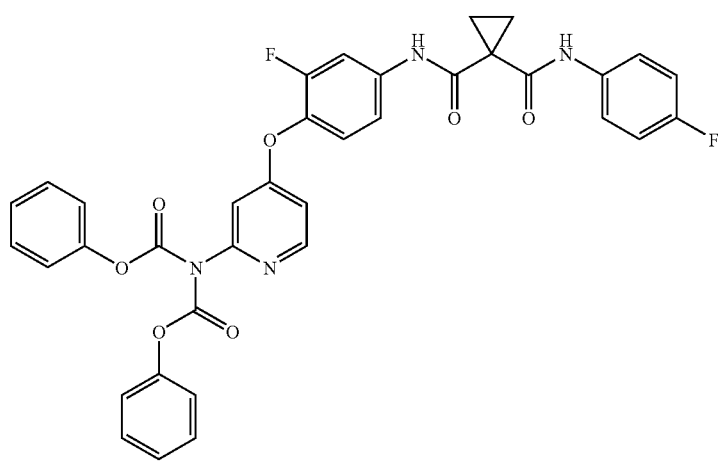
Pro. Ex. 29
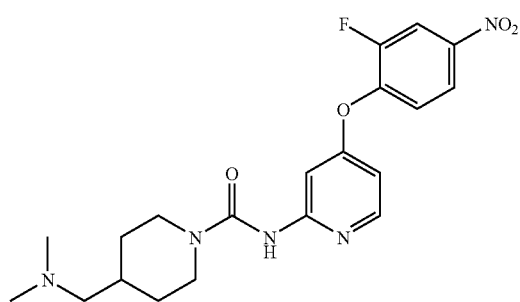
Pro. Ex. 30
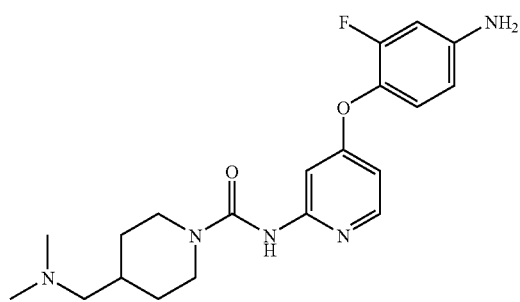
Pro. Ex. 31

TABLE 6-continued
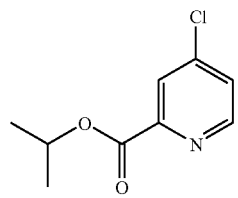
Pro. Ex. 32
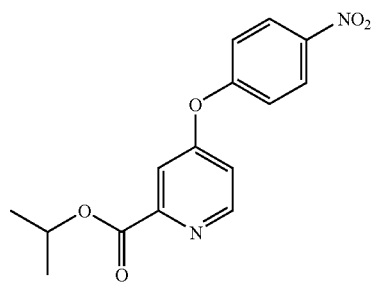
Pro. Ex. 33
TABLE 7
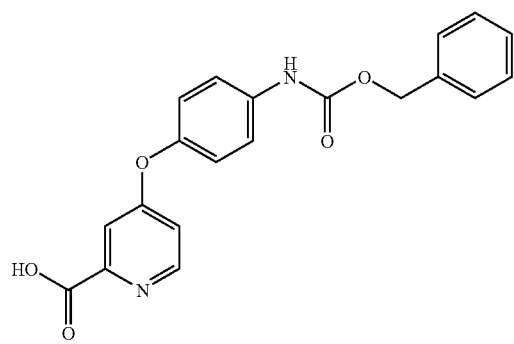
Pro. Ex. 34
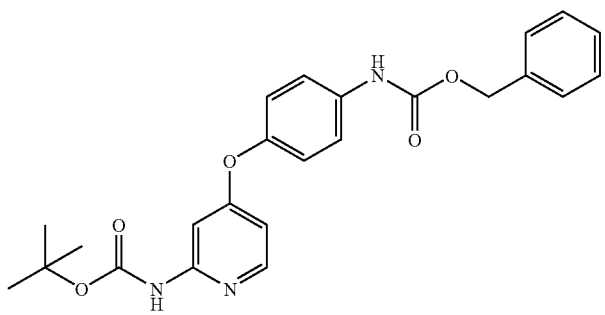
Pro. Ex. 35

TABLE 7-continued
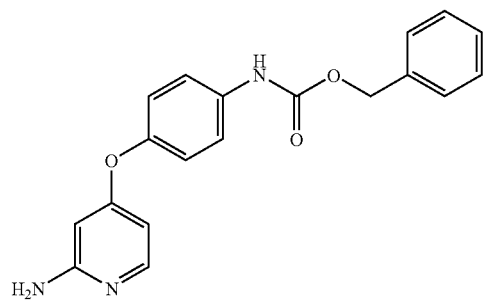
Pro. Ex. 36
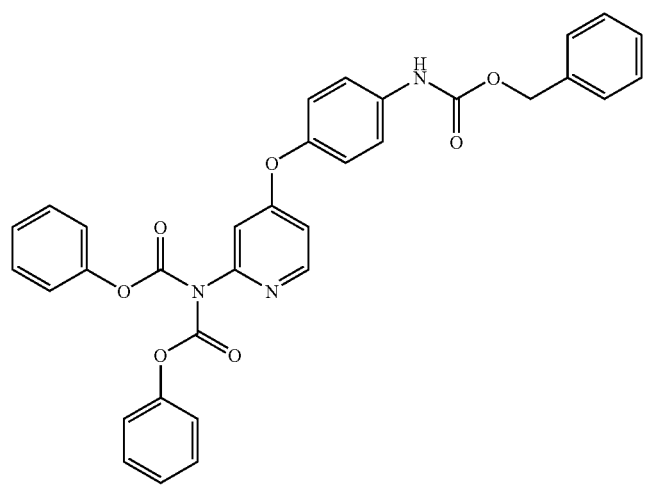
Pro. Ex. 37
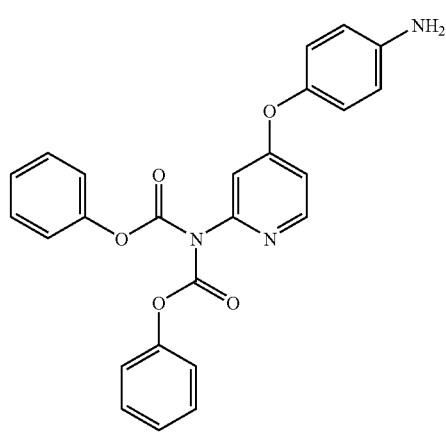
Pro. Ex. 38

TABLE 7-continued
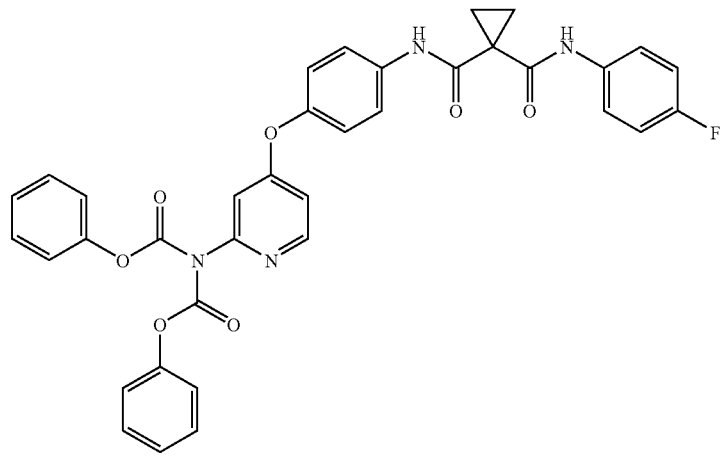
Pro. Ex. 39
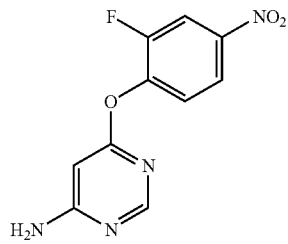
Pro. Ex. 40
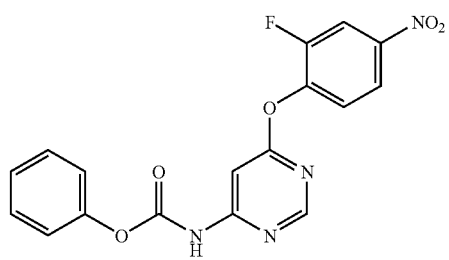
Pro. Ex. 41
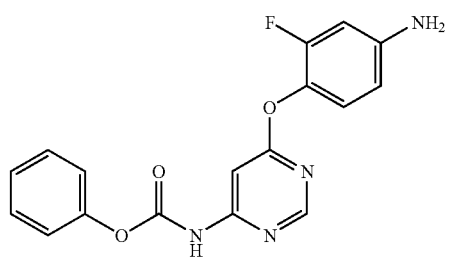
Pro. Ex. 42

TABLE 7-continued
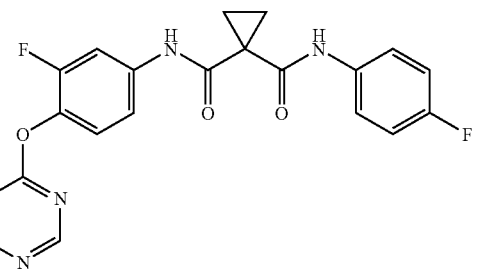
Pro. Ex. 43
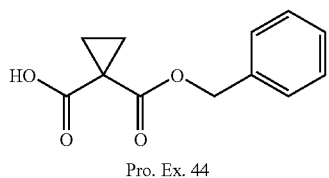
Pro. Ex. 44
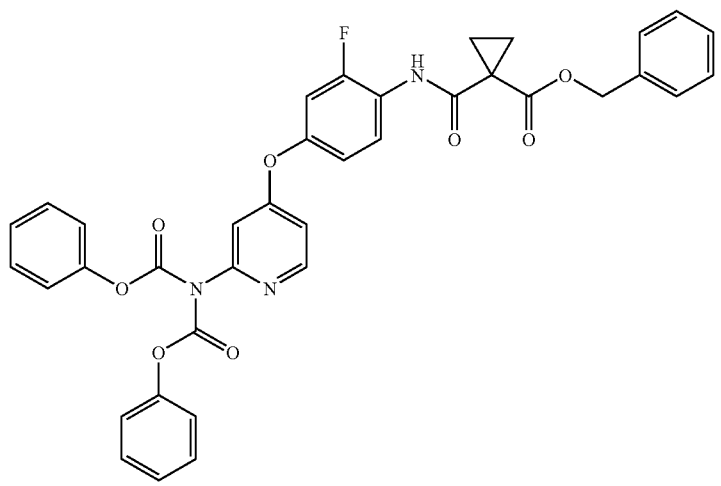
Pro. Ex. 45
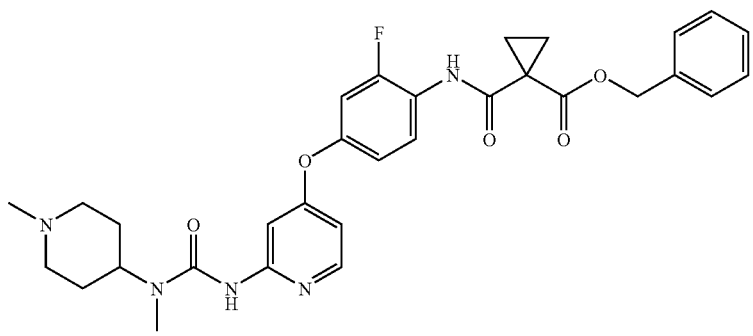
Pro. Ex. 46

TABLE 7-continued
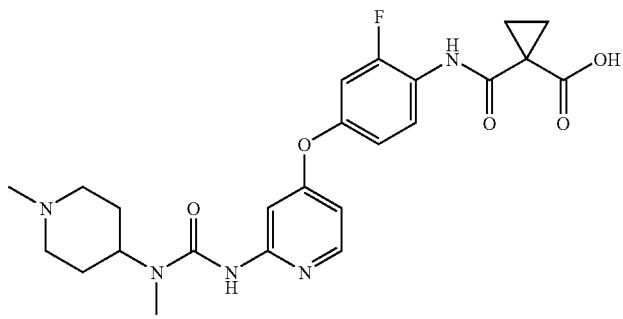
Pro. Ex. 47
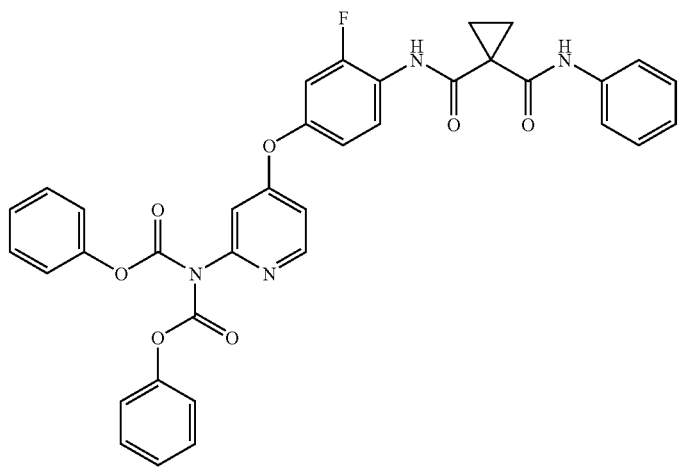
Pro. Ex. 48
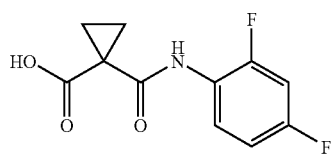
Pro. Ex. 49
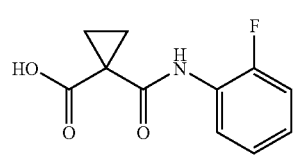
Pro. Ex. 50

TABLE 7-continued
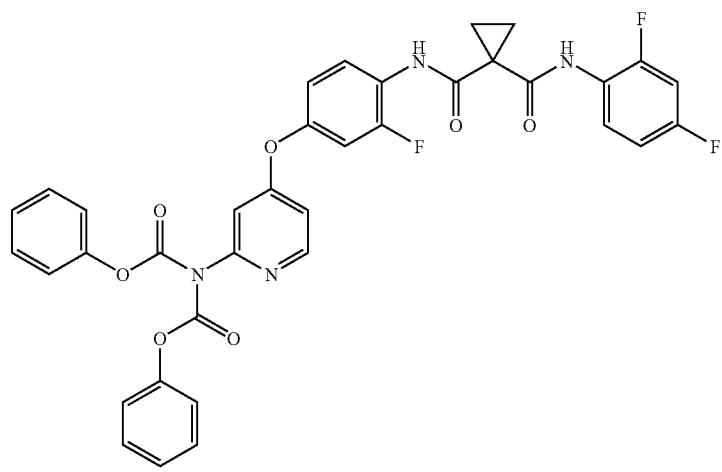
Pro. Ex. 51
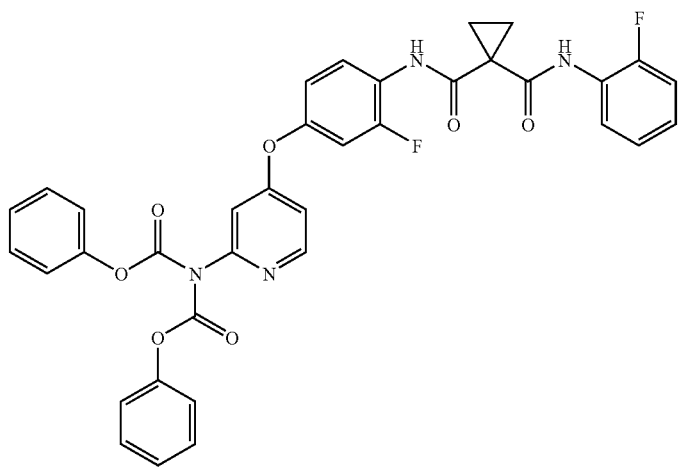
Pro. Ex. 52
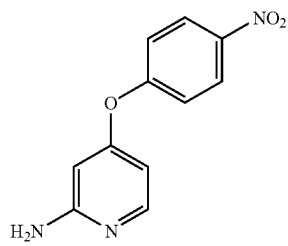
Pro. Ex. 53
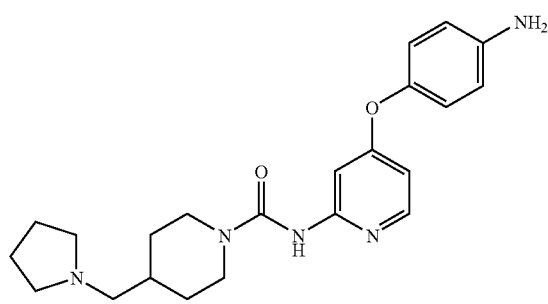
Pro. Ex. 54

TABLE 7-continued
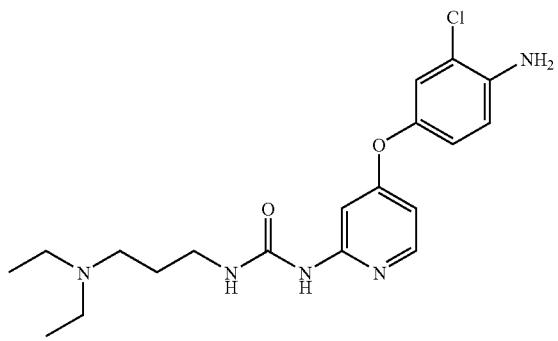
Pro. Ex. 55
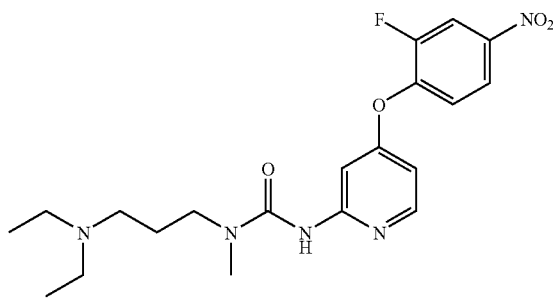
Pro. Ex. 56
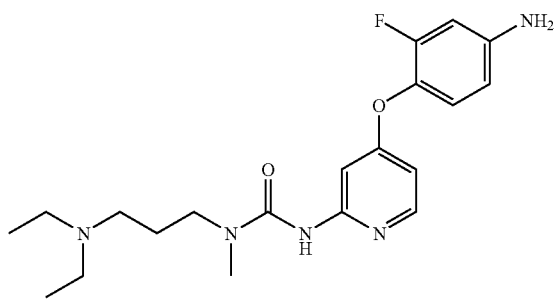
Pro. Ex. 57
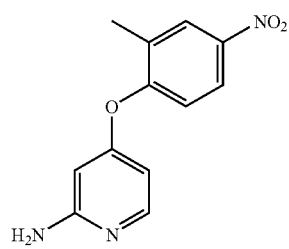
Pro. Ex. 58

TABLE 7-continued
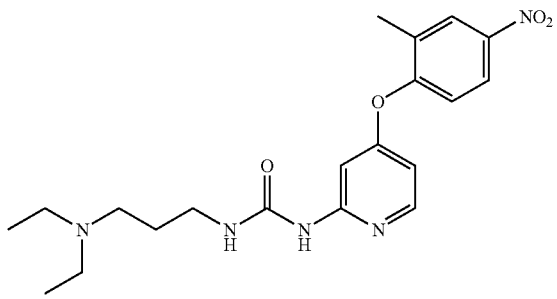
Pro. Ex. 59
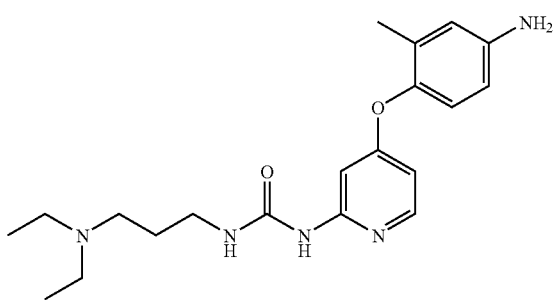
Pro. Ex. 60
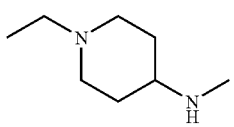
Pro. Ex. 61
TABLE 8
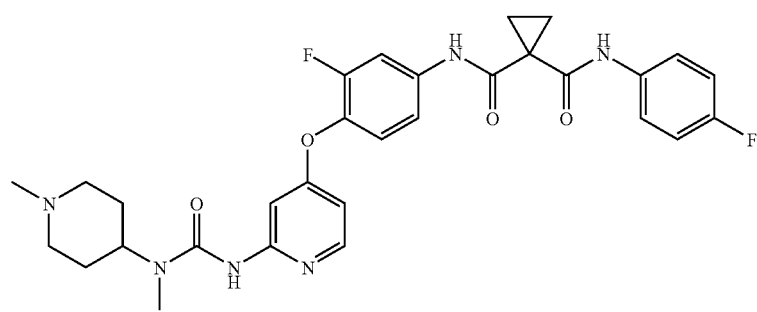
Example 1

TABLE 8-continued
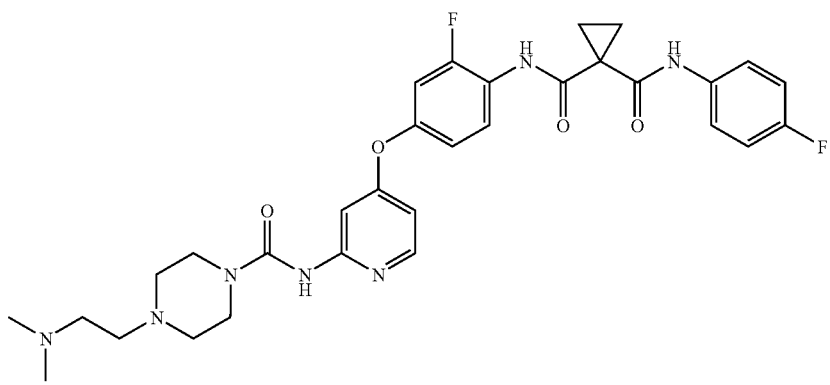
Example 2
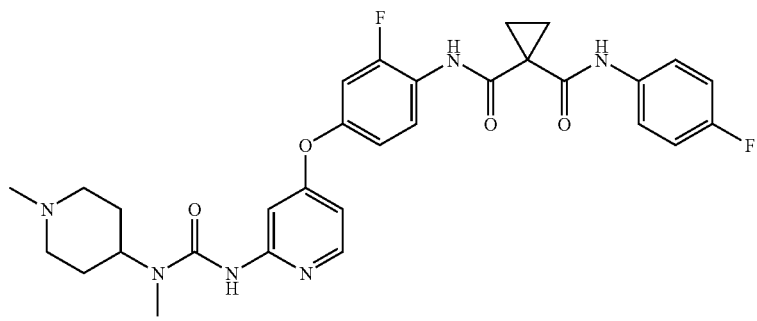
Example 3
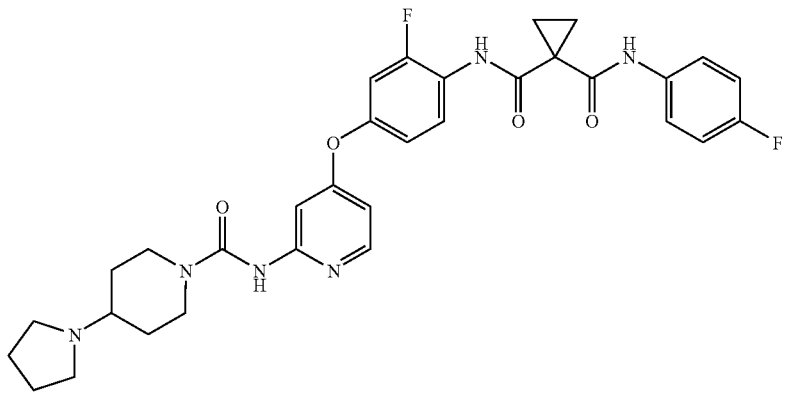
Example 4
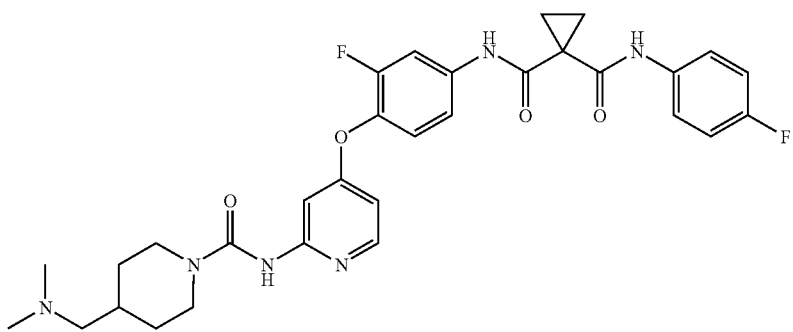
Example 5

TABLE 8-continued
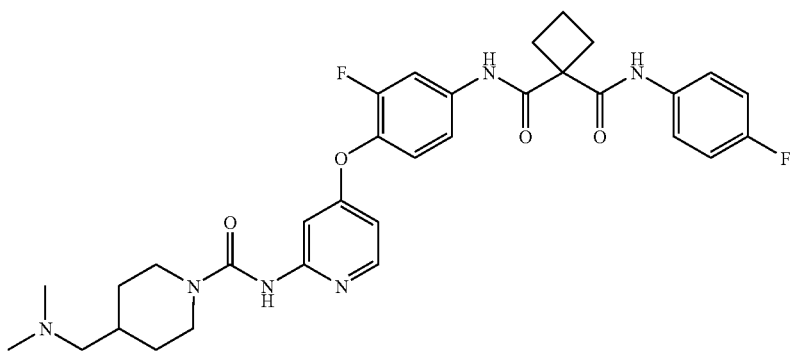
Example 6
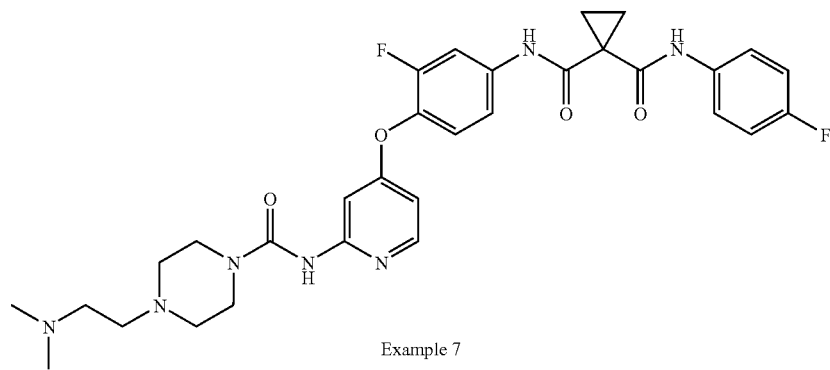
Example 7
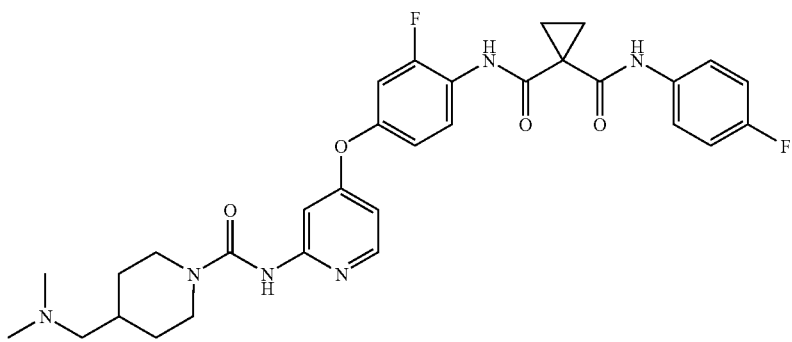
Example 8
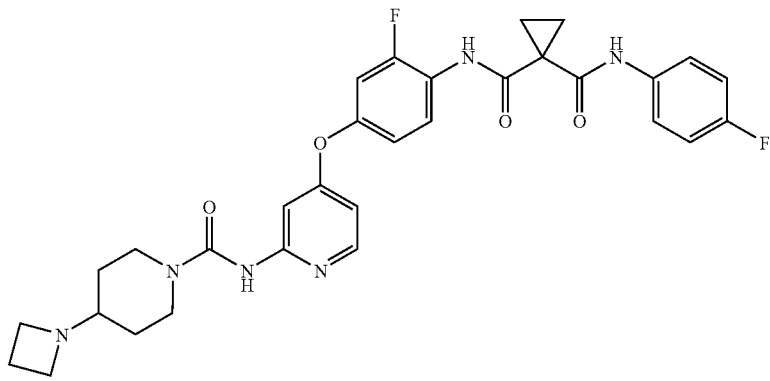
Example 9

TABLE 8-continued
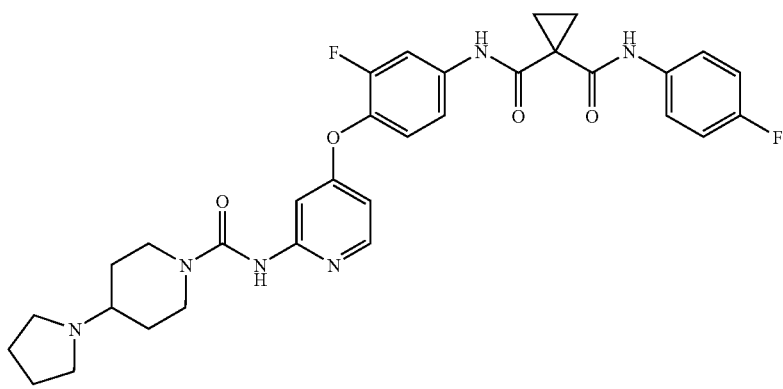
Example 10
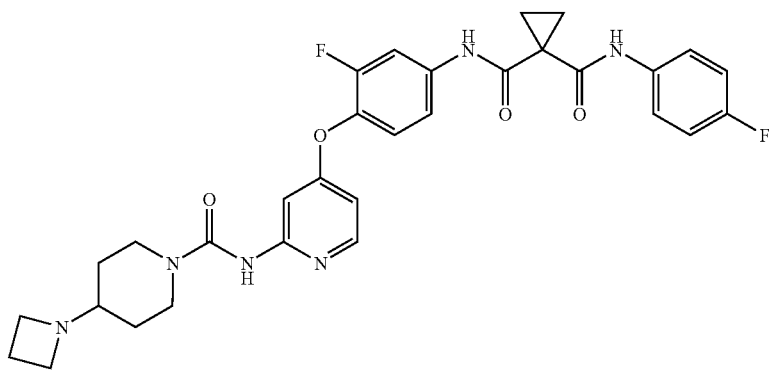
Example 11
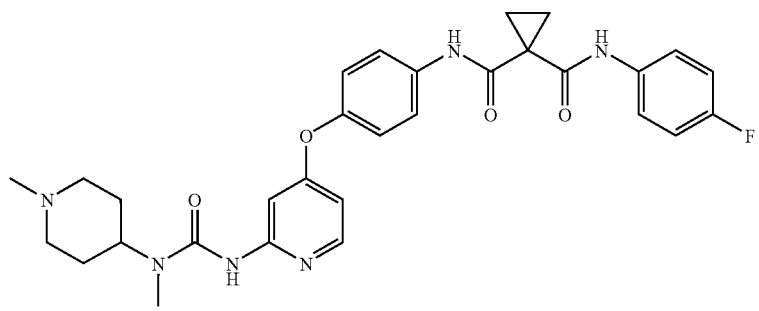
Example 12
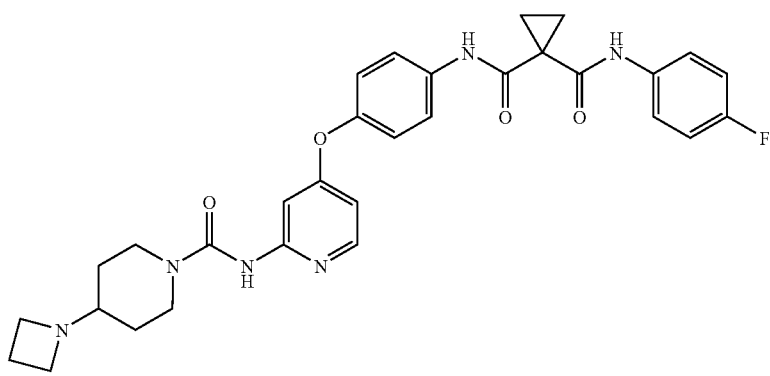
Example 13

TABLE 8-continued
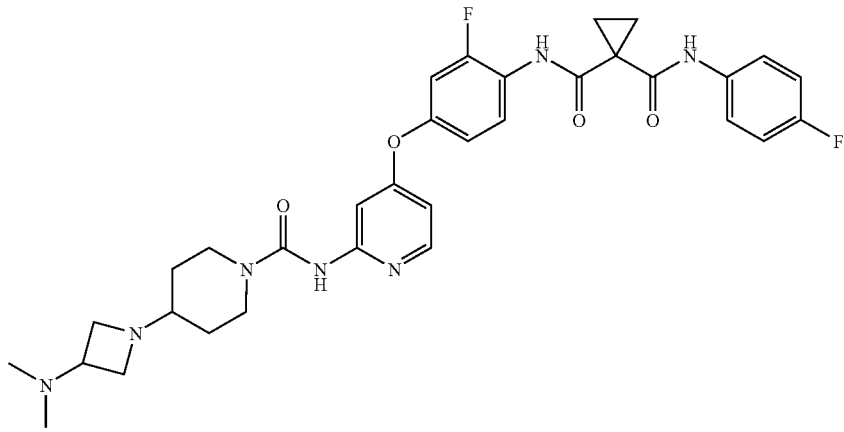
Example 14
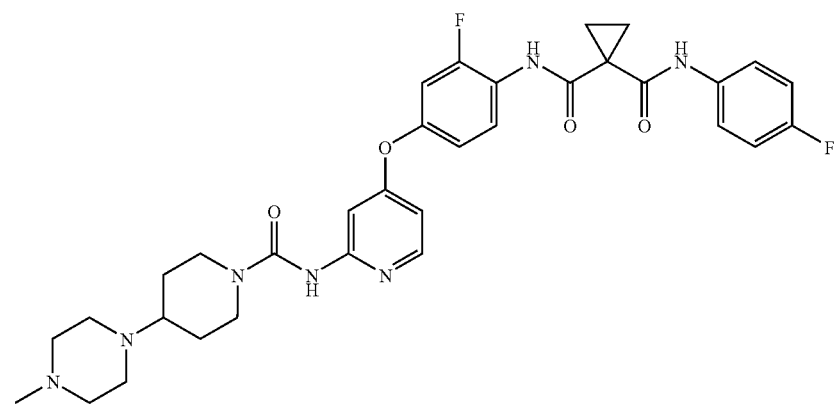
Example 15
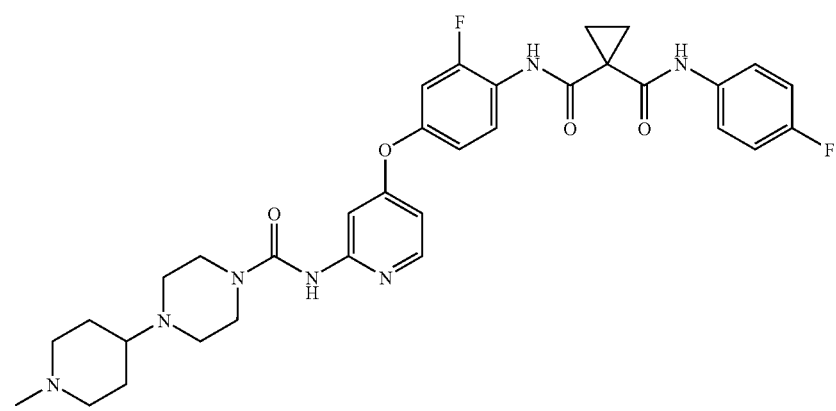
Example 16

TABLE 8-continued
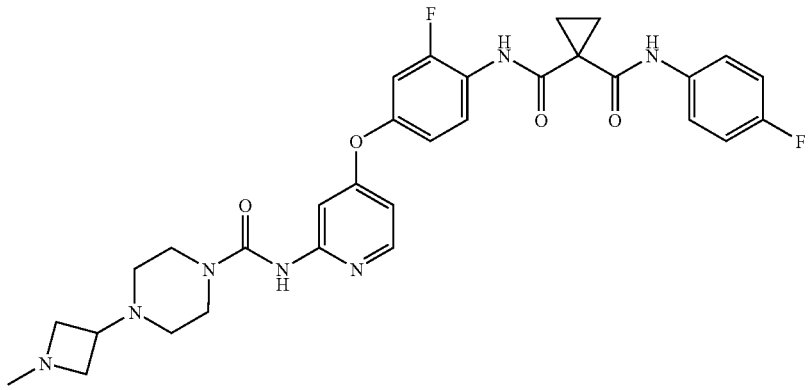
Example 17
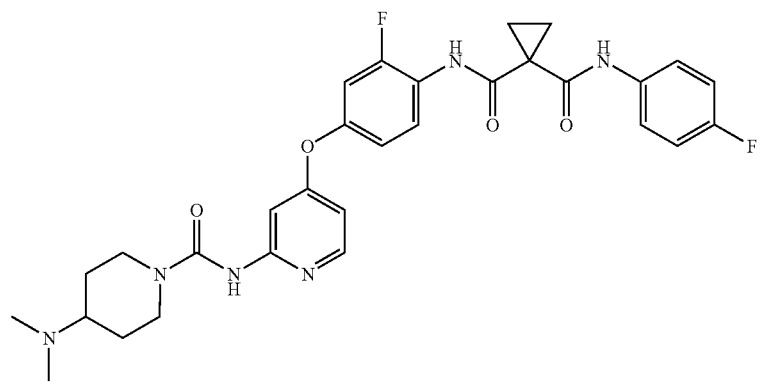
Example 18
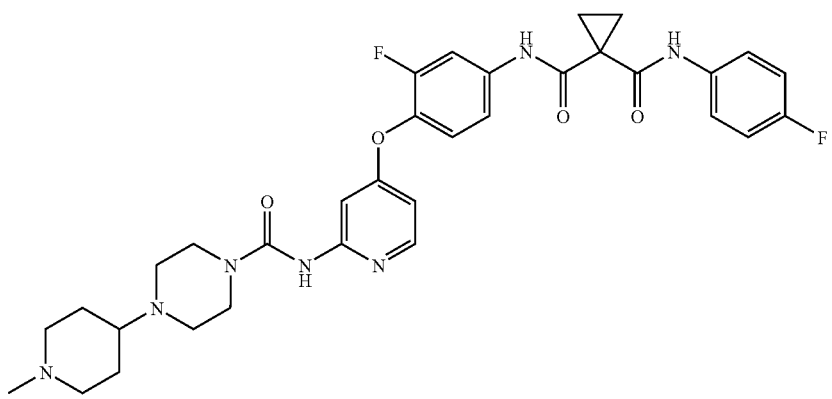
Example 19

TABLE 8-continued
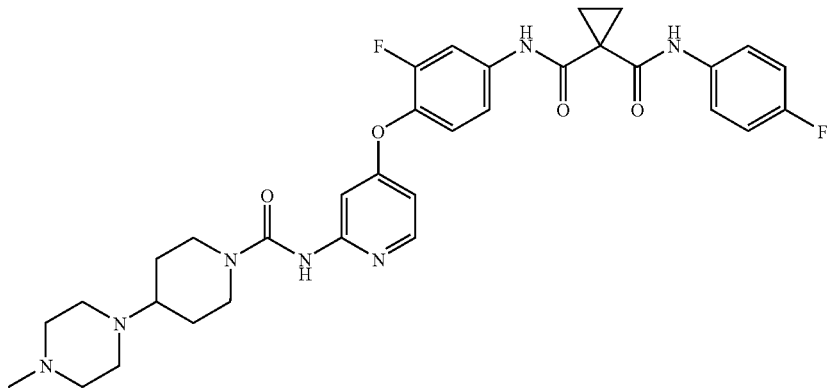
Example 20
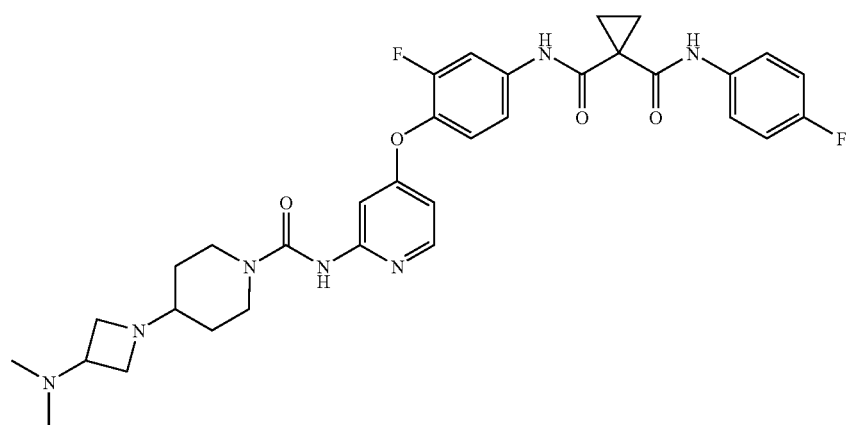
Example 21
TABLE 9
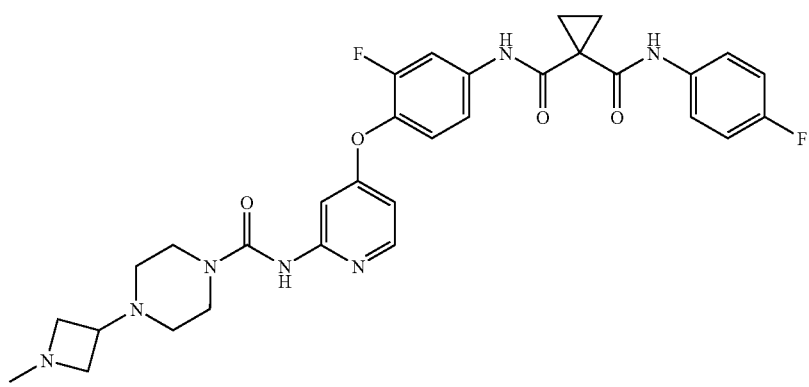
Example 22

TABLE 9-continued
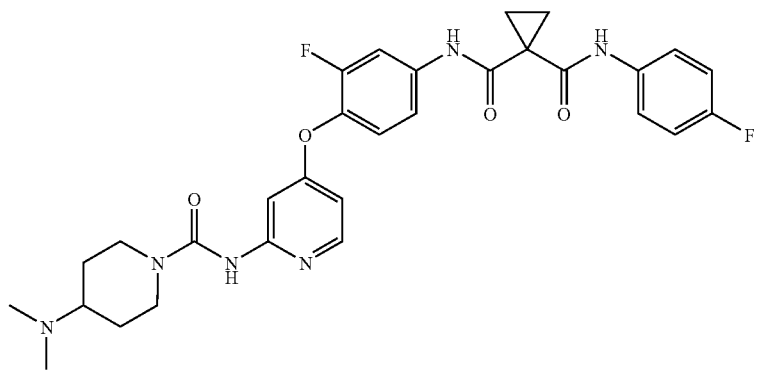
Example 23
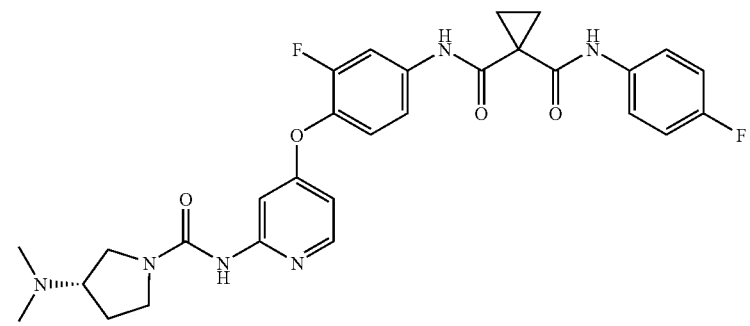
Example 24
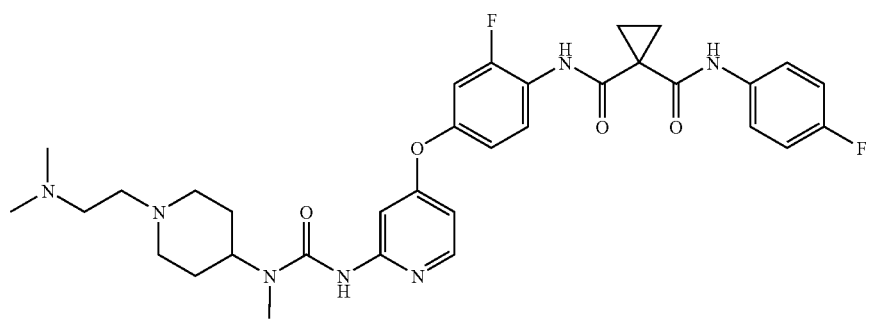
Example 25
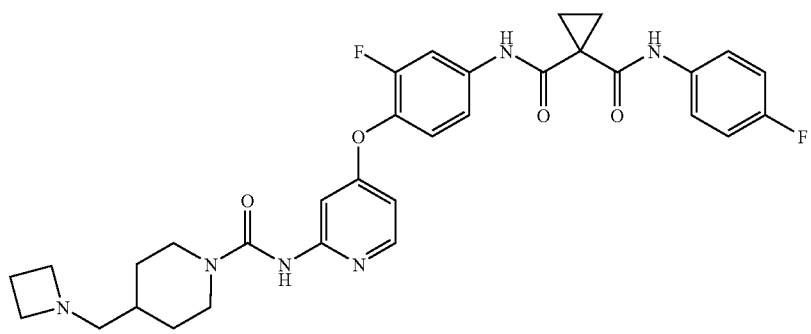
Example 26

TABLE 9-continued
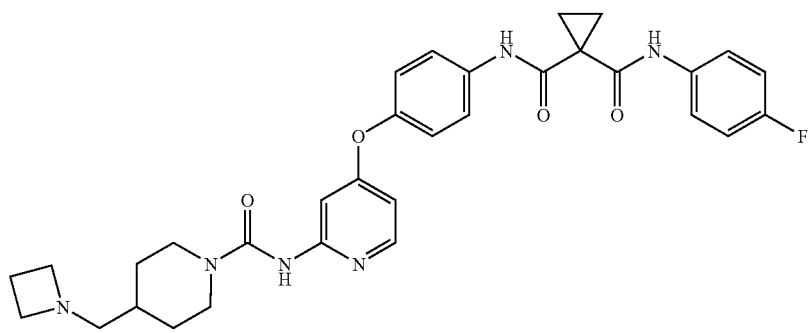
Example 27
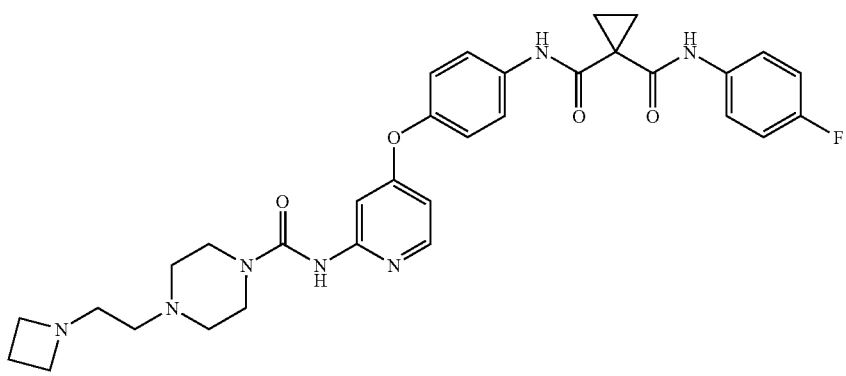
Example 28
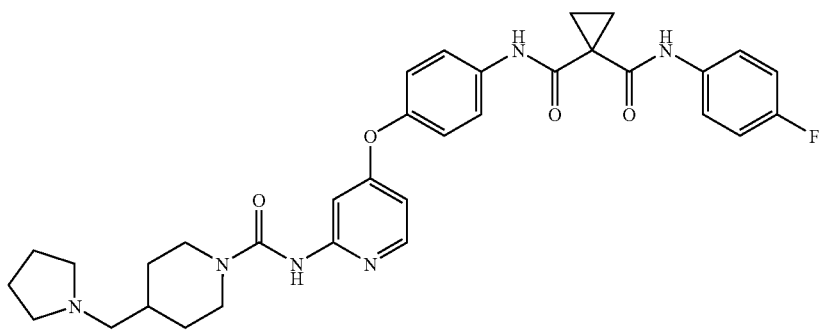
Example 29
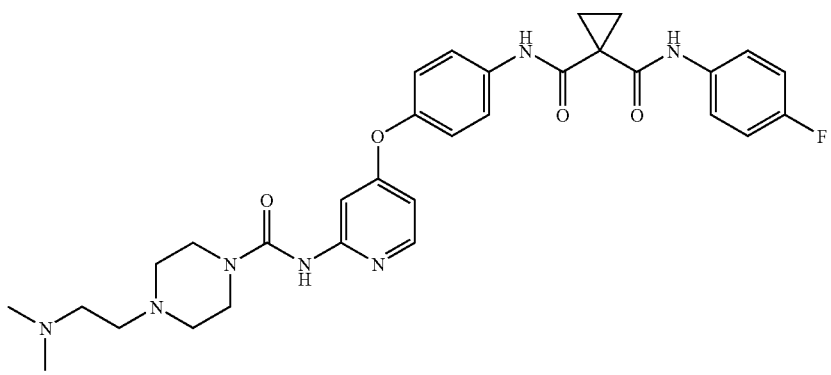
Example 30

TABLE 9-continued
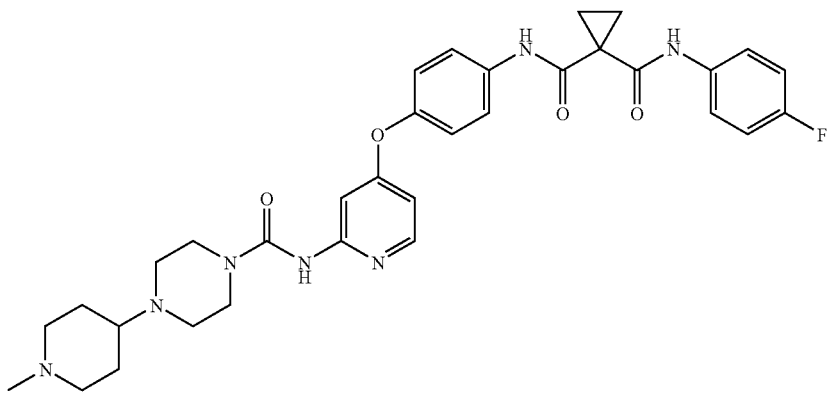
Example 31
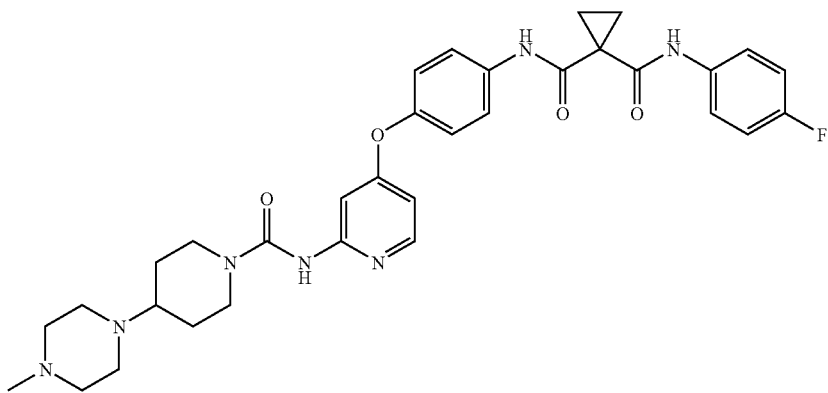
Example 32
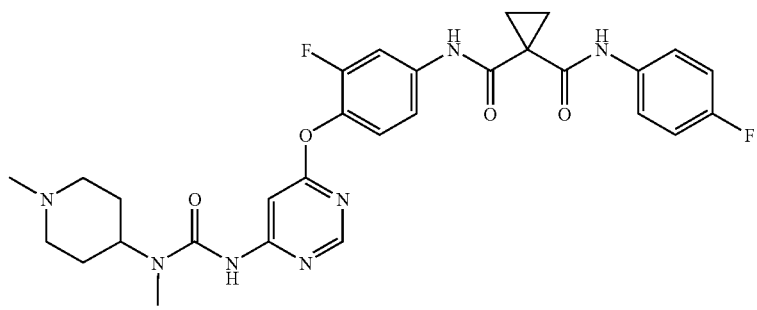
Example 33
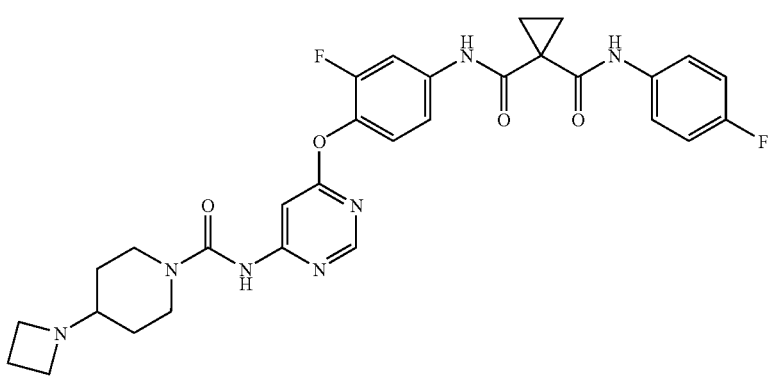
Example 34

TABLE 9-continued
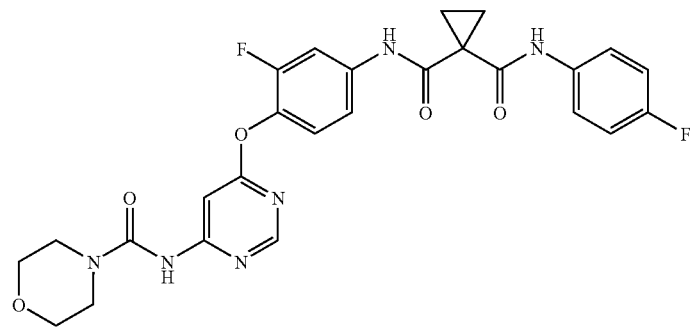
Example 35
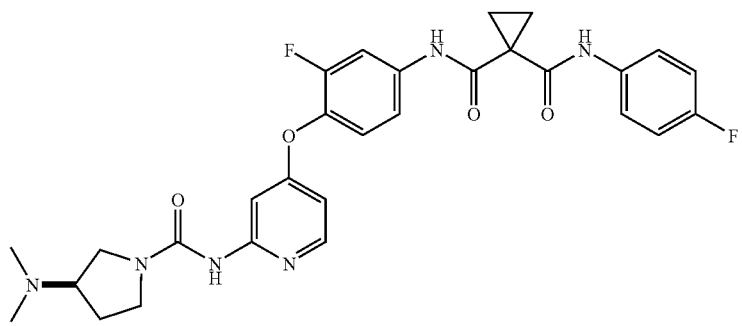
Example 36
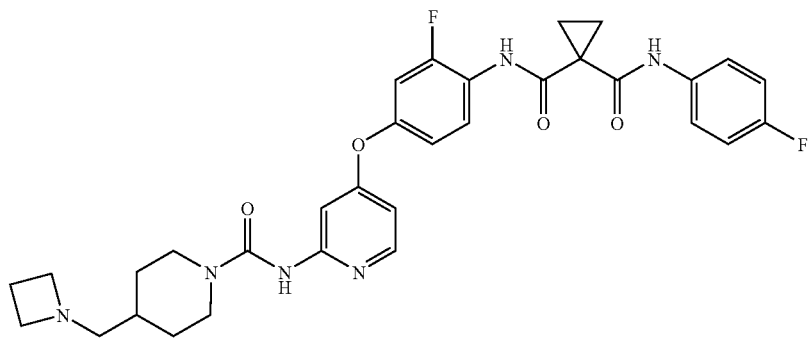
Example 37
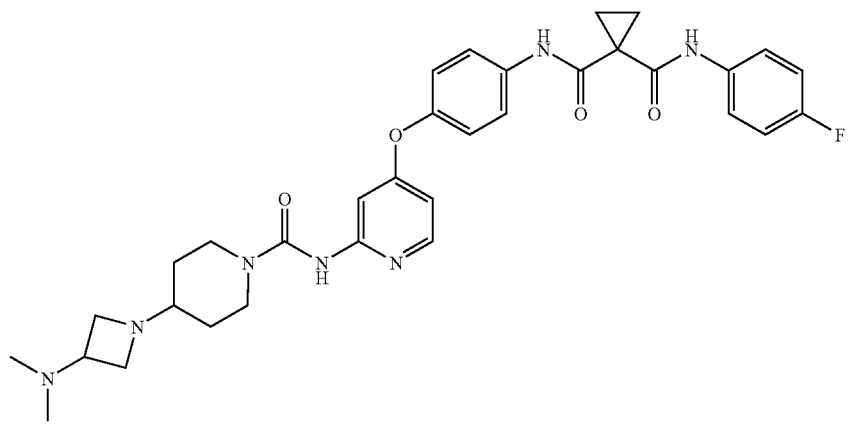
Example 38

TABLE 9-continued
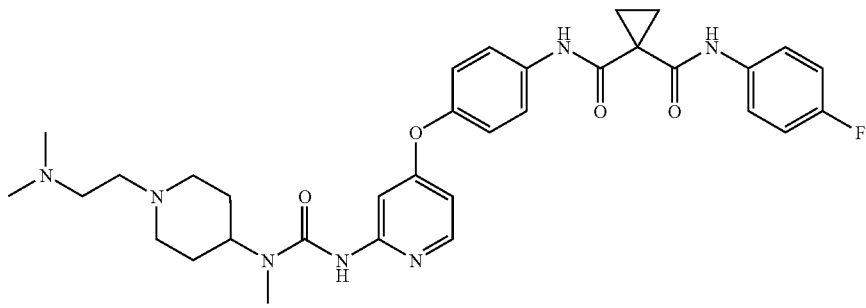
Example 39
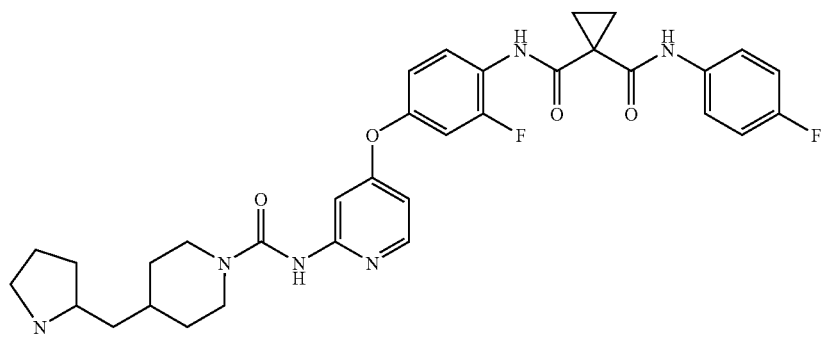
Example 40
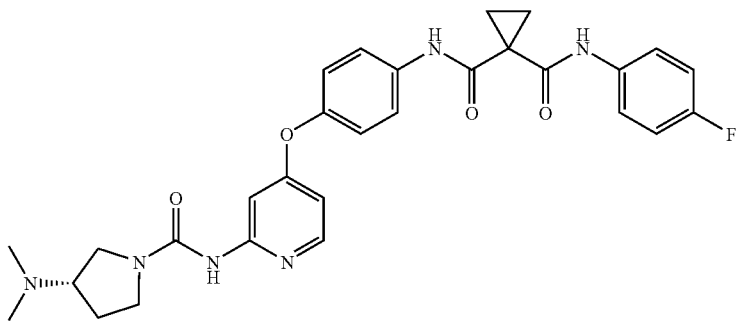
Example 41
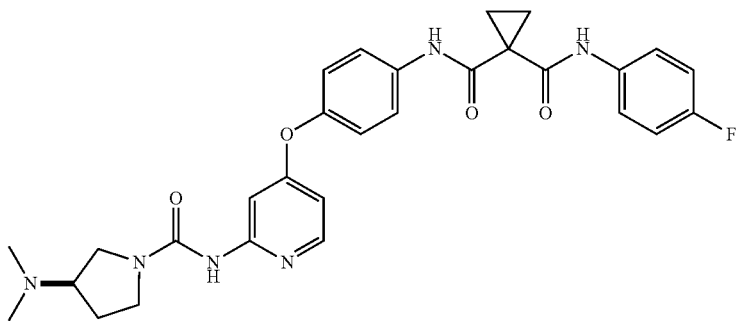
Example 42

TABLE 10
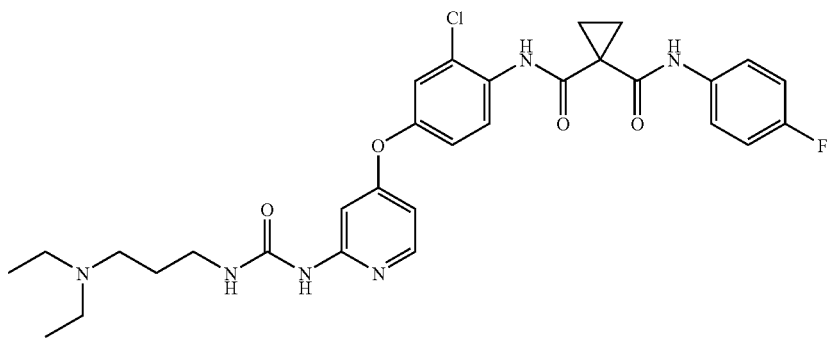
Example 43
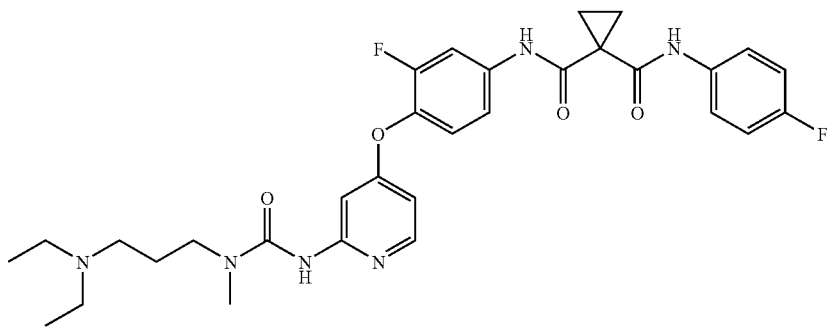
Example 44
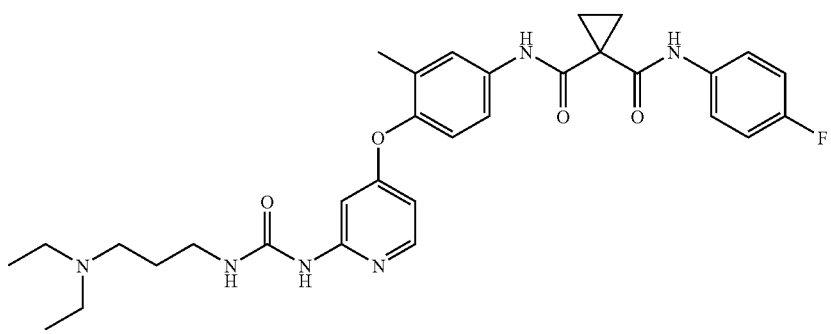
Example 45
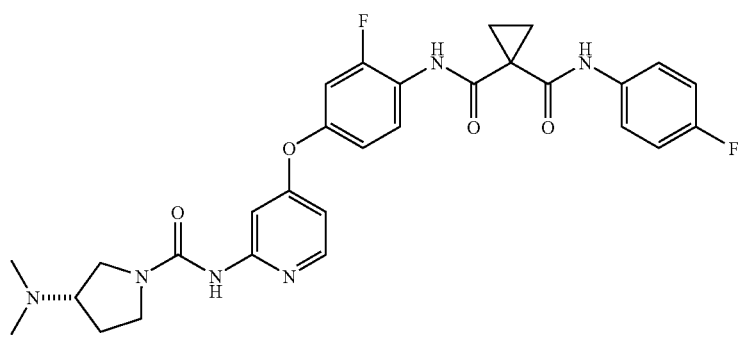
Example 46

TABLE 10-continued
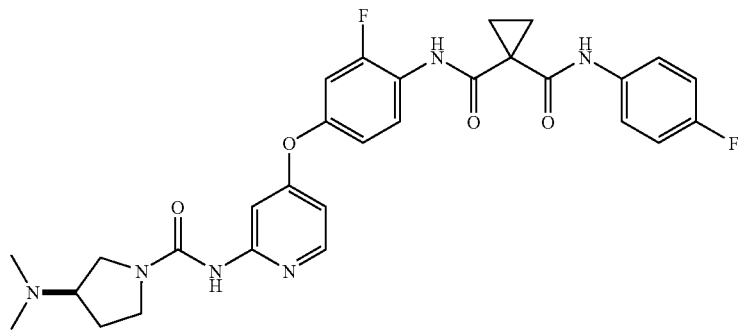
Example 47
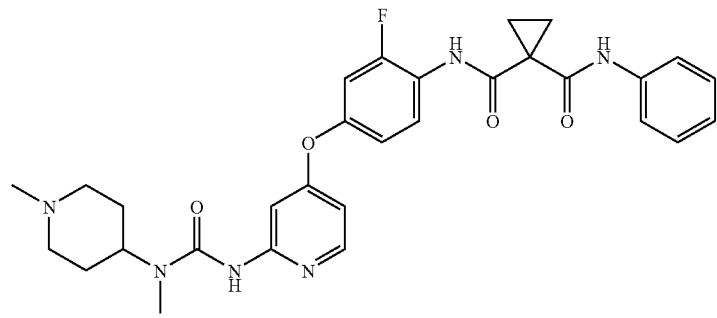
Example 48
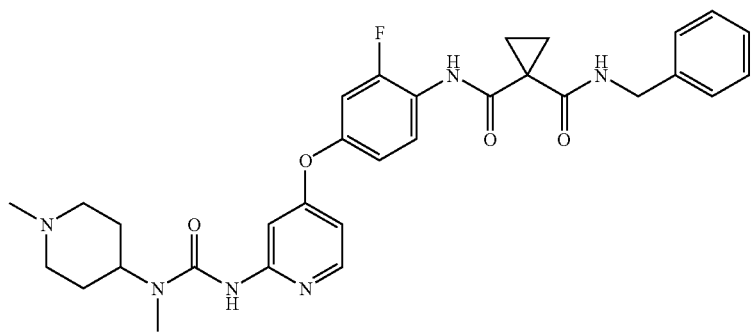
Example 49
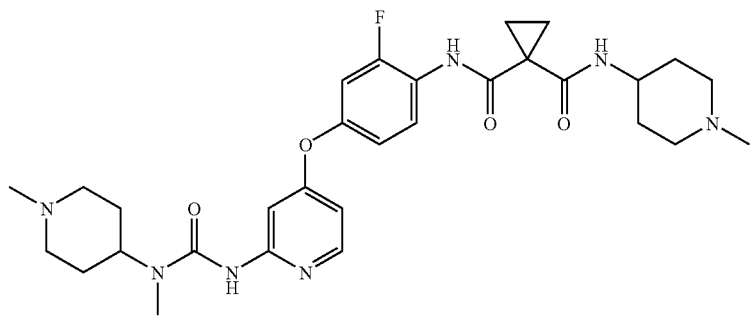
Example 50

TABLE 10-continued
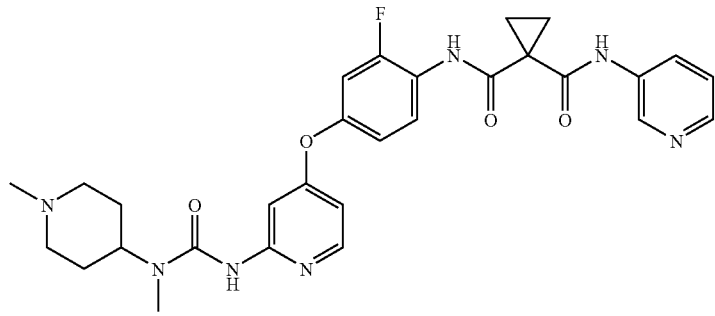
Example 51
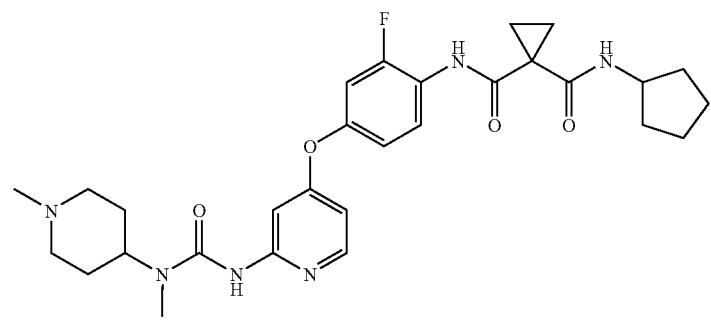
Example 52
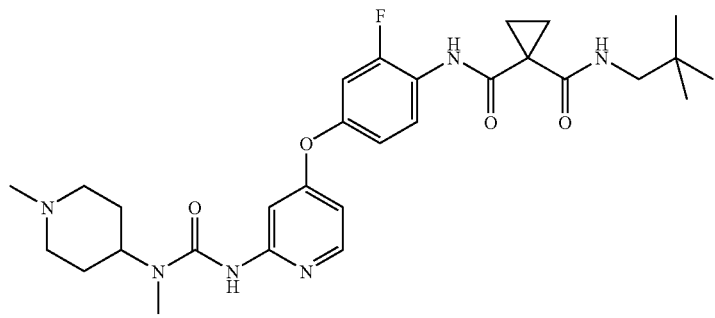
Example 53
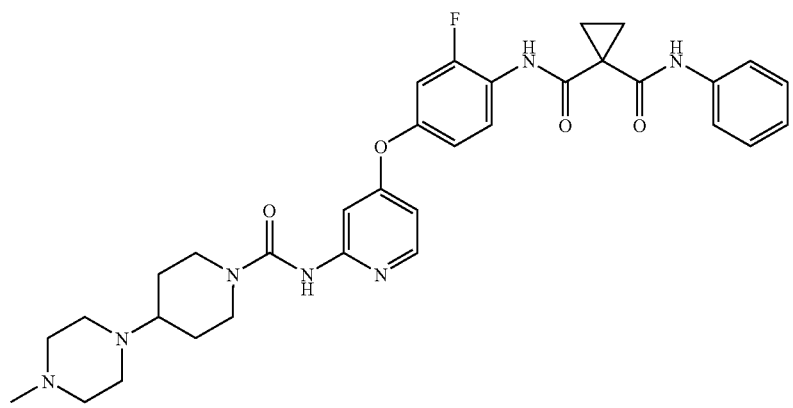
Example 54

TABLE 10-continued
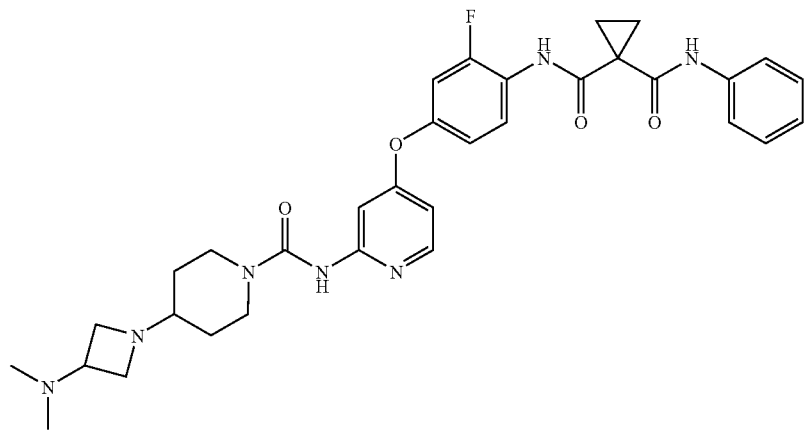
Example 55
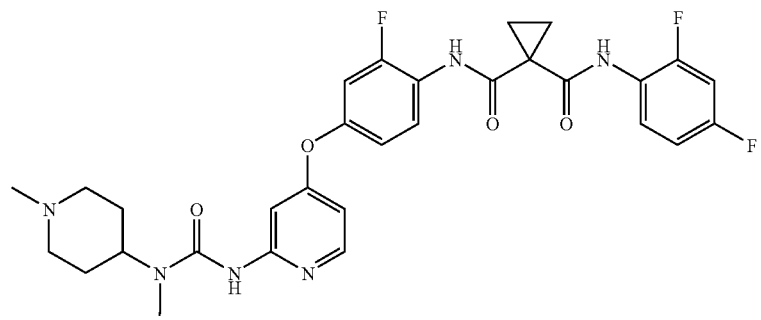
Example 56
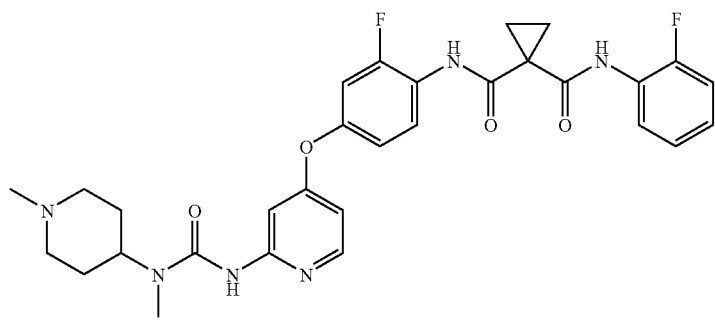
Example 57
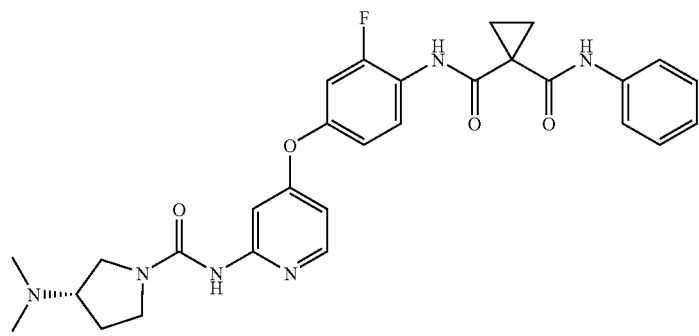
Example 58

TABLE 10-continued
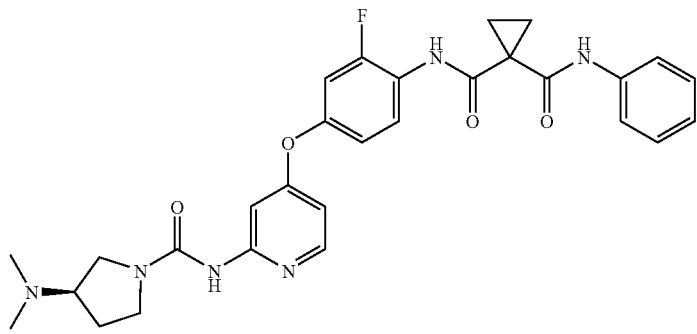
Example 59
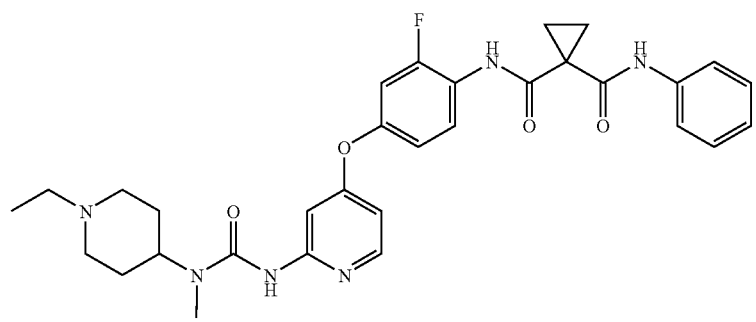
Example 60
TABLE 11
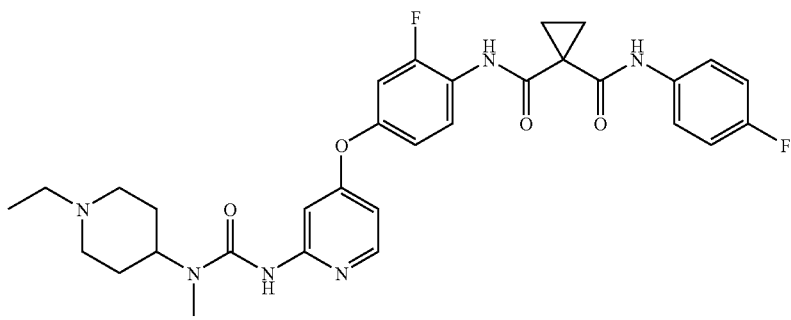
Illustrative Example 1
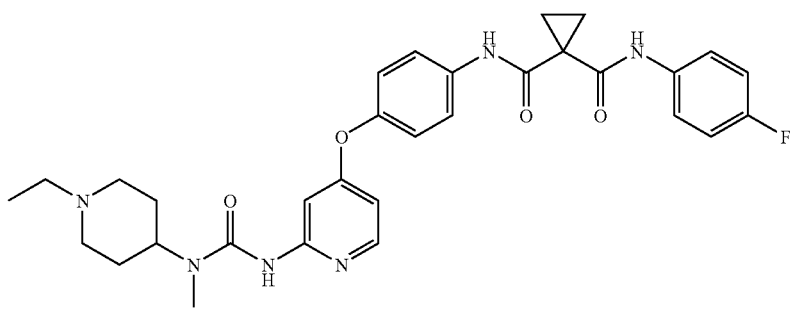
Illustrative Example 2

TABLE 11-continued
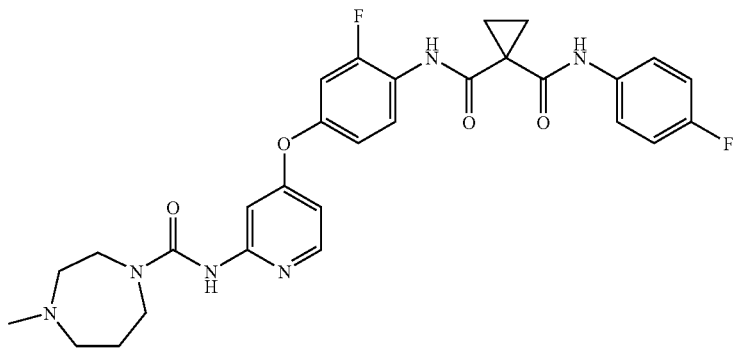
Illustrative Example 3
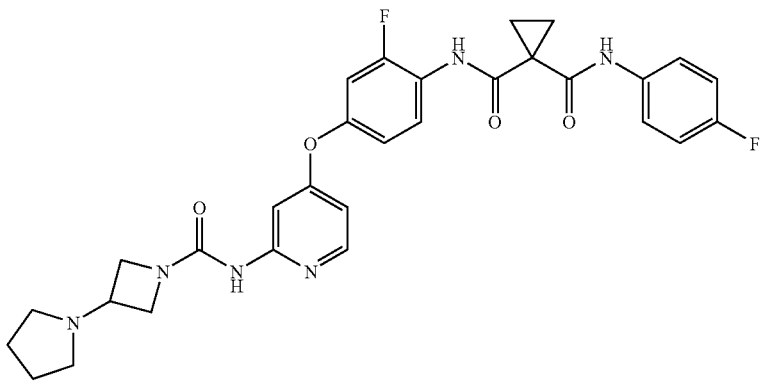
Illustrative Example 4
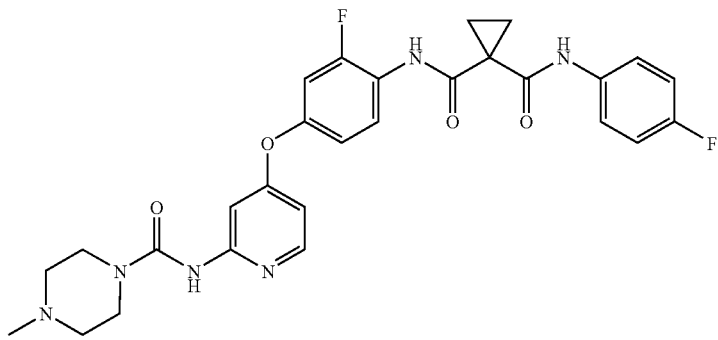
Illustrative Example 5
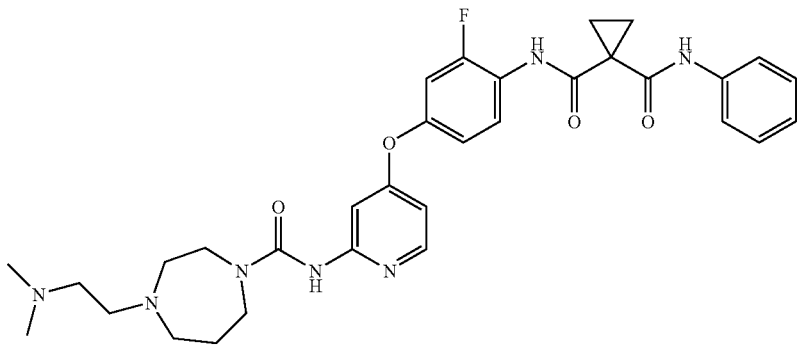
Illustrative Example 6

TABLE 11-continued
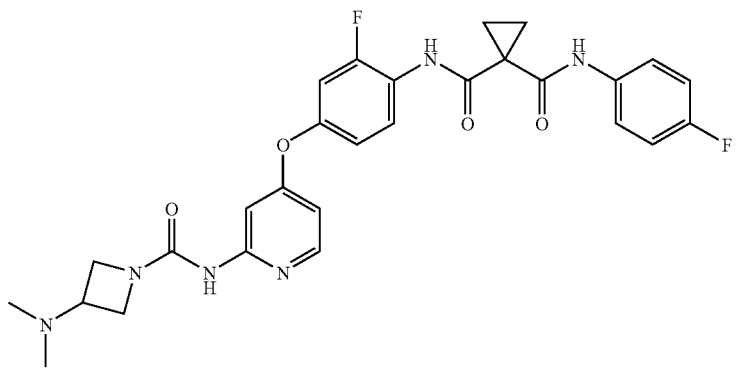
Illustrative Example 7
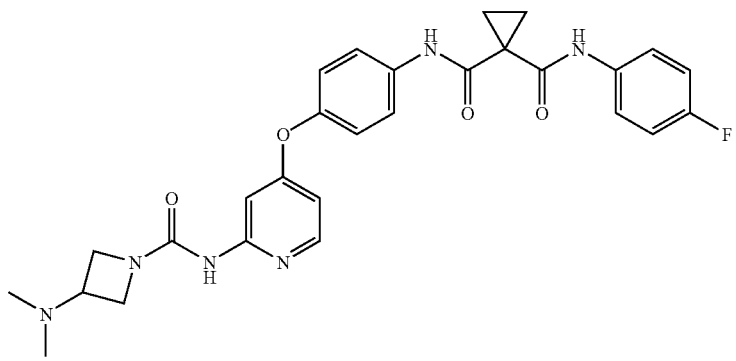
Illustrative Example 8
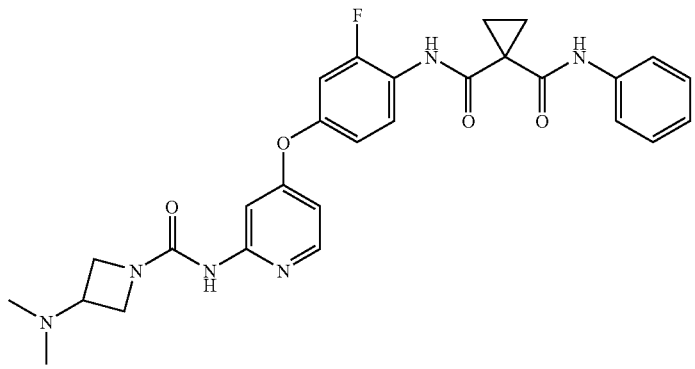
Illustrative Example 9
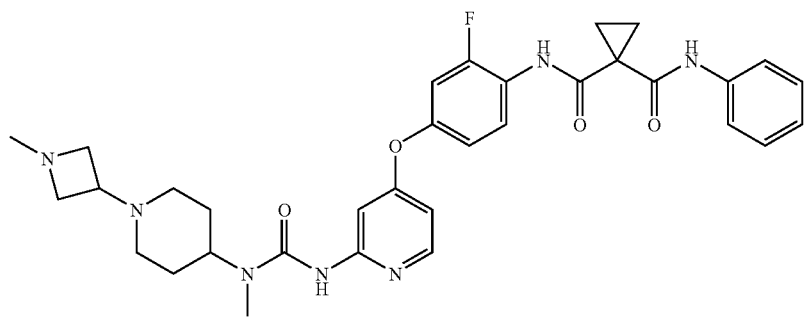
Illustrative Example 10

TABLE 11-continued
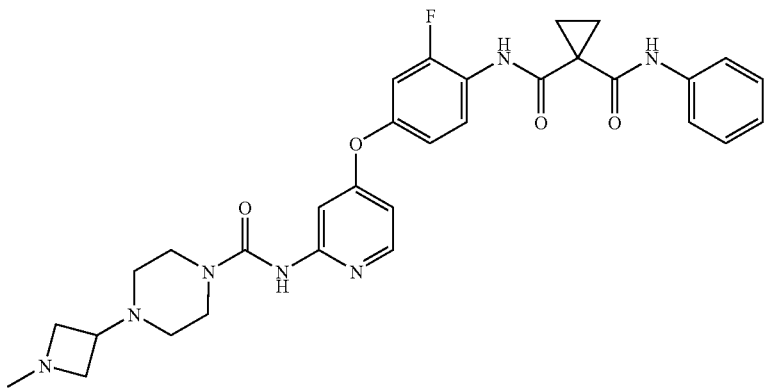
Illustrative Example 11
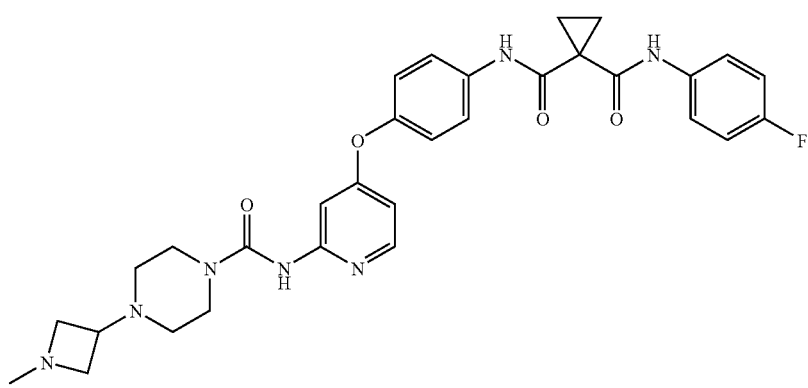
Illustrative Example 12
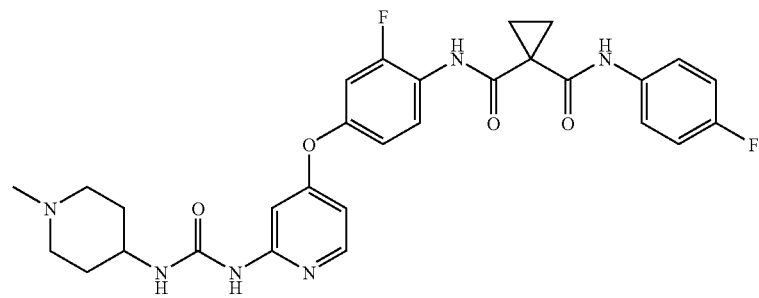
Illustrative Example 13
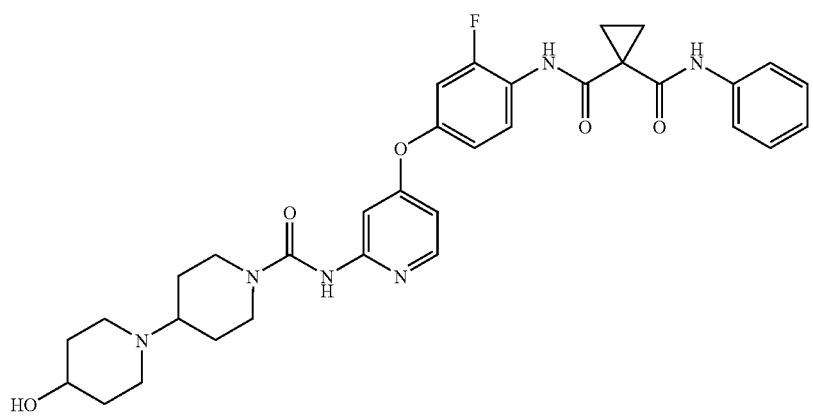
Illustrative Example 14

TABLE 11-continued
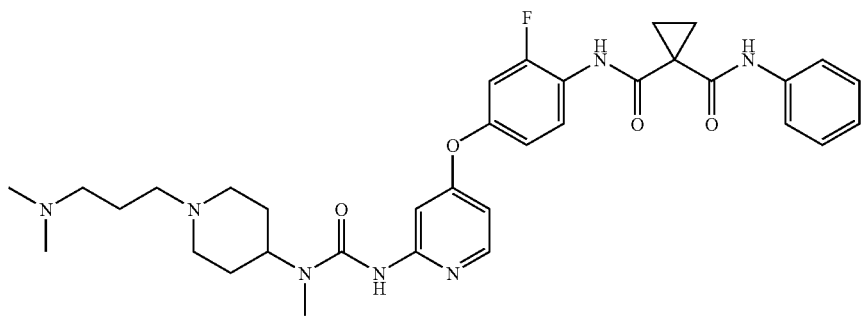
Illustrative Example 15
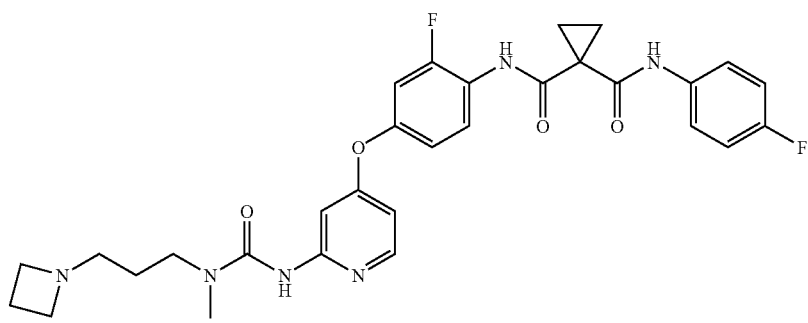
Illustrative Example 16
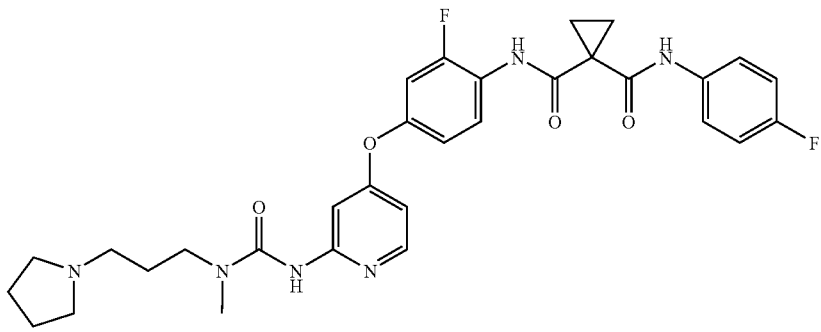
Illustrative Example 17
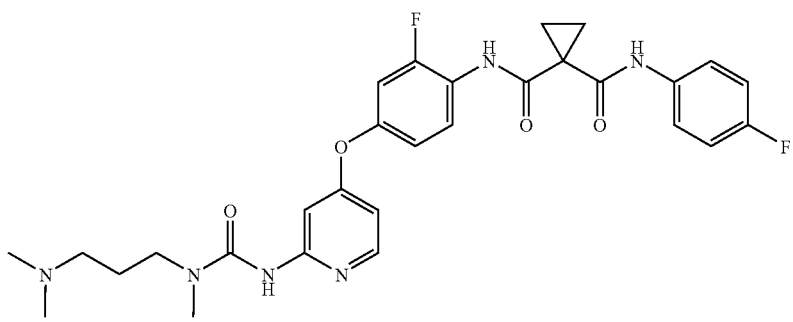
Illustrative Example 18

TABLE 12
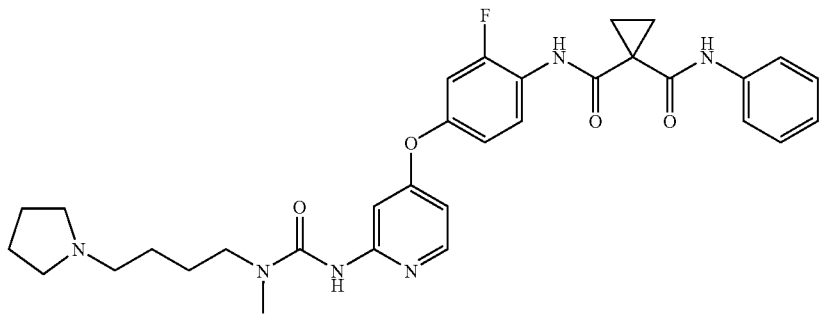
Illustrative Example 19
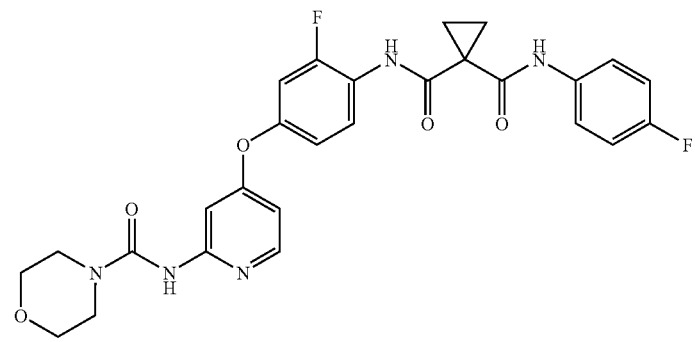
Illustrative Example 20
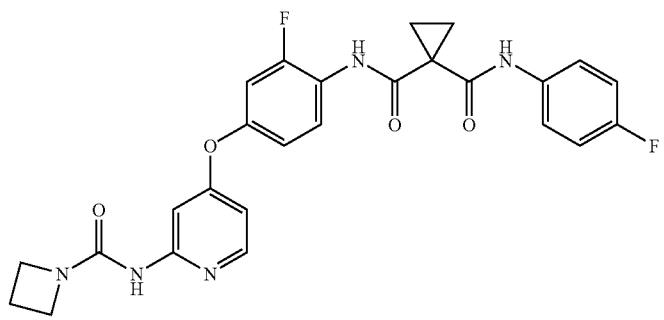
Illustrative Example 21
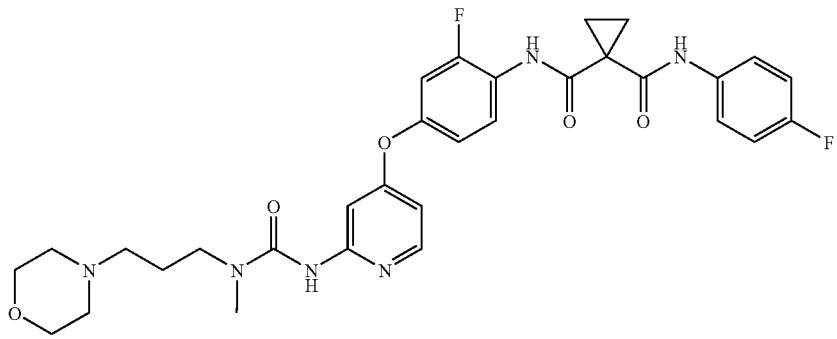
Illustrative Example 22

TABLE 12-continued
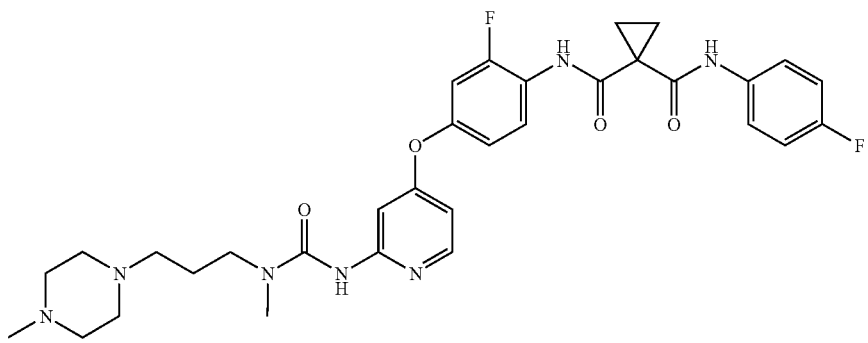
Illustrative Example 23
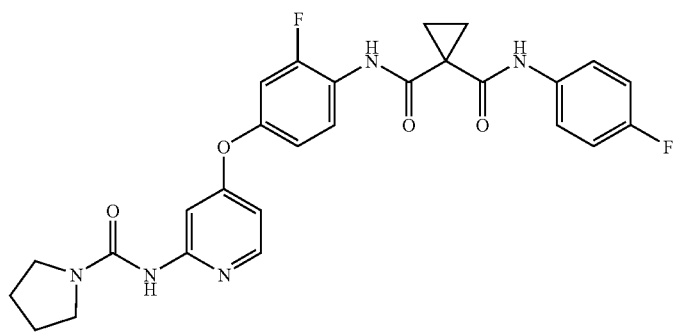
Illustrative Example 24
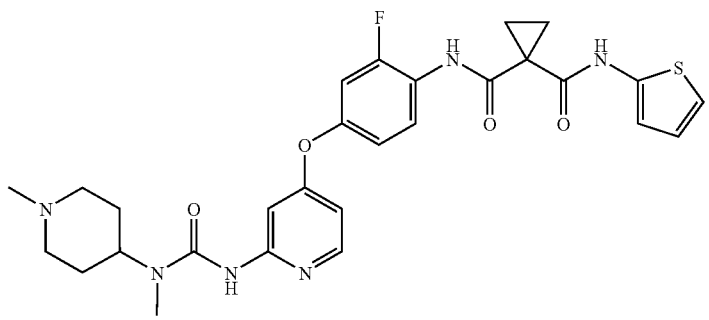
Illustrative Example 25
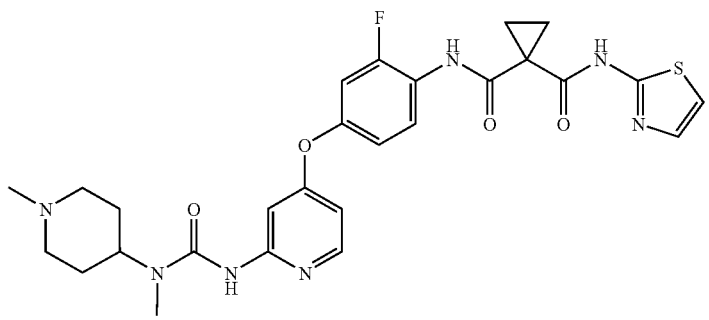
Illustrative Example 26

TABLE 12-continued
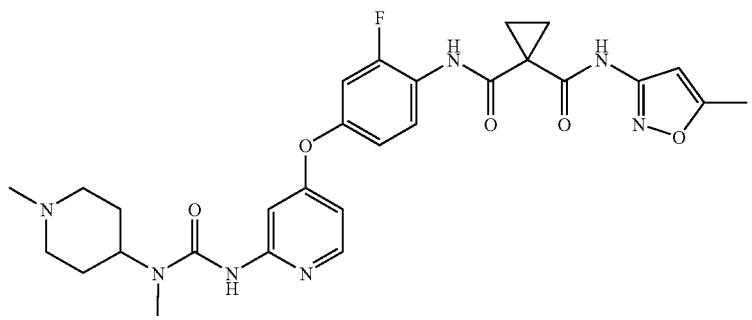
Illustrative Example 27
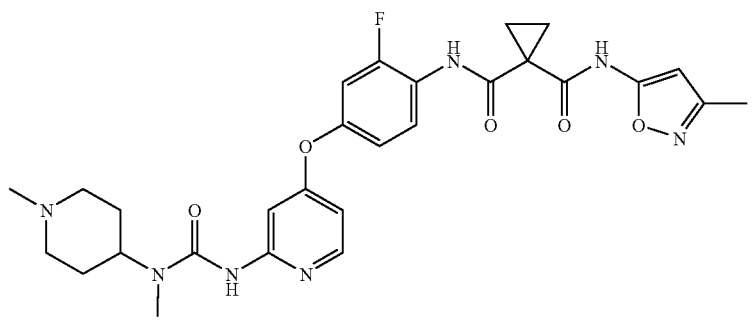
Illustrative Example 28
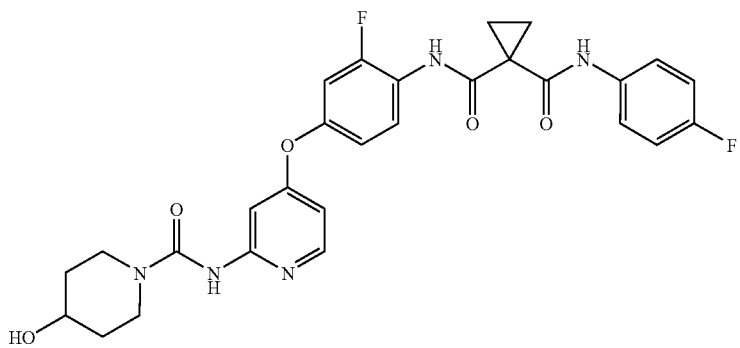
Illustrative Example 29
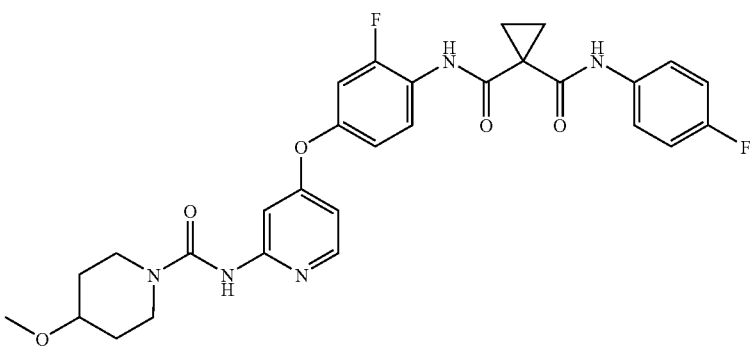
Illustrative Example 30

TABLE 12-continued
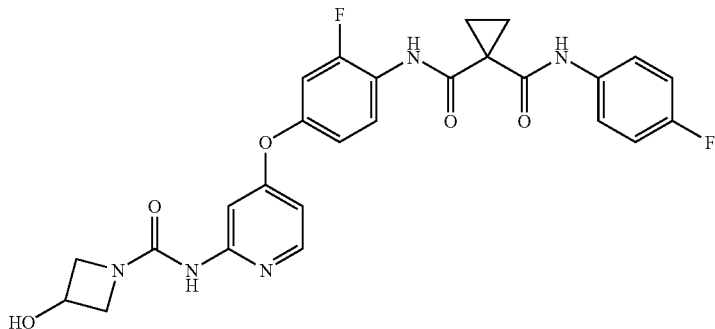
Illustrative Example 31
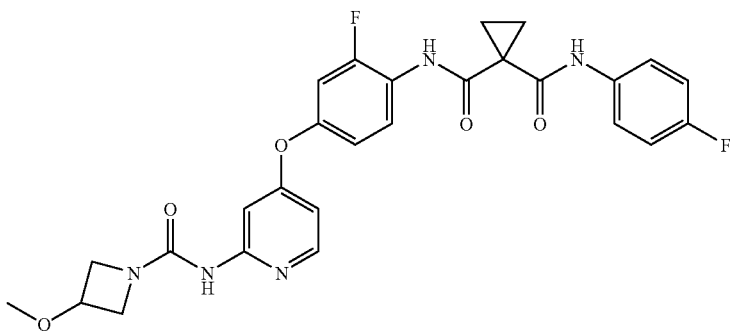
Illustrative Example 32
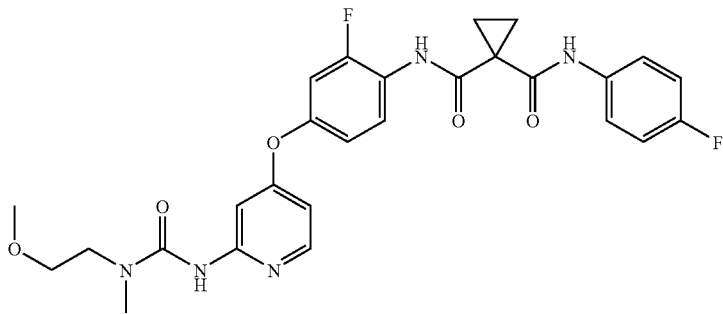
Illustrative Example 33
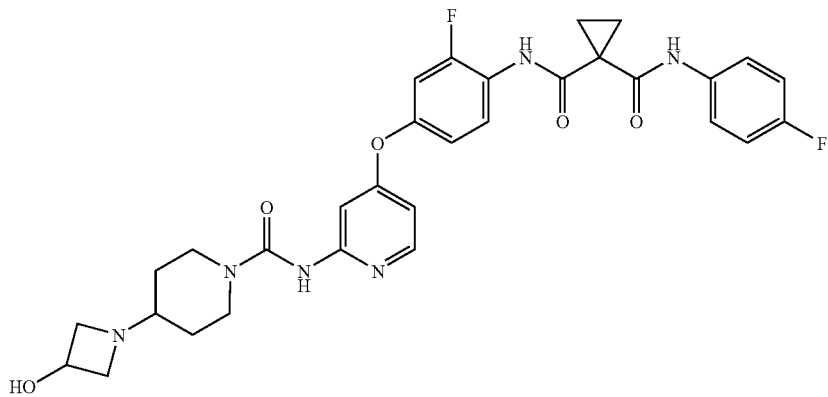
Illustrative Example 34

TABLE 12-continued
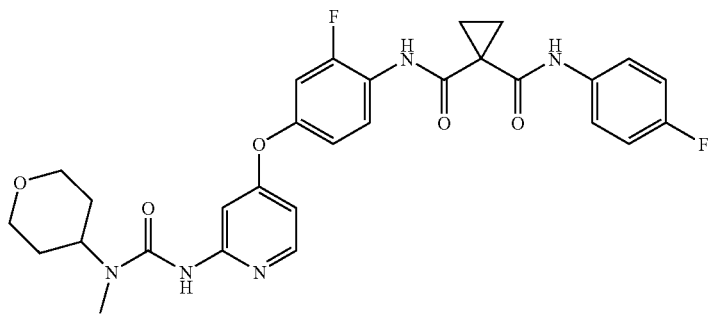
Illustrative Example 35
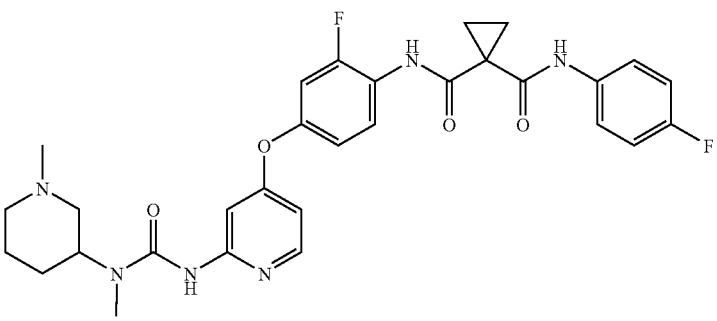
Illustrative Example 36
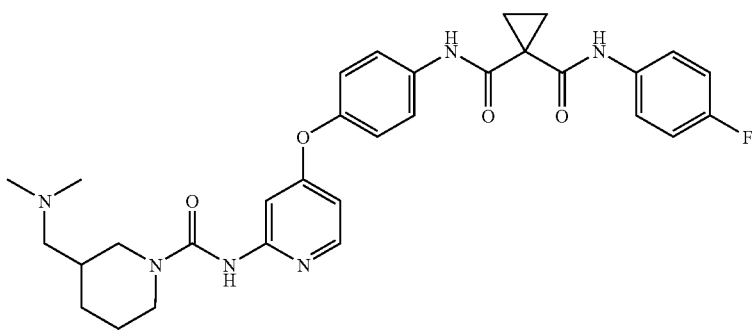
Illustrative Example 37
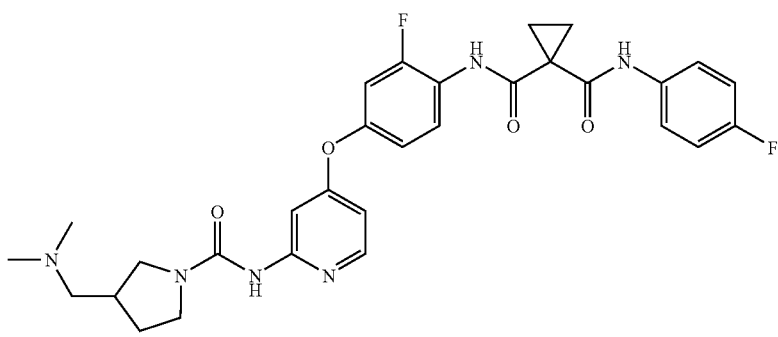
Illustrative Example 38

TABLE 12-continued
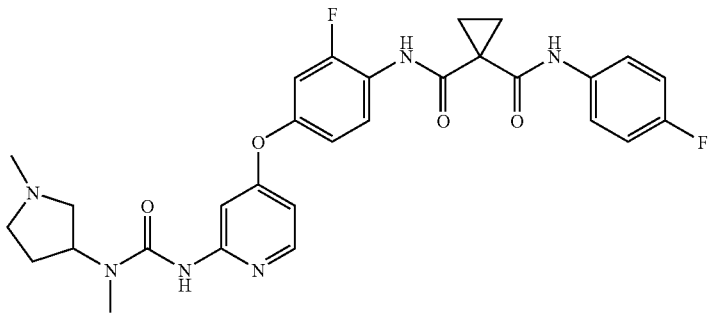
Illustrative Example 39
TABLE 13
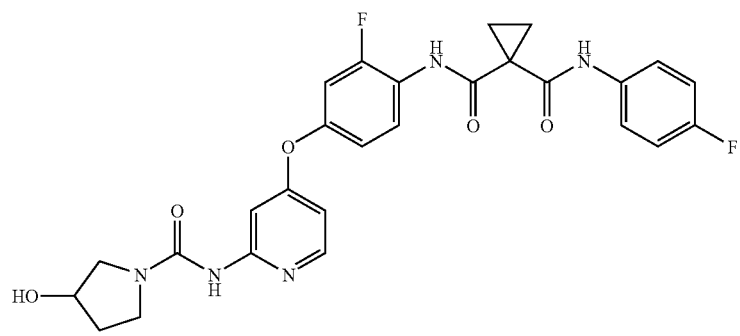
Illustrative Example 40
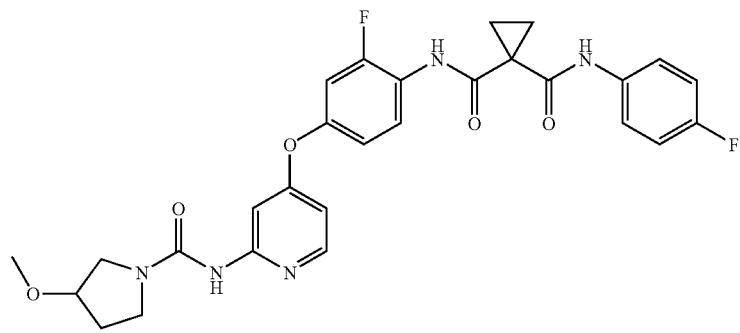
Illustrative Example 41
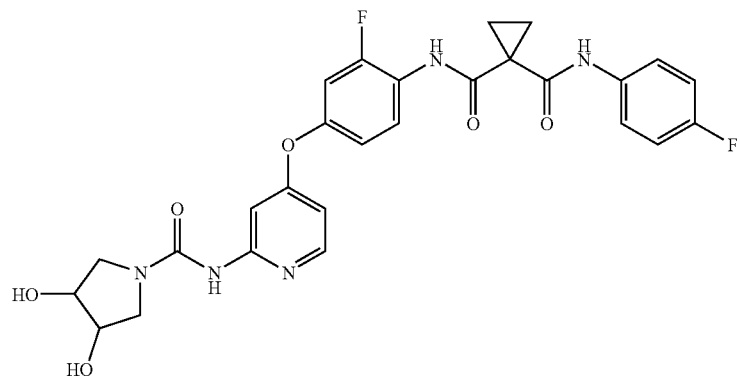
Illustrative Example 42

TABLE 13-continued
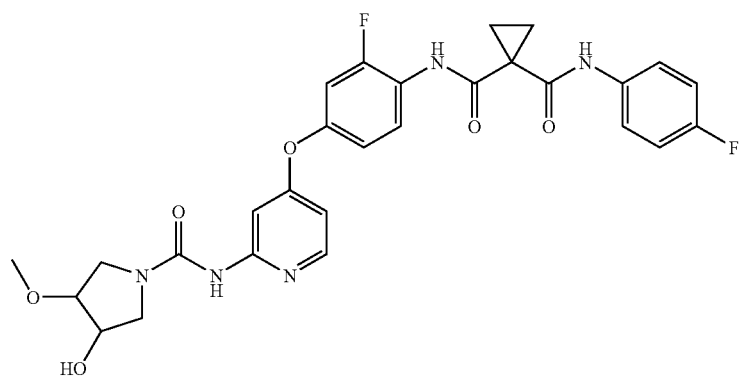
Illustrative Example 43
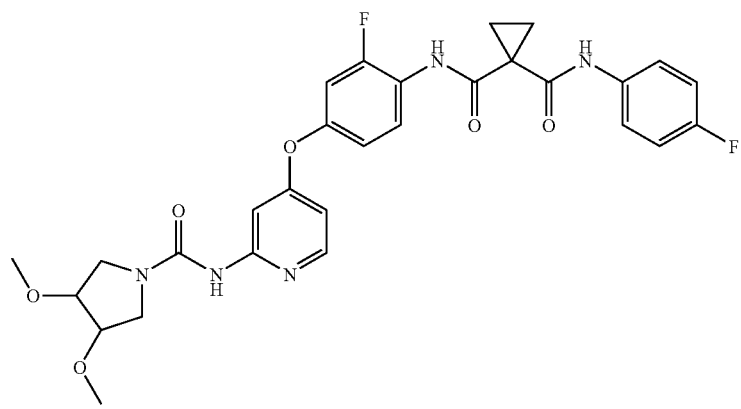
Illustrative Example 44
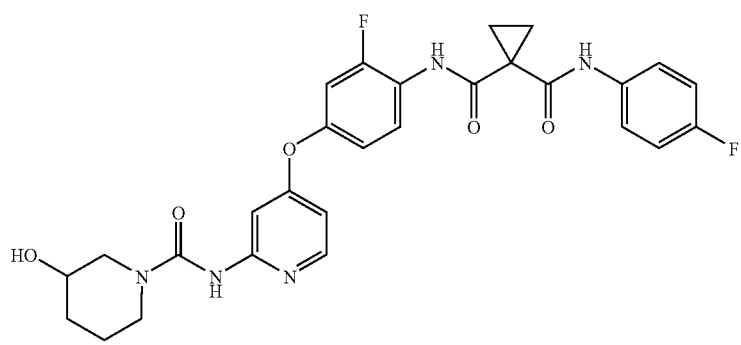
Illustrative Example 45
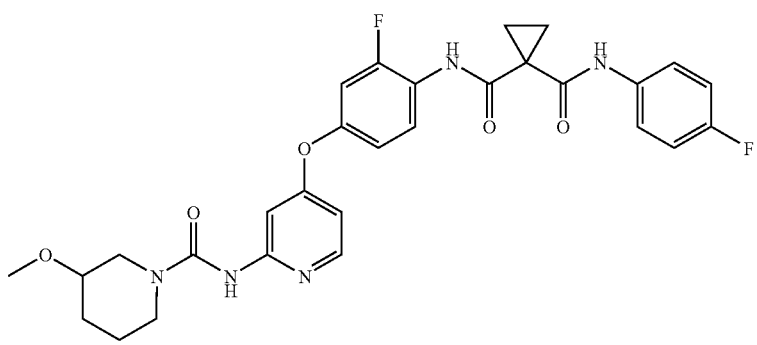
Illustrative Example 46

TABLE 13-continued
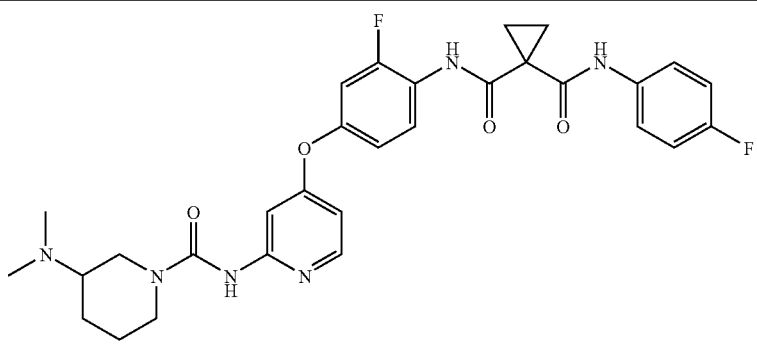
Illustrative Example 47
TABLE 14
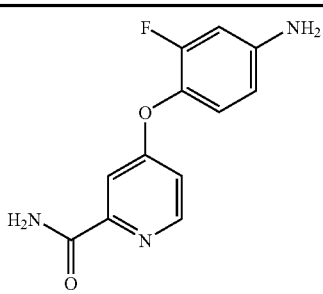
Pro. Ex. 62
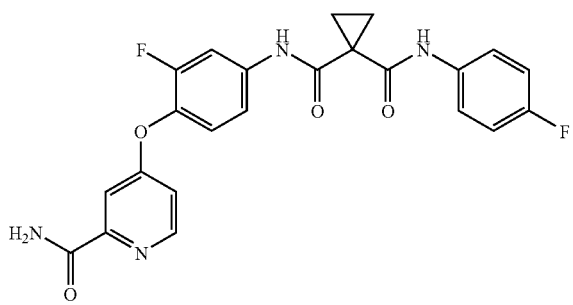
Pro. Ex. 63
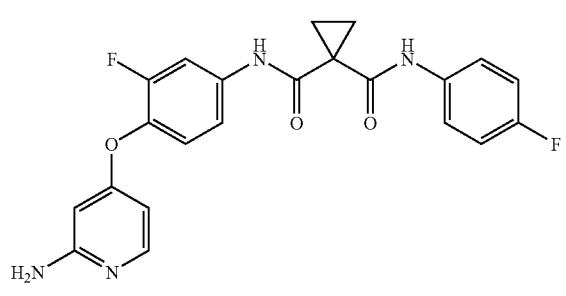
Pro. Ex. 64
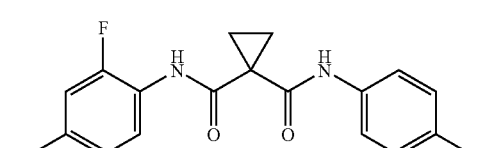
Pro. Ex. 65
TABLE 14-continued
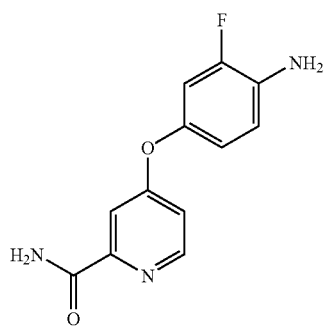
Pro. Ex. 66
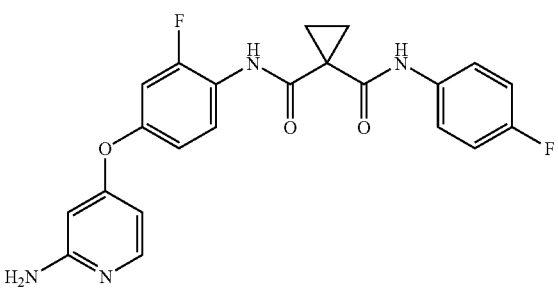
Pro. Ex. 67
Pro. Ex. 68

TABLE 14-continued
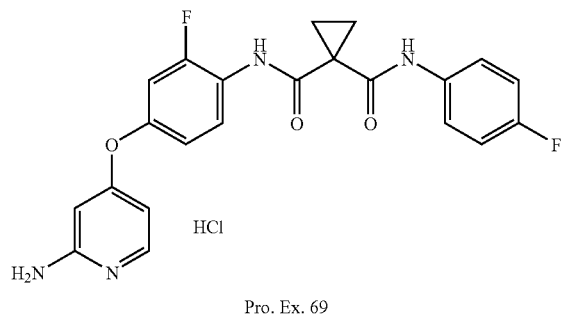
Pro. Ex. 69
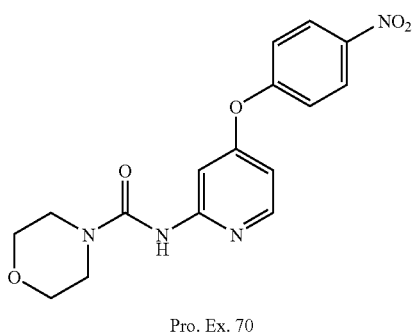
Pro. Ex. 70
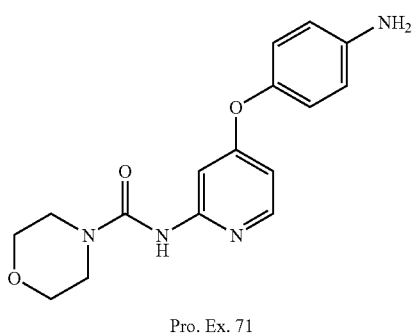
Pro. Ex. 71
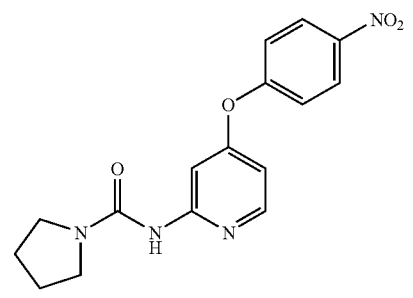
Pro. Ex. 72
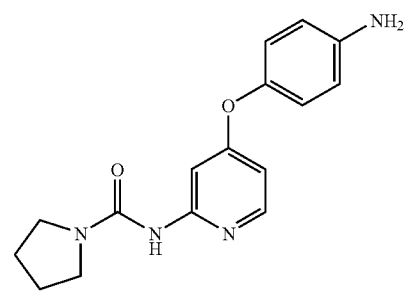
Pro. Ex. 73
TABLE 14-continued
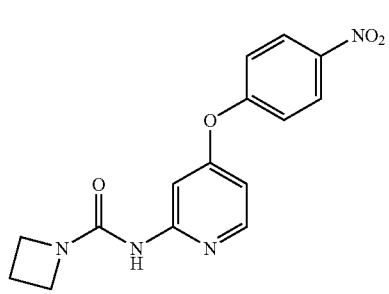
Pro. Ex. 74
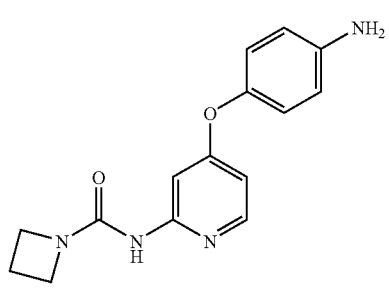
Pro. Ex. 75
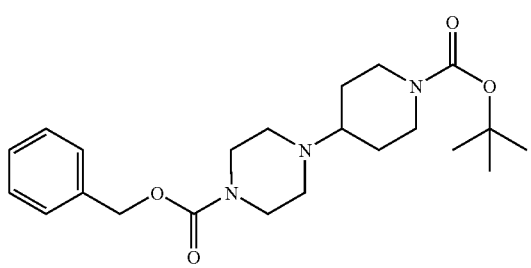
Pro. Ex. 76
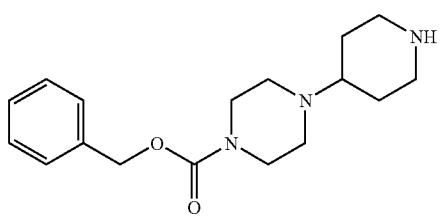
Pro. Ex. 77
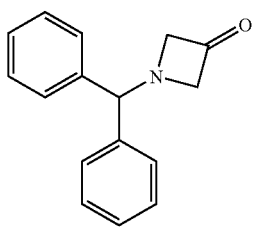
Pro. Ex. 78

TABLE 14-continued
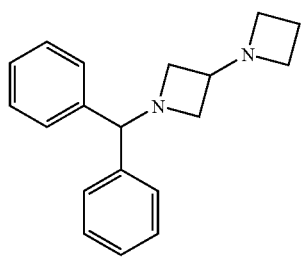
Pro. Ex. 79
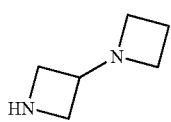
2HCl
Pro. Ex. 80
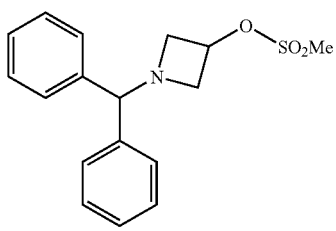
Pro. Ex. 81
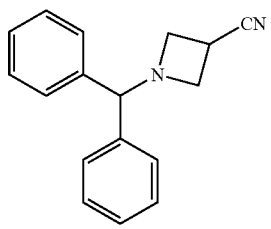
Pro. Ex. 82
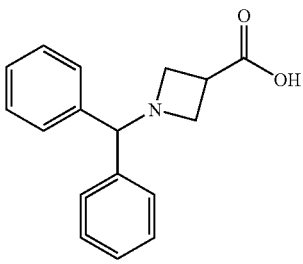
Pro. Ex. 83
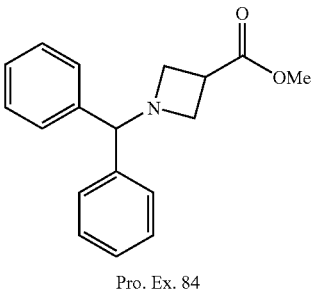
Pro. Ex. 84
TABLE 14-continued
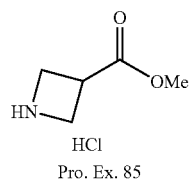
HCl
Pro. Ex. 85
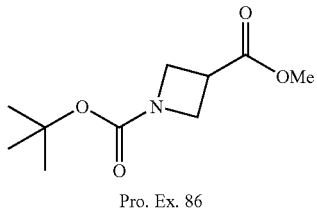
Pro. Ex. 86
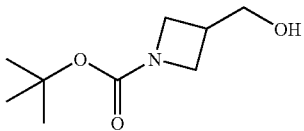
Pro. Ex. 87
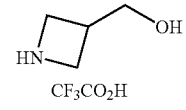
CF$_3$CO$_2$H
Pro. Ex. 88
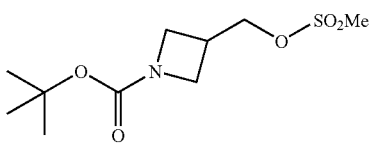
Pro. Ex. 89
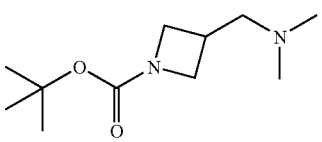
Pro. Ex. 90
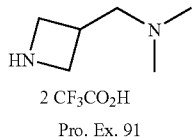
2 CF$_3$CO$_2$H
Pro. Ex. 91
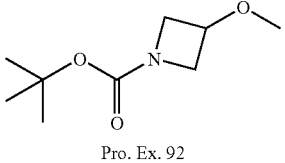
Pro. Ex. 92
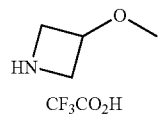
CF$_3$CO$_2$H
Pro. Ex. 93

TABLE 14-continued
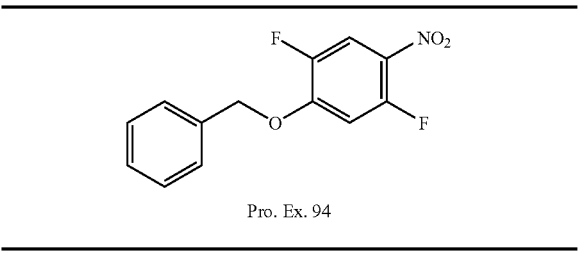
Pro. Ex. 94
TABLE 15
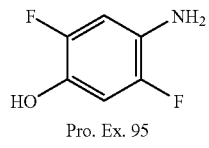
Pro. Ex. 95
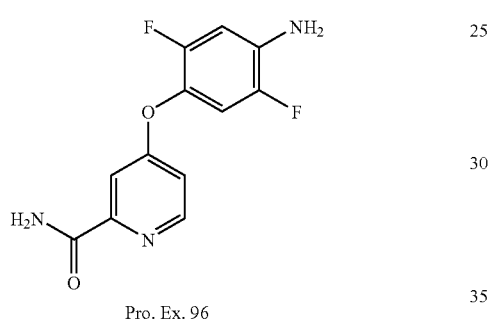
Pro. Ex. 96
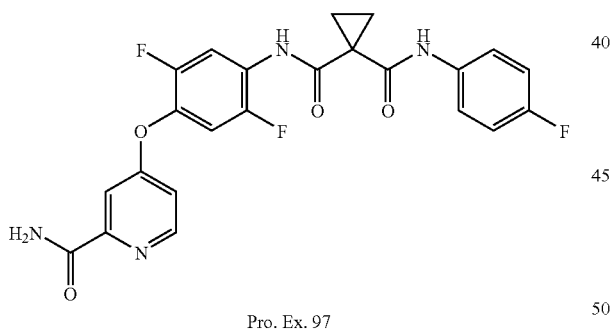
Pro. Ex. 97
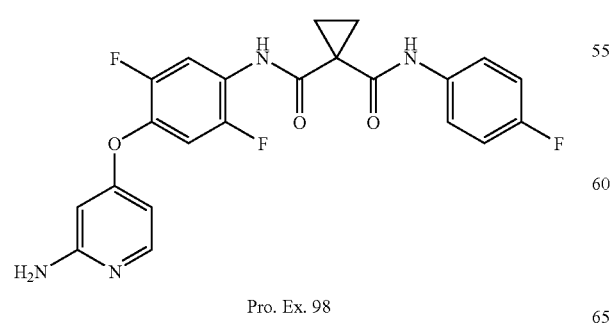
Pro. Ex. 98
TABLE 15-continued
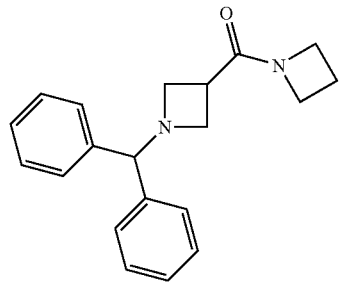
Pro. Ex. 99
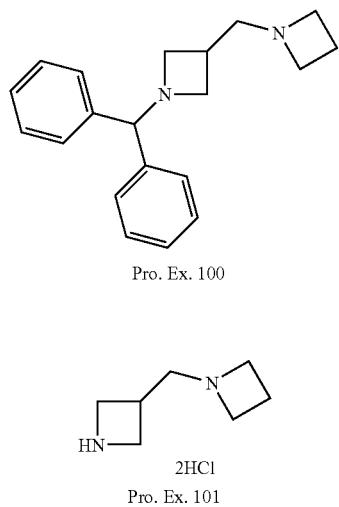
Pro. Ex. 100
2HCl
Pro. Ex. 101
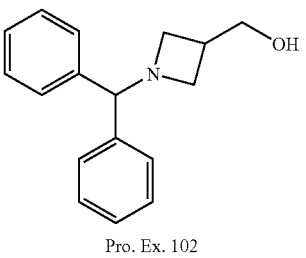
Pro. Ex. 102
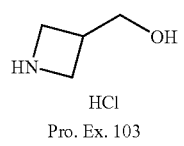
HCl
Pro. Ex. 103
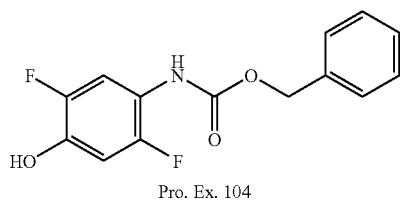
Pro. Ex. 104

TABLE 15-continued
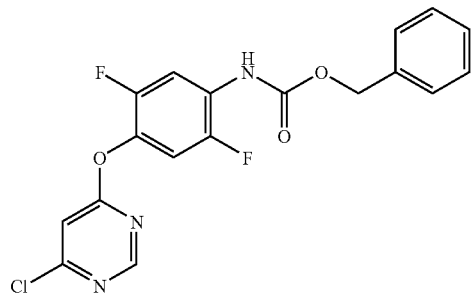
Pro. Ex. 105
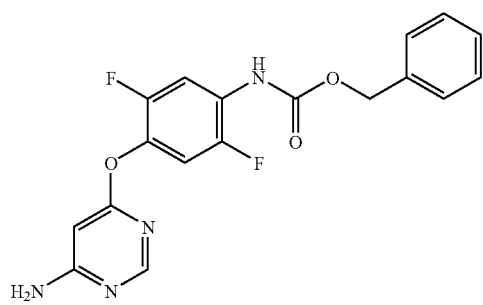
Pro. Ex. 106
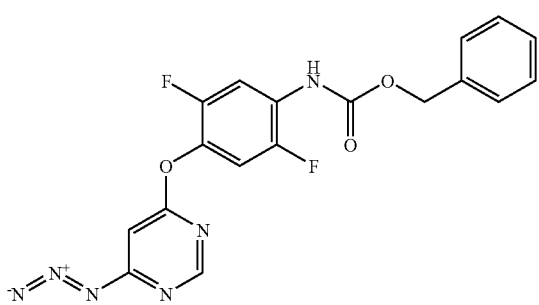
Pro. Ex. 107
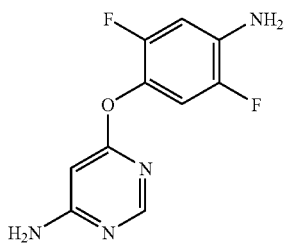
Pro. Ex. 108
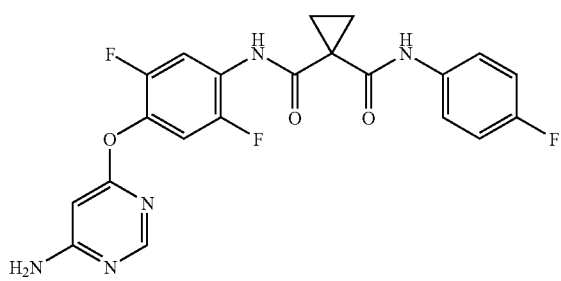
Pro. Ex. 109
TABLE 15-continued
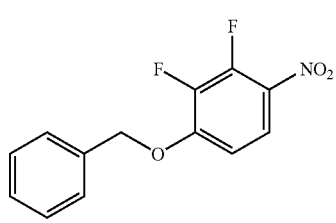
Pro. Ex. 110
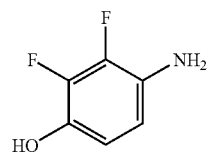
Pro. Ex. 111
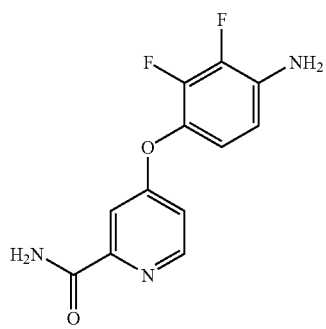
Pro. Ex. 112
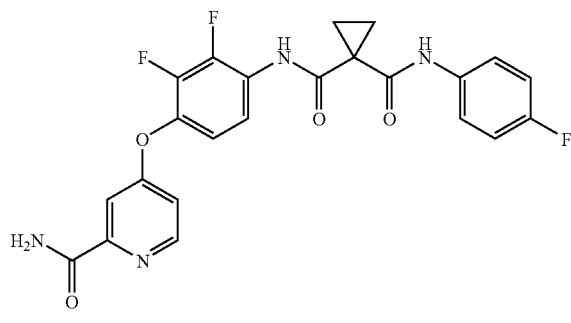
Pro. Ex. 113
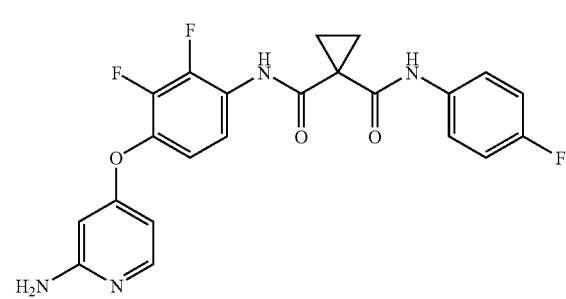
Pro. Ex. 114

TABLE 16
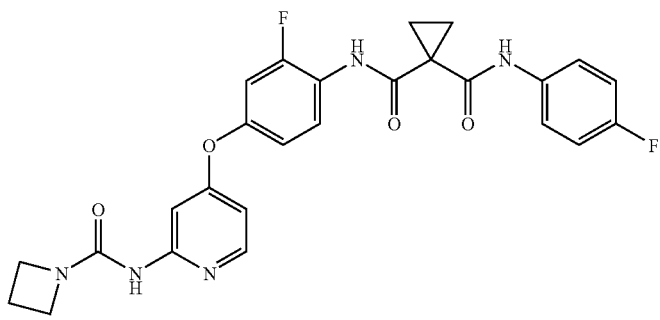
Example 61
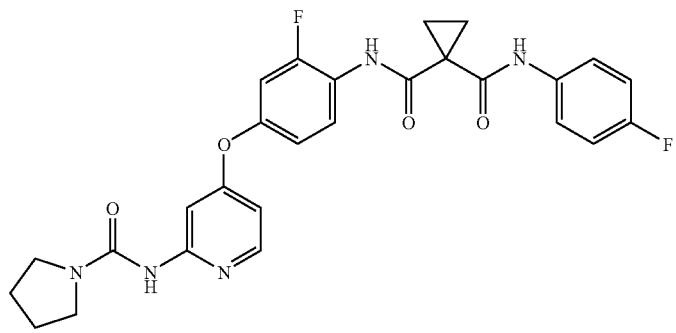
Example 62
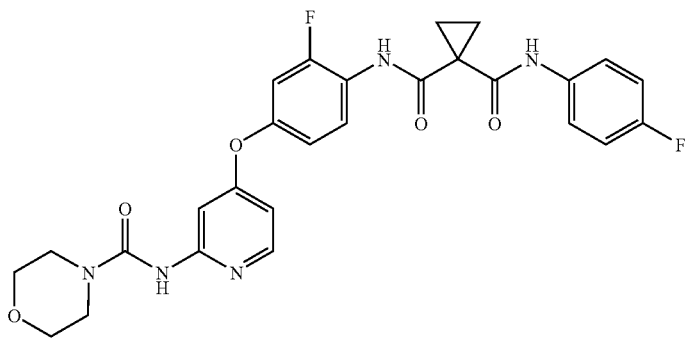
Example 63
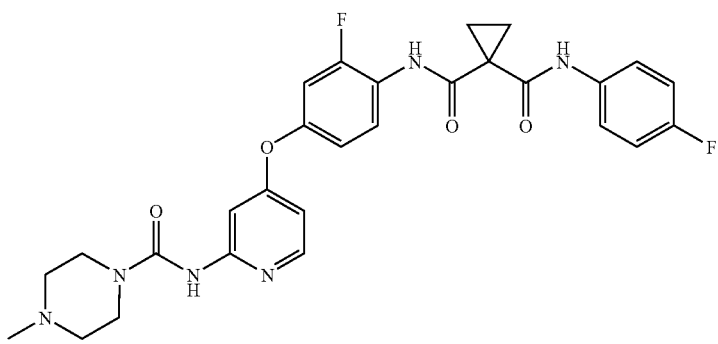
Example 64

TABLE 16-continued
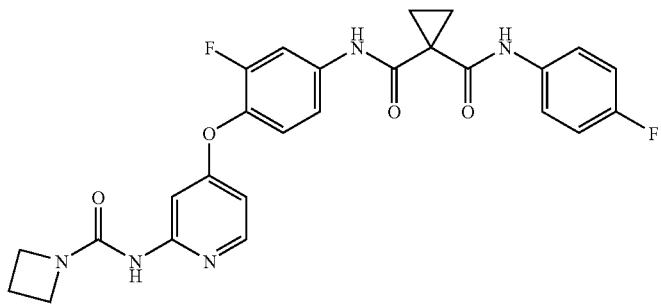
Example 65
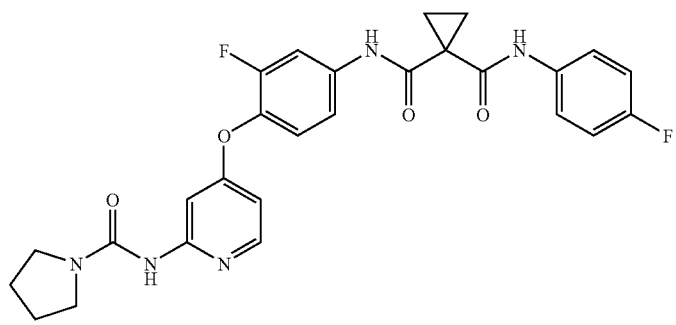
Example 66
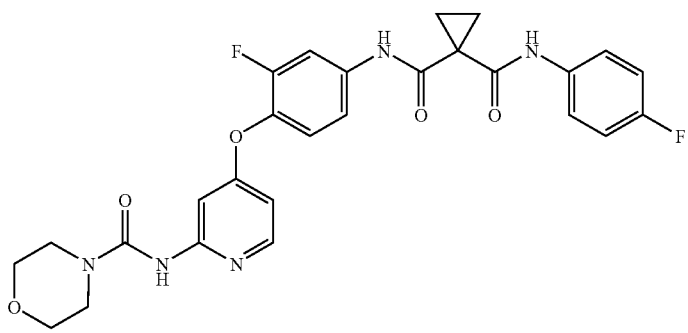
Example 67
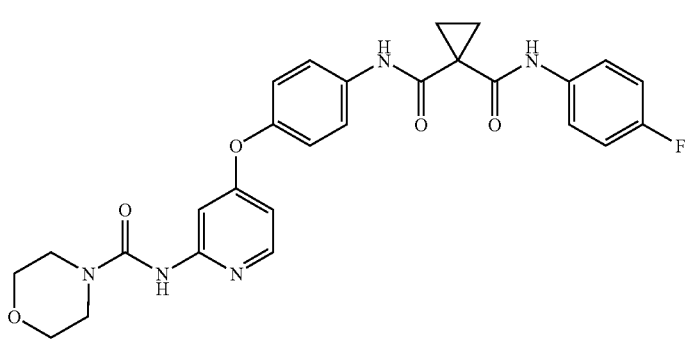
Example 68

TABLE 16-continued
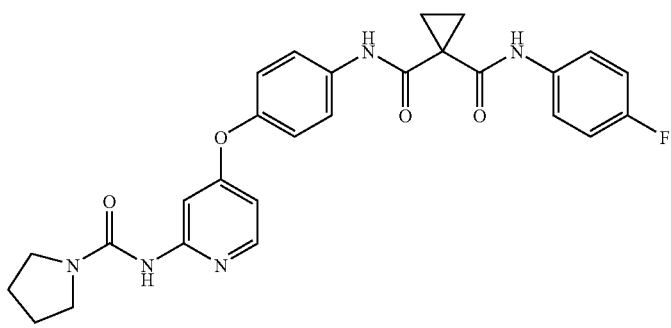
Example 69
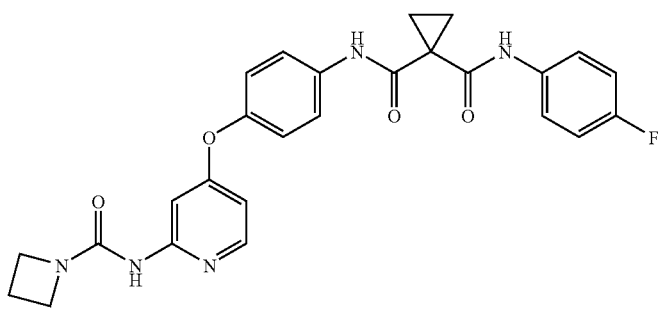
Example 70
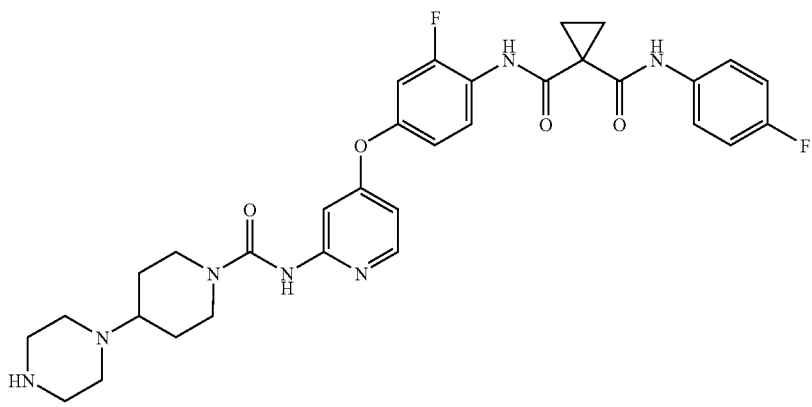
Example 71
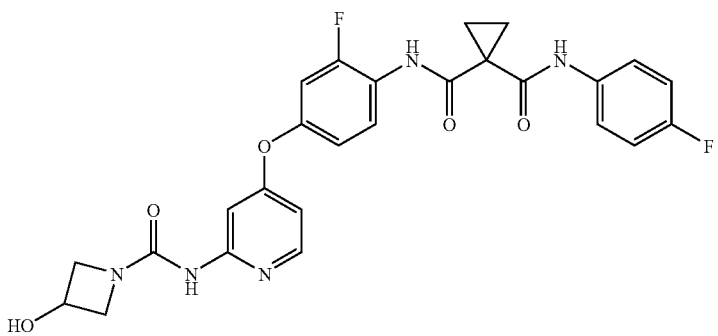
Example 72

TABLE 16-continued
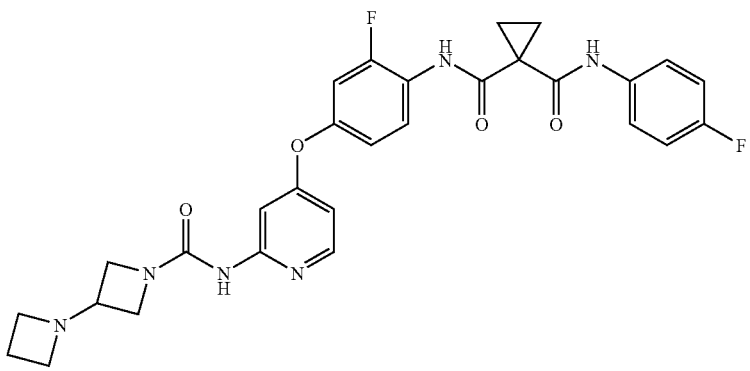
Example 73
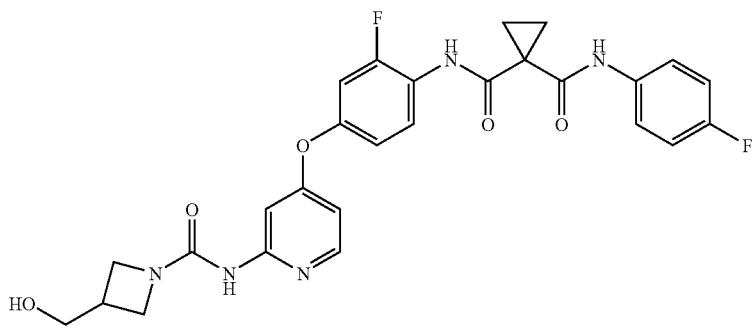
Example 75
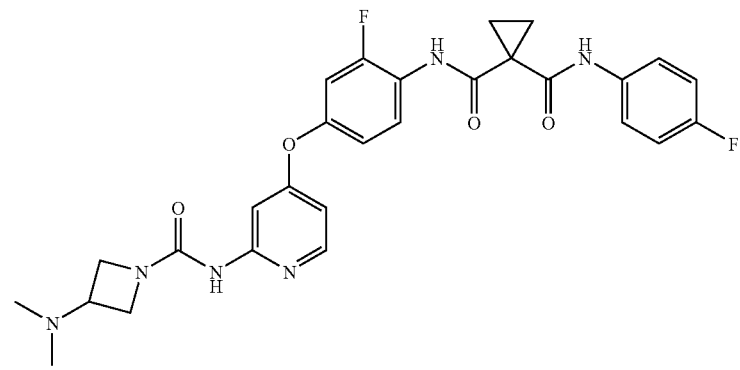
Example 76
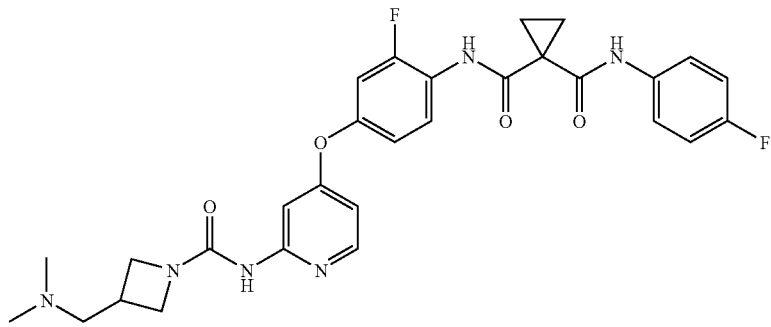
Example 77

TABLE 16-continued
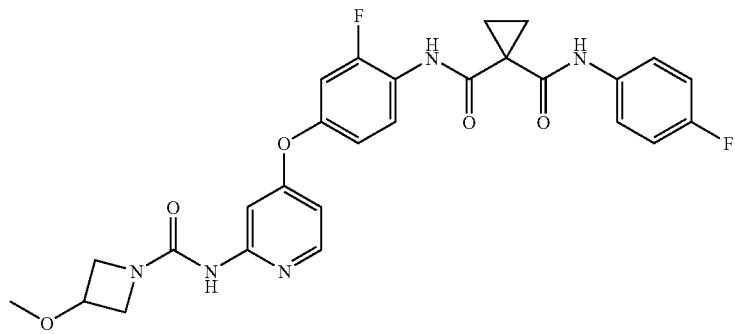
Example 78
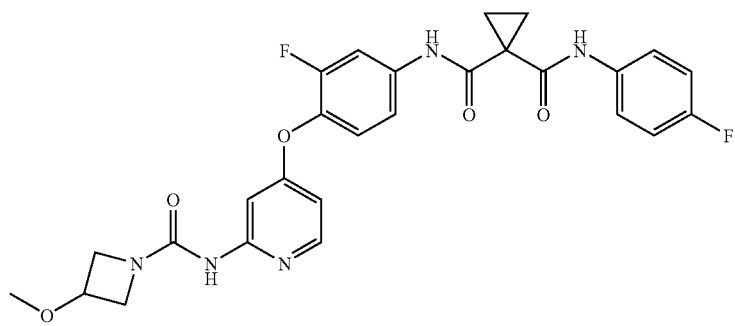
Example 79
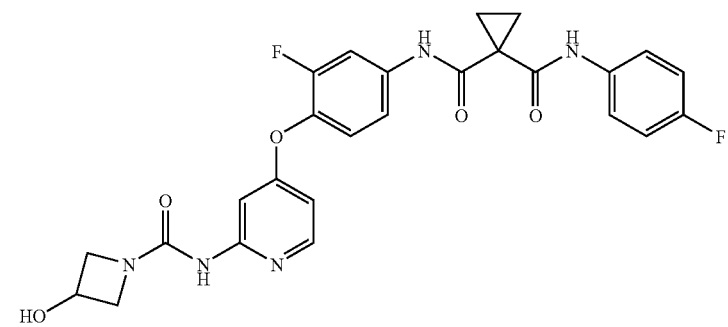
Example 80
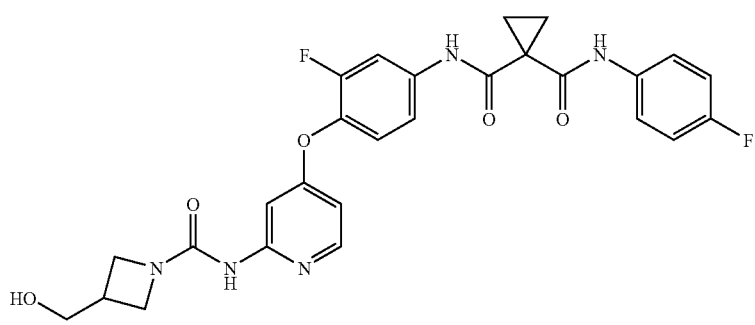
Example 81

TABLE 17
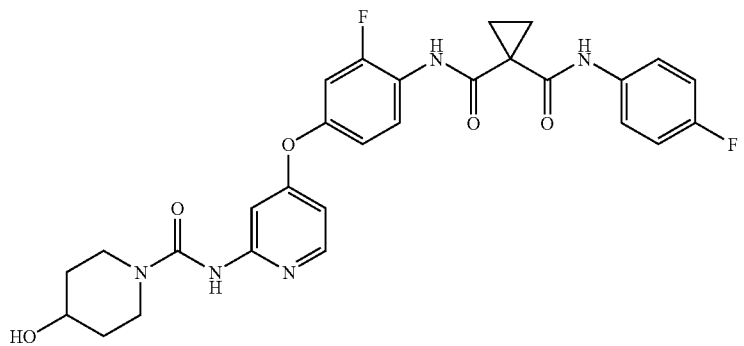
Example 82
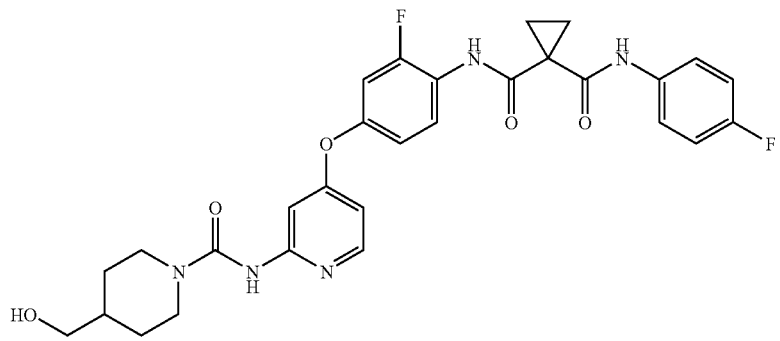
Example 83
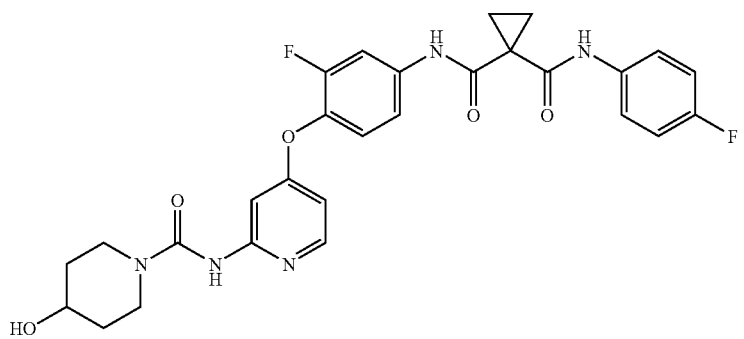
Example 84
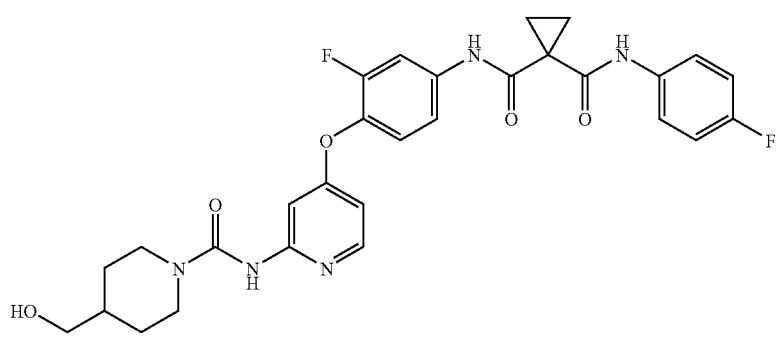
Example 85

TABLE 17-continued
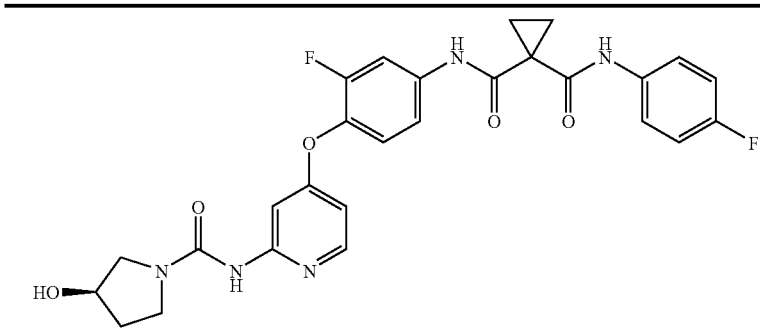
Example 86
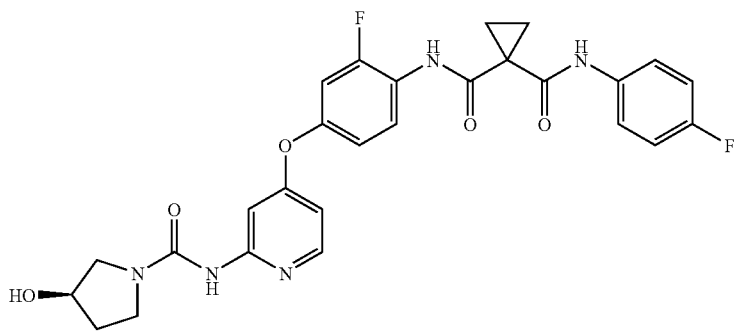
Example 87
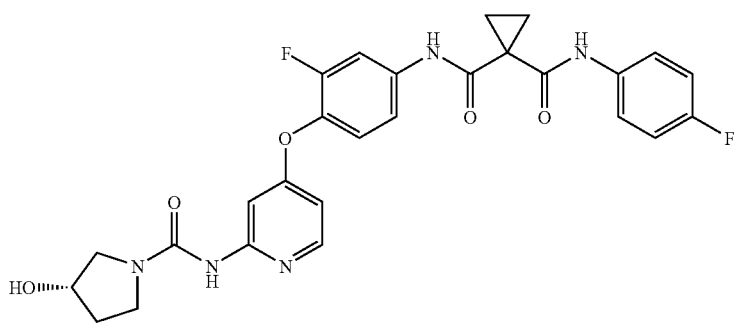
Example 88
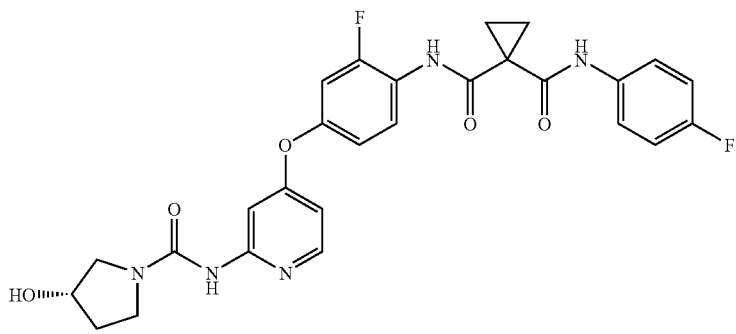
Example 89

TABLE 17-continued
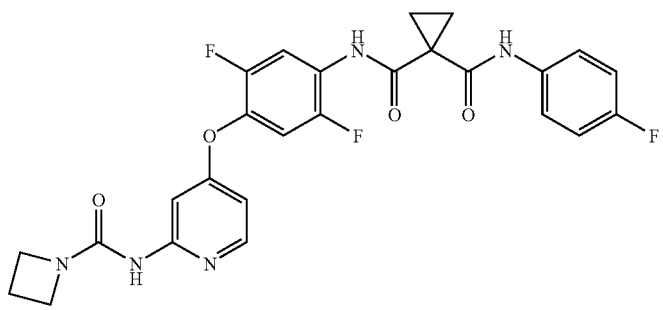
Example 90
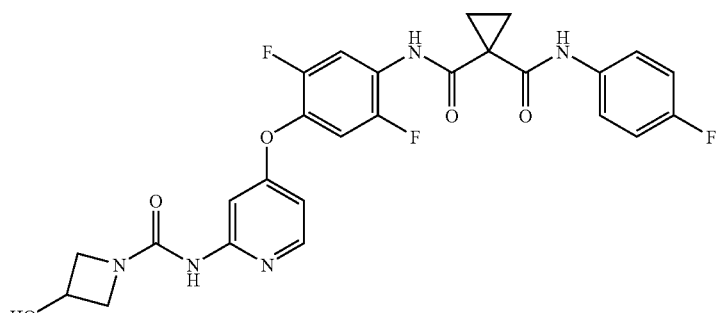
Example 91
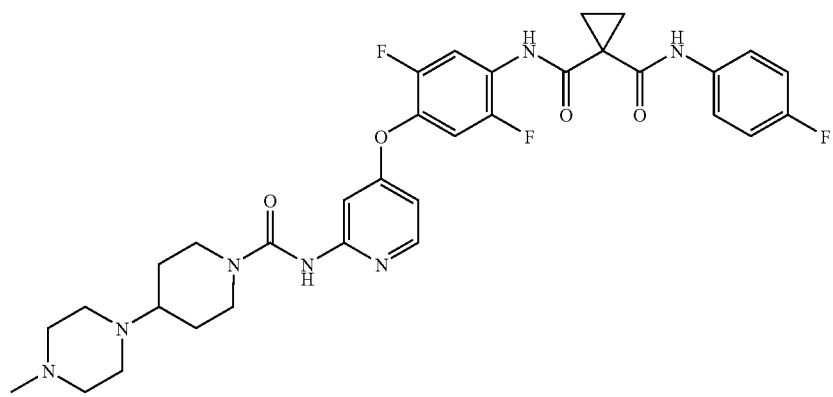
Example 92
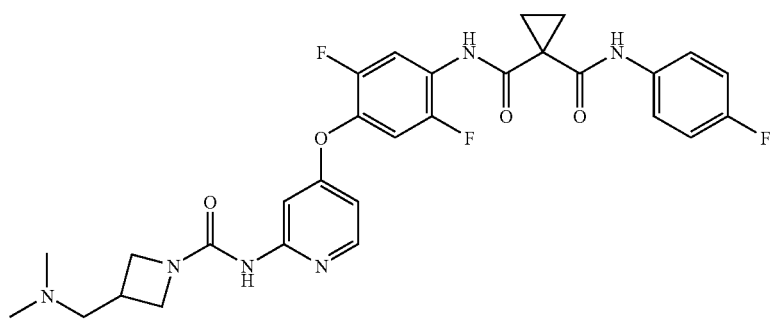
Example 93

TABLE 17-continued
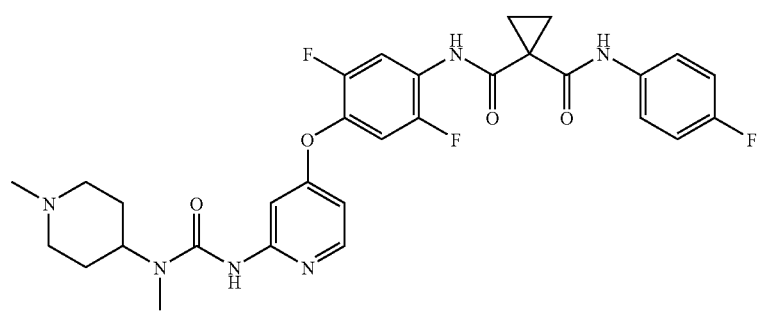
Example 94
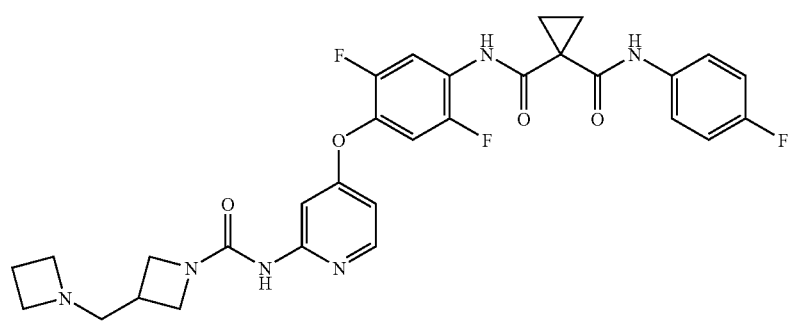
Example 95
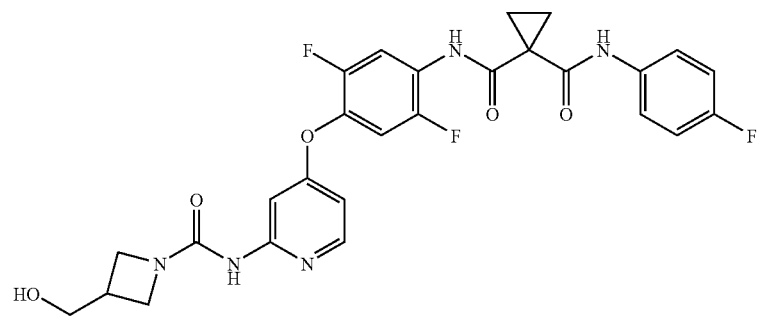
Example 96
TABLE 18
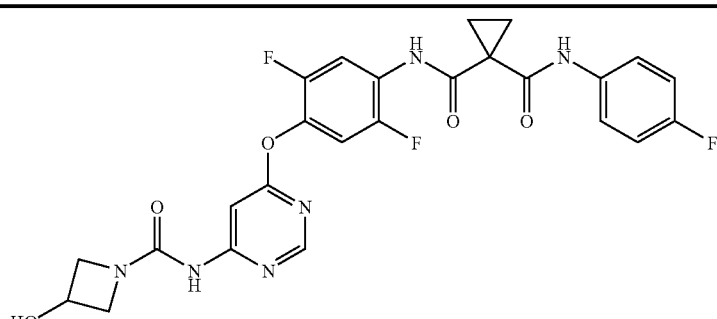
Example 97

TABLE 18-continued
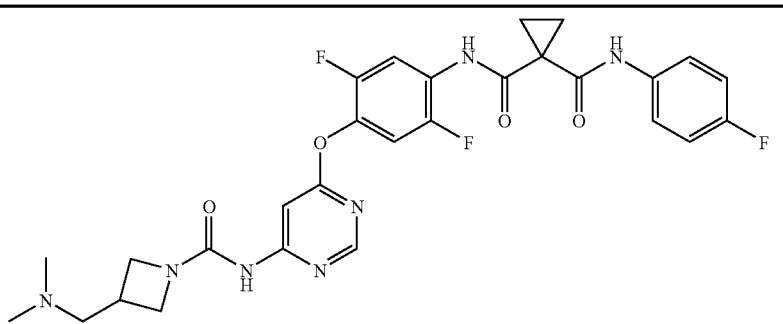
Example 98
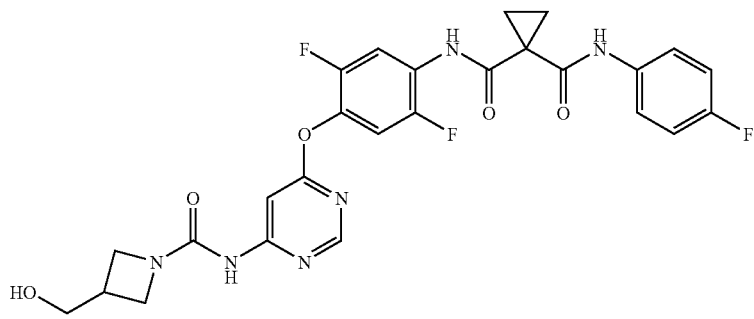
Example 99
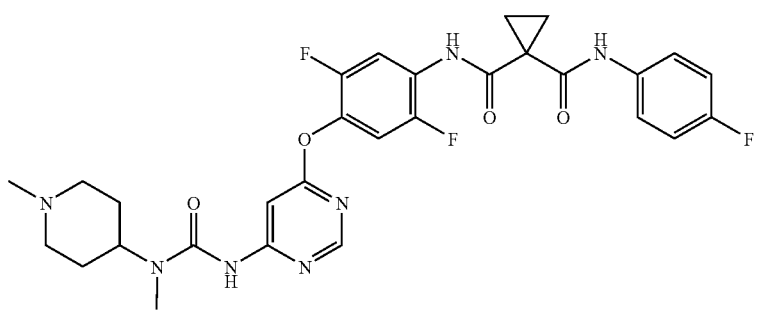
Example 100
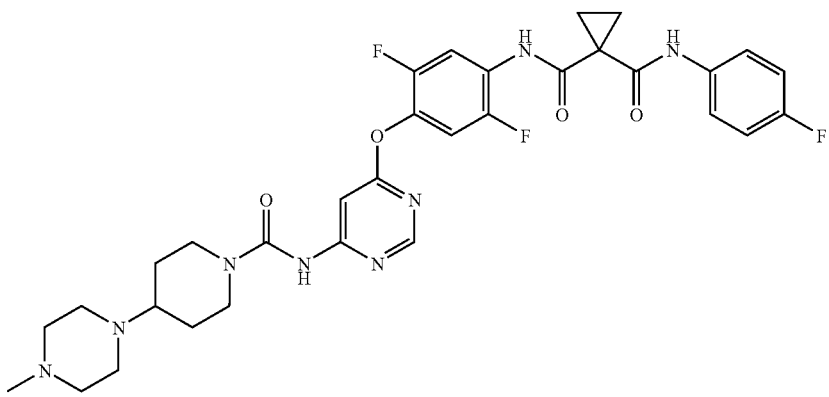
Example 101

TABLE 18-continued
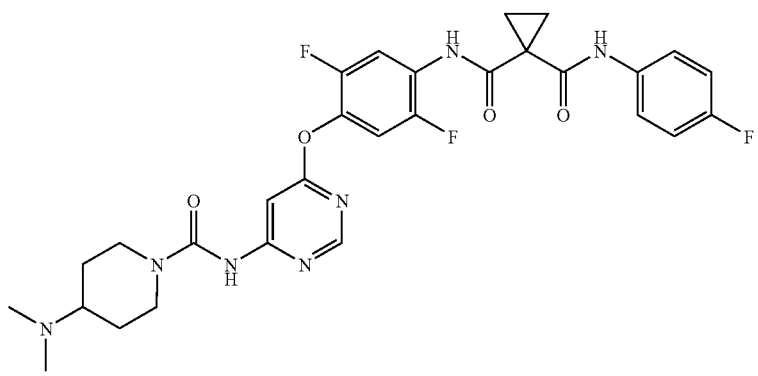
Example 102
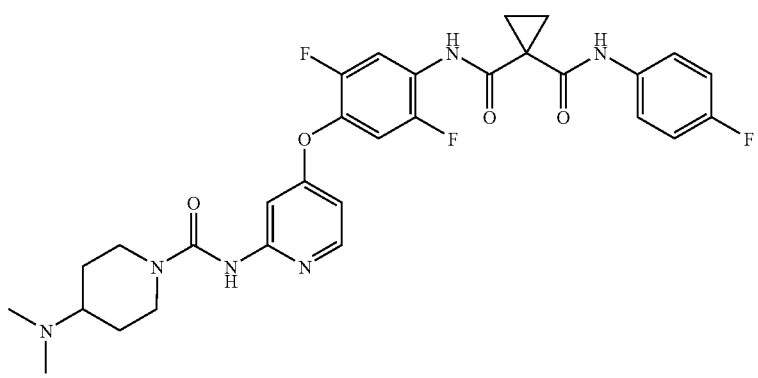
Example 103
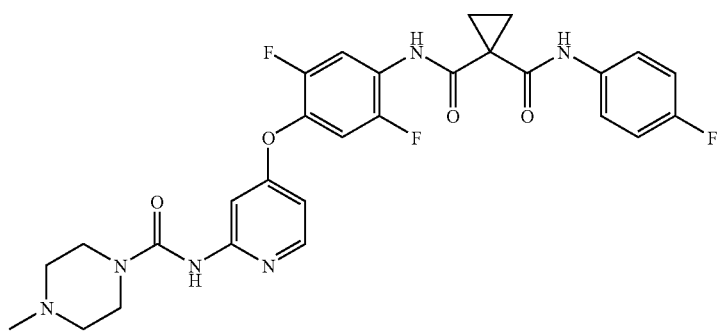
Example 104
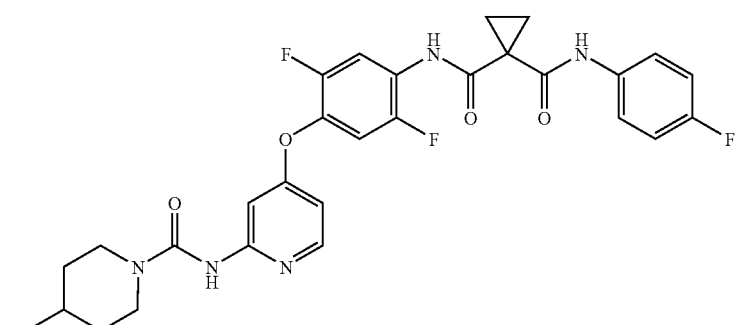
Example 105

TABLE 18-continued
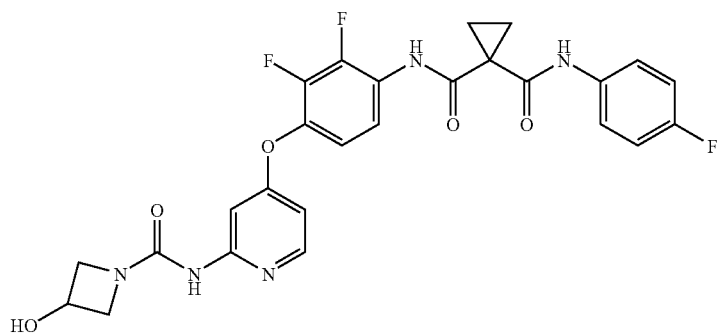
Example 106
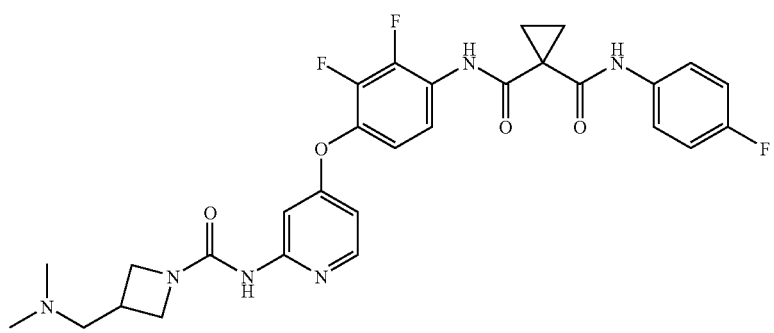
Example 107
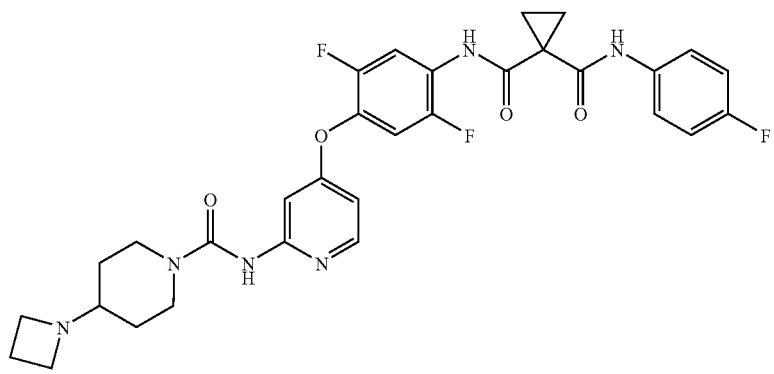
Example 108
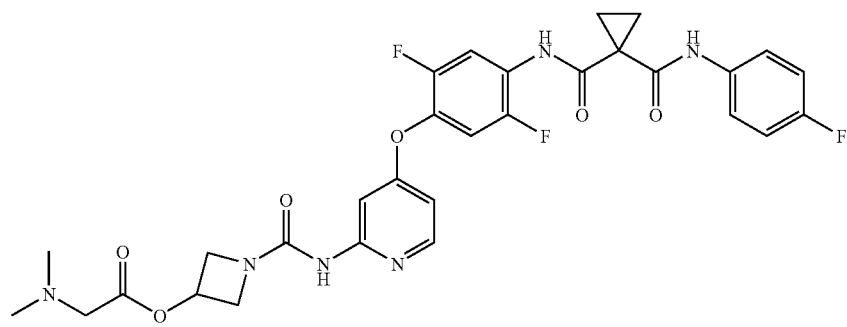
Example 109

TABLE 18-continued
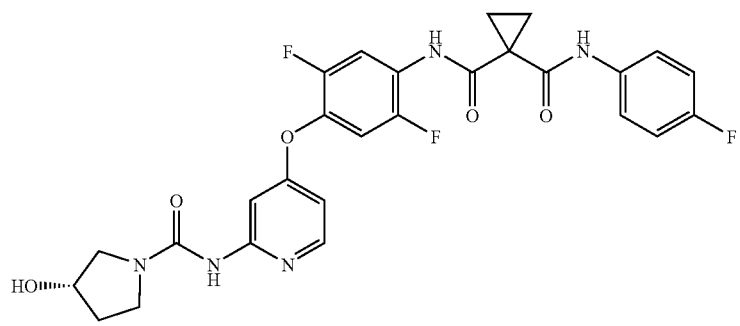
Example 110
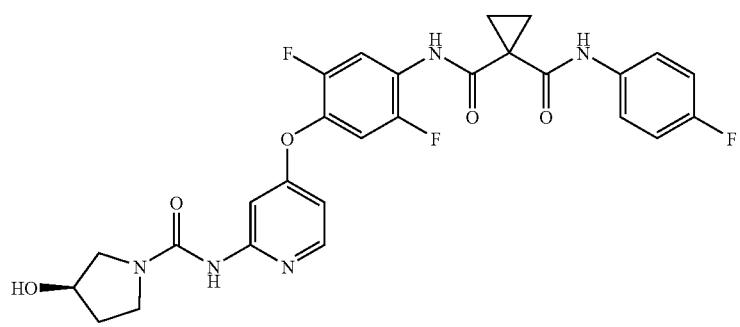
Example 111
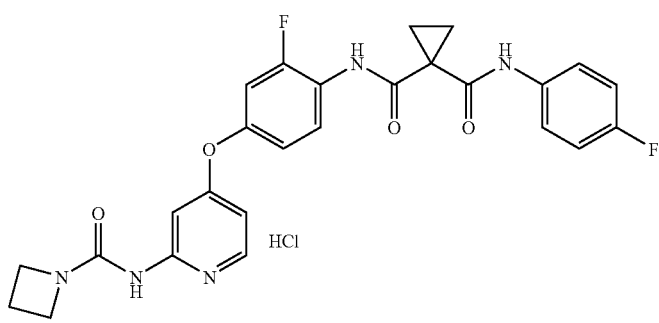
Example 112
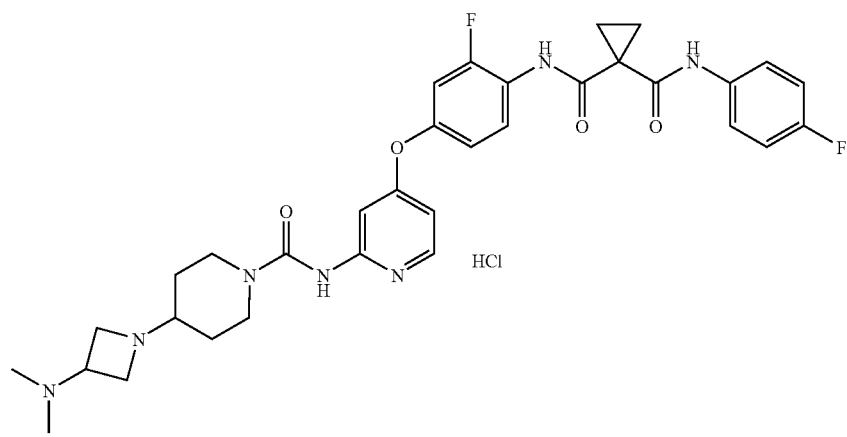
Example 113

TABLE 18-continued

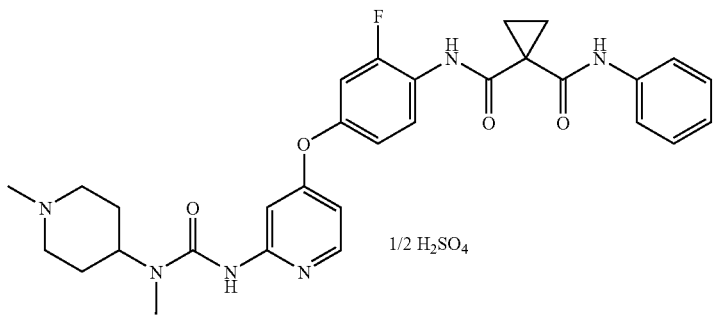

Example 114

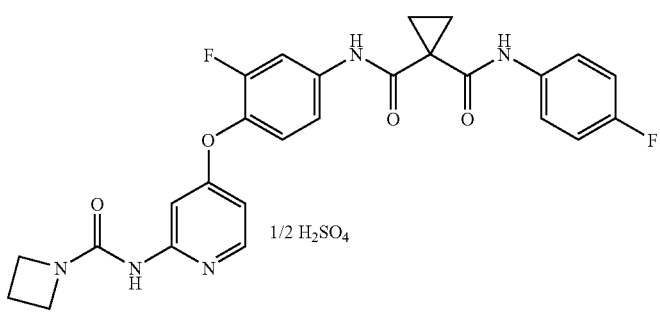

Example 115

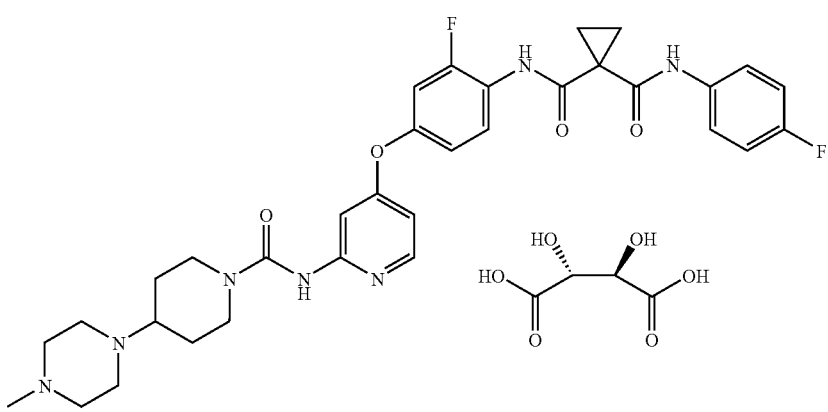

Example 116

INDUSTRIAL APPLICABILITY

A compound according to the present invention has excellent HGFR inhibitory activity, and is useful as an anti-tumor agent against various kinds of tumors such as a pancreatic cancer, a gastric cancer, a colorectal cancer, a breast cancer, a prostate cancer, a lung cancer, a renal cancer, a brain tumor and an ovarian cancer, an inhibitor against angiogenesis or a cancer metastasis inhibitor.

---

What is claimed is:

1. A compound represented by the following formula or a salt thereof:

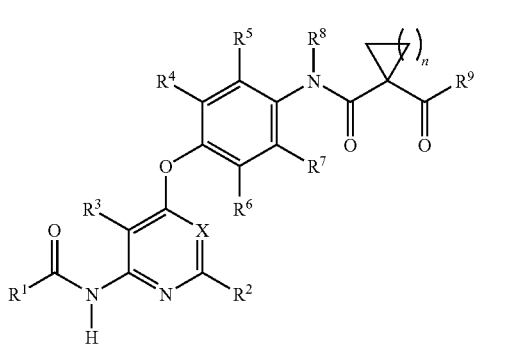

wherein $R^1$ represents azetidin-1-yl optionally substituted with a substituent selected from Substituent Group E, pyrrolidin-1-yl optionally substituted with a substituent selected from Substituent Group E, piperidin-1-yl optionally substituted with a substituent selected from Substituent Group E, piperazin-1-yl optionally substituted with a substituent selected from Substituent Group E, diazepan-1-yl optionally substituted with a substituent selected from Substituent Group E or morpholin-4-yl optionally substituted with a substituent selected from Substituent Group E wherein Substituent Group E substituents are methyl, ethyl, dimethylamino, azetidinyl, pyrrolidinyl, piperidinyl or piperazinyl, wherein each group included in Substituent Group E may be substituted with hydroxyl, methyl, dimethylamino, azetidinyl, pyrrolidinyl or piperidinyl or $R^1$ represents a group represented by the formula —$NR^{11e}R^{11f}$, wherein $R^{11e}$ represents hydrogen or $C_{1-6}$ alkyl, and $R^{11f}$ represents $C_{1-6}$ alkyl, pyrrolidin-3-yl, piperidin-3-yl, piperidin-4-yl or tetrahydropyran-4-yl, and $R^{11f}$ may be substituted with a substituent selected from Substituent Group D, wherein Substituent Group D substituents are halogen, hydroxyl, mercapto, cyano, formyl, oxo, $C_{1-6}$ alkyl, $C_{3-10}$ cycloalkyl, alkoxy, amino, mono-$C_{1-6}$ alkylamino, di-$C_{1-6}$ alkylamino, azetidinyl, pyrrolidinyl, piperidinyl, piperazinyl, diazepanyl or a group represented by -$T^4$-

$T^5$, wherein $T^4$ represents carbonyl or sulfonyl and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino, where each group included in Substituent Group D may be substituted with hydroxyl, $C_{1-6}$ alkyl, di-$C_{1-6}$ alkylamino, azetidinyl or pyrrolidinyl;

$R^2$ and $R^3$ represent hydrogen;

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino;

$R^8$ represents hydrogen or $C_{1-6}$ alkyl;

$R^9$ represents phenylamino optionally substituted with halogen;

n represents an integer of 1 or 2; and

X represents a group represented by the formula —C($R^{10}$)= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as recited above.

2. The compound according to claim 1 or a salt thereof wherein $R^1$ represent azetidin-1-yl optionally substituted with a substituent selected from Substituent Group E, pyrrolidin-1-yl optionally substituted with a substituent selected from Substituent Group E, piperidin-1-yl optionally substituted with a substituent selected from Substituent Group E, piperazin-1-yl optionally substituted with a substituent selected from Substituent Group E, diazepan-1-yl optionally substituted with a substituent selected from Substituent Group E or morpholin-4-yl optionally substituted with a substituent selected from Substituent Group E, wherein Substituent Group E substituents are methyl, ethyl, dimethylamino, azetidinyl, pyrrolidinyl, piperidinyl or piperazinyl, where each group included in Substituent Group E may be substituted with hydroxyl, methyl, dimethylamino, azetidinyl, pyrrolidinyl or piperidinyl.

3. The compound according to claim 1 or a salt thereof, wherein $R^1$ represents azetidin-1-yl optionally substituted with a substituent selected from Substituent Group G, pyrrolidin-1-yl optionally substituted with a substituent selected from Substituent Group G, piperidin-1-yl optionally substituted with a substituent selected from Substituent Group G or piperazin-1-yl optionally substituted with a substituent selected from Substituent Group G, wherein Substituent Group G substituents are dimethylamino, azetidinyl, pyrrolidinyl, piperidinyl, piperazinyl, dimethylaminomethyl, dimethylaminoethyl, azetidin-1-ylmethyl, pyrrolidin-1-ylmethyl or piperidin-1-ylmethyl, where each group included in Substituent Group G may be substituted with methyl or dimethylamino.

4. The compound according to claim 1 or a salt thereof, wherein $R^1$ represents a group represented by the formula —$NR^{11e}R^{11f}$, wherein $R^{11e}$ represents hydrogen or $C_{1-6}$ alkyl, and $R^{11f}$ represents $C_{1-6}$ alkyl, pyrrolidin-3-yl, piperidin-3-yl, piperidin-4-yl or tetrahydropyran-4-yl, and $R^{11f}$ may be substituted with a substituent selected from Substituent Group D, wherein Substituent Group D substituents are halogen, hydroxyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, or diazepanyl, where each group included in Substituent Group D may be substituted with hydroxyl, $C_{1-6}$ alkyl, di-$C_{1-6}$ alkylamino, azetidinyl or pyrrolidinyl.

5. The compound according to claim 1 or a salt thereof, wherein $R^1$ represents a group represented by the formula —$NR^{11g}R^{11h}$, wherein $R^{11g}$ represents hydrogen or methyl, and $R^{11h}$ represents n-propyl, n-butyl, pyrrolidin-3-yl, piperidin-3-yl, piperidin-4-yl or tetrahydropyran-4-yl, and $R^{11h}$ may be substituted with a substituent selected from Substituent Group F, wherein Substituent Group F substituents are methyl, ethyl, n-propyl, acetyl, dimethylamino, diethylamino, azetidinyl, pyrrolidinyl or piperazinyl, where each group included in Substituent Group F may be substituted with methyl or dimethylamino.

6. The compound according to claim 1 or a salt thereof, wherein $R^1$ represents a group represented by the formula —$N(CH_3)R^{11i}$, wherein $R^{11i}$ represents n-propyl, n-butyl, pyrrolidin-3-yl or piperidin-4-yl, and $R^{11i}$ may be substituted with a substituent selected from Substituent Group H, wherein Substituent Group H substituents are dimethylamino, diethylamino, dimethylaminoethyl, dimethylaminopropyl or 1-methylazetidin-3-yl.

7. The compound according to claim 1 or a salt thereof, wherein $R^1$ represents a group represented by the formula —$N(CH_3)R^{11j}$, wherein $R^{11j}$ represents 1-methylpiperidin-4-yl or 1-ethylpiperidin-4-yl.

8. The compound according to claim 1 or a salt thereof, wherein $R^4$, $R^5$, $R^6$ and $R^7$ may be the same or different and each represents hydrogen, halogen or $C_{1-6}$ alkyl.

9. The compound according to claim 1 or a salt thereof, wherein $R^8$ represents hydrogen.

10. The compound according to claim 1 or a salt thereof, wherein X represents a group represented by the formula —$C(R^{10a})$=, wherein $R^{10a}$ represents hydrogen, halogen or cyano.

11. The compound according to claim 1 or a salt thereof, wherein X represents nitrogen.

12. The compound according to claim 1 or a salt thereof, wherein n represents 1.

13. The compound according to claim 1 or a salt thereof, wherein $R^9$ represents phenylamino optionally substituted with fluorine.

14. The compound according to claim 1 or a salt thereof, wherein $R^9$ represents 4-fluorophenylamino.

\* \* \* \* \*